(12) United States Patent
Allan et al.

(10) Patent No.: US 12,365,666 B2
(45) Date of Patent: *Jul. 22, 2025

(54) PROCESS FOR PREPARING A Cot INHIBITOR COMPOUND

(71) Applicant: Gilead Sciences, Inc., Foster City, CA (US)

(72) Inventors: Kevin M. Allan, Belmont, CA (US); Lina Chan, Foster City, CA (US); Andrei Chtchemelinine, San Mateo, CA (US); Jeffrey T. Deignan, San Francisco, CA (US); Kelly J. Eberle, San Diego, CA (US); Timothy G. Elford, Sherwood Park (CA); Kevin D. Haggerty, St. Albert (CA); Jesse W. Li, Edmonton (CA); Andrew C. Stevens, Edmonton (CA); Ana F. Voica, Redwood City, CA (US); Kevin S. Williamson, San Mateo, CA (US); Boran Xu, Edmonton (CA)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/386,675

(22) Filed: Nov. 3, 2023

(65) Prior Publication Data

US 2024/0199579 A1    Jun. 20, 2024

Related U.S. Application Data

(63) Continuation of application No. 17/218,765, filed on Mar. 31, 2021, now Pat. No. 11,845,737.

(60) Provisional application No. 63/004,254, filed on Apr. 2, 2020.

(51) Int. Cl.
| | | |
|---|---|---|
| *C07D 401/14* | (2006.01) | |
| *C07D 217/02* | (2006.01) | |
| *C07D 217/24* | (2006.01) | |
| *C07D 249/04* | (2006.01) | |
| *C07D 401/06* | (2006.01) | |

(52) U.S. Cl.
CPC ......... *C07D 401/14* (2013.01); *C07D 217/02* (2013.01); *C07D 217/24* (2013.01); *C07D 249/04* (2013.01); *C07D 401/06* (2013.01)

(58) Field of Classification Search
CPC .. C07D 401/14; C07D 401/06; C07D 217/02; C07D 217/24; C07D 249/04
See application file for complete search history.

(56) References Cited

U.S. PATENT DOCUMENTS

| | | |
|---|---|---|
| 3,845,770 A | 11/1974 | Theeuwes et al. |
| 3,930,837 A | 1/1976 | Serban |
| 4,151,298 A | 4/1979 | Drabek et al. |
| 4,326,525 A | 4/1982 | Swanson et al. |
| 4,902,514 A | 2/1990 | Barclay et al. |
| 4,992,445 A | 2/1991 | Lawter et al. |
| 5,001,139 A | 3/1991 | Lawter et al. |
| 5,023,252 A | 6/1991 | Hseih |
| 5,565,408 A | 10/1996 | Hagen et al. |
| 5,616,345 A | 4/1997 | Geoghegan et al. |
| 7,297,795 B2 | 11/2007 | Sutherland et al. |
| 7,432,279 B2 | 10/2008 | Green et al. |
| 7,741,354 B2 | 6/2010 | Thormann et al. |
| 8,008,481 B2 | 8/2011 | Ericsson et al. |
| 9,173,395 B2 | 11/2015 | Frackenpohl et al. |
| 9,453,026 B2 | 9/2016 | Harriman et al. |
| 9,815,818 B2 | 11/2017 | Bacon et al. |
| 9,878,995 B2 | 1/2018 | Bacon et al. |
| 9,878,996 B2 | 1/2018 | Silverman |
| 10,059,695 B2 | 8/2018 | Balan et al. |
| 10,316,017 B2 | 6/2019 | Bacon et al. |
| 10,577,352 B2 | 3/2020 | Balan et al. |
| 10,702,503 B2 | 7/2020 | Haneda et al. |

(Continued)

FOREIGN PATENT DOCUMENTS

| | | |
|---|---|---|
| CN | 101790518 | 7/2010 |
| CN | 102040550 | 5/2011 |

(Continued)

OTHER PUBLICATIONS

Akriviadis et al., "Treatment of alcoholic hepatitis: is this a "dead-end"?," Ann Gastroenterol., 2016, 29(2):236-237.

Alkhouri et al. "GS-0976 (Firsocostat): an investigational liver-directed acetyl-CoA carboxylase (ACC) inhibitor for the treatment of non-alcoholic steatohepatitis (NASH)," Expert opinion on investigational drugs, Feb. 2020, 29(2): 135-141.

Bates et al., "Acetyl-CoA carboxylase inhibition disrupts metabolic reprogramming during hepatic stellate cell activation," Journal of Hepatology, Oct. 2020, 73(4):896-905.

Brown et al., "Bromination of Isoquinoline, Quinoline, Quinazoline and Quinoxaline in Strong Acid," Synthesis, 2002, 1:83-86.

(Continued)

*Primary Examiner* — D Margaret M Seaman
(74) *Attorney, Agent, or Firm* — Fish & Richardson P.C.

(57) ABSTRACT

Disclosed are syntheses of a Cot (cancer Osaka thyroid) inhibitor, which has the following formula:

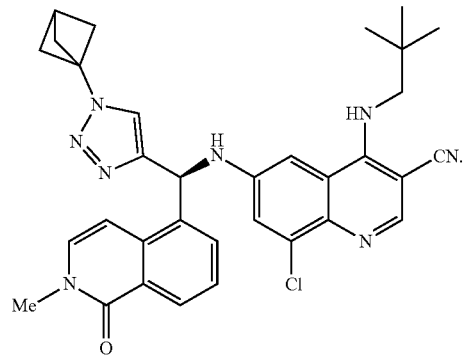

20 Claims, No Drawings

(56) References Cited

U.S. PATENT DOCUMENTS

| | | | |
|---|---|---|---|
| 10,947,259 B2 | 3/2021 | Canales et al. | |
| 11,066,414 B2 | 7/2021 | Bacon et al. | |
| 11,325,930 B2 | 5/2022 | Canales et al. | |
| 11,655,237 B2 | 5/2023 | Dempah et al. | |
| 11,845,737 B2* | 12/2023 | Allan | C07D 217/24 |
| 11,905,299 B2 | 2/2024 | Bacon et al. | |
| 2005/0043537 A1 | 2/2005 | Sutherland et al. | |
| 2006/0264460 A1 | 11/2006 | Green et al. | |
| 2011/0009410 A1 | 1/2011 | Corkey et al. | |
| 2013/0116206 A1 | 5/2013 | Pisaneschi et al. | |
| 2013/0123231 A1 | 5/2013 | Harriman et al. | |
| 2013/0197037 A1 | 8/2013 | Notte | |
| 2013/0225579 A1 | 8/2013 | Zhang et al. | |
| 2014/0171422 A1 | 6/2014 | Otsubo et al. | |
| 2014/0221659 A1 | 8/2014 | Kinzel et al. | |
| 2014/0275006 A1 | 9/2014 | Yoshinaga et al. | |
| 2015/0297573 A1 | 10/2015 | Dalle et al. | |
| 2016/0244430 A1 | 8/2016 | Brown et al. | |
| 2016/0280683 A1 | 9/2016 | Andres et al. | |
| 2016/0297809 A1 | 10/2016 | Coburn et al. | |
| 2017/0008873 A1 | 1/2017 | Bacon et al. | |
| 2017/0008905 A1 | 1/2017 | Bacon et al. | |
| 2017/0152240 A1 | 6/2017 | Bacon et al. | |
| 2017/0267690 A1 | 9/2017 | Alexander et al. | |
| 2017/0268069 A1 | 9/2017 | Garraway et al. | |
| 2017/0273952 A1 | 9/2017 | Watkins | |
| 2017/0362201 A1 | 12/2017 | Bacon et al. | |
| 2018/0002316 A1 | 1/2018 | Balan et al. | |
| 2018/0013320 A1 | 1/2018 | Brooks et al. | |
| 2018/0021341 A1 | 1/2018 | Harriman et al. | |
| 2018/0237455 A1 | 8/2018 | Bacon et al. | |
| 2018/0280394 A1 | 10/2018 | Bates et al. | |
| 2018/0298025 A1 | 10/2018 | Geier et al. | |
| 2018/0333401 A1 | 11/2018 | Bates et al. | |
| 2019/0016705 A1 | 1/2019 | Balan et al. | |
| 2019/0031612 A1 | 1/2019 | Li et al. | |
| 2019/0134041 A1 | 5/2019 | Bates et al. | |
| 2019/0248807 A1 | 8/2019 | Bacon et al. | |
| 2020/0123172 A1 | 4/2020 | Bacon et al. | |
| 2020/0281911 A1 | 9/2020 | Dalton et al. | |
| 2020/0392170 A1 | 12/2020 | Canales et al. | |
| 2021/0061831 A1 | 3/2021 | Canales et al. | |
| 2021/0147454 A1 | 5/2021 | Canales et al. | |
| 2021/0309637 A1 | 10/2021 | Dempah et al. | |
| 2022/0235078 A1 | 7/2022 | Canales et al. | |
| 2022/0259234 A1 | 8/2022 | Canales et al. | |
| 2022/0380340 A1 | 12/2022 | Allan et al. | |
| 2023/0000848 A1 | 1/2023 | Breckenridge et al. | |
| 2023/0002407 A1 | 1/2023 | Bacon et al. | |
| 2023/0322727 A1 | 10/2023 | Dempah et al. | |
| 2024/0043458 A1 | 2/2024 | Canales et al. | |
| 2024/0066016 A1 | 2/2024 | Breckenridge et al. | |
| 2024/0174702 A1 | 5/2024 | Carra et al. | |
| 2024/0254137 A1 | 8/2024 | Bacon et al. | |

FOREIGN PATENT DOCUMENTS

| | | |
|---|---|---|
| CN | 103408572 | 11/2013 |
| CN | 103483363 | 1/2014 |
| CN | 106512014 | 3/2017 |
| CN | 109928956 | 6/2019 |
| CN | 112300072 | 2/2021 |
| EG | 1437/2007 | 12/2007 |
| JP | H20-36181 | 2/1990 |
| JP | 2005526097 | 9/2005 |
| JP | 2009513659 | 4/2009 |
| WO | WO 1994/027969 | 12/1994 |
| WO | WO 1998/043960 | 10/1998 |
| WO | WO 1999/011124 | 3/1999 |
| WO | WO 2000/002887 | 1/2000 |
| WO | WO 2000/018740 | 4/2000 |
| WO | WO 2004/078176 | 9/2004 |
| WO | WO 2005/019201 | 3/2005 |
| WO | WO 2005/028443 | 3/2005 |
| WO | WO 2005/082891 | 9/2005 |
| WO | WO 2006/030032 | 3/2006 |
| WO | WO 2006/124692 | 11/2006 |
| WO | WO 2008/055950 | 5/2008 |
| WO | WO 2008/092292 | 8/2008 |
| WO | WO 2010/055164 | 5/2010 |
| WO | WO 2015/089170 | 6/2015 |
| WO | WO 2015/134710 | 9/2015 |
| WO | WO 2016/044331 | 3/2016 |
| WO | WO 2017/007689 | 1/2017 |
| WO | WO 2017/007694 | 1/2017 |
| WO | WO 2018/005435 | 1/2018 |
| WO | WO 2020/185685 | 9/2020 |
| WO | WO 2020/252151 | 12/2020 |
| WO | WO 2021/030142 | 2/2021 |
| WO | WO 2021/202224 | 10/2021 |
| WO | WO 2021/202688 | 10/2021 |

OTHER PUBLICATIONS

Bunz et al., "Bridgehead-Coupled Bicyclo[1.1.1]pentanes: Synthesis and Structure," Chem Ber, 1988, 121(10):1785-1790 (with English abstract).

Chemical Abstract Registry No. 1092351-39-7, dated Dec. 31, 2008, retrieved on Mar. 25, 2020.

Chemical Abstract Registry No. 1349435-18-2, indexed in the Registry File on STN CAS Online Dec. 6, 2011.

Chemical Abstract Registry No. 1415564-65-6, dated Dec. 27, 2012, retrieved on Mar. 25, 2020.

Chemical Abstract Registry No. 2102019-37-2, dated Jul. 14, 2017, retrieved on Dec. 5, 2022, 1 page.

Chemical Abstracts, Database accession No. 292605-14-2.

Cohen et al., "Targeting protein kinases for the development of anti-inflammatory drugs", Curr Opin Cell Biol., 2009, 21:317-24.

Cooksey et al., "N-Substituted Heterocyclic Cations. Part VIII. Substituent Effects and the Acidity of Quinolinium Ions. Hydroxide Addition versus Proton Loss," J. Chem. Soc. (B), 1968, pp. 1191-1197.

Cusack et al., "Identification of a selective thieno[2,3-c]pyridine inhibitor of Cot kinase and TNF-oc production" Bioorganic & Medicinal Chemistry Letters, 2009, 19:1722-25.

Della et al., "Experimental and Theoretical Study of Substituent Effects on $^3J(^{13}C1-^1H)$ Coupling Constants in 1-X-bicyclo[1.1.1]pentanes", Journal of Physical Organic Chemistry, 1996, 9(3):168-178.

Detz et al., "Enantioselective Copper-Catalyzed Propargylic Amination," Angew. Chem. Int. Ed., 2008, 47:3777-3780.

Eisenberg et al., "Why can't we find a new treatment for SLE?", J Autoimmun, 2009, 32:223-30.

Eller et al., "Ober die Einwirkung von Sulfurylchlorid auf aromatische Amine," Berichte der Deutschen Chemischen Gesellschaft [Abteilung] B: Abhandlungen, 1922, 55B:217-224 (English-language machine translation of the first page).

Foster, "Deuterium Isotope Effects in Studies of Drug Metabolism," Trends Pharmacol. Sci., 1984, 5(12):524-527.

Gamage et al., "Structure-Activity Relationships for Pyrido-, lmidazo-, Pyrazolo-, Pyrazino-, and Pyrrolophenazinecarboxamides as Topoisomerase-Targeted Anticancer Agents", J Med Chem, 2002, 45(3):740-743.

Gantke et al., "Regulation and function of TPL-2, an lkB kinase-regulated MAP kinase kinase kinase", Cell Res., 2010, 21 (1):131-45.

Garofalo et al., "Discovery of 4-alkylamino-7-aryl-3-cyanoquinoline LRRK2 kinase inhibitors," Bioorganic & Medicinal Chemistry Letters, 2013, 23:1974-1977.

Gavrin et al., "Inhibition of Tp12 kinase and TNF-oc production with 1,7-naphthyridine-3-carbonitriles: Synthesis and structure-activity relationships" Bioorganic & Medicinal Chemistry Letters, 2005, 15:5288-5292.

GenBank Accession No. NP_004985, "matrix metalloproteinase-9 preproprotein [*Homo sapiens*]," Jul. 4, 2020, 3 pages.

George et al., "Cot/Tpl-2 Protein Kinase as a Target for the Treatment of Inflammatory Disease", Current Topics in Medicinal Chemistry, 2009, 9:611-622.

(56) References Cited

OTHER PUBLICATIONS

George et al., "Discovery of thieno[2,3-c]pyridines as potent Cot inhibitors" Bioorganic & Medicinal Chemistry Letters, 2008, 18:4952-4955.
Ghosh, "Anti-TNF therapy in Crohn's disease," Inflammatory Bowel Disease: Crossroads of Microbes, Epithelium and Immune Systems, Novartis Foundation Symposium, Nov. 2004, 263:193-205.
Gianatassio et al., "Strain Release Amination," Science, 2016, 351(6270):241-246.
Gisbert et al., "Vedolizumab en el tratamiento de la enfermedad de Crohn," Gastroenterologia y Hepatologia, Jan. 2015, 38(5): 338-348 (with English abstract).
Glatthar et al., "Discovery of Imidazoquinolines as a Novel Class of Potent, Selective, and in Vivo Efficacious Cancer Osaka Thyroid (COT) Kinase Inhibitors", Journal of Medicinal Chemistry, 2016, 59:7544-7560.
Goh et al., "A New Route to Bicyclo[1.1.1]pentan-l-amine from l-Azido-3-iodobicyclo[1.1.1]pentane," Organic Letters, 2014, 16(7):1884-1887.
Gonzalez-Cabrera et al., "SIP signaling: new therapies and opportunities," F1000Prime Reports, Dec. 2014, 6(109):1-7.
Goyal et al., "Models for anti-inflammatory activity of 8-substituted-4-anilino-6-aminoquinoline-3-carbonitriles", Med Chem Res, 2011, 21:1044-55.
Green et al., "Inhibitors of Tumor Progression Loci-2 (Tpl2) Kinase and Tumor Necrosis Factor oc (TNF-oc) Production: Selectivity and in Vivo Antiinflammatory Activity of Novel 8-Substituted-4-anilino-6-aminoquinoline-3-carbonitriles," J. Med. Chem., 2007, 50:4728-4745.
Grignard et al., "Sur le monomagnesien de l'acetylene," Academie Des Sciences, Sep. 24, 1928, pp. 517-520 (English-language machine translation).
Gu et al., "A highly specific inhibitor of matrix metalloproteinase-9 rescues laminin from proteolysis and neurons from apoptosis in transient focal cerebral ischemia," The Journal of Neuroscience, 2005, 25(27):6401-6408.
Gupta et al., "Homolytic displacement at carbon. Part 3. First example of alpha-attack on the allenyl- and prop-2-ynyl-cobaloximes," J. Chem. Soc., Perkin Trans. 2, 1988, 1377-1383.
Guyatt et al., "A new measure of health status for clinical trials in inflammatory bowel disease," Gastroenterology, 1989, 96:804-810.
Hall et al., "Pharmacologic Inhibition of Tpl2 Blocks Inflammatory Responses in Primary Human Monocytes, Synoviocytes, and Blood", The Journal of Biological Chemistry, 2007, 282(46): 33295-33304.
Hamad Elgazwy, "Studies of (Pd0-Mediated) Stille Cross-Coupling Reactions of Thiophenestannane with Aryl Halide Derivatives," Phosphorus, Sulfur, and Silicon and the Related Elements.; 164(1):131-143.
Hanselmann et al., "Synthesis of an Antibacterial Compound Containing a 1,4-Substituted 1H-1,2,3-Triazole: A Scaleable Alternative to the "Click" Reaction," Organic Process Research & Development, 2010, 14(1):152-158.
Hirata et al., "Inhibition of tumor progression locus 2 protein kinase decreases lipopolysaccharide-induced tumor necrosis factor alpha production due to the inhibition of the tip-associated protein induction in RAW264.7 cells", Biol Pharm Bull, 2010, 33(7):1233-7.
Hirayama, "Organic Compound Crystallization Process—Principle of Crystallization of Organic Compounds," Jul. 25, 2018, pp. 57-79 (with English translation).
Horváth et al., "Regioexhaustive Functionalization of the Carbocyclic Core of Isoquinoline: Concise Synthesis of Oxoaporphine Core and Ellipticine," Synthesis, Jun. 2018, 50(11):2181-2190.
Hu et al., "Discovery of indazoles as inhibitors of Tpl2 kinase", Bioorganic & Medicinal Chemistry Letters, 2011, 21(16): 4758-4761.
Hu et al., "Inhibition of Tp12 kinase and TN Fa production with quinoline-3-carbonitriles for the treatment of rheumatoid arthritis," Bioorganic & Medicinal Chemistry Letters, 2006, 16:6067-6072.

Jin et al., "Visible-Light-Mediated Aerobic Oxidation of N-Alkylpyridinium Salts under Organic Photocatalysis," Journal of the American Chemical Society, Oct. 2017, 139(40):14237-14243.
Kaila et al., "Identification of a novel class of selective Tpl2 kinase inhibitors: 4-Alkvlamino-fl, 7lnaohthvridine-3-carbonitriles", Bioorganic & Medicinal Chemistry, 2007, 15:6425-6442.
Kakino et al. "Pivotal Role of TNF-α in the Development and Progression of Nonalcoholic Fatty Liver Disease in a Murine Model," Hormone and Metabolic Research, Jan. 2018, 50(01): 80-87.
Kitamura et al., "A reagent for safe and efficient diazo-transfer to primary amines: 2-azido-1,3-dimethylimidazolinium hexafluorophosphate", Org. Biomol. Chem., 2014, 12:4397-4406.
Kitamura et al., "Synthesis of a,a-diarylacetamides from benzyl aryl ketones using 2-azido-1,3-dimethylimidazolinium hexafluorophosphate," Tetrahedron Letters, 2011, 52(24):3158-3161.
Kokhan et al., "Bicyclo[1.1.1]pentane-Derived Building Blocks for Click Chemistry," European Journal of Organic Chemistry, 2017, 43:6450-6456.
Körner et al., "a-Halogenated p-nitroaniline and its derivatives," Atti della Accademia Nazionale dei Lincei, Classe di Scienze Fisiche, Matematiche e Naturali, Rendiconti, 1913, 22(1):823-836 (English-language machine translation of the first page).
Kötz et al., "Gleichzeitige Reduktion und Oxydation. (Erste Abhandlung.) Dichlorbrenztraubensaure, -nitril und -ester aus Trichlormilchsaure, -nitril und—ester," Journal Fuerraktische Chemie-chemiker-zeitung, Sep. 19, 1913, 88:531-552 (English-language machine translation of the first page).
Kranenburg et al., "The Effect of the Bite Angle of Diphosphane Ligands on Activity and Selectivity in Palladium-Catalyzed Cross-Coupling," Eur. J. Inorg. Chem., 1998, 2:155-157.
Lopchuk et al., "Strain-Release Heteroatom Functionalization: Development, Scope, and Stereospecificity," Journal of the American Clinical Society, 2017, 139(8):3209-3226.
Marshall et al., "Selective Allosteric Inhibition of MMP9 Is Efficacious in Preclinical Models of Ulcerative Colitis and Colorectal Cancer," PLoS One, May 2015, 10(5): pp. 1-26.
McMahon et al., "VEGF Receptor Signaling in Tumor Angiogensis", The Oncologist, 2000, 5:3-10.
Mitter et al., "Condensation of Amidines with Ethoxymethylene Derivatives of B-Ketonic Esters, B-Diketones and Cyanacetic Ester. Part II", Quarterly Journal of the Indian Chemical Society, 1925, 2:61-70.
Nathubhai et al., "N3-alkylation during formation of quinazolin-4-ones from condensation of anthranilamides and orthoamides," Organic and Biomolecular Chemistry, 2011, 9(17):6089-6099.
Newton et al.,"Theoretical Studies of Tricyclo[1.1.1.01.3]pentane and Bicyclo[1.1.1]pentane," J Am Chem Soc, 1972, 94(3):773-778.
Nunes et al., "Oral locally active steroids in inflammatory bowel disease," Journal of Crohn's and Colitis, Apr. 2013, 7(3): 183-191.
Osborn et al., "Studies of the Amino-isoquinolines, -cinnolines, and -quinazolines," J. Chem. Soc., 1956, pp. 4191-4206.
Passalacqua, "Ethoxymethylenemalononitrile and its Derivatives," Gazzetta Chimica Italiana, 1914, 43(11):566-569 (English-language machine translation of the first page).
Perfield et al. "Tumor Progression Locus 2 (TPL2) Regulates Obesity-Associated Inflammation and Insulin Resistance," Diabetes, Apr. 2011, 60(4): 1168-1176.
Perugorria et al., "Tumor progression locus 2/Cot is required for activation of extracellular regulated kinase in liver injury and toll-like receptor-induced TIMP-1 gene transcription in hepatic stellate cells in mice," Hepatology, 2013, 57:1238-1249.
Petyunin et al., "Chemistry of heterocycles. XXX. 2,4-Dihalo derivatives of 9-phenylacridine," Zhurnal Obshchei Khimii, 1957, 27:1558-1562 (English-language machine translation of the first page).
Pinedo et al., "Translational Research: The Role of VEGF in Tumor Angiogenesis", The Oncologist, 2000,5:1-2.
Pisarenko et al., "Synthesis and hydroxylation of 1-alkyl- and 7-alkyl-1,3,7-triazapyrenium salts," Chemistry of Heterocyclic Compounds, 2009, 45(5):580-586.

(56) References Cited

OTHER PUBLICATIONS

PubChem Database (2006) 4-Chloro-3-cyano-7-ethoxy-6-nitroquinoline, CID11011305, 14 pages.
PubChem Database (2006) 4-Chloro-6-nitro-quinoline-3-carbonitrile, CID11085690, 20 pages.
PubChem Database (2006) 4-Chloro-7-methoxy-6-nitroquinoline-3-carbonitrile, CID11139975, 20 pages.
PubChem Database (2006) 4-Chloro-8-methoxy-6-nitro-quinoline-3-carbonitrile, CID11129151, 20 pages.
PubChem Database (2007) 4,8-Dichloro-6-nitroquinoline-3-carbonitrile, CID 17759323, 20 pages.
PubChem Database (2007) 4-Chloro-8-methyl-6-nitro-3 quinolinecarbonitrile, CID22466621, 20 pages.
PubChem Database (2013) 4-Chloro-7-[3-(morpholin-4-yl)propoxy]-6-nitroquinoline-3-carbonitrile, CID71425067, 9 pages.
Qian et al., "Asymmetric glyoxylate-ene reaction catalyzed by C2-symmetric chiral bis(oxazoline)-lanthanide complexes," Tetrahedron Asymmetry, 2000, 11(11):2347-2357.
Robak et al., "Synthesis and Applications of tert-Butanesulfinamide", Chem Rev, 2010, 110(6):3600-3740.
Saal et al., "Pharmaceutical salts: A summary on doses of Salt formers from the Orange Book," Eur. J. Pharm. Sci., 2013, 49(4):614-623.
Sakai et al., "Reactions of a-Polyhalo Ketone Tosylhydrazones with Sulfide Ion and Primary Amines. Cyclization to 1,2,3-Thiadiazoles and 1,2,3-Triazoles," Bull Chem Soc Jpn, 1986, (59)1:179-183.
Semmler et al., "Tetracyclo[5.1.0.01.6.02.7]octane, a [1.1.1]Propellane Derivative, and a New Route to the Parent Hydrocarbon," J Am Chem Soc, 1985, 107(22):6410-6411.
Smith et al., "Vedolizumab: An α4β7 Integrin Inhibitor for Inflammatory Bowel Diseases", Annals of Pharmacotherapy, Sep. 2014, 7 pages.
Teli et al., "Pharmacophore generation and atom-based 3D-QSAR of novel quinoline-3-carbonitrile derivatives as Tpl2 kinase inhibitors", Journal of Enzyme Inhibition and Medicinal Chemistry, 2012, 27(4): 558-570.
Thirumoorthi et al., "Expedient synthesis of 3-phenylbicyclo[1.1.1]pentan-1-amine via metal-free homolytic aromatic alkylation of benzene," Chem. Commun., 2015, 51:3139-3142.
Tomisawa et al., "Studies on 1-Alkyl-2(1H)-pyridone Derivatives. XVI. The Friedel-Crafts Reaction of 2-Methyl-1 (2H)-isoquinolone," Chem. Pharm. Bull., 1973, 21(12):2585-2589.
Truelove et al., "Cortisone in ulcerative colitis; final report on a therapeutic trial," Br Med J., 1955, 2(4947):1041-1048.
Van Berkel et al., "Traceless Tosylhydrazone-Based Triazole Formation: A Metal-Free Alternative to Strain-Promoted Azide-Alkyne Cycloaddition," Angew Chem Int Ed, 2012, 51 (22):5343-5346.
Vyrla et al., "TPL2 Kinase Is a Crucial Signaling Factor and Mediator of NKT Effector Cytokine Expression in Immune-Mediated Liver Injury," The Journal of Immunology, 2016, 196(10):4298-310.
Walter et al., "The Reduction of Cyanides," J Am Chem Soc, 1934, 56(7):1614-1616.
Wang et al., "Carbene-catalyzed aerobic oxidation of isoquinolinium salts: efficient synthesis of isoquinolinones," Green Chemistry, Jun. 2018, 20(14):3302-3307.
Wang et al., "Cyanoacetamide Multicomponent Reaction (I): Parallel Synthesis of Cyanoacetamides," J. Comb. Chem., 2009, 11(5):920-927.
Wiberg et al., "Bicyclo[1.1.1]pentane Derivatives," J. Org. Chem., 1970, 35(2):369-373.
Wissner et al., "Syntheses and EGFR kinase inhibitory activity of 6-substituted-4-anilino [1,7] and [1,8] naphthyridine-3-carbonitriles", Bioorg. Med. Chem. Lett., 2004, 14(6):1411-6.
Wu et al., "Selective inhibitors of tumor progression loci-2 (Tpl2) kinase with potent inhibition of TNF-oc production in human whole blood", Bioorganic & Medicinal Chemistry Letters, 2009, 19(13):3485-3488.
Xu et al., "Iodination of Isoquinoline by Trifluoromethanesulfonic Acid," Organic & Supramolecular Chemistry, Nov. 2020, 5(43):13768-13780.
Zhu et al., "Anti-TNF-alpha therapies in systemic lupus erythematosus", J Biomed Biotechnol., 2010, 8 pages.
Argentinian Office Action in Argentinian Appln. No. 20160102051, dated Jan. 26, 2024, 12 pages (with English translation).
Chinese Office Action in CN Appln No. 202180026128.3, dated Feb. 22, 2024, 11 pages (with English translation).
Exam Report dated Dec. 21, 2018 for New Zealand Appl. No. 738525, 1 page.
Exam Report dated Jul. 25, 2019 for Indian Appl. No. 201817004204, 6 pages (with English translation).
Exam Report dated Oct. 24, 2019 for Australian Appl. No. 2019203122, 6 pages.
Exam Report dated Jul. 12, 2021 for Indian Appl. No. 201817004204, 3 pages.
Exam Report in Pakastani Appln. No. 401/2016, dated Nov. 30, 2019, 2 pages.
International Search Report and Written Opinion in International Appln. No. PCT/US2016/040520, dated Aug. 16, 2018, 11 pages.
International Search Report and Written Opinion in International Appln. No. PCT/US2016/040552, dated Sep. 23, 2016, 9 pages.
International Search Report and Written Opinion in International Appln. No. PCT/US2017/039418, dated Sep. 20, 2017, 9 pages.
International Search Report and Written Opinion in International Appln. No. PCT/US2020/037214, dated Aug. 25, 2020, 13 pages.
International Search Report and Written Opinion in International Appln. No. PCT/US2021/024067, mailed Jul. 5, 2021, 10 pages.
International Search Report and Written Opinion in International Appln. No. PCT/US2021/025118, mailed on Jul. 27, 2021, 15 pages.
International Search Report and Written Opinion in International Appln. No. PCT/US2022/031963, dated Aug. 31, 2022, 15 pages.
Isreali Office Action in Isreal Appln. No. 288310, dated Dec. 27, 2023, 4 pages.
New Zealand Office Action in New Zealand Appln. No. 782835, dated Feb. 28, 2024, 4 pages.
Notice of Allowance dated Jun. 9, 2017 for U.S. Appl. No. 15/199,779, 11 pages.
Notice of Allowance dated Oct. 25, 2017 for U.S. Appl. No. 15/429,086, 10 pages.
Notice of Allowance dated Apr. 26, 2018 for U.S. Appl. No. 15/634,314, 5 pages.
Notice of Allowance dated Mar. 14, 2019 for U.S. Appl. No. 15/697,755, 12 pages.
Office Action in AR Appln. No. 20160102051, dated Jun. 1, 2020, 7pages (with English translation).
Office Action in ARIPO Appln. No. AP/P/2017/010402, dated Jun. 16, 2020, 5 pages.
Office Action in AU Appln. No. 2020290461, dated Jan. 11, 2023, 5 pages.
Office Action in AU Appln. No. 2020290461, dated Nov. 6, 2023, 2 pages.
Office Action in AU Appln. No. 2021245924, dated Apr. 17, 2023, 2 pages.
Office Action in AU Appln. No. 2021249010, dated Nov. 1, 2023, 4 pages.
Office Action in AU Appln. No. 2022204050, dated Apr. 19, 2023, 2 pages.
Office Action in AU Appn. No. 2020257055, dated Mar. 30, 2021, 3 pages.
Office Action in BR Appln. No. BR102016015656-4, dated Mar. 30, 2021, 16 pages (with English translation).
Office Action in CA Appln. No. 2,991,572, dated Mar. 14, 2023, 3 pages.
Office Action in CA Appln. No. 3,142,478, dated Jan. 11, 2023, 4 pages.
Office Action in CA Appln. No. 3175541, dated Dec. 1, 2023, 4 pages.
Office Action in CA Appln. No. 3176061, dated Jan. 8, 2024, 4 pages.

(56) References Cited

OTHER PUBLICATIONS

Office Action in CL Appl. No. 201703356, dated Feb. 14, 2019, 23 pages (with English translation).
Office Action in CL Appln. No. 202103336, dated Feb. 14, 2023, 22 pages (with English translation).
Office Action in CN Appln. No. 201910292757.5, dated Dec. 23, 2020, 15 pages (with English translation).
Office Action in CN Appln. No. 201910292757.5, dated Jul. 27, 2021, 12 pages (with English translation).
Office Action in CN Appln. No. 202080043370.7, dated Jun. 8, 2023, 18 pages (with English translation).
Office Action in CN Appln. No. 202180025717.X, dated Dec. 29, 2023, 19 pages (with English translation).
Office Action in CN Appln. No. 202180026128.3, dated Jul. 19, 2023, 17 pages (with English translation).
Office Action in CN Appln. No. 202210008753.1, dated Dec. 19, 2023, 16 pages (with English translation).
Office Action in CO Appl. No. NC2017/0013351, 6 pages.
Office Action in CR Application No. 2017-0599, dated Apr. 13, 2021, 21 pages (with English translation).
Office Action in CR Appln No. 2017-0599, dated Apr. 20, 2023, 41 pages (with English translation).
Office Action in CR Appln. No. 2017-0599, dated Oct. 28, 2020, 17 pages (with English translation).
Office Action in DO Appln,. No. P2017-0311, dated Jul. 7, 2021, 6 pages (with English Translation).
Office Action in DO Appln. No. 2017-0311, dated Aug. 24, 2020, 5 pages (with English translation).
Office Action in DO Appln. No. P2021-0259, dated May 29, 2023, 17 pages (with English translation).
Office Action in EA Appln. No. 202092495, dated Nov. 25, 2022, 6 pages (with English translation).
Office Action in EA Appln. No. 202193143, dated Feb. 16, 2023, 7 pages (with English translation).
Office Action in EG Appln. No. 2017122179, dated Sep. 15, 2022, 5 pages (English translation).
Office Action in EP Appln No. 16741446.5, dated Sep. 27, 2019, 4 pages.
Office Action in EP Appln. No. 18186568.4, dated May 5, 2020, 4 pages.
Office Action in GC Appln No. 39905, dated Aug. 8, 2021, 4 pages.
Office Action in GC Appln. No. 2016-31644, dated May 6, 2020, 3 pages (English translation).
Office Action in IL Appln. No. 274568, dated Jul. 12, 2020, 5 pages (English translation).
Office Action in IL Appln. No. 288310, dated Aug. 6, 2023, 4 pages (English translation).
Office Action in IN Appln. No. 201817004197, dated Aug. 26, 2019, 7 pages (with English translation).
Office Action in IN Appln. No. 202217060101, dated Jan. 24, 2024, 6 pages (with English translation).
Office Action in JP Appln No. 2022-065168, dated May 12, 2023, 4 pages (with English translation).
Office Action in JP Appln. No. 2018-171794, dated Jun. 23, 2020, 6 pages (with English translation).
Office Action in JP Appln. No. 2019-137759, dated Jun. 16, 2020, 4 pages (with Enlgish translation).
Office Action in JP Appln. No. 2022-560069, dated Sep. 28, 2023, 6 pages (with English translation).
Office Action in Korean Appln. No. 10-2023-7041219, dated Feb. 5, 2024, 13 pages (with English translation).
Office Action in KR Appln. No. 2022-7031078, dated Aug. 4, 2023, 2 pages (with English translation).
Office Action in MX Appl No. MX/a/2017/004737, dated Aug. 2, 2019, 6 pages (with English translation).
Office Action in MX Appln. No. MX/a/2020/000232, dated Mar. 25, 2021, 9 pages (with partial English translation).
Office Action in MX Appln. No. MX/a/2020/000232, dated Sep. 28, 2021, 20 pages (with English translation).
Office Action in MX Appln. No. MX_a_2020-000232, dated Oct. 8, 2020, 5 pages.
Office Action in MY Appln. No. PI2018700007, dated Apr. 19, 2023, 3 pages.
Office Action in NZ Appln. No. 750707, dated Feb. 22, 2023, 3 pages.
Office Action in PA Appl. No. 91923, dated Apr. 25, 2019, 8 pages (with English translation).
Office Action in PE Appln. No. 002804-2017/DIN, dated Jun. 30, 2021, 14 pages (with English translation).
Office Action in PH Appln. No. 1-2018-500031, dated Jun. 23, 2020, 4 pages.
Office Action in SA Appln. No. 517381350, dated Sep. 20, 2020, 7 pages (with English translation).
Office Action in SG Appln. No. 11202113307T, dated Jan. 10, 2023, 5 pages.
Office Action in Taiwanese Appl. No. 110111737, dated Jan. 22, 2022, 10 pages (with English translation).
Office Action in TW Appl No. 107117905, dated Aug. 7, 2019, 4 pages.
Office action in TW Appl. No. 105121281, dated Oct. 18, 2017, 3 pages (with English translation).
Office Action in TW Appln No. 109119416, dated Aug. 11, 2021, 20 pages (with English translation).
Office Action in TW Appln No. 111120005, dated Feb. 9, 2023, 14 pages (with English translation).
Office Action in TW Appln. No. 111121600, dated Nov. 21, 2023, 10 pages (with English translation).
Office Action in U.S. Appl. No. 15/199,534, dated Sep. 7, 2017, 37 pages.
Office Action in U.S. Appl. No. 15/429,086, dated Mar. 23, 2017, 19 pages.
Office Action in U.S. Appl. No. 15/429,086, dated Jun. 30, 2017, 15 pages.
Office Action in U.S. Appl. No. 15/634,314, dated Dec. 18, 2017, 10 pages.
Office Action in U.S. Appl. No. 15/697,755, dated Jul. 5, 2018, 54 pages.
Office Action in U.S. Appl. No. 15/891,163, dated Oct. 4, 2019, 24 pages.
Office Action in U.S. Appl. No. 16/045,518, dated Jun. 19, 2019, 12 pages.
Office Action in U.S. Appl. No. 16/391,673, dated Aug. 22, 2019, 7 pages.
Office Action in UA Appln. No. a 2021 07612, dated Jun. 19, 2023, 6 pages (with English translation).
Office Action in UK Appln. No., a201712984, dated Mar. 12, 2020, 6 pages (with English translation).
PCT International Preliminary Report on Patentability in International Application No. PCT/US2016/040520, dated Jan. 9, 2019, 8 pages.
PCT International Preliminary Report on Patentability in International Application No. PCT/US2016/040552, dated Jan. 9, 2018, 7 pages.
PCT International Preliminary Report on Patentability in International Application No. PCT/US2017/039418, dated Jan. 1, 2019, 6 pages.
Preliminary Rejection dated Jun. 17, 2019 for Korean Appl. No. 10-2018-7003220, 12 pages (with English translation).
Restriction Requirement dated Feb. 16, 2017 for U.S. Appl. No. 15/199,534, 13 pages.
Restriction Requirement dated Mar. 8, 2017 for U.S. Appl. No. 15/199,779, 10 pages.
Restriction Requirement dated Aug. 11, 2017 for U.S. Appl. No. 15/634,314, 6 pages.
Restriction Requirement dated Mar. 26, 2018 for U.S. Appl. No. 15/697,755, 6 pages.
Restriction Requirement dated Jun. 29, 2018 for U.S. Appl. No. 15/891,163, 12 pages.
Restriction Requirement dated Feb. 8, 2019 for U.S. Appl. No. 16/045,518, 5 pages.
Search Report dated Feb. 5, 2019 for European Appl. No. 18186568.4, 5 pages.

(56) References Cited

OTHER PUBLICATIONS

Taiwanese Office Action in Taiwanese Appln. No. 112117450, dated Dec. 20, 2023, 8 pages (with English translation).
Vietnamese Office Action in Vietnamese Appln. No. 1-2021-08005, dated Feb. 26, 2024, 4 pages (with English translation).
U.S. Appl. No. 15/199,534, filed Jun. 30, 2016, Elizabeth M. Bacon.
U.S. Appl. No. 15/429,086, filed Feb. 9, 2017, Elizabeth M. Bacon.
U.S. Appl. No. 15/890,091, filed Feb. 6, 2018, Elizabeth M. Bacon.
U.S. Appl. No. 15/891,163, filed Feb. 7, 2018, Elizabeth M. Bacon.
U.S. Appl. No. 16/391,673, filed Apr. 23, 2019, Elizabeth M. Bacon.
U.S. Appl. No. 16/717,074, filed Dec. 17, 2019, Elizabeth M. Bacon.
U.S. Appl. No. 17/317,041, filed May 11, 2021, Elizabeth M. Bacon.
U.S. Appl. No. 15/634,314, filed Jun. 27, 2017, Gayatri Balan.
U.S. Appl. No. 16/045,518, filed Jul. 25, 2018, Gayatri Balan.
U.S. Appl. No. 15/199,779, filed Jun. 30, 2016, Elizabeth M. Bacon.
U.S. Appl. No. 15/697,755, filed Sep. 7, 2017, Elizabeth M. Bacon.
U.S. Appl. No. 16/898,981, filed Jun. 11, 2020, Eda Y. Canales.
U.S. Appl. No. 16/994,889, filed Aug. 17, 2020, Eda Y. Canales.
U.S. Appl. No. 17/162,754, filed Jan. 29, 2021, Eda Y. Canales.
U.S. Appl. No. 17/715,366, filed Apr. 7, 2022, Eda Y. Canales.
U.S. Appl. No. 18/374,108, filed Sep. 28, 2023, Eda Y. Canales.
U.S. Appl. No. 17/618,696, filed Dec. 13, 2021, Eda Y. Canales.
U.S. Appl. No. 17/218,765, filed Mar. 31, 2021, Kevin M. Allan.
U.S. Appl. No. 18/386,675, filed Nov. 3, 2023, Kevin M. Allan.
U.S. Appl. No. 17/212,228, filed Mar. 25, 2021, Kassibla E. Dempah.
U.S. Appl. No. 18/132,722, filed Apr. 10, 2023, Kassibla E. Dempah.
U.S. Appl. No. 17/831,044, filed Jun. 2, 2022, David G. Breckenridge.
U.S. Appl. No. 18/372,242, filed Sep. 25, 2023, David G. Breckenridge.
Extended Search Report in European Appln. No. 24154495.6, dated Jul. 19, 2024, 7 pages.
Office Action in Argentinian Appln. No. 20160102051, dated May 30, 2024, 6 pages (with English translation).
Office Action in BR Appln. No. 112021025039-5, dated Aug. 6, 2024, 5 pages (with English translation).
Office Action in CA Appln. No. 3,142,478, dated Aug. 1, 2024, 3 pages.
Office Action in CA Appln. No. 3029457, dated Jun. 12, 2024, 4 pages.
Office Action in Israeli Appln. No. 288310, dated Jun. 24, 2024, 5 pages.
Office Action in JP Appln No. 2022-557743, dated Jul. 1, 2024, 8 pages (with English translation).
Office Action in MX Appln. No. MX/a/2021/015545, dated Jul. 18, 2024, 6 pages (with machine translation).
Office Action in TW Appln. No. 111121600, dated Jun. 25, 2024, 7 pages (with English translation).
Indian Hearing Notice in Indian Appln. No. 202217000592, dated May 30, 2024, 2 pages.
Office Action in Egyptian Appln. No. 2179/2017, dated Mar. 27, 2024, 11 pages (with English translation).
Office Action in Indian Appln. No. 202217055847, dated Apr. 24, 2024, 6 pages.
Caira, "Crystalline Polymorphism of Organic Compounds," Topics in Current Chemistry, Jan. 1998, 198:163-208.
Feuerstein et al., "Ulcerative Colitis: Epidemiology, Diagnosis, and Management," Mayo Clinic Proceedings, 2014, 89(11): 1553-1563.
Gong et al., "Tumor progression locus 2 in hepatocytes potentiates both liver and systemic metabolic disorders in mice," Hepatology, Feb. 2019, 69(2):524-544.
Hearing Notice in Indian Appln. No. 202217055847, dated Nov. 28, 2024, 2 pages.
International Preliminary Report on Patentability in International Appln. No. PCT/US2023/021659, mailed on Nov. 21, 2024, 8 pages.
International Search Report and Written Opinion in International Appln. No. PCT/US2023/021659, mailed on Aug. 14, 2023, 9 pages.
Office Action in AR Appln. No. 20160102051, dated Sep. 9, 2024, 7 pages (with English translation).
Office Action in Australian Appln. No. 2022286966, dated Aug. 29, 2024, 3 pages.
Office Action in Australian Appln. No. 2024202085, dated Nov. 20, 2024, 4 pages.
Office Action in CL Appln. No. 202300112, dated Sep. 4, 2024, 26 pages (with English translation).
Office Action in Eurasian Appln. No. 202490132, dated Sep. 19, 2024, 4 pages (with English translation).
Office Action in Japanese Appln. No. 2023-049724, mailed on Nov. 12, 2024, 6 pages (with English translation).
Office Action in Japanese Appln. No. 2023-574433, mailed on Nov. 21, 2024, 10 pages (with English translation).
Office Action in Korean Appln. No. 10-2022-7037591, dated Jan. 17, 2025, 7 pages (with English translation).
Office Action in Korean Appln. No. 10-2022-7037824, dated Jan. 23, 2025, 9 pages (with English translation).
Office Action in Mexican Appln. No. MX/a/2021/015545, dated Dec. 2, 2024, 12 pages (with machine translation).
Office Action in Mexican Appln. No. MX/a/2021/015545, dated Feb. 4, 2025, 12 pages (with machine translation).
Office Action in Mexican Appln. No. MX/a/2021/015545, dated Sep. 24, 2024, 10 pages (with machine translation).
Office Action in Uzbekistan Appln. No. IAP20220009, dated Dec. 12, 2024, 7 pages (with English translation).

\* cited by examiner

PROCESS FOR PREPARING A Cot INHIBITOR COMPOUND

CROSS-REFERENCES TO RELATED APPLICATIONS

This application is a continuation of U.S. Ser. No. 17/218,765, filed Mar. 31, 2021, which claims the benefit of U.S. Provisional Application 63/004,254 filed on Apr. 2, 2020, the entirety of each is incorporated herein by reference.

FIELD

The present disclosure relates to the field of organic synthetic methodology for a process for the preparation of Cot (cancer Osaka thyroid) inhibitor compounds and their synthetic intermediates.

BACKGROUND

Cot (cancer Osaka thyroid) protein is a serine/threonine kinase that is a member of the MAP kinase kinase kinase (MAP3K) family. It is also known as "Tpl2" (tumor progression locus), "MAP3K8" (mitogen-activated protein kinase kinase kinase 8) or "EST" (Ewing sarcoma transformant). Cot was identified by its oncogenic transforming activity in cells and has been shown to regulate oncogenic and inflammatory pathways.

Cot is known to be upstream in the MEK-ERK pathway and is essential for LPS induced tumor necrosis factor-α (TNF-α) production. Cot has been shown to be involved in both production and signaling of TNFα. TNFα is a pro-inflammatory cytokine and plays an important role in inflammatory diseases, such as rheumatoid arthritis (RA), multiple sclerosis (MS), inflammatory bowel disease (IBD), diabetes, sepsis, psoriasis, misregulated TNFα expression and graft rejection.

Agents and methods that modulate the expression or activity of Cot, therefore, may be useful for preventing or treating such diseases.

There remains a need to develop methods of preparing Cot inhibitor compounds, including the preparation of Compound 1:

Compound 1

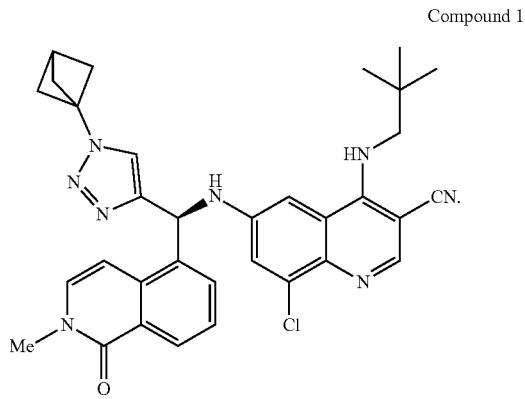

SUMMARY

Provided in one aspect is a process for preparing Compound 1, the process comprising:

(2a) contacting Compound 2A with Compound 2B:

2A

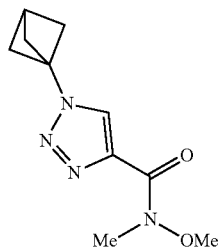

2B

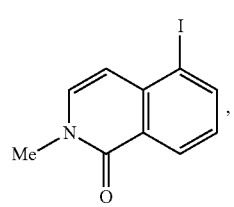

in the presence of an organometallic reagent and a Lewis base in a solvent at temperature sufficient to provide Compound 2C:

2C

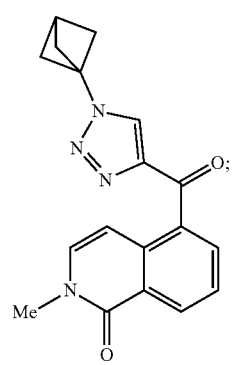

(2b) contacting Compound 2C with

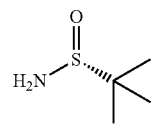

in the presence of a titanium- or zirconium-based reagent in a solvent at a temperature sufficient to provide Compound 2D:

2D

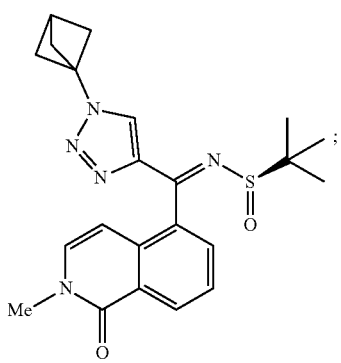

(2c) contacting Compound 2D with a reducing agent and optionally, a ruthenium, palladium, rhodium, or platinum catalyst in a solvent at a temperature sufficient to provide Compound 2E:

2E

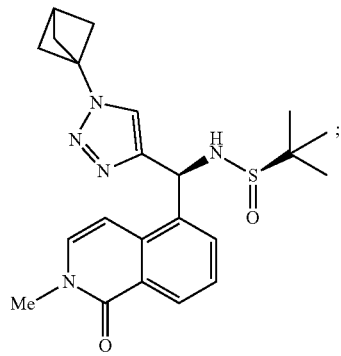

(2d) contacting Compound 2E with an acid in a solvent at a temperature sufficient to provide Compound 2F:

2F

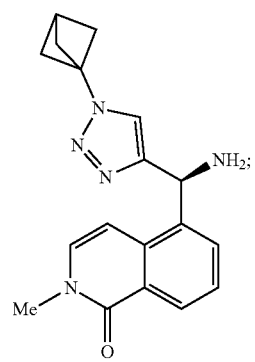

and (2e) contacting Compound 2F with Compound 2G:

2G

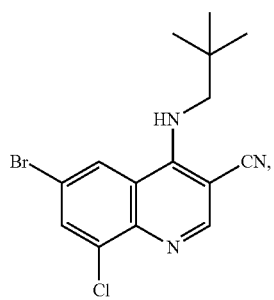

in the presence of a palladium catalyst and a base in a solvent at a temperature sufficient to provide Compound 1:

Compound 1

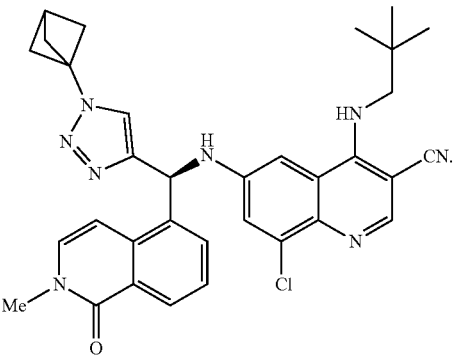

In another aspect is a process for preparing Compound 1, the process comprising:

(2a) contacting Compound 2A with Compound 2B:

2A

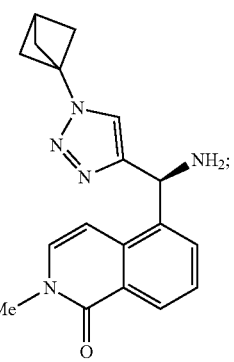

2B

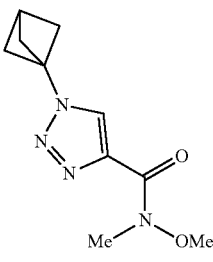

in the presence of an organometallic reagent and a Lewis base in a solvent at temperature sufficient to provide Compound 2C:

2C

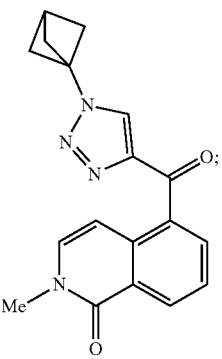

(2b) contacting Compound 2C with

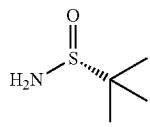

in the presence of a titanium- or zirconium-based reagent in a solvent at a temperature sufficient to provide Compound 2D:

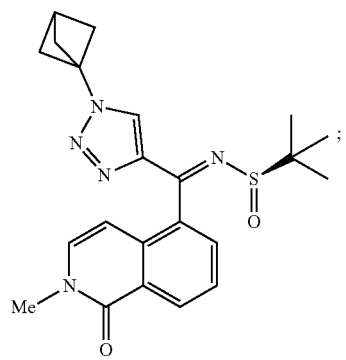

2D (2c) contacting Compound 2D with a reducing agent and optionally, a ruthenium, palladium, rhodium, or platinum catalyst in a solvent at a temperature sufficient to provide Compound 2E:

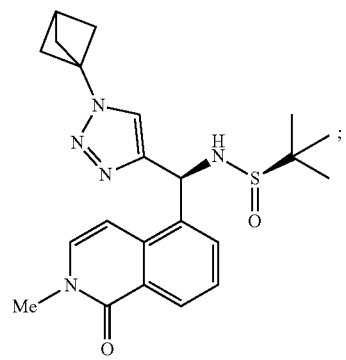

2E (2d) contacting Compound 2E with an acid in a solvent at a temperature sufficient to provide Compound 2F:

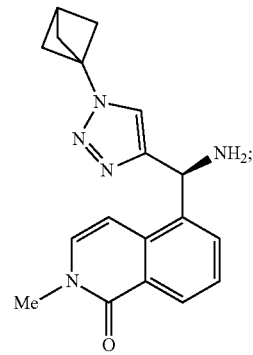

2F and (2e) contacting Compound 2F with Compound 2G:

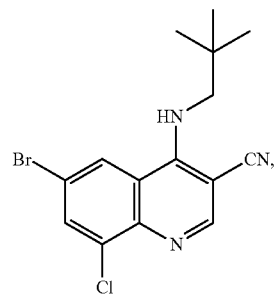

2G in the presence of a copper catalyst, a copper catalyst ligand, and a base in a solvent at a temperature sufficient to provide Compound 1:

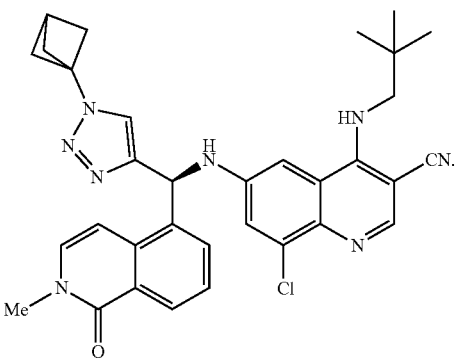 [SMILES: Cn1ccc2c([C@H](Nc3cc(Cl)c4ncc(C#N)c(NCC(C)(C)C)c4c3)c3cn(C45CC(C4)C5)nn3)cccc2c1=O]

Compound 1

In another aspect is a process for preparing Compound 1, the process comprising:

(3a) contacting Compound 2M:

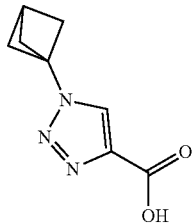

2M with a chlorinating reagent and an additive in a solvent at a temperature sufficient to provide Compound 3A:

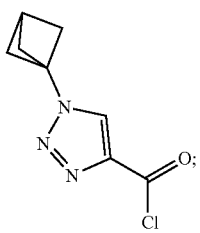

3A (3b) contacting Compound 3A with Compound 2B:

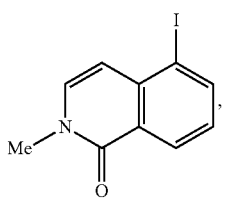

2B in the presence of an organometallic reagent, then followed by the addition of a copper or palladium catalyst, optionally, a zinc additive, and optionally, a Lewis base in a solvent at a temperature sufficient to provide Compound 2C:

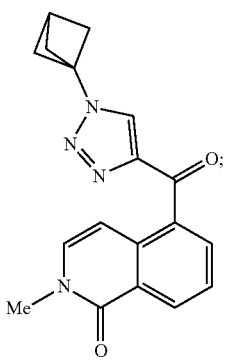

2C (3c) contacting Compound 2C with

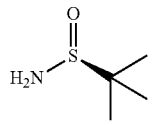

in the presence of a titanium-based reagent in a solvent at a temperature sufficient to provide Compound 3B:

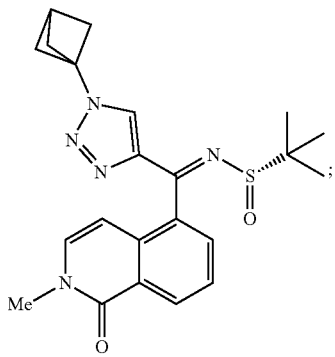

3B (3d) contacting Compound 3B with a reducing agent, and optionally a ruthenium, palladium, or platinum catalyst in a solvent at a temperature sufficient to provide Compound 3C:

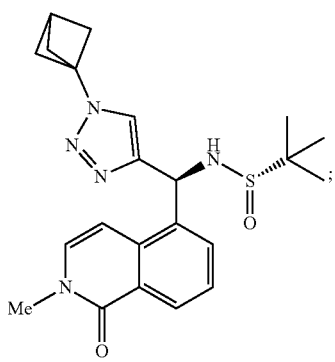

3C (3e) contacting Compound 3C with an acid in a solvent at a temperature sufficient to provide Compound 2F:

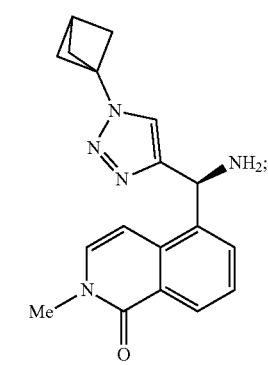

2F and (3f) contacting Compound 2F with Compound 2G:

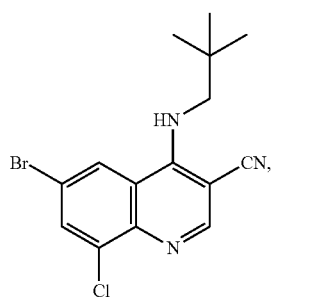

2G in the presence of a palladium catalyst and a base in a solvent at a temperature sufficient to provide Compound 1:

Compound 1

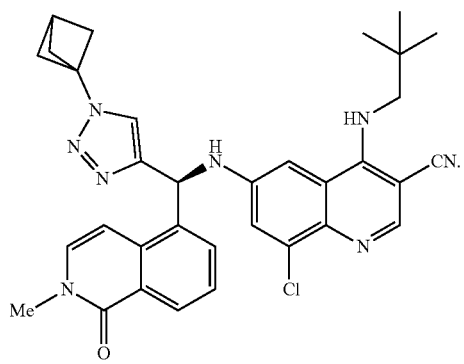

In another aspect is a process for preparing Compound 1, the process comprising:

(3a) contacting Compound 2M:

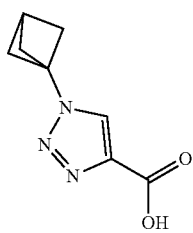

2M with a chlorinating reagent and an additive in a solvent at a temperature sufficient to provide Compound 3A:

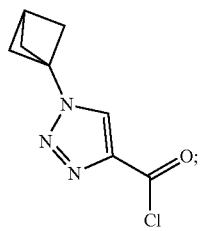

3A (3b) contacting Compound 3A with Compound 2B:

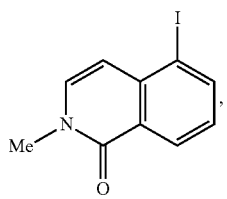

2B in the presence of an organometallic reagent, then followed by the addition of a copper or palladium catalyst, optionally, a zinc additive, and optionally, a Lewis base in a solvent at a temperature sufficient to provide Compound 2C:

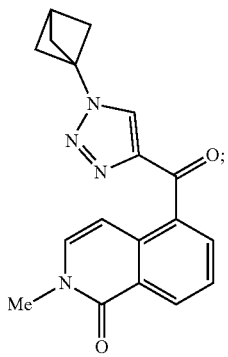

2C (3c) contacting Compound 2C with

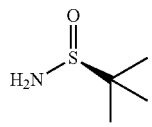

in the presence of a titanium-based reagent in a solvent at a temperature sufficient to provide Compound 3B:

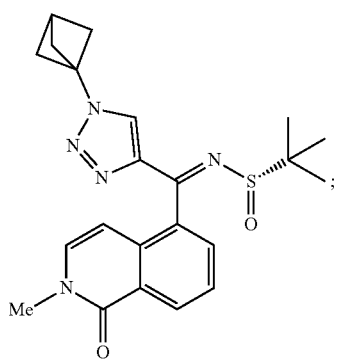

3B (3d) contacting Compound 3B with a reducing agent, and optionally a ruthenium, palladium, or platinum catalyst in a solvent at a temperature sufficient to provide Compound 3C:

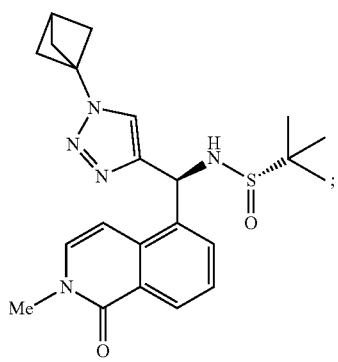

3C (3e) contacting Compound 3C with an acid in a solvent at a temperature sufficient to provide Compound 2F:

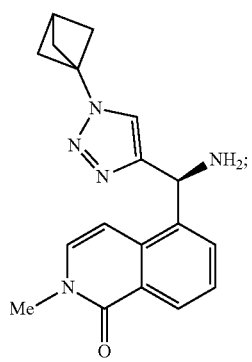

2F and (3f) contacting Compound 2F with Compound 2G:

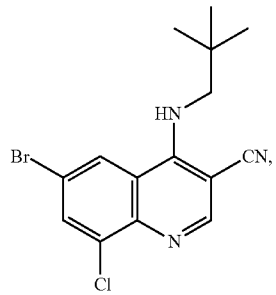

2G in the presence of a copper catalyst, a copper catalyst ligand, and a base in a solvent at a temperature sufficient to provide Compound 1:

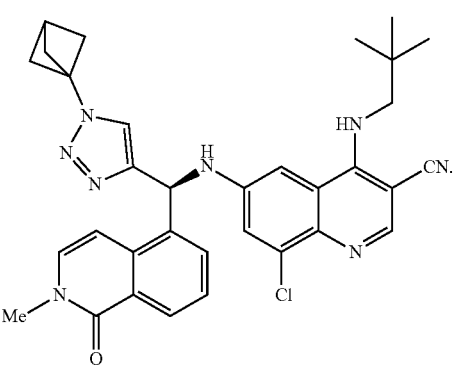

Compound 1

In another aspect is a process for preparing Compound 1, the process comprising:

(4a) contacting Compound 1H:

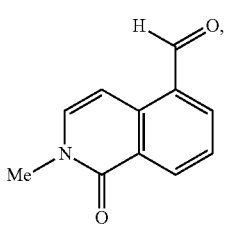

1H in the presence of

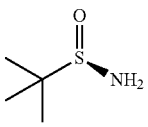

in the presence of a catalyst in a solvent at a temperature sufficient to provide Compound 4A:

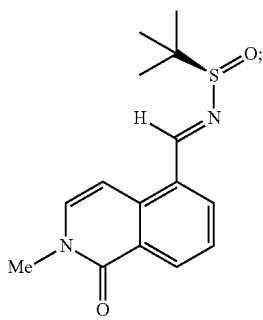

4A (4b) contacting Compound 4A with Compound 4B:

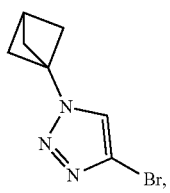

4B in the presence of a base, followed by optionally, a copper catalyst, optionally, a Lewis base additive, and optionally, a zinc additive in a solvent at a temperature sufficient to provide Compound 2E:

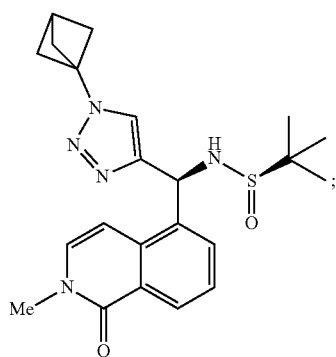

2E (4c) contacting Compound 2E with an acid in a solvent at a temperature sufficient to provide Compound 2F:

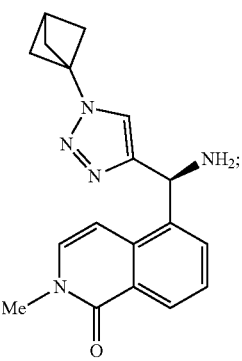

2F and (4d) contacting Compound 2F with Compound 2G:

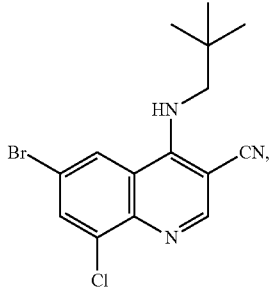

2G in the presence of a palladium catalyst and a base in a solvent at a temperature sufficient to provide Compound 1:

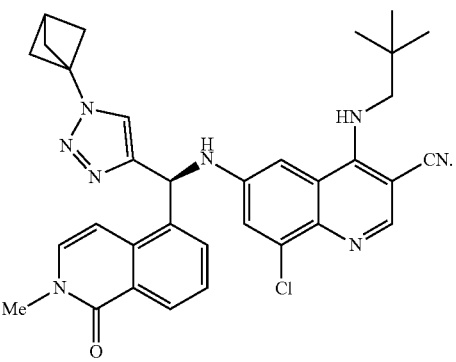

Compound 1

In another aspect is a process for preparing Compound 1, the process comprising:

(4a) contacting Compound 1H:

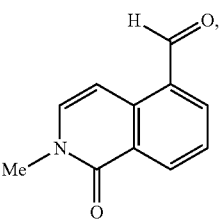

1H in the presence of

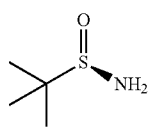

in the presence of a catalyst in a solvent at a temperature sufficient to provide Compound 4A:

(4b) contacting Compound 4A with Compound 4B:

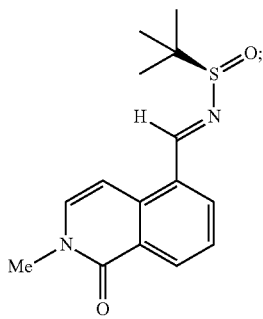

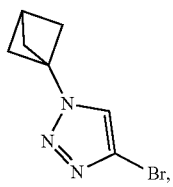

in the presence of a base, followed by optionally, a copper catalyst, optionally, a Lewis base additive, and optionally, a zinc additive in a solvent at a temperature sufficient to provide Compound 2E:

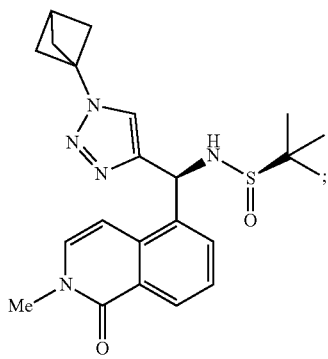

(4c) contacting Compound 2E with an acid in a solvent at a temperature sufficient to provide Compound 2F:

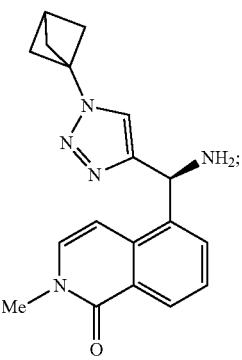

and (4d) contacting Compound 2F with Compound 2G:

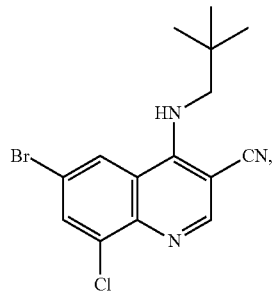

in the presence of a copper catalyst, a copper catalyst ligand, and a base in a solvent at a temperature sufficient to provide Compound 1:

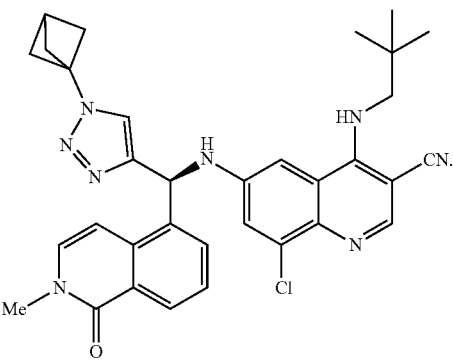

In another aspect is a process for preparing Compound 2M, the process comprising:

(5a) contacting Compound 2H:

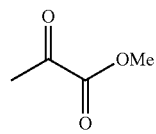

with a chlorinating reagent, optionally an amine catalyst, and optionally an acidic additive in a solvent at a temperature sufficient to provide Compound 2I:

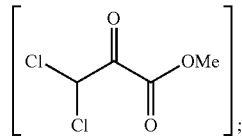

(5b) contacting Compound 2I with TsHNNH$_2$ in a solvent at a temperature sufficient to provide Compound 2J:

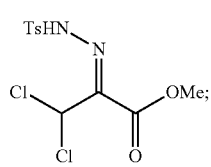
2J (5c) contacting Compound 2J with Compound 2K:

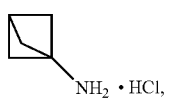
2K in the presence of a base in a solvent at a temperature sufficient to provide Compound 2L:

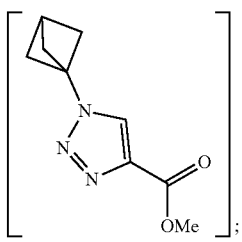
2L (5d) contacting Compound 2L with a base in a solvent at a temperature sufficient to provide Compound 2M:

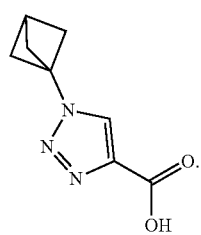
2M

In another aspect is a process for preparing Compound 2B, the process comprising:

(6a) contacting Compound 1E:

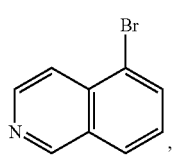
1E with a copper catalyst, an amine ligand, and an iodide additive in a solvent at a temperature sufficient to provide Compound 2O:

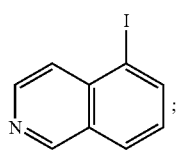
2O (6b) contacting Compound 2O with an alkylating agent in a solvent at a temperature sufficient to provide Compound 2P:

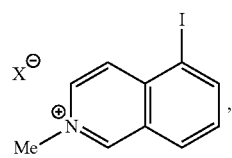
2P wherein X is iodide, chloride, bromide, methylsulfate, sulfate, methylcarbonate, carbonate, methanesulfonate, trifluoromethanesulfonate, toluenesulfonate, or tetrafluoroborate;

(6c) contacting Compound 2P with an oxidant and a base in a solvent at a temperature sufficient to provide Compound 2B:

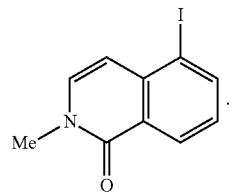
2B

In another aspect is a process for preparing Compound 1, the process comprising:

(7a) contacting Compound 2C with Compound 1B:

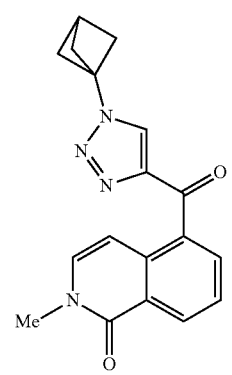
2C

-continued

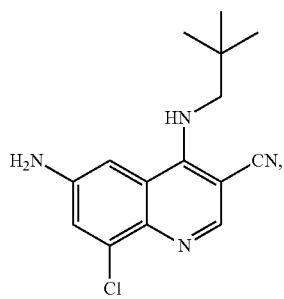
1B in the presence of a titanium catalyst and a base in a solvent at a temperature sufficient to provide Compound 5A:

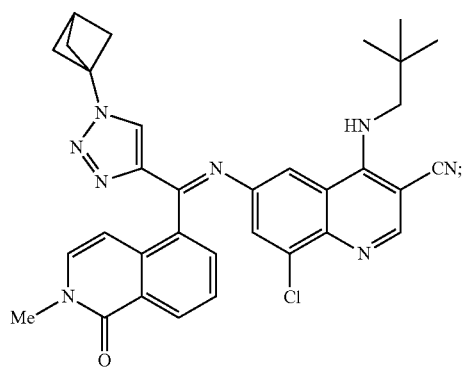
5A and (7b) contacting Compound 5A in the presence of a catalyst and a reagent in a solvent at a temperature sufficient to provide Compound 1:

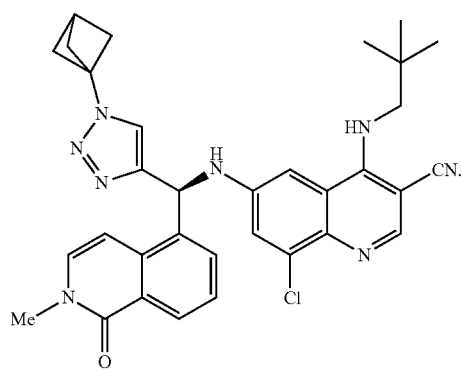
Compound 1

In another aspect is a process for preparing Compound 1, the process comprising:

(8a) contacting Compound 6A with Compound 1B:

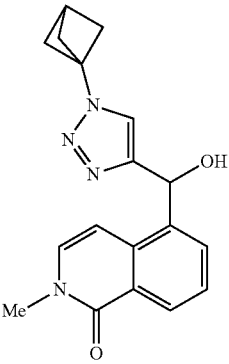
6A

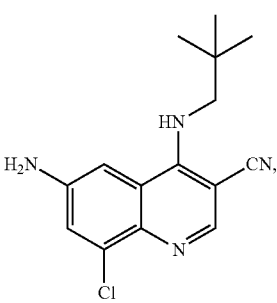
1B in the presence of a reagent, and optionally an additive, in a solvent at a temperature sufficient to provide Compound 1:

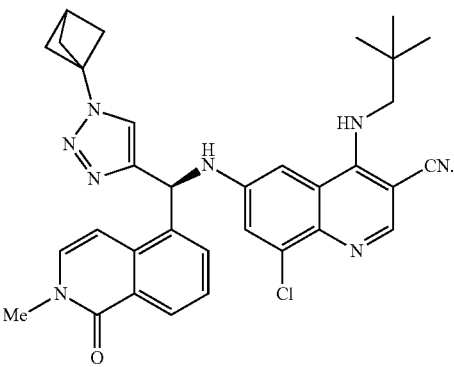
Compound 1

In another aspect is a process for preparing Compound 1, the process comprising:

(9a) contacting Compound 6A:

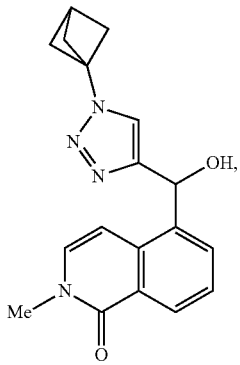

6A with an activating reagent and a base in a solvent at a temperature sufficient to provide Compound 7A:

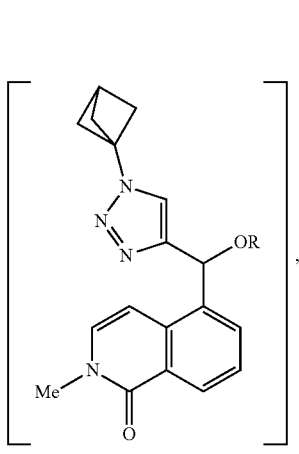

7A wherein R is methylsulfonyl, ethylsulfonyl, toluenesulfonyl, phenylsulfonyl, 4-chlorobenzenesulfonyl, or 4-nitrobenzenesulfonyl; and (9b) contacting Compound 7A with Compound 1B:

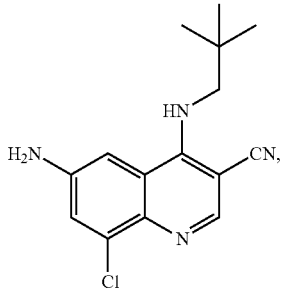

1B in the presence of a base in a solvent at a temperature sufficient to provide Compound 1:

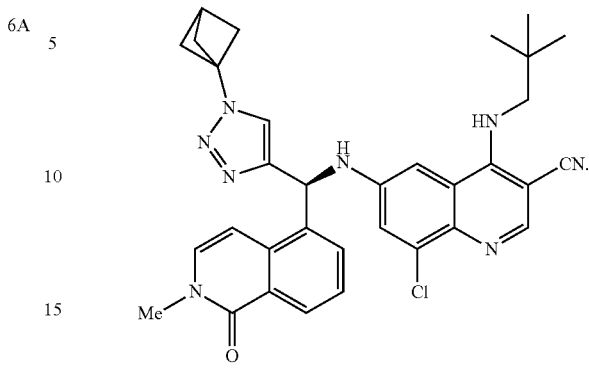

Compound 1

In another aspect is a process for preparing Compound 1, the process comprising:

(22a) contacting Compound 2A with Compound 2B:

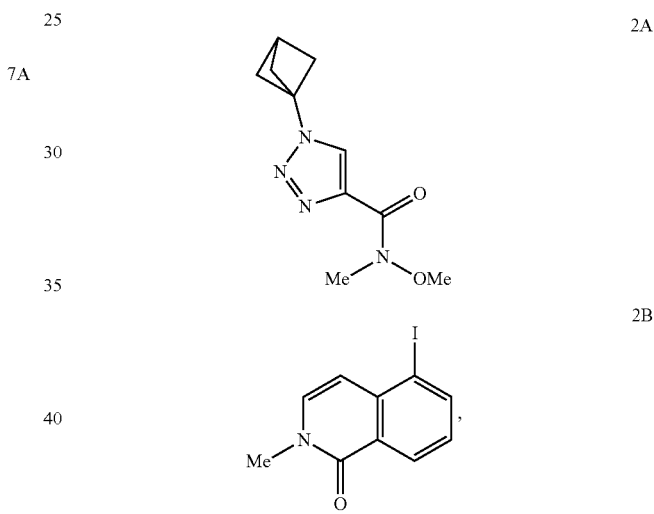

2A

2B in the presence of an organometallic reagent and a Lewis base in a solvent at temperature sufficient to provide Compound 2C:

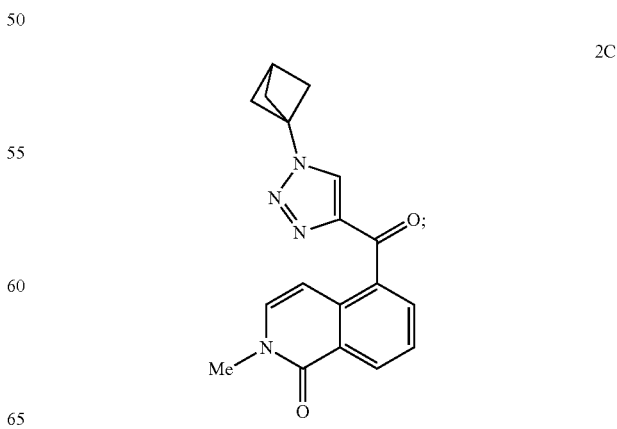

2C (22b) contacting Compound 2C with

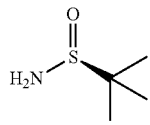

in the presence of a titanium-based or zirconium-based reagent in a solvent at a temperature sufficient to provide Compound 3B:

3B

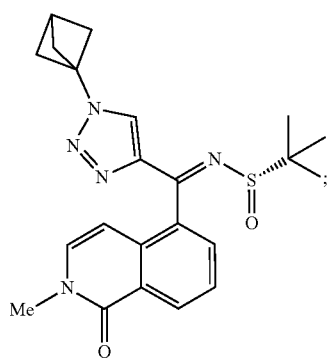

(22c) contacting Compound 3B with a reducing agent, and optionally a ruthenium, palladium, or platinum catalyst in a solvent at a temperature sufficient to provide Compound 3C:

3C

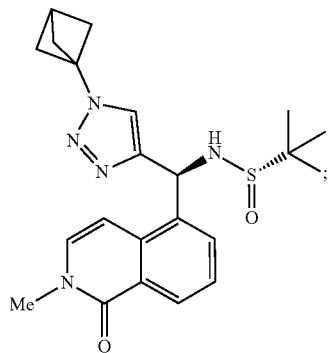

(22d) contacting Compound 3C with an acid in a solvent at a temperature sufficient to provide Compound 2F:

2F

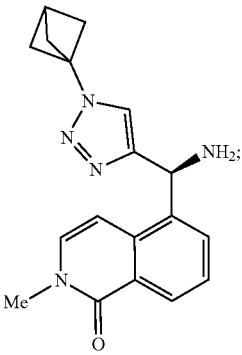

and (22e) contacting Compound 2F with Compound 2G:

2G

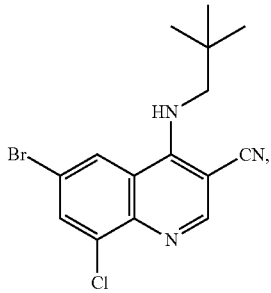

in the presence of a palladium catalyst and a base in a solvent at a temperature sufficient to provide Compound 1:

Compound 1

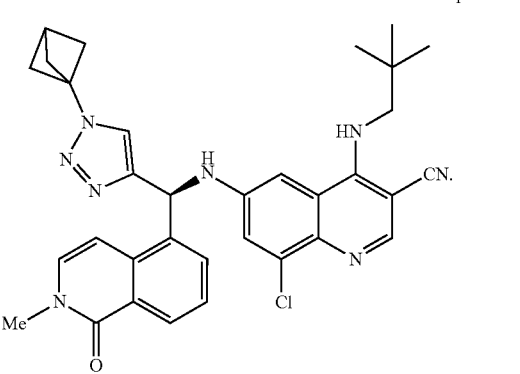

In another aspect is a process for preparing Compound 1, the process comprising:

(22a) contacting Compound 2A with Compound 2B:

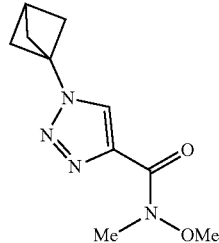

2A

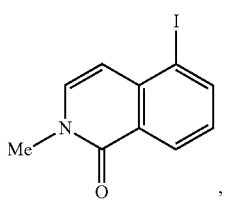

2B in the presence of an organometallic reagent and a Lewis base in a solvent at temperature sufficient to provide Compound 2C:

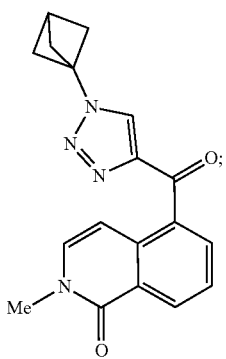

2C (22b) contacting Compound 2C with

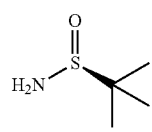

in the presence of a titanium-based or zirconium-based reagent in a solvent at a temperature sufficient to provide Compound 3B:

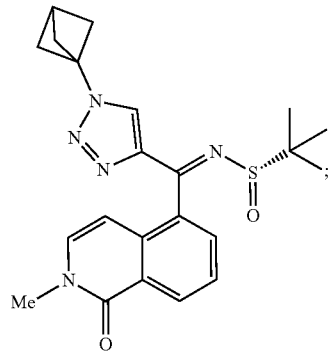

3B (22c) contacting Compound 3B with a reducing agent, and optionally a ruthenium, palladium, or platinum catalyst in a solvent at a temperature sufficient to provide Compound 3C:

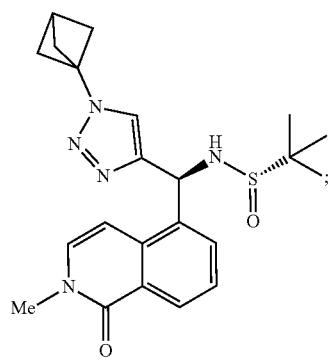

3C (22d) contacting Compound 3C with an acid in a solvent at a temperature sufficient to provide Compound 2F:

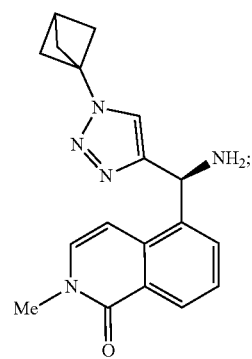

2F and (22e) contacting Compound 2F with Compound 2G:

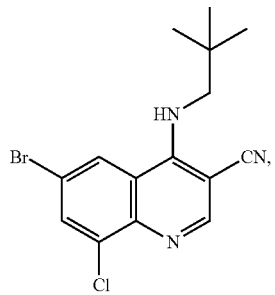

in the presence of a copper catalyst, a copper catalyst ligand, and a base in a solvent at a temperature sufficient to provide Compound 1:

Compound 1

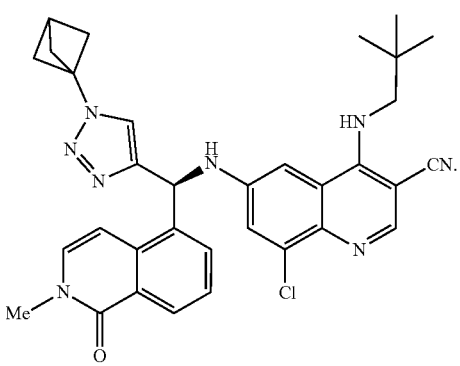

In another aspect is a process for preparing Compound 1, the process comprising:

(23a) contacting Compound 2M:

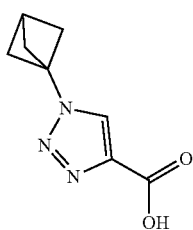

with a chlorinating reagent and an additive in a solvent at a temperature sufficient to provide Compound 3A:

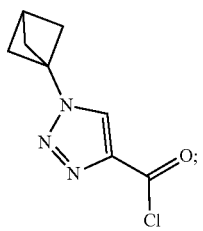

(23b) contacting Compound 3A with Compound 2B:

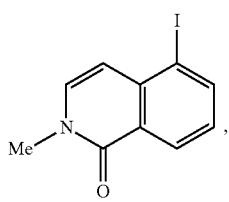

in the presence of an organometallic reagent, then followed by the addition of a copper or palladium catalyst, optionally, a zinc additive, and optionally, a Lewis base in a solvent at a temperature sufficient to provide Compound 2C:

[Compound 2C structure]

(23c) contacting Compound 2C with

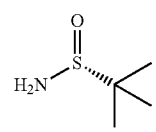

in the presence of a titanium- or zirconium-based reagent in a solvent at a temperature sufficient to provide Compound 2D:

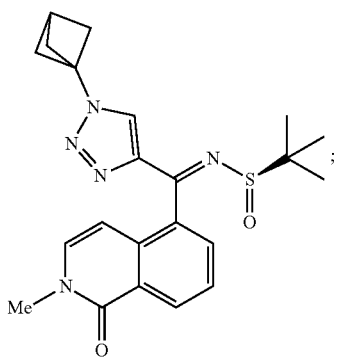

2D (23d) contacting Compound 2D with a reducing agent and optionally, a ruthenium, palladium, rhodium, or platinum catalyst in a solvent at a temperature sufficient to provide Compound 2E:

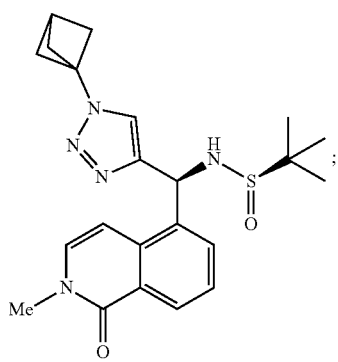

2E (23e) contacting Compound 2E with an acid in a solvent at a temperature sufficient to provide Compound 2F:

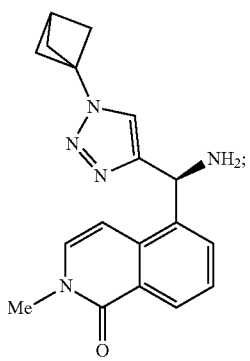

2F and (23f) contacting Compound 2F with Compound 2G:

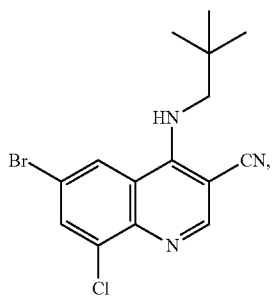

2G in the presence of a palladium catalyst and a base in a solvent at a temperature sufficient to provide Compound 1:

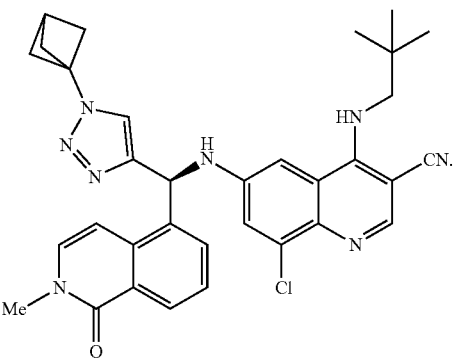

Compound 1

In another aspect is a process for preparing Compound 1, the process comprising:

(23a) contacting Compound 2M:

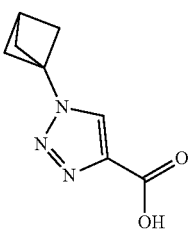

2M with a chlorinating reagent and an additive in a solvent at a temperature sufficient to provide Compound 3A:

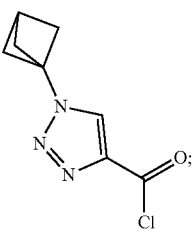

3A (23b) contacting Compound 3A with Compound 2B:

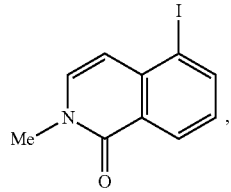
2B in the presence of an organometallic reagent, then followed by the addition of a copper or palladium catalyst, optionally, a zinc additive, and optionally, a Lewis base in a solvent at a temperature sufficient to provide Compound 2C:

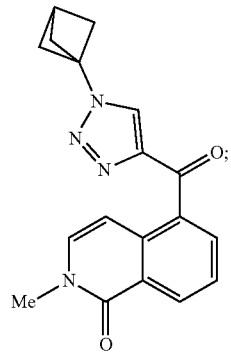
2C (23c) contacting Compound 2C with

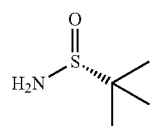

in the presence of a titanium- or zirconium-based reagent in a solvent at a temperature sufficient to provide Compound 2D:

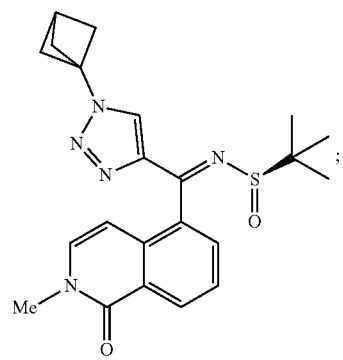
2D (23d) contacting Compound 2D with a reducing agent and optionally, a ruthenium, palladium, rhodium, or platinum catalyst in a solvent at a temperature sufficient to provide Compound 2E:

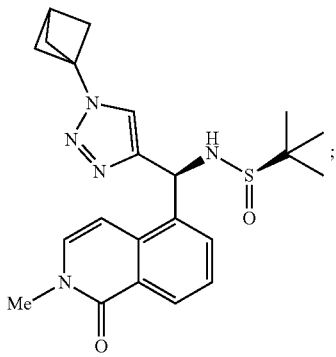
2E (23e) contacting Compound 2E with an acid in a solvent at a temperature sufficient to provide Compound 2F:

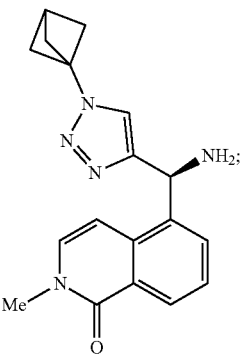
2F and (23f) contacting Compound 2F with Compound 2G:

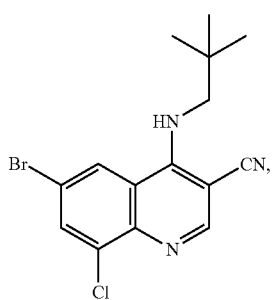
2G in the presence of a copper catalyst, a copper catalyst ligand, and a base in a solvent at a temperature sufficient to provide Compound 1:

Compound 1

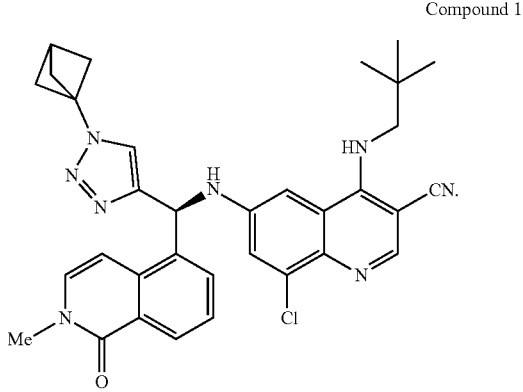 [SMILES: Cn1ccc2c([C@H](Nc3cc(Cl)c4ncc(C#N)c(NCC(C)(C)C)c4c3)c3cn(C45CC(C4)C5)nn3)cccc2c1=O]

In another aspect is a compound according to the following formula 2F salt:

2F

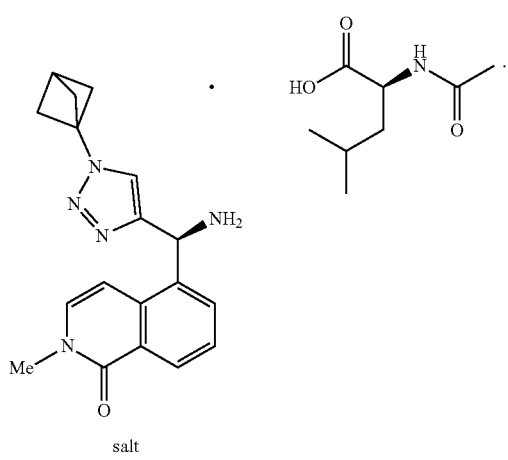

salt

In another aspect is a process for preparing Compound 2O, the process comprising: contacting Compound 14A:

14A

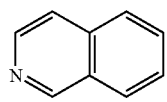

with an iodide reagent comprising N-iodosuccinimide, iodine, iodine with iodic acid, bis(pyridine)iodonium(I) tetrafluoroborate, sodium iodide with bleach, sodium iodide with oxidant (e.g., oxone, sodium periodate, and periodic acid), 1,3-diiodo-5,5-dimethylhydantoin, iodine monochloride, or pyridine iodine monochloride with

- a solvent comprising trifluoromethanesulfonic acid, sulfuric acid, trifluoroacetic acid, acetic acid, methanesulfonic acid, acid in combination with water, dimethylformamide, methanol, acetonitrile, dichloromethane, tetrahydrofuran, or toluene, at a temperature from about −30 C to about 60 C to provide Compound 2O:

2O

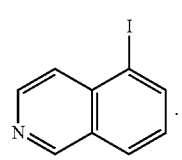

DETAILED DESCRIPTION

Triazole containing compounds, such as Compound 1 disclosed herein, are frequently prepared from azides. The use of azide-containing materials can be inherently hazardous, for example due to potential explosiveness of azides. Processes that avoid the use of azides can be desirable, for example, to avoid such hazards.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Definitions

As used above, throughout the disclosure, the following abbreviations, unless otherwise indicated, has the following meanings:

2-MeTHF 2-methyltetrahydrofuran
Ac acetyl
ACN acetonitrile (MeCN)
ADMP 2-azido-1,3-dimethylimidazolium hexafluorophosphate
BIQ 5-bromo-isoquinoline
CAA 3-chloroanthranilic acid
CBS Corey-Bakshi-Shibata
CNA 2-chloro-4-nitroaniline
DBN diazabicyclo[4.3.0]non-5-ene
DBU 1,8-diazabicyclo[5.4.0]undec-7-ene
DCM dichloromethane ($CH_2Cl2$)
DIAD diisopropylazodicarboxylate
DIBAL diisobutylaluminum hydride
DIPEA diisopropylethylamine
DME 1,2-dimethoxyethane
DMF dimethylformamide
DMF-DMA N,N-dimethylformamide dimethyl acetal
DMP Dess-Martin periodinane
DMPAO 2,6-dimethylanilino(oxo)acetic acid
DMPU N,N'-dimethylpropyleneurea
DMSO dimethylsulfoxide
(dppf)$PdCl_2$ [1,1'-bis(diphenylphosphino)ferrocene]palladium(II) dichloride
ECEA ethyl (ethoxymethylene)cyanoacetate
EDC·HCl 1-(3-dimethylaminopropyl)-3-ethylcarbodiimide hydrochloride
EDCP ethyl dichloropyruvate
equiv equivalent(s)
EtOAc Ethyl acetate
EtOH ethanol
Et ethyl
HCl Hydrochloric acid
IIQ 5-iodo-isoquinoline
IPAc isopropyl acetate
IPE isopropyl ether IPA isopropyl alcohol
iPr isopropyl
LiHMDS lithium bis(trimethylsilyl)amide
LTBA lithium tri-tert-butoxyaluminum hydride
MDCP methyl dichloropyruvate
MeOH methanol
Me methyl
MsCl methanesulfonyl chloride
MTBE methyl tert-butyl ether
NaOAc sodium acetate
NBS N-bromosuccinimide
NIS N-iodosuccinimide
NMBI N-methyl bromoisoquinolinium iodide
NMP methyl-2-pyrrolidinone
NMR nuclear magnetic resonance
Sigamide S—N-(3,5-di-tert-butylphenyl)-3-methyl-2-(N-formyl-N-methylamino)butanamide
TfOH triflic acid
THF tetrahydrofuran
Volume 1 liter per kilogram scaling factor
XantPhos 4,5-bis(diphenylphosphino)-9,9-dimethylxanthene
XantPhos-Pd-G2 chloro[(4,5-bis(diphenylphosphino)-9,9-dimethylxanthene)-2-(2'-amino-1,1'-biphenyl)]palladium(II)

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, an "activating reagent" is compound that increases the leaving group ability of a leaving group by chemical modification. Non-limiting examples of activating reagents, include but are not limited to, methanesulfonyl chloride, methanesulfonic anhydride, ethylsulfonyl chloride, toluenesulfonyl chloride, phenylsulfonyl chloride, 4-chlorobenzenesulfonyl chloride, and 4-nitrobenzenesulfonyl chloride.

As used herein, an "acid" or an "acidic additive" refers to a compound that is a proton donor that yields hydronium ions in water solution or an electron-pair acceptor that combines with an electron-pair donors or a base. Non-limiting examples of acids include, but are not limited to, hydrochloric acid, hydrobromic acid, methanesulfonic acid, p-toluenesulfonic acid, benzenesulfonic acid, trifluoroacetic acid, phosphoric acid, formic acid, and oxalic acid.

As used herein, an "alkylating agent" refers to compound that can install an alkyl group into a compound. Non-limiting examples of the alkylating agents include, but are not limited to, iodomethane, trimethylsulfoxonium iodide, diazomethane, dimethylsulfate, 2,2-dimethoxypropane, dimethylcarbonate, dimethyldicarbonate, methyl fluorosulfonate, methyl methanesulfonate, chloromethane, bromomethane, and trimethyloxonium tetrafluoroborate As used herein, an "amine catalyst" refers to a compound used to facilitate a reaction, such as chlorination. Non-limiting examples of amine catalysts include, but are not limited to, L-proline amide and (2R,5R)-diphenylpyrrolidine.

As used herein, an "amine ligand" refers to compound that can bind to a metal complex, such as copper. Non-limiting examples of amine ligands include, but are not limited to, trans-N,N'-dimethylcyclohexane-1,2-diamine, N1,N2-dimethylethane-1,2-diamine, N1,N3-dimethylpropane-1,3-diamine, and N1-(2-aminoethyl)ethane-1,2-diamine.

As used herein, "base" can refer to metal oxides or other compounds that react with an acid to neutralize it and produce water and a salt. "Base" can also refer to compounds and functional groups that contain a basic nitrogen atom with a lone pair. Bases can include tertiary amine bases, aromatic amine bases, hydroxide bases, and alkoxide bases. Non-limiting examples of bases include, but are not limited to, potassium tert-butoxide, sodium tert-butoxide, sodium methoxide, lithium tert-butoxide, potassium tert-pentoxide, sodium tert-pentoxide, potassium propionate, potassium pivalate, N-methylmorpholine, tri-n-propylamine, N,N-diisopropylethylamine, triethylamine, tri-n-butylamine, 1,8-diazabicyclo[5.4.0]undec-7-ene, 1,4-diazabicyclo[2.2.2]octane, pyridine, 2,6-lutidine, collidine, sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, cesium carbonate, sodium hydroxide, lithium hydroxide, potassium hydroxide, ammonium hydroxide, or lithium bis(trimethylsilyl)amide. Additional examples include, but are not limited to, phenyllithium, mesityllithium, tert-butyllithium, sec-butyllithium, isopropylmagnesium chloride, isopropylmagnesium bromide, isopropylmagnesium chloride lithium chloride complex, phenylmagnesium chloride, sec-butylmagnesium chloride, 2,2,6,6-tetramethylpiperidinylmagnesium chloride lithium chloride complex, lithium diisopropylamide, potassium bis(trimethylsilyl)amide, or sodium bis(trimethylsilyl)amide.

As used herein, a "brominating agent" refers to a compound that can install a bromine group into a compound. Non-limiting examples of brominating agents include, but are not limited to, N-bromosuccinimide, 1,3-dibromo-5,5-dimethylhydantoin, pyridinium tribromide, or bromine; potassium bromide/hypochlorous acid, and dibromoisocyanuric acid.

As used herein, a "carbonyl source" is a compound that can provide a carbonyl group into a compound. Non-limiting examples of carbonyl sources include, but are not limited to, carbon monoxide, iron pentacarbonyl, dicobalt octacarbonyl, N-formylsaccharine, paraformaldehyde, and formic acid.

As used herein, a "catalyst" is a compound that facilitate other reactions, such as bond-forming reactions, and also include the metal catalysts described here. Non-limiting examples of catalysts include. but are not limited to, Sigamide ((S)—N-(3,5-Di-tert-butylphenyl)-3-methyl-2-(N-formyl-N-methylamino)butanamide), RuCl(mesitylene)[(S,S)-Ts-DPEN], RuCl(p-cymene)[(R,R)-Teth-Ts-DPEN], CBS type catalysts, copper hydride-bisoxazoline complexes with stoichiometric reductants, chiral phosphine ligands (BINAP, DIPAMP, Segphos, Phanephos, Norphos, Me-DuPhos, PPhos, Josiphos, MeBoPhoz, Chenphos) with transition metals Pd, Ru, Rh, or Ir, or chiral formamide catalysts. Other examples include but are not limited to cesium carbonate, magnesium sulfate, cesium carbonate, potassium carbonate, sodium carbonate, potassium hydroxide, lithium hydroxide, sodium hydroxide, titanium(IV) isopropoxide, pyrrolidine, piperidine, proline, diisopropylamine, dibutylamine, acetic acid, trifluoroacetic acid, benzoic acid, 4-nitrobenzoic acid, methoxyacetic acid, propionic acid, isobutyric acid, pivalic acid, decanoic acid, hexanoic acid, phenyl boronic acid, or a combination thereof.

As used herein, a "copper catalyst" is a compound that contains copper and can facilitate other reactions, such as bond-forming reactions. Non-limiting examples of copper catalyst include, but are not limited to, copper(I) iodide, copper(I) bromide, copper(I) chloride, copper(I) oxide, copper(I) acetate, copper(I) bromide dimethyl sulfide complex, copper(I) triflate, copper(I) iodide tetrabutylammonium iodide complex, tetrakis(acetonitrile)copper(I) hexafluorophosphate, copper(I) iodide triethylphosphite complex, and copper(I) bromide triphenylphosphine complex. Additional examples include copper(I) cyanide di(lithium chloride) complex, copper(I) trifluoromethanesulfonate toluene complex, copper(I) chloride bis(lithium chloride) complex, copper(I) bromide bis(lithium bromide) complex, copper(I) thiocyanate, copper(I) thiophene-2-carboxylate, copper(I) thiophenolate, copper(I) diphenylphosphinate, (1,10-phenanthroline)bis(triphenylphosphine)copper(I) nitrate DCM adduct, copper(I) 3-methylsalicylate, chloro[1,3-bis(2,6-diisopropylphenyl)imidazol-2-ylidene]copper(I), chloro(1,5-cyclooctadiene)copper(I) dimer, copper(II) chloride, and copper(II) acetate with triphenylphosphine, tributylphosphine, tri(2-furyl)phosphine, tri(p-tolyl)phosphine, or tri(o-tolyl)phosphine.

As used herein, a "copper catalyst ligand" refers to a compound that can bind to a metal complex, such as copper. Non-limiting examples of copper catalyst ligands include, but are not limited to, diamines (N,N'-dimethylethane-1,2-diamine, trans-N,N'-dimethyl-cyclohexane-1,2-diamine), diols (ethan-1,2-diol, propane-1,3-diol), diketones (2-acetylcyclohexanone, acetoacetonate,2,2,6,6-tetramethylheptane-3,5-dione), glycine derivatives (N-methylglycine, N,N-dimethylglycine), ethyl 2-oxocyclohexanecarboxylate, ethylene glycol, pyridine, 2,2'-bipyridine, 1,10-phenanthroline, neocuproine, 8-hydroxyquinoline, picolinic acid, glyoxal bis(phenylhydrazone), 2,6-dimethylanilino(oxo)acetic acid, 2,6-difluoroanilino(oxo)acetic acid, 2,6-dimethyloxyaniliono(oxo)acetic acid, 2,3,4,5,6-pentafluoroanilino(oxo)acetic acid, 3,5-bis(trifluoromethyl)anilino(oxo)acetic acid, 2-fluoro-6-(piperidine-1-sulfonyl)anilino(oxo)acetic acid, $N^1,N^2$-di([1,1'-biphenyl]-2-yl)oxalamide, $N^1,N^2$-bis(2-phenoxyphenyl)oxalamide, thiophene-2-carboxylic acid, and a pyridine bisoxazoline ligand, such as (2,6-bis((4S,5R)-4,5-diphenyl-4,5-dihydrooxazol-2-yl)pyridine), 2,6-bis((S)-4-phenyl-4,5-dihydrooxazol-2-yl)pyridine, 2,6-bis((S)-4-tert-butyl-4,5-dihydrooxazol-2-yl)pyridine, 2,6-bis((S)-4-isopropyl-4,5-dihydrooxazol-2-yl)pyridine, 2,6-bis((S)-4-benzyl-4,5-dihydrooxazol-2-yl)pyridine, 2,6-bis((S)-4-methyl-4,5-dihydrooxazol-2-yl)pyridine, 2,6-bis((S)-4-isobutyl-4,5-dihydrooxazol-2-yl)pyridine, 2,6-bis((S)-4-phenethyl-4,5-dihydrooxazol-2-yl)pyridine, 2,6-bis((4S,5R)-4-methyl-5-phenyl-4,5-dihydrooxazol-2-yl)pyridine, 2,6-bis((S)-4-isopropyl-5,5-diphenyl-4,5-dihydrooxazol-2-yl)pyridine, and 2,6-bis((3aS,8aR)-3a,8a-dihydro-8H-indeno[1,2-d]oxazol-2-yl)pyridine.

As used herein, a "chlorinating agent" or "chlorinating reagent" refers to a compound that can install a chlorine group into a compound. Non-limiting examples of chlorinating agents include, but are not limited to, sulfuryl chloride, chlorine gas, acetyl chloride/ceric ammonium nitrate, lithium diisopropylamide/4-toluenesulfonyl chloride, iodosobenzene dichloride, trichloromethanesulfonyl chloride, 1,3-dichloro-5,5-dimethylhydantoin/ammonium chloride, tetrachlorosilane/urea-hydrogen peroxide, N-chlorosuccinimide, trichloroisocyanuric acid, and 3,5-dichloro-2-hydroxy-4,6-s-triazinedione sodium salt. Additional examples include, but not limited to, oxalyl chloride, phosphorus oxychloride, thionyl chloride, phosgene, triphosgene, methanesulfonyl chloride, and cyanuric chloride.

As used herein, a "coupling agent" is a compound that improves the coupling of an carboxylic acid and amine. Non-limiting examples of coupling agents include, but are not limited to, 1-(3-Dimethylaminopropyl)-3-ethylcarbodiimide hydrochloride (EDC HCl), carbonyl diimidazole, oxalyl chloride, thionyl chloride, dicyclohexylcarbodiimide, diisopropylcarbodiimide, isobutyl chloroformate, 1-[Bis(dimethylamino)methylene]-1H-1,2,3-triazolo[4,5-b]pyridinium 3-oxid hexafluorophosphate, N,N,N',N'-Tetramethyl-O-(1H-benzotriazol-1-yl)uronium hexafluorophosphate, (Benzotriazol-1-yloxy)tris(dimethylamino)phosphonium hexafluorophosphate, (Benzotriazol-1-yloxy)tripyrrolidinophosphonium hexafluorophosphate, tri-n-propylphosphonic anhydride, and 2-chloro-4,6-dimethoxy-1,3,5-triazine.

As used herein, a "formamide-based reagent" refers to a compound that can install a one carbon synthon into a compound. Non-limiting examples of formamide-based reagents include, but are not limited to, N,N-dimethylformamide dimethyl acetal, N,N-dimethylformamide diethyl acetal, and N,N-dimethylformamide diisopropyl acetal.

As used herein, a "hydride source" refers to a compound that can install a hydride into a compound. Non-limiting examples of hydride sources include, but are not limited to, triethylsilane, methyldiethoxysilane, trichlorosilane, polymethylhydrosiloxane, dimethyl(phenyl)silane, 1,1,2,2-tetramethyldisilane, diphenylsilane, and hydrogen gas.

As used herein, a "hydroxide base" refers to a metal oxide that react with an acid to neutralize it and produce water and a salt. Non-limiting examples, include but are not limited to, potassium hydroxide, lithium hydroxide, and sodium hydroxide, ammonium hydroxide.

As used herein, an "iodide additive" refers to a compound that can install an iodine group into a compound. Non-limiting examples of iodide additives include, but are not limited to, sodium iodide, lithium iodide, or potassium iodide.

As used herein, a "Lewis base" or "Lewis base additive" refers to a compound or ionic species which can donate an electron pair to an acceptor compound. Non-limiting examples of Lewis bases include, but are not limited to, N,N'-dimethylpropyleneurea (DMPU), hexamethylphosphoramide, 2,6-lutidine, pyridine, diglyme, N-methylmorpholine, diisopropylethylamine, and 1,2-dimethoxyethane.

As used herein, a "nitrile reagent" refers to a compound that can install a two carbon synthon into a compound. Non-limiting examples of the nitrile reagent include, but are not limited to, acetonitrile.

As used herein, an "organometallic reagent" is a compound that contains a carbon-metal bond. Non-limiting examples of organometallic reagents include, but are not limited to, isopropylmagnesium chloride, cyclohexylmagnesium chloride, butylmagnesium chloride, tert-butylmagnesium chloride, isopropylmagnesium chloride lithium chloride complex, sec-butylmagnesium chloride lithium chloride complex, isopropylmagnesium bromide, ethylmagnesium bromide, phenyllithium, mesityllithium, tert-butyllithium, and sec-butyllithium.

As used herein, an "oxidant" is a compound that can oxidize other compounds. Non-limiting examples of oxidant include but are not limited to, potassium ferricyanide, oxone, lead tetraacetate, peracetic acid, hydrogen peroxide, molecular oxygen, air, sodium hypochlorite, sodium chlorite, sodium periodate, potassium peroxymonosulfate, 2,3-dichloro-5,6-dicyano-1,4-benzoquinone, 1,4-benzoquinone, periodic acid, potassium bromate, meta-chloroperoxybenzoic acid, and magnesium monoperoxypthalate.

As used herein, a "palladium catalyst" is a compound that contains pallidum, or a combination of a palladium catalyst and a palladium catalyst ligand, and can facilitate other reactions, such as bond-forming reactions. Non-limiting examples of palladium catalysts, include be are not limited to, palladium on carbon, chloro[(4,5-bis(diphenylphosphino)-9,9-dimethylxanthene)-2-(2'-amino-1,1'-biphenyl)] palladium(II) (XantPhos Pd G2), $Pd(acac)_2$, $Pd(OAc)_2$, $Pd(hfac)_2$, PdCl(allyl), $PdCl_2$, $PdSO_4 \cdot 2H_2O$, Pd(XantPhos)$Cl_2$, XantPhos Pd G3, N-XantPhos Pd G4, tBuXPhos Pd G3, tBuBrettPhos Pd G3, RockPhos Pd G3, JosiPhos-J009 Pd G3, AdBrettPhos Pd G3, TrixiePhos Pd G3, tetrakis(triphenylphosphine)palladium(0)/Pd($PPh_3)_4$, and bis(dibenzylideneacetone)palladium(0)/$Pd_2(dba)_3$. Other examples include, but not limited to, 1,1'-bis(diphenylphosphino)ferrocene)palladium(II) chloride, palladium dichloride bis(acetonitrile), bis(triphenylphosphine)palladium chloride, tris(dibenzylideneacetone)dipalladium(0)-chloroform adduct, [1,1'-Bis(di-tert-butylphosphino)ferrocene]dichloropalladium(II), dichlorobis(tricyclohexylphosphine)palladium(II), bis(benzonitrile)palladium dichloride, [1,3-Bis(2,6-Diisopropylphenyl)imidazol-2-ylidene](3-chloropyridyl)palladium(II) dichloride, and tris(dibenzylideneacetone)dipalladium(0) in combination with triphenylphosphine, tributylphosphine, tri(2-furyl)phosphine, tri(p-tolyl)phosphine, or tri(o-tolyl)phosphine.

As used herein, a "palladium catalyst ligand" refers to compound that can bind to a palladium complex. Non-limiting examples of palladium catalyst ligands include, but are not limited to, 4,5-bis(diphenylphosphino)-9,9-dimethylxanthene (Xantphos) and other phosphine ligands understood by one skilled in the art.

As used herein, a "platinum catalyst" is a compound that contains platinum and can facilitate other reactions, such as hydrogenation. Non-limiting examples include, but are not limited to, platinum on alumina and platinum dioxide.

As used herein, a "reducing agent" is a compound that can reduce other compounds. Non-limiting examples of reducing agents include, but are not limited to, borane tetrahydrofuran complex, borane dimethylsulfide complex, $NaBH_4$/$I_2$, ammonia borane, diethylphenylamine-borane, $NaBH_4$, $LiBH_4$, $KBH_4$, lithium triethylborohydride, potassium tri-sec-butylborohydride, diisobutylaluminum hydride, sodium bis(2-methoxyethoxy)aluminum hydride, lithium tri-tert-butoxyaluminum hydride, lithium tris[(3-ethyl-3-pentyl)oxy]aluminohydride, hydrogen gas, formic acid/triethylamine, or 2-propanol.

As used herein, a "rhodium catalyst" is a compound that contains rhodium and can facilitate other reactions, such as hydrogenation. Non-limiting examples of rhodium catalysts include, but are not limited to, rhodium on alumina.

As used herein, a "ruthenium catalyst" is a compound that contains ruthenium and that can facilitate other reactions, such as hydrogenation. Non-limiting examples of ruthenium catalysts include but are not limited to, RuCl(mesitylene)[(S,S)-Ts-DPEN] and RuCl(p-cymene)[(R,R)-Teth-Ts-DPEN].

As used herein, a "solvent" is a substance that can dissolve a solute to a solution. A solvent can be a polar solvent or a non-polar solvent. Solvents can include esters, ethers, chlorinated solvents, aromatic solvents, nitriles, water, polar aprotic solvents, and alcohols. Non-limiting examples of solvents include, but are not limited to, water, alkanes such as heptanes, hexanes, and cyclohexane, petroleum ether, alcohols such as methanol, ethanol, propanol, isopropanol, ethylene glycol and polyethylene glycol such as PEG400, alkanoates such as ethyl acetate, propyl acetate, isopropyl acetate, and butyl acetate, acetonitrile, alkanones such as acetone, methyl ethyl ketone (MEK), methyl propyl ketone (MPK) and methyl iso-butyl ketone (MIBK), ethers such as diethyl ether, methyl-t-butyl ether, tetrahydrofuran, methyltetrahydrofuran, 1,2-dimethoxy ethane and 1,4-dioxane, aromatics such as benzene and toluene, halogenated solvents such as methylene chloride, chloroform and carbon tetrachloride, dimethylsulfoxide (DMSO), and dimethylformamide (DMF). Other examples include but are not limited to, diglyme, cyclopentyl methyl ether, diphenyl ether, trifluorotoluene, xylenes, acetic acid, trifluoroacetic acid, propionic acid, dichloroethane, chlorobenzene, tert-butanol, acetonitrile, propionitrile, and butyronitrile.

As used herein, a "titanium-based reagent" is a compound that contains titanium. Non-limiting examples of titanium-based reagents include but are not limited to, titanium(IV) ethoxide, titanium(IV) isopropoxide, titanium(IV) butoxide, and titanium(IV) tetrachloride.

As used herein, a "zinc additive" is a compound that contains zinc. Non-limiting examples of zinc additives include but are not limited to, zinc chloride, and zinc bromide.

As used herein, a "zirconium-based reagent" is a compound that contains zirconium. Non-limiting examples of zirconium-based reagents include but are not limited to, zirconium(IV) tert-butoxide.

The compounds disclosed herein also include mixtures of all stereoisomers, including enantiomers and diastereomers. As used herein, "stereoisomers" refer to compounds which have identical chemical constitution, but differ with regard to the arrangement of the atoms or groups in space. Examples of stereoisomers include diastereomers and enantiomers. In some embodiments, the compounds described herein are produced in at least greater than about 50%, at least greater than about 60%, at least greater than about 70%, at least greater than about 80%, at least greater than about 90%, at least greater than about 91%, at least greater than about 92%, at least greater than about 93%, at least greater than about 94%, at least greater than about 95%, at least greater than about 96%, at least greater than about 97%, at least greater than about 98%, at least greater than about 99%, at least greater than about 99.5%, or at least greater about 99.9% diastereomeric or chiral purity.

As used herein, a "diastereomer" refers to a stereoisomer with two or more centers of chirality and whose molecules are not mirror images of one another. Diastereomers have different physical properties, e.g., melting points, boiling points, spectral properties, and reactivities.

As used herein, "enantiomers" refer to two stereoisomers of a compound which are non-superimposable mirror images of one another.

As used herein, "chiral" refers to molecules which have the property of non-superimposability of the mirror image partner, while the term "achiral" refers to molecules which are superimposable on their mirror image partner.

Nomenclature

The structure of the compound (S)-6-(((1-(bicyclo[1.1.1]pentan-1-yl)-1H-1,2,3-triazol-4-yl)(2-methyl-1-oxo-1,2-dihydroisoquinolin-5-yl)methyl)amino)-8-chloro-4-(neopentylamino)quinoline-3-carbonitrile is as follows:

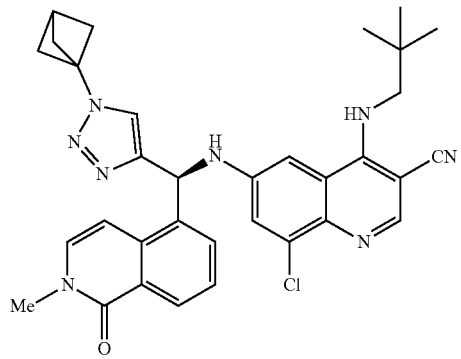

In this disclosure, the above compound is referred to as Compound 1.

Compound 1 Manufacturing Route 1

In a non-limiting example, Scheme 1 is a scheme depicting one embodiment of Compound 1 Manufacturing Route 1. In a non-limiting example, Schemes 1, 2, and 3 depict one embodiment for the synthesis of Compound 1.

Scheme 1

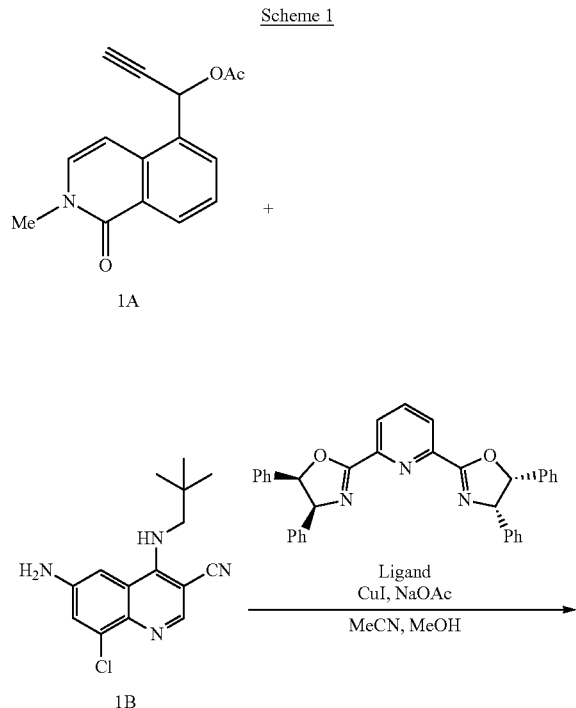

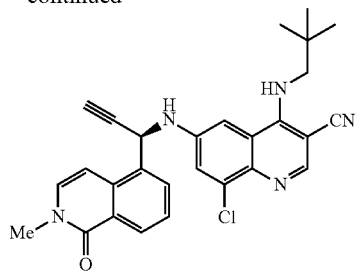

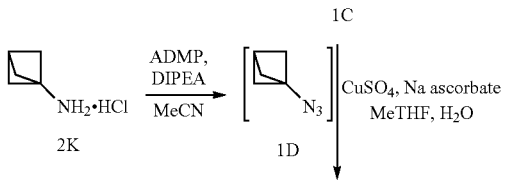

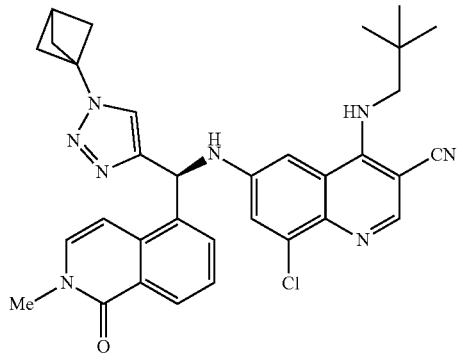 [SMILES: Cn1ccc2c([C@H](Nc3cc(Cl)c4ncc(C#N)c(NCC(C)(C)C)c4c3)c3cn(C45CC(C4)C5)nn3)cccc2c1=O]

Compound 1

One method for the synthesis of Compound 1 is a process comprising: (1a) contacting Compound 1A with Compound 1B in the presence of a copper source, a ligand and a base in a solvent at a temperature sufficient to provide Compound 1C; and (1b) contacting Compound 1C with Compound 1D in the presence of a copper catalyst and sodium ascorbate in a solvent at a temperature sufficient to provide Compound 1.

In some embodiments for step (1a): (i) the copper source comprises copper(I) iodide, copper(I) bromide, copper(I) chloride, copper(I) oxide, copper(I) acetate, copper(I) bromide dimethyl sulfide complex, copper(I) triflate, copper(I) iodide tetrabutylammonium iodide complex, tetrakis(acetonitrile)copper(I) hexafluorophosphate, copper(I) iodide triethylphosphite complex, copper(I) bromide triphenylphosphine complex, copper(II) chloride, copper(II) bromide, copper(II) acetate, or copper(II) sulfate; (ii) the ligand comprises a pyridine bisoxazoline ligand, such as (2,6-bis((4S,5R)-4,5-diphenyl-4,5-dihydrooxazol-2-yl)pyridine), 2,6-bis((S)-4-phenyl-4,5-dihydrooxazol-2-yl)pyridine, 2,6-bis((S)-4-tertbutyl-4,5-dihydrooxazol-2-yl)pyridine, 2,6-bis((S)-4-isopropyl-4,5-dihydrooxazol-2-yl)pyridine, 2,6-bis((S)-4-benzyl-4,5-dihydrooxazol-2-yl)pyridine, 2,6-bis((S)-4-methyl-4,5-dihydrooxazol-2-yl)pyridine, 2,6-bis((S)-4-isobutyl-4,5-dihydrooxazol-2-yl)pyridine, 2,6-bis((S)-4-phenethyl-4,5-dihydrooxazol-2-yl)pyridine, 2,6-bis((4S,5R)-4-methyl-5-phenyl-4,5-dihydrooxazol-2-yl)pyridine, 2,6-bis((S)-4-isopropyl-5,5-diphenyl-4,5-dihydrooxazol-2-yl)pyridine, and 2,6-bis((3aS,8aR)-3a,8a-dihydro-8H-indeno[1,2-d]oxazol-2-yl)pyridine; (iii) the base comprises sodium acetate, lithium acetate, potassium acetate, a tertiary amine (e.g., N-methylmorpholine, tri-n-propylamine, N,N-diisopropylethylamine, triethylamine, tri-n-butylamine, 1,8- diazabicyclo[5.4.0]undec-7-ene, and 1,4-diazabicyclo [2.2.2]octane), an aromatic amine (e.g., pyridine, 2,6-lutidine, and collidine), an inorganic base (e.g., sodium bicarbonate, sodium carbonate, sodium phosphate monobasic, sodium phosphate dibasic, sodium phosphate tribasic, potassium bicarbonate, potassium carbonate, potassium phosphate monobasic, potassium phosphate dibasic, potassium phosphate tribasic, potassium fluoride, lithium carbonate, and cesium carbonate), or an alkoxide base (e.g., sodium methoxide, sodium ethoxide, sodium isopropoxide, sodium tert-amylate, and sodium tert-butoxide); (iv) the solvent comprises an alcoholic solvent (e.g., methanol, ethanol, isopropanol, and tert-butanol), an ester (e.g., ethyl acetate, isopropyl acetate, n-propyl acetate, butyl acetate, and isobutyl acetate), an ether (e.g., diethyl ether, methyl tert-butyl ether, tetrahydrofuran, 2-methyltetrahydrofuran, and 1,4-dioxane), an aromatic solvent (e.g., toluene, benzene, and xylenes), a polar aprotic solvent (e.g., N,N-dimethylformamide, N,N-dimethylacetamide, N-methylpyrrolidinone, and dimethylsulfoxide), a chlorinated solvent (e.g., dichloromethane, chloroform, dichloroethane, and chlorobenzene), a nitrile (e.g., acetonitrile, propionitrile, and butyronitrile), or a combination thereof; and/or (v) the temperature is from about −20° C. to about 60° C.

In some embodiments for step (1a), the copper source comprises copper(I) iodide. In some embodiments for step (1a), the ligand comprises 2,6-bis((4S,5R)-4,5-diphenyl-4,5-dihydrooxazol-2-yl)pyridine. In some embodiments for step (1a), the base comprises sodium acetate. In some embodiments for step (1a), the solvent comprises acetonitrile and methanol. In some embodiments for step (1a), the temperature is from about 0° C. to about 20° C. In some embodiments for step (1a), the temperature is from about −20° C. to about 60° C. In some embodiments for step (1a), the temperature is about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., or about 60° C.

In some embodiments for step (1b): (i) the copper catalyst comprises copper(II) sulfate, copper(II) acetate, copper(I) chloride, copper(I) bromide, copper (I) bromide dimethyl sulfide complex, copper(I) triflate toluene complex, copper (I) iodide tetrabutylammonium iodide complex, tetrakis (acetonitrile)copper(I) hexafluorophosphate, copper(I) iodide triethylphosphite complex, or copper(I) bromide triphenylphosphine complex; (ii) the solvent comprises water, an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), an alcohol (e.g., methanol, ethanol, isopropanol, and tert-butanol), a polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, and butyronitrile), a hydrocarbon solvent (e.g., toluene, trifluorotoluene, cyclohexane, n-heptane, and xylenes), or a combination thereof, and/or (iii) the temperature is from about 0° C. to about 50° C.

In some embodiments, Compound 1D is prepared from Compound 2K as described throughout the specification, such as in the Alternate Synthesis 1 of Compound 6A (Scheme 18).

In some embodiments for step (1b), the copper catalyst comprises copper(II) sulfate. In some embodiments for step (1b), the solvent comprises 2-methyltetrahydrofuran, acetonitrile, and water. In some embodiments for step (1b), the temperature is about 20° C. In some embodiments for step (1b), the temperature is from about 0° C. to about 50° C. In some embodiments for step (1b), the temperature is from about 0° C., about 5° C., about 10° C., about 15° C., about 20° C., about 25° C., about 30° C., about 35° C., about 40° C., about 45° C., or about 50° C.

Synthesis of Compound 1A

In a non-limiting example, Scheme 2 is a scheme depicting one embodiment of the synthesis of Compound 1A.

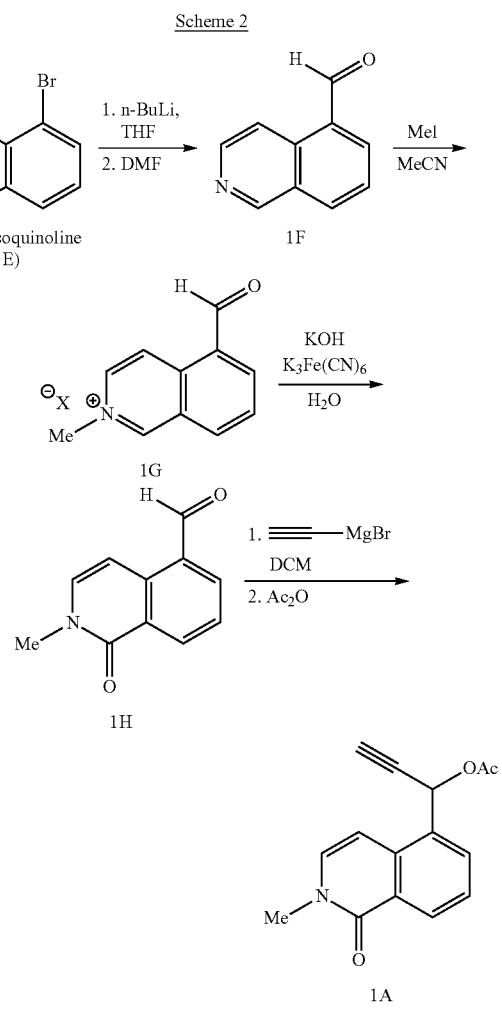

In some embodiments, Compound TA is prepared from a process comprising: (1c) contacting Compound 1E with an organometallic reagent and an electrophile in a solvent at temperature sufficient to provide Compound 1F; (1d) contacting Compound 1F with a methylation reagent in a solvent at a temperature sufficient to provide Compound 1G, wherein X is iodide, chloride, bromide, methylsulfate, sulfate, methylcarbonate, carbonate, methanesulfonate, trifluoromethanesulfonate, toluenesulfonate, or tetrafluoroborate; (1e) contacting Compound 1G with an oxidant and a base in a solvent at a temperature sufficient to provide Compound 1H; and (1f) contacting Compound 1H with an alkylating reagent in a solvent followed by the addition of an acetylating reagent at a temperature sufficient to provide Compound TA.

In some embodiments for step (1c), (i) the organometallic reagent comprises an organolithium reagent (e.g., n-butyllithium, n-hexyllithium, phenyllithium, mesityllithium, tert-butyllithium, and sec-butyllithium) or a Grignard (e.g., isopropylmagnesium chloride, isopropylmagnesium bromide, isopropylmagnesium chloride lithium chloride complex, phenylmagnesium chloride, sec-butylmagnesium chloride, and 2,2,6,6-tetramethylpiperidinylmagnesium chloride lithium chloride complex); (ii) the electrophile comprises a formylated amine (e.g., N,N'-dimethylformamide, N, N-diethylformamide, 1-formylpyrrolidine, 4-formylmorpholine, and N-methylformanilide), a formate ester (e.g., cyanomethyl formate, phenyl formate, ethyl formate, and trifluoroethyl formate), an ortho ester (e.g., trimethyl orthoformate, triethyl orthoformate, and diethyl phenyl orthoformate), a formamide acetal (e.g., N,N-dimethylformamide dipropyl acetal, and N,N-dimethylformamide dimethylacetal), or (chloromethylene)dimethyliminium chloride; (iii) the solvent comprises an ether (e.g., diethyl ether, methyl tert-butyl ether, cyclopentyl methyl ether, 1,4-dioxane, tetrahydrofuran, and 2-methyltetrahydrofuran), or a hydrocarbon solvent (e.g., toluene, trifluorotoluene, n-heptane, and xylenes); and/or (iv) the temperature is from about −100° C. to about −50° C.

In some embodiments for step (1c), the organometallic regent comprises n-butyllithium. In some embodiments for step (1c), the electrophile comprises N,N'-dimethylformamide. In some embodiments for step (1c), the solvent comprises tetrahydrofuran. In some embodiments for step (1c), the temperature is from about −80° C. to about −60° C. In some embodiments for step (1c), the temperature is from about −100° C. to about −50° C. In some embodiments, the temperature is about −100° C., about −95° C., about −90° C., about −85° C., about −80° C., about −75° C., about −70° C., about −65° C., about −60° C., about −55° C., or about −50° C.

In some embodiments for step (1d): (i) the methylation reagent comprises iodomethane, bromomethane, chloromethane, trimethylsulfoxonium iodide, diazomethane, dimethylsulfate, a carbonate (e.g., dimethylcarbonate, and dimethyldicarbonate), a sulfonate (e.g., methyl fluorosulfonate, methyl methanesulfonate, methyl trifluoromethanesulfonate, and methyl toluenesulfonate), or trimethyloxonium tetrafluoroborate; (ii) the solvent comprises an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a chlorinated solvent (e.g., dichloromethane, chloroform, dichloroethane, and chlorobenzene); and/or (iii) the temperature is from about −20° C. to about 45° C.

In some embodiments for step (1d), the methylation reagent comprises iodomethane. In some embodiments for step (1d), the solvent comprises acetonitrile. In some embodiments for step (1d), the temperature is from about 5° C. to about 45° C. In some embodiments for step (1d), the temperature is from about −20° C. to about 45° C. In some embodiments for step (1d), the temperature is about −20° C., about −15° C., about −10° C., about −5° C., about 0° C., about 5° C., about 10° C., about 15° C., about 20° C., about 25° C., about 30° C., about 35° C., about 40° C., or about 45° C. In some embodiments for step (1d), X is iodide.

In some embodiments for step (1e): (i) the oxidant comprises potassium ferricyanide, oxone, lead tetraacetate, peracetic acid, hydrogen peroxide, molecular oxygen, air, sodium hypochlorite, sodium chlorite, sodium periodate, potassium peroxymonosulfate, 2,3-dichloro-5,6-dicyano-1,4-benzoquinone, 1,4-benzoquinone, periodic acid, potassium bromate, meta-chloroperoxybenzoic acid, or magnesium monoperoxyphthalate; (ii) the base comprises a hydroxide base (e.g., potassium hydroxide, lithium hydroxide, sodium hydroxide, cesium hydroxide, and ammonium hydroxide); (iii) the solvent comprises water, an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (iv) the temperature is from about −5° C. to about 70° C.

In some embodiments for step (1e), the oxidant comprises potassium ferricyanide. In some embodiments for step (1e), the base comprises potassium hydroxide. In some embodiments for step (1e), the solvent comprises water. In some embodiments for step (1e), the temperature is from about 0° C. to about 20° C. In some embodiments for step (1e), the temperature is from about −5° C. to about 70° C. In some embodiments for step (1e), the temperature is about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., or 70° C.

In some embodiments for step (1f), (i) the alkylating reagent comprises a Grignard (e.g., ethynylmagnesium bromide, and ethynylmagnesium chloride), or an organolithium reagent (e.g., lithium acetylide, lithium (trimethylsilyl) acetylide), and sodium acetylide); (ii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a hydrocarbon solvent (e.g., toluene, trifluorotoluene, cyclohexane, n-heptane, and xylenes), a nitrile (e.g., acetonitrile, propionitrile, and butyronitrile), or a chlorinated solvent (e.g., dichloromethane dichloroethane, and chloroform); (iii) the acetylating reagent comprises acetic anhydride, an ester (e.g., methyl acetate, ethyl acetate, isopropyl acetate, 1-methylvinyl acetate, ethenyl acetate, acetoxybenzene, and 4-acetoxychlorobenzene), acetyl chloride, or acetyl bromide; and/or (iv) the temperature is from about −20° C. to about 50° C.

In some embodiments for step (1f), the alkylating reagent comprises ethynylmagnesium bromide. In some embodiments for step (1f), the solvent comprises dichloromethane. In some embodiments for step (1f), the acetylating reagent comprises acetic anhydride. In some embodiments for step (1f), the temperature is about 20° C. In some embodiments for step (1f), the temperature is from about −20° C. to about 50° C. In some embodiments for step (1f), the temperature is about −20° C., about −15° C., about −10° C., about −5° C., about 0° C., about 5° C., about 10° C., about 15° C., about 20° C., about 25° C., about 30° C., about 35° C., about 40° C., about 45° C., or about 50° C.

Synthesis of Compound 1B

In a non-limiting example, Scheme 3 is a scheme depicting one embodiment of the synthesis of Compound 1B for Manufacturing Route 1.

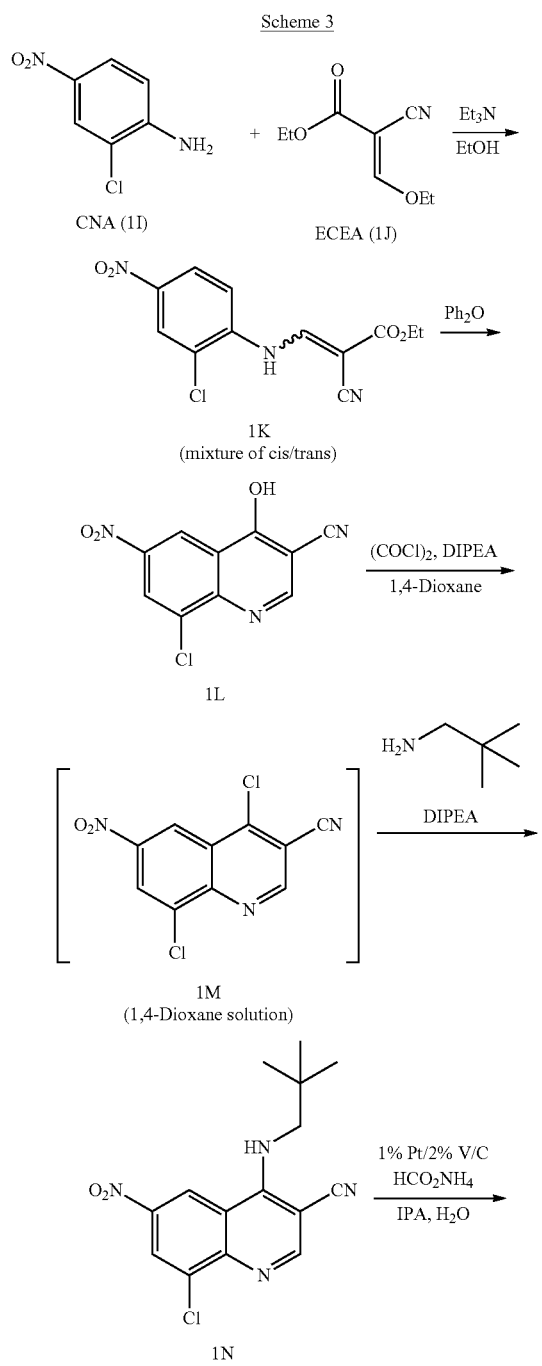

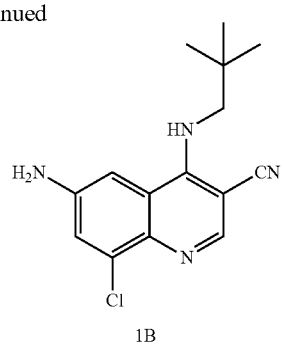

In some embodiments, Compound 1B is prepared from a process comprising: (1g) contacting Compound 1I with Compound 1J in the presence of an amine or carbonate base in a solvent at a temperature sufficient to provide Compound 1K as a mixture of cis and trans compounds; (1h) contacting Compound 1K with a solvent under a high temperature sufficient to provide Compound 1L; (1i) contacting Compound 1L with a chlorinating agent and a base in a solvent at a temperature sufficient to provide Compound 1M; (1j) contacting Compound 1M with 2,2-dimethylpropan-1-amine and a base in a solvent at a temperature sufficient to provide Compound 1N: and (1k) contacting Compound 1N with a metal catalyst and a hydrogen source in a solvent at a temperature sufficient to provide Compound 1B.

In some embodiments for step (1g): (i) the amine or carbonate base comprises a tertiary amine (e.g., triethylamine, N-methylmorpholine, tri-n-propylamine, N,N-diisopropylethylamine, tri-n-butylamine, 1,8-diazabicyclo[5.4.0]undec-7-ene, and 1,4-diazabicyclo[2.2.2]octane) or a carbonate base (e.g., sodium carbonate, cesium carbonate, and potassium carbonate); (ii) the solvent comprises an alcohol (e.g., ethanol, methanol, isopropanol, and tert-butanol), or a polar aprotic solvent (e.g., N,N-dimethylformamide, N,N-dimethylacetamide, N-methyl-2-pyrrolidinone, and dimethyl sulfoxide), and/or (iii) the temperature is from about 20° C. to about 120° C.

In some embodiments for step (1g), the base comprises triethylamine. In some embodiments for step (1g), the solvent comprises ethanol. In some embodiments for step (1g), the temperature is about 75° C. In some embodiments for step (1g), the temperature is from about 20° C. to about 120° C. In some embodiments for step (1g), the temperature is about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C.

In some embodiments for step (1h): (i) the solvent comprises a high boiling solvent (e.g., diphenyl ether, di(ethyleneglycol) dibutyl ether, paraffin oil, xylenes, polyphosphoric acid, Eaton's reagent (phosphorus pentoxide solution in methanesulfonic acid), sulfuric acid/acetic anhydride, and triethyl phosphite), or an eutectic mixture (e.g. Dowtherm®); and/or (ii) the high temperature is from about 50° C. to about 300° C.

In some embodiments for step (1h), the solvent comprises diphenyl ether. In some embodiments for step (1h), the high temperature is about 260° C. In some embodiments for step (1h), the high temperature is from about 50° C. to about 300° C. In some embodiments for step (1h), the high temperature is about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., about 150° C., about 155° C., about 160° C., about 165° C., about 170° C., about 175° C., about 180° C., about 185° C., about 190° C., about 195° C., about 200° C., about 205° C., about 210° C., about 215° C., about 220° C., about 225° C., about 230° C., about 235° C., about 240° C., about 245° C., about 250° C., about 255° C., about 260° C., about 265° C., about 270° C., about 275° C., about 280° C., about 285° C., about 290° C., or about 300° C.

In some embodiments for step (1i), (i) the chlorinating agent comprises oxalyl chloride, phosphorus oxychloride, thionyl chloride, sulfuryl chloride, phosgene, methanesulfonyl chloride, cyanuric chloride, or triphenylphosphine dichloride; (ii) the base comprises a tertiary amine (e.g., N,N-diisopropylethylamine 1-methylimidazole, N-methylmorpholine, tri-n-propylamine, triethylamine, tri-n-butylamine, 1,8-diazabicyclo[5.4.0]undec-7-ene, and 1,4-diazabicyclo[2.2.2]octane), or an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate); (iii) the solvent comprises an ether (e.g., 1,4-dioxane, diethyl ether, tetrahydrofuran, 2-methyltetrahydrofuran, dimethoxyethane, methyl tert-butyl ether, cyclopentyl methyl ether, and diphenyl ether), or a polar aprotic solvent (e.g., N,N-dimethylformamide, N,N-dimethylacetamide, N-methyl-2-pyrrolidinone, and dimethyl sulfoxide); and/or (iv) the temperature is from about 20° C. to about 80° C.

In some embodiments for step (1i), the chlorinating agent comprises oxalyl chloride. In some embodiments for step (1i), the base comprises N,N-diisopropylethylamine. In some embodiments for step (1i), the solvent comprises 1,4-dioxane. In some embodiments for step (1i), the temperature is about 60° C. In some embodiments for step (1i), the temperature is from about 20° C. to about 80° C. In some embodiments for step (1i), the temperature is about 20° C., about 25° C., about 30° C., about 35° C., about 40° C., about 45° C., about 50° C., about 55° C., about 60° C., about 65° C., about 70° C., about 75° C., or about 80° C.

In some embodiments for step (1j): (i) the base comprises a tertiary amine (e.g., N,N-diisopropylethylamine, 1-methylimidazole, N-methylmorpholine, tri-n-propylamine, triethylamine, tri-n-butylamine, 1,8-diazabicyclo[5.4.0]undec-7-ene, and 1,4-diazabicyclo[2.2.2]octane), or a inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate); (ii) the solvent comprises an ether (e.g., 1,4-dioxane, diethyl ether, tetrahydrofuran, 2-methyltetrahydrofuran, dimethoxyethane, methyl tert-butyl ether, cyclopentyl methyl ether, and diphenyl ether), or a polar aprotic solvent (e.g., N,N-dimethylformamide, N,N-dimethylacetamide, N-methyl-2-pyrrolidinone, and dimethyl sulfoxide); and/or (iii) the temperature is from about 20° C. to about 80° C.

In some embodiments for step (1j), the base comprises N,N-diisopropylethylamine. In some embodiments for step (1j), the solvent comprises 1,4-dioxane. In some embodiments for step (1j), the temperature is about 60° C. In some embodiments for step (1j), the temperature is from about 20° C. to about 80° C. In some embodiments, the temperature is about 20° C., about 25° C., about 30° C., about 35° C., about 40° C., about 45° C., about 50° C., about 55° C., about 60° C., about 65, about 70° C., about 75° C., or about 80° C.

In some embodiments for step (1k): (i) the metal catalyst comprises platinum and vanadium on carbon, palladium on carbon, platinum on alumina, palladium hydroxide on carbon, platinum dioxide, or rhodium on alumina; (ii) the hydrogen source comprises ammonium formate, hydrogen gas, formic acid, formic acid triethylamine complex, or 1,4-cyclohexadiene; (iii) the solvent comprises an alcohol (e.g., methanol, ethanol, tert-butanol, and isopropanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), a halogenated solvent (e.g., dichloromethane, chloroform, dichloroethane, chlorobenzene, and dibromoethane), water, or a combination thereof, and/or (iv) the temperature is from about 0° C. to about 120° C.

In some embodiments for step (1k), the metal catalyst comprises platinum and vanadium on carbon. In some embodiments for step (1k), the hydrogen source comprises ammonium formate. In some embodiments for step (1k), the solvent comprises isopropanol and water. In some embodiments for step (1k), the temperature is from about 50° C. to about 70° C. In some embodiments for step (1k), the temperature is from about 0° C. to about 120° C. In some embodiments for step (1k), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C.

Compound 1 Manufacturing Route 2

In a non-limiting example, Scheme 4 is a scheme depicting one embodiment of Compound 1 Manufacturing Route 2. In a non-limiting example, Schemes 4, 5, 6 and 7 depict one embodiment of the synthesis of Compound 1.

Scheme 4
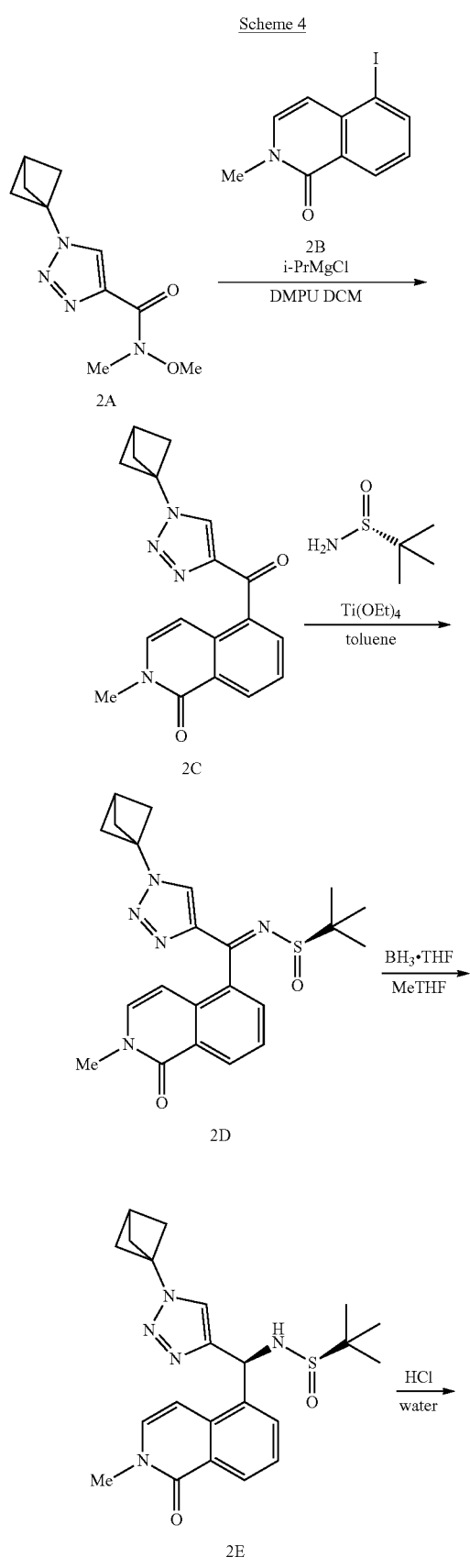
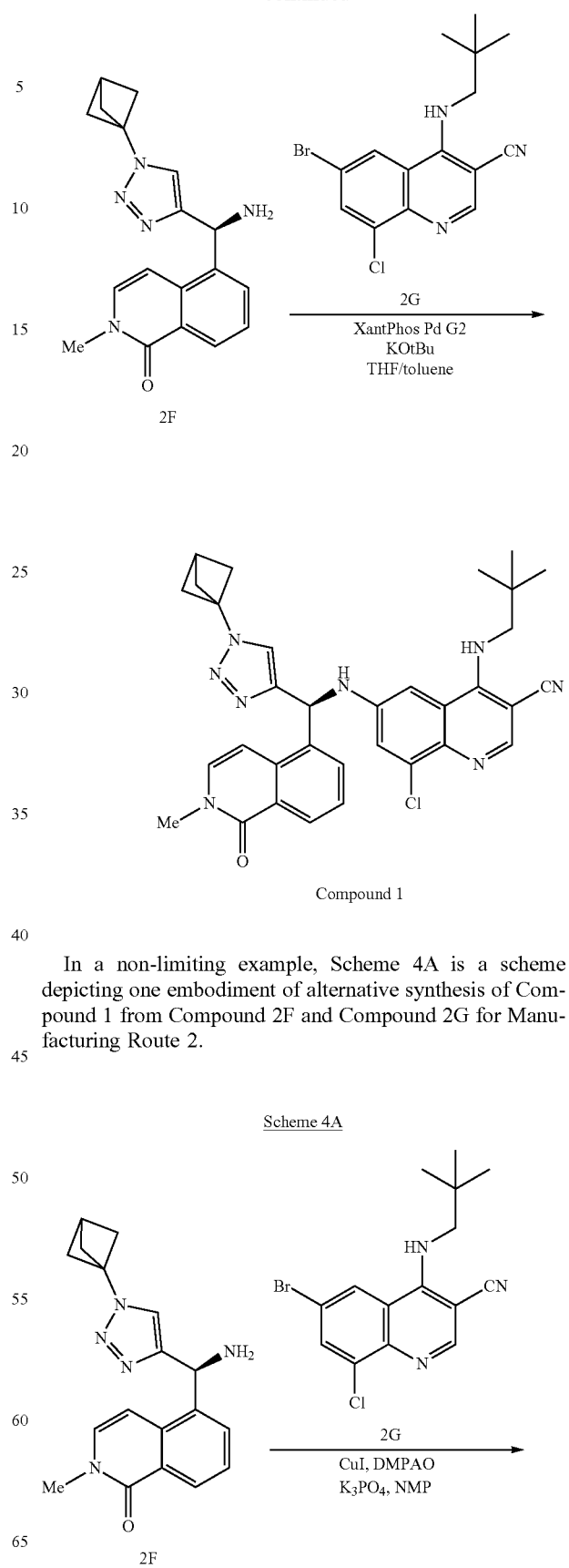
In a non-limiting example, Scheme 4A is a scheme depicting one embodiment of alternative synthesis of Compound 1 from Compound 2F and Compound 2G for Manufacturing Route 2.
Scheme 4A

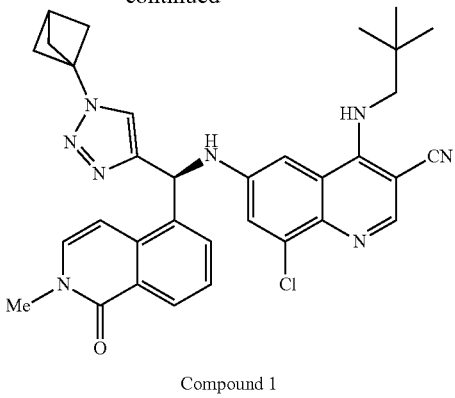

Compound 1

One method for the synthesis of Compound 1 is a process comprising: (2a) contacting Compound 2A with Compound 2B in the presence of an organometallic reagent and a Lewis base in a solvent at temperature sufficient to provide Compound 2C; (2b) contacting Compound 2C with

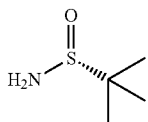

in the presence of a titanium or zirconium based reagent in a solvent at a temperature sufficient to provide Compound 2D; (2c) contacting Compound 2D with a reducing agent and optionally, a ruthenium, palladium, rhodium, or platinum catalyst in a solvent at a temperature sufficient to provide Compound 2E; (2d) contacting Compound 2E with an acid in a solvent at a temperature sufficient to provide Compound 2F; and (2e) contacting Compound 2F with Compound 2G in the presence of a palladium catalyst and a base in a solvent at a temperature sufficient to provide Compound 1.

One method for the synthesis of Compound 1 is a process comprising: (2a) contacting Compound 2A with Compound 2B in the presence of an organometallic reagent and a Lewis base in a solvent at temperature sufficient to provide Compound 2C; (2b) contacting Compound 2C with

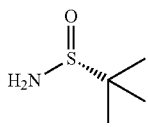

in the presence of a titanium or zirconium based reagent in a solvent at a temperature sufficient to provide Compound 2D; (2c) contacting Compound 2D with a reducing agent and optionally, a ruthenium, palladium, rhodium, or platinum catalyst in a solvent at a temperature sufficient to provide Compound 2E; (2d) contacting Compound 2E with an acid in a solvent at a temperature sufficient to provide Compound 2F; and (2e) contacting Compound 2F with Compound 2G in the presence of a copper catalyst, a copper catalyst ligand, and a base in a solvent at a temperature sufficient to provide Compound 1.

In some embodiments for step (2a): (i) the organometallic reagent comprises an organomagnesium reagent (e.g., iso-propylmagnesium chloride, cyclohexylmagnesium chloride, butylmagnesium chloride, tert-butylmagnesium chloride, isopropylmagnesium chloride lithium chloride complex, sec-butylmagnesium chloride lithium chloride complex, iso-propylmagnesium bromide, and ethylmagnesium bromide), or an organolithium reagent (e.g., phenyllithium, mesityl-lithium, tert-butyllithium, and sec-butyllithium); (ii) the Lewis base comprises N,N'-dimethylpropyleneurea (DMPU), hexamethylphosphoramide, 2,6-lutidine, pyridine, diglyme, N-methylmorpholine, diisopropylethylamine, 1,2-dimethoxyethane, or lithium chloride; (iii) the solvent comprises dichloromethane, an ether (e.g., diglyme, diethyl ether, 1,4-dioxane, tetrahydrofuran, 2-methyltetrahydrofuran, dimethoxyethane, methyl tert-butyl ether, cyclopentyl methyl ether, and diphenyl ether), or a hydrocarbon solvent (e.g., n-hexane, toluene, trifluorotoluene, cyclohexane, n-heptane, and xylenes); and/or (iv) the temperature is from about −80° C. to about 40° C.

In some embodiments for step (2a), the organometallic reagent comprises isopropylmagnesium chloride. In some embodiments for step (2a), the Lewis base comprises N,N'-dimethylpropyleneurea (DMPU). In some embodiments for step (2a), the solvent comprises dichloromethane. In some embodiments for step (2a), the temperature is from about −5° C. to about 20° C. In some embodiments for step (2a), the temperature is from about −80° C. to about 40° C. In some embodiments for step (2a), the temperature is about −80° C., about −75° C., about −70° C., about −65° C., about −60° C., about −55° C., about −50° C., about −45° C., about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., or about 40° C.

In some embodiments for step (2b): (i) the titanium or zirconium based reagent comprises titanium(IV) ethoxide, titanium(IV) isopropoxide, titanium(IV) butoxide, zirconium(IV) tert-butoxide, or zirconium(IV) ethoxide; (ii) the solvent comprise a hydrocarbon solvent (e.g., toluene, trifluorotoluene, cyclohexane, n-heptane, and xylenes), a chlorinated solvent (e.g., dichloromethane, chloroform, dichloroethane, and chlorobenzene), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), an ester (e.g., ethyl acetate, isopropyl acetate, n-propyl acetate, and isobutyl acetate), a polar aprotic solvent (e.g., N,N-dimethylformamide, N,N-dimethylacetamide, N-methyl-2-pyrrolidinone, and dimethyl sulfoxide), or a nitrile (e.g., acetonitrile, propionitrile, and butyronitrile); and/or (iii) the temperature is from about 25° C. to about 110° C.

In some embodiments for step (2b), the titanium or zirconium based reagent comprises titanium(IV) ethoxide. In some embodiments for step (2b), the solvent comprises toluene. In some embodiments for step (2b), the temperature is from about 70° C. to about 75° C. In some embodiments, the temperature is from about 25° C. to about 110° C. In some embodiments, the temperature is about 25° C., about 30° C., about 35° C., about 40° C., about 45° C., about 50° C., about 55° C., about 60° C., about 65° C., about 70° C., about 75° C., about 80° C., about 85° C., about 90° C., about 100° C., about 105° C., or about 110° C.

In some embodiments for step (2c): (i) the reducing agent comprises borane tetrahydrofuran complex, borane dimethylsulfide complex, $NaBH_4/I_2$, a amine·borane complex (e.g., Ammonia Borane, and Diethylphenylamine-borane), a borohydride reagent (e.g., $NaBH_4$, $LiBH_4$, $KBH_4$, Lithium triethylborohydride, and potassium tri-sec-butylborohydride), an aluminum hydride reagent (e.g., Diisobutylaluminum hydride, Sodium bis(2-methoxyethoxy)aluminum hydride, Lithium tri-tert-butoxyaluminum hydride, and Lithium tris [(3-ethyl-3-pentyl)oxy]aluminohydride), hydrogen gas, formic acid/triethylamine, or 2-propanol; (ii) the ruthenium, palladium, rhodium, or platinum catalyst, if present, comprises Noyori Type Ru catalysts (e.g., RuCl(mesitylene)[(S, S)-Ts-DPEN], RuCl(p-cymene)[(R,R)-Teth-Ts-DPEN]), or heterogeneous hydrogenation catalysts (e.g., palladium on carbon, rhodium on alumina, and platinum on carbon); (iii) the solvent comprises an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, and tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (iv) the temperature is from about −40° C. to about 100° C. In some embodiments, for step (2c), Compound 2E is produced in at least greater than about 50%, at least greater than about 60%, at least greater than about 70%, at least greater than about 80%, at least greater than about 90%, at least greater than about 95%, or at least greater than about 99% diastereomeric purity.

In some embodiments for step (2c), the reducing agent comprises borane tetrahydrofuran complex. In some embodiments for step (2c), no ruthenium, palladium, rhodium, or platinum catalyst is present. In some embodiments for step (2c), the solvent comprises 2-methyltetrahydrofuran. In some embodiments for step (2c), the temperature is from about −10° C. to about 0° C. In some embodiments for step (2c), the temperature is from about −40° C. to about 100° C. In some embodiments for step (2c), the temperature is about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C. In some embodiments, for step (2c), Compound 2E is produced in at least greater than about 99% diastereomeric purity.

In some embodiments for step (2d): (i) the acid comprises hydrochloric acid, hydrobromic acid, a sulfonic acid (e.g., methanesulfonic acid, p-toluenesulfonic acid, and benzenesulfonic acid), a trifluoroacetic acid, phosphoric acid, formic acid, or oxalic acid; (ii) the solvent comprises water, an ester (e.g., ethyl acetate, isopropyl acetate, n-propyl acetate, and isobutyl acetate), an alcohol (e.g., ethanol, ethylene glycol, propylene glycol, methanol, isopropanol, and tert-butanol), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (iii) the temperature is from about 0° C. to about 70° C.

In some embodiments for step (2d), the acid comprises hydrochloric acid. In some embodiments for step (2d), the solvent comprises water. In some embodiments for step (2d), the temperature is from about 20° C. to about 50° C. In some embodiments for step (2d), the temperature is from about 0° C. to about 70° C. In some embodiments for step (2d), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., or about 70° C.

In some embodiments for step (2e): (i) the palladium catalyst comprises a palladium(II) catalyst (e.g., XantPhos Pd G2, Pd(acac)$_2$, Pd(OAc)$_2$, Pd(hfac)$_2$, PdCl(allyl), PdCl$_2$, PdSO$_4$·2H$_2$O), a palladium pre-catalyst (e.g., Pd(XantPhos)Cl$_2$, XantPhos Pd G3, N-XantPhos Pd G4, tBuXPhos Pd G3, tBuBrettPhos Pd G3, RockPhos Pd G3, JosiPhos-J009 Pd G3, AdBrettPhos Pd G3, and TrixiePhos Pd G3), or a palladium(0) catalyst (e.g., Pd$_2$(dba)$_3$, Pd(PPh$_3$)$_4$); (ii) the base comprises an alkoxide base (e.g., potassium tert-butoxide, sodium tert-butoxide, sodium methoxide, lithium tert-butoxide, potassium tert-pentoxide, sodium tert-pentoxide, potassium propionate, and potassium pivalate), a tertiary amine (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), an aromatic amine (e.g., pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), a hydroxide base (e.g., sodium hydroxide, lithium hydroxide, potassium hydroxide, and ammonium hydroxide), or lithium bis(trimethylsilyl)amide; (iii) the solvent comprises an alcohol (e.g., methanol, ethanol, tert-amyl alcohol, isopropanol, and tert-butanol), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a combination thereof, and/or (iv) the temperature is from about 20° C. to about 120° C.

In some embodiments for step (2e), the palladium catalyst comprises chloro[(4,5-bis(diphenylphosphino)-9,9-dimethylxanthene)-2-(2'-amino-1,1'-biphenyl)]palladium(II) (XantPhos Pd G2). In some embodiments for step (2e), the base comprises potassium tert-butoxide. In some embodiments for step (2e), the solvent comprises tetrahydrofuran and toluene. In some embodiments for step (2e), the temperature is from about 60° C. to about 75° C. In some embodiments for step (2e), the temperature is from about 20° C. to about 120° C. In some embodiments, the temperature is about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C.

In some embodiments for step (2e): (i) the copper catalyst comprises a copper(II) acetate, copper(I) chloride, copper(I) bromide, copper(I) bromide dimethyl sulfide complex, copper(I) triflate toluene complex, copper(I) iodide, copper(I) iodide tetrabutylammonium iodide complex, tetrakis(acetonitrile)copper(I) hexafluorophosphate, copper(I) iodide triethylphosphite complex, copper(I) bromide triphenylphosphine complex, copper(I) oxide, or copper(II) oxide; (ii) the copper catalyst ligand comprises a diamine (e.g., N,N'-dimethylethane-1,2-diamine, and trans-N,N'-dimethyl-cyclohexane-1,2-diamine), a diol (e.g., ethan-1,2-diol, and propane-1,3-diol), a diketone (e.g., 2-acetylcyclohexanone, and acetoacetonate,2,2,6,6-tetramethylheptane-3,5-dione), a glycine derivative (e.g., N-methylglycine, and N,N-dimethylglycine), ethyl 2-oxocyclohexanecarboxylate, ethylene glycol, pyridine, 2,2'-bipyridine, 1,10-phenanthroline, neocuproine, 8-hydroxyquinoline, picolinic acid, glyoxal bis(phenylhydrazone), 2,6-dimethylanilino(oxo)acetic acid, 2,6-difluoroanilino(oxo)acetic acid, 2,6-dimethyloxyaniliono(oxo)acetic acid, 2,3,4,5,6-pentafluoroanilino(oxo) acetic acid, 3,5-bis(trifluoromethyl)anilino(oxo)acetic acid, 2-fluoro-6-(piperidine-1-sulfonyl)anilino(oxo)acetic acid, N1,N2-di([1,1'-biphenyl]-2-yl)oxalamide, N1,N2-bis(2-phenoxyphenyl)oxalamide, or thiophene-2-carboxylic acid; (iii) the base comprises an alkoxide base (e.g, sodium tert-butoxide, lithium tert-butoxide, potassium tert-pentoxide, sodium tert-pentoxide, potassium propionate, and potassium pivalate), a tertiary amine (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), an aromatic amine (pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), a hydroxide base (e.g., sodium hydroxide, lithium hydroxide, potassium hydroxide, and ammonium hydroxide), or lithium bis(trimethylsilyl) amide; (iv) the solvent comprises an alcohol (e.g., tert-amyl alcohol, isopropanol, and tert-butanol), an ether (e.g., diethyl ether, 1,4-dioxane, 2-methyltetrahydrofuran, dimethoxyethane, methyl tert-butyl ether, cyclopentyl methyl ether, diphenyl ether, dibutyl ether, and 1,4-dioxane), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a combination thereof; and/or (v) the temperature is from about 0° C. to about 140° C.

In some embodiments for step (2e), the copper catalyst comprises Copper(I) iodide. In some embodiments for step (2e), the copper catalyst ligand comprises 2,6-dimethylanilino(oxo)acetic acid (DMPAO). In some embodiments for step (2e), the base comprises potassium phosphate tribasic. In some embodiments for step (2e), the solvent comprises N-methyl-2-pyrrolidinone. In some embodiments for step (2e), the temperature is from about 100° C. to about 120° C. In some embodiments for step (2e), the temperature is from about 0° C. to about 140° C. In some embodiments, the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., or about 140° C.

Synthesis of Compound 2A

In a non-limiting example, Scheme 5 is a scheme depicting one embodiment of the synthesis of Compound 2A via Compound 2M for Manufacturing Route 2.

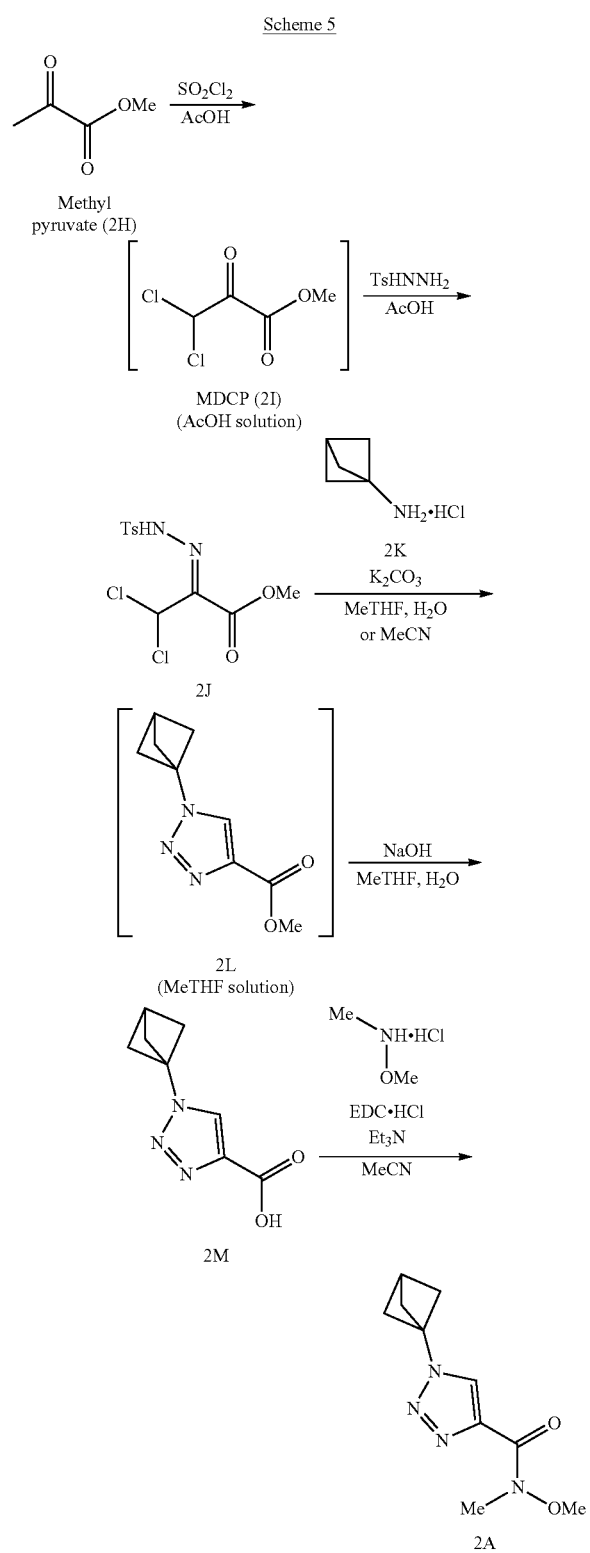

In some embodiments, Compound 2A is prepared from a process comprising: (2f) contacting Compound 2H with a chlorinating agent, optionally an amine catalyst, and optionally an acidic additive in a solvent at a temperature sufficient to provide Compound 2I; (2g) contacting Compound 2I with TsHNNH$_2$ in a solvent at a temperature sufficient to provide Compound 2J; (2h) contacting Compound 2J with Compound 2K in the presence of a base in a solvent at a temperature sufficient to provide Compound 2L; (2i) contacting Compound 2L with a base in a solvent at a temperature sufficient to provide Compound 2M; and (2j) contacting Compound 2M with MeNHOMe·HCl, a coupling agent, and a base in a solvent at a temperature sufficient to provide Compound 2A.

In some embodiments for step (2f): (i) the chlorinating agent comprises sulfuryl chloride, chlorine gas, or a source of electrophilic chlorine (e.g., acetyl chloride/ceric ammonium nitrate, lithium diisopropylamide/4-toluenesulfonyl chloride, iodosobenzene dichloride, trichloromethanesulfonyl chloride, 1,3-dichloro-5,5-dimethylhydantoin/ammonium chloride, tetrachlorosilane/urea-hydrogen peroxide, N-chlorosuccinimide, trichloroisocyanuric acid, and 3,5-dichloro-2-hydroxy-4,6-s-triazinedione sodium salt); (ii) the amine catalyst, if present, comprises a pyrrolidine type organocatalyst (e.g., L-proline amide, and (2R,5R)-diphenylpyrrolidine); (iii) the acidic additive, if present, comprises a Brønsted Acid (e.g., methanesulfonic acid, p-toluenesulfonic acid, and hydrochloric acid); (iv) the solvent comprises a carboxylic acid (e.g., acetic acid, trifluoroacetic acid, and propionic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, and tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (v) the temperature is from about 30° C. to about 70° C.

In some embodiments for step (2f), the chlorinating agent comprises sulfuryl chloride. In some embodiments for step (2f), the amine catalyst is absent. In some embodiments for step (2f), the acidic additive is absent. In some embodiments for step (2f), the solvent comprises acetic acid. In some embodiments for step (2f), the temperature is from about 35° C. to about 50° C. In some embodiments for step (2f), the temperature is from about 30° C. to about 70° C. In some embodiments for step (2f), the temperature is about 30° C., about 35° C., about 40° C., about 45° C., about 50° C., about 55° C., about 60° C., about 65° C., or about 70° C.

In some embodiments for step (2g): (i) the solvent comprises a carboxylic acid (e.g., acetic acid, trifluoroacetic acid, and propionic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (ii) the temperature is from about 30° C. to about 70° C.

In some embodiments for step (2g), the solvent comprises acetic acid. In some embodiments for step (2g), the temperature is from about 35° C. to about 50° C. In some embodiments for step (2g), the temperature is from about 30° C. to about 70° C. In some embodiments for step (2g), the temperature is about 30° C., about 35° C., about 40° C., about 45° C., about 50° C., about 55° C., about 60° C., about 65° C., or about 70° C.

In some embodiments for step (2h): (i) the base comprises a tertiary amine base (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), a hydroxide base (e.g., lithium hydroxide, potassium hydroxide, and sodium hydroxide), a carbonate base (e.g., potassium carbonate, sodium carbonate, and cesium carbonate), a bicarbonate base (e.g., sodium bicarbonate, and potassium bicarbonate), a tetraalkylammonium hydroxide (e.g., tetrabutylammonium hydroxide, benzyltrimethylammonium hydroxide, and choline hydroxide), an alkoxide base (e.g., sodium or potassium methoxide, and sodium or potassium ethoxide), or a phosphate base (e.g., sodium phosphate monobasic, sodium phosphate dibasic, potassium phosphate monobasic, and potassium phosphate dibasic); (ii) the solvent comprises water, a nitrile (e.g., acetonitrile, propionitrile, and butyronitrile), a hydrocarbon solvent (e.g., toluene, 2-methyltetrahydrofuran, trifluorotoluene, cyclohexane, n-heptane, and xylenes), a chlorinated solvent (e.g., dichloromethane, chloroform, dichloroethane, and chlorobenzene), an ether solvent (e.g., diethyl ether, 1,4-dioxane, tetrahydrofuran, dimethoxyethane, methyl tert-butyl ether, cyclopentyl methyl ether, diphenyl ether, and dibutyl ether), an alcohol solvent (e.g., methanol, ethanol, isopropanol, and tert-butanol), or a combination thereof, and/or (iii) the temperature is from –20° C. to about 60° C.

In some embodiments for step (2h), the base comprises potassium carbonate. In some embodiments for step (2h), the solvent comprises 2-methyltetrahydrofuran and water, or acetonitrile. In some embodiments for step (2h), the temperature is from about –20° C. to about 20° C. In some embodiments for step (2h), the temperature is from about –20° C. to about 60° C. In some embodiments for step (2h), the temperature is about –20° C., about –15° C., about –10° C., about –5° C., about 0° C., about 5° C., about 10° C., about 15° C., about 20° C., about 25° C., about 30° C., about 35° C., about 40° C., about 45° C., about 50° C., about 55° C., or about 60° C.

In some embodiments wherein for step (2i): (i) the base comprises a hydroxide base (e.g., sodium hydroxide, lithium hydroxide, and potassium hydroxide); (ii) the solvent comprises water, a nitrile solvent (e.g., acetonitrile, propionitrile, and butyronitrile), a hydrocarbon solvent (e.g., toluene, trifluorotoluene, cyclohexane, n-heptane, and xylenes), a chlorinated solvent (e.g., dichloromethane, chloroform, dichloroethane, and chlorobenzene), an ether solvent (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an alcohol solvent (e.g., methanol, ethanol, isopropanol, and tert-butanol), or a combination thereof, and/or (iii) the temperature is from about –10° C. to about 80° C.

In some embodiments wherein for step (2i), the base comprises sodium hydroxide. In some embodiments wherein for step (2i), the solvent comprises 2-methyltetrahydrofuran and water. In some embodiments for step (2i), the temperature is from about 15° C. to about 25° C. In some embodiments wherein for step (2i), the temperature is about 20° C. In some embodiments wherein for step (2i), the temperature is from about −10° C. to about 80° C. In some embodiments wherein for step (2i), the temperature is about about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., or about 80° C.

In some embodiments wherein for step (2j): (i) the coupling agent comprises a peptide coupling agent (e.g., 1-(3-Dimethylaminopropyl)-3-ethylcarbodiimide hydrochloride (EDC HCl), carbonyl diimidazole, oxalyl chloride, thionyl chloride, dicyclohexylcarbodiimide, diisopropylcarbodiimide, isobutyl chloroformate, 1-[Bis(dimethylamino)methylene]-1H-1,2,3-triazolo[4,5-b]pyridinium 3-oxid hexafluorophosphate, N,N,N',N'-Tetramethyl-O-(1H-benzotriazol-1-yl)uronium hexafluorophosphate, (Benzotriazol-1-yloxy)tris(dimethylamino)phosphonium hexafluorophosphate, (Benzotriazol-1-yloxy)tripyrrolidinophosphonium hexafluorophosphate, tri-n-propylphosphonic anhydride, and 2-chloro-4,6-dimethoxy-1,3,5-triazine); (ii) the base comprises a tertiary amine (e.g., N-methylmorpholine, triethylamine, tri-n-propylamine, N,N-diisopropylethylamine, tri-n-butylamine, 1,8-diazabicyclo[5.4.0]undec-7-ene, and 1,4-diazabicyclo[2.2.2]octane), or an aromatic amine (e.g., pyridine, 2,6-lutidine, and collidine); (iii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a hydrocarbon solvent (e.g., benzene, toluene, trifluorotoluene, cyclohexane, n-heptane, and xylenes), a polar aprotic solvent (e.g., N,N-dimethylformamide, N,N-dimethylacetamide, N-methyl-2-pyrrolidinone, and dimethyl sulfoxide), a chlorinated solvent (e.g., dichloromethane, chloroform, dichloroethane, and chlorobenzene), or nitrile (e.g., acetonitrile propionitrile, and butyronitrile); and/or (iv) the temperature is from about −20° C. to about 120° C.

In some embodiments wherein for step (2j), the coupling agent comprises 1-(3-dimethylaminopropyl)-3-ethylcarbodiimide hydrochloride (EDC HCl). In some embodiments wherein for step (2j), the base comprises triethylamine. In some embodiments wherein for step (2j), the solvent comprises acetonitrile. In some embodiments wherein for step (2j), the temperature is from about 0° C. to about 20° C. In some embodiments wherein for step (2j), the temperature is from about −20° C. to about 120° C. In some embodiments wherein for step (2j), the temperature is about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C.

Synthesis of Compound 2B

In a non-limiting example, Scheme 6 is a scheme depicting one embodiment of the synthesis of Compound 2B for Manufacturing Route 2.

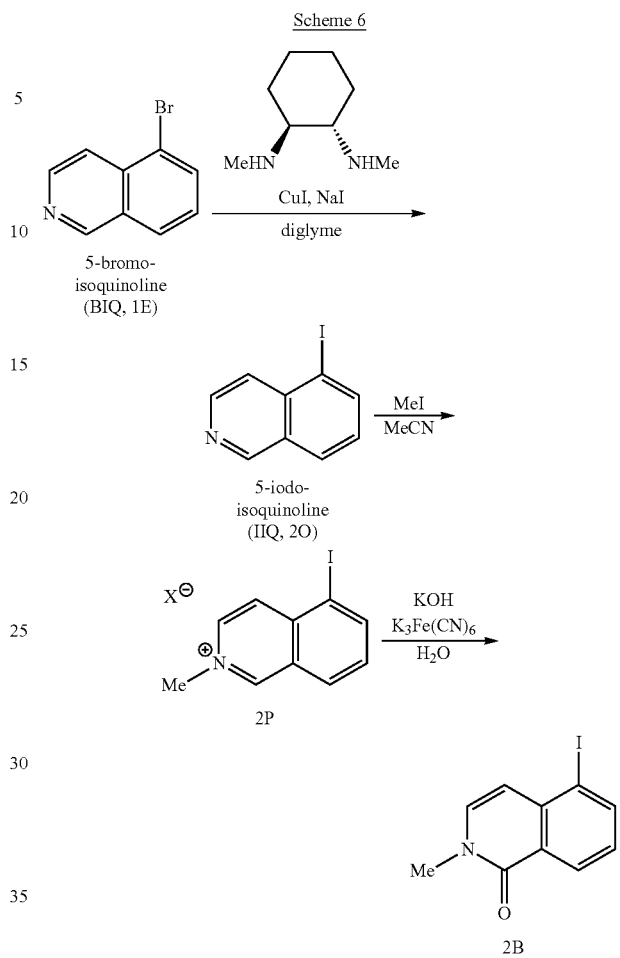

Scheme 6

In some embodiments, Compound 2B is prepared from a process comprising: (2k) contacting Compound 1E with a copper catalyst, an amine ligand, and an iodide additive in a solvent at a temperature sufficient to provide Compound 2O; (2l) contacting Compound 2O with an alkylating agent in a solvent at a temperature sufficient to provide Compound 2P, wherein X is iodide, chloride, bromide, methylsulfate, sulfate, methylcarbonate, carbonate, methanesulfonate, trifluoromethanesulfonate, toluenesulfonate, or tetrafluoroborate; (2m) contacting Compound 2P with an oxidant and a base in a solvent at a temperature sufficient to provide Compound 2B.

In some embodiments for step (2k): (i) the copper catalyst comprises copper(I) iodide, copper(I) bromide, copper(I) chloride, copper(I) oxide, copper(I) acetate, copper(I) bromide dimethyl sulfide complex, copper(I) triflate, copper(I) iodide tetrabutylammonium iodide complex, tetrakis(acetonitrile)copper(I) hexafluorophosphate, copper(I) iodide triethylphosphite complex, or copper(I) bromide triphenylphosphine complex; (ii) the amine ligand comprises trans-N,N'-dimethylcyclohexane-1,2-diamine, N1,N2-dimethylethane-1,2-diamine, N1,N3-dimethylpropane-1,3-diamine, or N1-(2-aminoethyl)ethane-1,2-diamine; (iii) the iodide additive comprises sodium iodide, lithium iodide, or potassium iodide; (iv) the solvent comprises an ether (e.g., diethylene glycol dimethylether, diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (v) the temperature is from about 50° C. to about 150° C.

In some embodiments for step (2k), the copper catalyst comprises copper(I) iodide. In some embodiments for step (2k), the amine ligand comprises trans-N,N'-dimethylcyclohexane-1,2-diamine. In some embodiments for step (2k), the iodide additive comprises sodium iodide. In some embodiments for step (2k), the solvent comprises diethylene glycol dimethylether. In some embodiments for step (2k), the temperature is from about 80° C. to about 130° C. In some embodiments for step (2k), the temperature is from about 50° C. to about 150° C. In some embodiments for step (2k), the temperature is about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about 150° C.

In some embodiments for step (2l): (i) the alkylating agent comprises iodomethane, trimethylsulfoxonium iodide, diazomethane, dimethylsulfate, 2,2-dimethoxypropane, a carbonate (e.g., dimethylcarbonate, and dimethyldicarbonate), a sulfonate (e.g., methyl fluorosulfonate, and methyl methanesulfonate), chloromethane, bromomethane, or trimethyloxonium tetrafluoroborate; (ii) the solvent comprises an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a chlorinated solvent (e.g., dichloromethane, chloroform, dichloroethane, and chlorobenzene); and/or (iii) the temperature is from about 0° C. to about 100° C.

In some embodiments for step (2l), the alkylating agent comprises iodomethane. In some embodiments for step (2l), the solvent comprises acetonitrile. In some embodiments for step (2l), the temperature is from about 20° C. to about 40° C. In some embodiments for step (2l), the temperature is from about 0° C. to about 100° C. In some embodiments for step (2l), the temperature is about 30° C. In some embodiments for step (2l), the temperature is about 0° C., about 5° C., about 10° C., about 15° C., about 20° C., about 25° C., about 30° C., about 35° C., about 40° C., about 45° C., about 50° C., about 55° C., around 60° C., about 65° C., about 70° C., about 75° C., about 80° C., about 85° C., about 90° C., about 95° C., or about 100° C. In some embodiments for step (2l), X is iodide.

In some embodiments for step (2m): (i) the oxidant comprises potassium ferricyanide, oxone, lead tetraacetate, peracetic acid, hydrogen peroxide, molecular oxygen, air, sodium hypochlorite, sodium chlorite, sodium periodate, potassium peroxymonosulfate, 2,3-dichloro-5,6-dicyano-1,4-benzoquinone, 1,4-benzoquinone, periodic acid, potassium bromate, meta-chloroperoxybenzoic acid, or magnesium monoperoxypthalate; (ii) the base comprises a hydroxide base (e.g., lithium hydroxide, potassium hydroxide, and ammonium hydroxide); (iii) the solvent comprises water, an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (iv) the temperature is from about 0° C. to about 70° C.

In some embodiments for step (2m), the oxidant comprises potassium ferricyanide. In some embodiments for step (2m), the base comprises potassium hydroxide. In some embodiments for step (2m), the solvent comprises water. In some embodiments for step (2m), the temperature is from about 5° C. to about 20° C. In some embodiments for step (2m), the temperature is from about 0° C. to about 70° C. In some embodiments for step (2m), the temperature is from about 0° C., about 5° C., about 10° C., about 15° C., about 20° C., about 25° C., about 30° C., about 35° C., about 40° C., about 45° C., about 50° C., about 55° C., about 60° C., about 65° C., or about 70° C.

Synthesis of Compound 2G

In a non-limiting example, Scheme 7 is a scheme depicting one embodiment of the synthesis of Compound 1B via Compound 2G for Manufacturing Route 2.

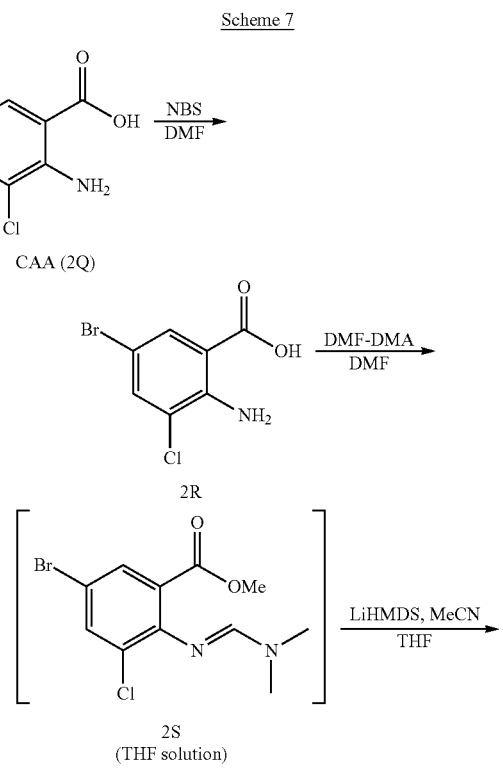

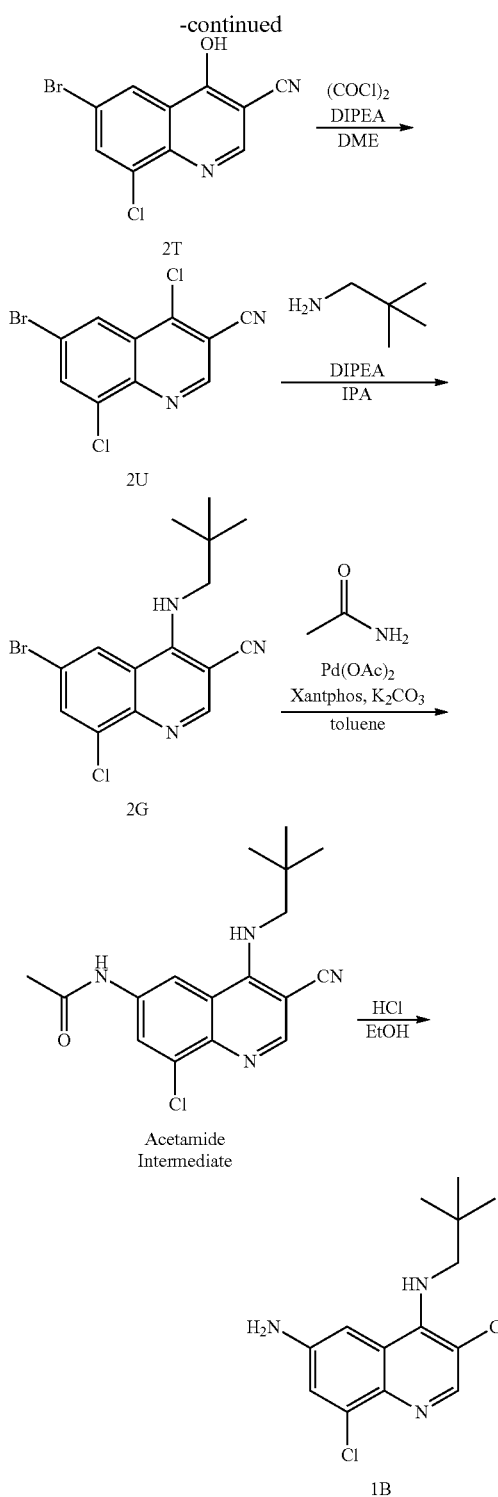

In some embodiments, Compound 2G is prepared from a process comprising: (2n) contacting Compound 2Q with a brominating agent in a solvent at a temperature sufficient to provide Compound 2R; (2o) contacting Compound 2R with a formamide-based reagent in a solvent at a temperature sufficient to provide Compound 2S; (2p) contacting Compound 2S with optionally, a nitrile reagent and a base in a solvent at a temperature sufficient to provide Compound 2T; (2q) contacting Compound 2T with a chlorinating reagent and a base in a solvent at a temperature sufficient to provide Compound 2U; and (2r) contacting Compound 2U with 2,2-dimethylpropan-1-amine and a base in a solvent at a temperature sufficient to provide Compound 2G.

In some embodiments for step (2n), (i) the brominating agent comprises N-bromosuccinimide, 1,3-dibromo-5,5-dimethylhydantoin, pyridinium tribromide, or bromine; (ii) the solvent comprises a polar aprotic solvent (e.g., N,N-dimethylformamide, N,N-dimethylacetamide, N-methyl-2-pyrrolidinone, and dimethyl sulfoxide), or a chlorinated solvent (e.g., dichloromethane, chloroform, dichloroethane, and chlorobenzene); and/or (iii) the temperature is from about 0° C. to about 40° C.

In some embodiments for step (2n), the brominating agent comprises N-bromosuccinimide. In some embodiments for step (2n), the solvent comprises N,N-dimethylformamide. In some embodiments for step (2n), the temperature is from about 15° C. to about 25° C. In some embodiments for step (2n), the temperature is about 20° C. In some embodiments for step (2n), the temperature is the temperature is from about 0° C. to about 40° C. In some embodiments for step (2n), the temperature is the temperature is about 0° C., about 5° C., about 10° C., about 15° C., about 20° C., about 25° C., about 30° C., about 35° C., or about 40° C.

In some embodiments for step (2o): (i) the formamide-based reagent comprises N,N-dimethylformamide dimethyl acetal, N,N-dimethylformamide diethyl acetal, or N,N-dimethylformamide diisopropyl acetal; (ii) the solvent comprises a polar aprotic solvent (e.g., N,N-dimethylformamide N,N-dimethylacetamide, N-methyl-2-pyrrolidinone, and dimethyl sulfoxide), N,N-dimethylformamide dimethyl acetal, N,N-dimethylformamide diethyl acetal, or N,N-dimethylformamide diisopropyl acetal; and/or (iii) the temperature is from about 20° C. to about 150° C.

In some embodiments for step (2o), the formamide-based reagent comprises N,N-dimethylformamide dimethyl acetal. In some embodiments for step (2o), the solvent comprises N,N-dimethylformamide. In some embodiments for step (2o), the temperature is from about 100° C. to about 120° C. In some embodiments for step (2o), the temperature is about 110° C. In some embodiments for step (2o), the temperature is from about 20° C. to about 150° C. In some embodiments for step (2o), the temperature is about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about 150° C.

In some embodiments for step (2p): (i) the nitrile reagent, if present, comprises acetonitrile; (ii) the base comprises an organolithium reagent (e.g., phenyllithium, mesityllithium, tert-butyllithium, and sec-butyllithium), a Grignard (e.g., isopropylmagnesium chloride, isopropylmagnesium bromide, isopropylmagnesium chloride lithium chloride complex, phenylmagnesium chloride, sec-butylmagnesium chloride, and 2,2,6,6-tetramethylpiperidinylmagnesium chloride lithium chloride complex), an alkoxide base (e.g., potassium tert-butoxide, and potassium tert-amylate), or an amide base (e.g., lithium diisopropylamide, potassium bis(trimethylsilyl)amide, sodium bis(trimethylsilyl)amide, and lithium bis(trimethylsilyl)amide); (iii) the solvent comprises an ether (e.g., tetrahydrofuran, diethyl ether, 1,4-dioxane, 2-methyltetrahydrofuran, dimethoxyethane, methyl tert-butyl ether, cyclopentyl methyl ether, diphenyl ether, and dibutyl ether); and/or (iv) the temperature is from about −80° C. to about 40° C.

In some embodiments for step (2p), the nitrile reagent, if present, comprises acetonitrile. In some embodiments for step (2p), the base comprises lithium bis(trimethylsilyl) amide. In some embodiments for step (2p), the solvent comprises tetrahydrofuran. In some embodiments for step (2p), the temperature is from about −10° C. to about 0° C. In some embodiments for step (2p), the temperature is from about −80° C. to about 40° C. In some embodiments for step (2p), the temperature is from about −80° C., about −75° C., about −70° C., about −65° C., about −60° C., about −55° C., about −50° C., about −45° C., about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., or about 40° C.

In some embodiments for step (2q): (i) the chlorinating reagent comprises oxalyl chloride, phosphorus oxychloride, thionyl chloride, sulfuryl chloride, phosgene, triphosgene, methanesulfonyl chloride, or cyanuric chloride; (ii) the base comprises an amine base (e.g., N,N-Diisopropylethylamine 1-methylimidazole, N-methylmorpholine, tri-n-propylamine, triethylamine, tri-n-butylamine, 1,8-diazabicyclo[5.4.0] undec-7-ene, and 1,4-diazabicyclo[2.2.2]octane), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), or an aromatic amine (e.g., pyridine, 2,6-lutidine, and collidine); (iii) the solvent comprises an ether (e.g., 1,2-dimethoxyethane, diethyl ether, 1,4-dioxane, tetrahydrofuran, 2-methyltetrahydrofuran, methyl tert-butyl ether, cyclopentyl methyl ether, diphenyl ether, and dibutyl ether), an ester solvent (e.g., ethyl acetate, isopropyl acetate, n-propyl acetate, and isobutyl acetate), a hydrocarbon (e.g., toluene, trifluorotoluene, cyclohexane, n-heptane, and xylenes), a chlorinated solvent (e.g., dichloromethane, chloroform, dichloroethane, and chlorobenzene), or a polar aprotic solvent (e.g., N,N-dimethylformamide); and/or (iv) the temperature is from about 20° C. to about 80° C.

In some embodiments for step (2q), the chlorinating reagent comprises oxalyl chloride. In some embodiments for step (2q), the base comprises N,N-Diisopropylethylamine. In some embodiments for step (2q), the solvent comprises 1,2-dimethoxyethane. In some embodiments for step (2q), the temperature is from about 55° C. to about 65° C. In some embodiments for step (2q), the temperature is about 60° C. In some embodiments for step (2q), the temperature is from about 20° C. to about 80° C. In some embodiments for step (2q), the temperature is about 20° C., about 25° C., about 30° C., about 35° C., about 40° C., about 45° C., about 50° C., about 55° C., about 60° C., about 65° C., about 70° C., about 75° C., or about 80° C.

In some embodiments for step (2r): (i) the base comprises an amine base (e.g., N,N-Diisopropylethylamine, 1-methylimidazole, N-methylmorpholine, tri-n-propylamine, triethylamine, tri-n-butylamine, 1,8-diazabicyclo[5.4.0]undec-7-ene, and 1,4-diazabicyclo[2.2.2]octane), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), or an aromatic amine (e.g., pyridine, 2,6-lutidine, and collidine); (ii) the solvent comprises an alcohol (e.g., methanol, ethanol, tert-butanol, sec-butanol, and isopropanol), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), a hydrocarbon (e.g., toluene, trifluorotoluene, cyclohexane, n-heptane, and xylenes), a polar aprotic solvent (e.g., N,N-dimethylformamide, N,N-dimethylacetamide, N-methyl-2-pyrrolidinone, and dimethyl sulfoxide), or a nitrile (e.g., acetonitrile, propionitrile, and butyronitrile); and/or (iii) the temperature is from about 20° C. to about 100° C.

In some embodiments for step (2r), the base comprises N,N-Diisopropylethylamine. In some embodiments for step (2r), the solvent comprises isopropanol. In some embodiments for step (2r), the temperature is from about 70° C. to about 80° C. In some embodiments for step (2r), the temperature is about 75° C. In some embodiments for step (2r), the temperature is from about 20° C. to about 100° C. In some embodiments for step (2r), the temperature is about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

In some embodiments, Compound 1B is prepared from a process comprising: (2s) contacting Compound 2G with acetamide, a palladium catalyst or copper catalyst, a palladium catalyst or copper catalyst ligand, and a base in a solvent at a temperature sufficient to provide Acetamide Intermediate; and (2t) contacting Acetamide Intermediate with a reagent in a solvent at a temperature sufficient to provide Compound 2G.

In some embodiments for step (2s): (i) the palladium catalyst or copper catalyst comprises a copper source (e.g., copper(I) iodide, copper(I) bromide, and copper(I) chloride), or a palladium source (e.g., palladium(II) acetate, palladium (II) chloride, palladium(II) bromide, palladium(II) bis(triphenylphosphine) dichloride, allylpalladium(II) chloride, and tetrakis(triphenylphosphine)palladium(0)); (ii) the palladium catalyst or copper catalyst ligand comprises 1,2-dimethylethylenediamine, 1,2-transcyclohexanediamide, or an amino acid for a copper catalyst or a phosphine ligand (e.g., 4,5-bis(diphenylphosphino)-9,9-dimethylxanthene (Xantphos)) for a palladium catalyst (iii) the base comprises a tertiary amine (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), an aromatic amine (e.g., pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium phosphate monobasic, potassium phosphate dibasic, potassium phosphate tribasic, potassium acetate, potassium fluoride, lithium carbonate, lithium acetate, cesium carbonate, and potassium carbonate), or an alkoxide base (e.g., sodium methoxide, sodium ethoxide, sodium isopropoxide, sodium tert-amylate, and sodium tert-butoxide); (iv) the solvent comprises a hydrocarbon solvent (e.g., toluene, trifluorotoluene, cyclohexane, n-heptane, xylenes, and benzene), a polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, butyronitrile, and benzonitrile), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether); and/or (iv) the temperature is from about about 20° C. to about 100° C.

In some embodiments for step (2s), the palladium catalyst or copper catalyst comprises palladium(II) acetate. In some embodiments for step (2s), the palladium catalyst or copper catalyst ligand comprises 4,5-bis(diphenylphosphino)-9,9-dimethylxanthene (Xantphos)). In some embodiments for step (2s), the base comprises potassium carbonate. In some embodiments for step (2s), the temperature is from about about 80° C. In some embodiments for step (2s), the temperature is from about 20° C. to about 100° C. In some embodiments for step (2s), the temperature is about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

In some embodiments for step (2t): (i) the reagent comprises an acid (e.g., hydrochloric acid, hydrobromic acid, sulfuric acid, phosphoric acid, methanesulfonic acid, benzenesulfonic acid, para-toluenesulfonic acid, and trifluoroacetic acid), or a base (e.g., sodium hydroxide, potassium hydroxide, lithium hydroxide, and ammonium hydroxide); (ii) the solvent comprises an alcohol (e.g., methanol, ethanol, isopropanol, tert-butanol, 1-butanol, and 2-butanol), or water; and/or (iii) the temperature is from about about 50° C. to about 100° C.

In some embodiments for step (2t), the reagent comprises hydrochloric acid. In some embodiments for step (2t), the solvent comprises ethanol. In some embodiments for step (2t), the temperature is from about about 60° C. to about 75° C. In some embodiments for step (2t), the temperature is from about about 50° C. to about 100° C. In some embodiments for step (2t), the temperature is about 50° C., about 55° C., about 60° C., about 65° C., about 70° C., about 75° C., about 80° C., about 85° C., about 90° C., about 95° C., or about 100° C.

Compound 1 Manufacturing Route 3

In a non-limiting example, Scheme 8 is a scheme depicting one embodiment of the alternate synthesis of Compound 2F for Manufacturing Route 3. In a non-limiting example, Schemes 8, 5, 6, and 7 depict one embodiment of a synthesis of Compound 1.

Scheme 8

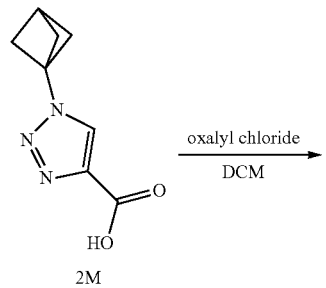
2M

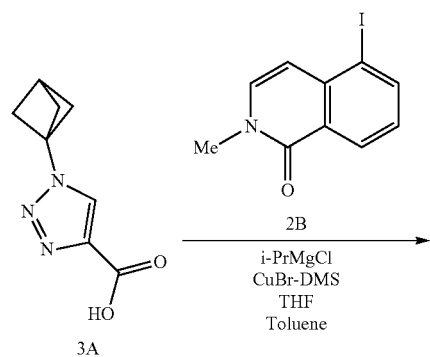
3A

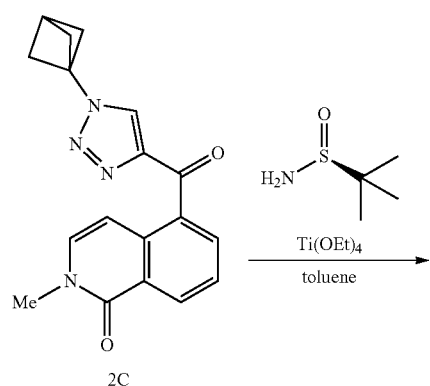
2C

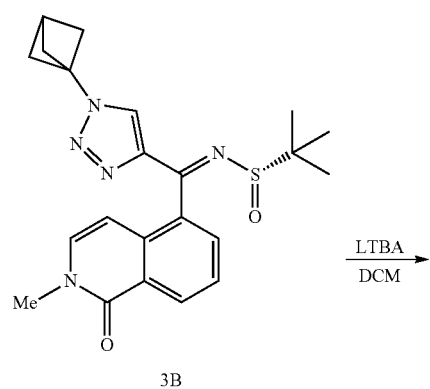
3B

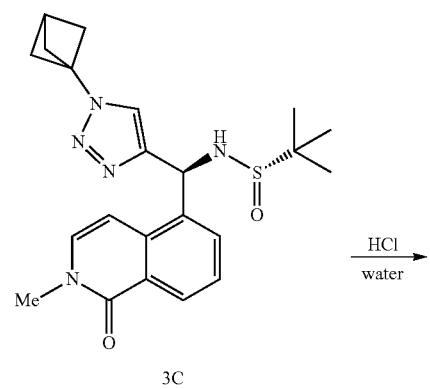
3C

-continued

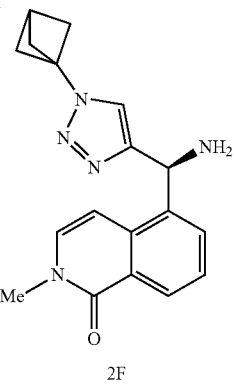

2F

One method for the synthesis of Compound 1 is a process comprising (3a) contacting Compound 2M with a chlorinating reagent and an additive in a solvent at a temperature sufficient to provide Compound 3A; (3b) contacting Compound 3A with Compound 2B in the presence of an organometallic reagent, then followed by the addition of a copper or palladium catalyst, optionally, a zinc additive, and optionally, a Lewis base in a solvent at a temperature sufficient to provide Compound 2C; (3c) contacting Compound 2C with

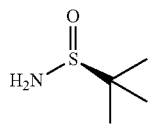

in the presence of a titanium-based or zirconium-based reagent in a solvent at a temperature sufficient to provide Compound 3B; (3d) contacting Compound 3B with a reducing agent, and optionally a ruthenium, palladium, or platinum catalyst in a solvent at a temperature sufficient to provide Compound 3C; (3e) contacting Compound 3C with an acid in a solvent at a temperature sufficient to provide Compound 2F; and (3f) contacting Compound 2F with Compound 2G in the presence of a palladium catalyst and a base in a solvent at a temperature sufficient to provide Compound 1.

One method for the synthesis of Compound 1 is a process comprising (3a) contacting Compound 2M with a chlorinating reagent and an additive in a solvent at a temperature sufficient to provide Compound 3A; (3b) contacting Compound 3A with Compound 2B in the presence of an organometallic reagent, then followed by the addition of a copper or palladium catalyst, optionally, a zinc additive, and optionally, a Lewis base in a solvent at a temperature sufficient to provide Compound 2C; (3c) contacting Compound 2C with

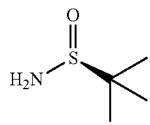

in the presence of a titanium-based or zirconium-based reagent in a solvent at a temperature sufficient to provide Compound 3B; (3d) contacting Compound 3B with a reducing agent, and optionally a ruthenium, palladium, or platinum catalyst in a solvent at a temperature sufficient to provide Compound 3C; (3e) contacting Compound 3C with an acid in a solvent at a temperature sufficient to provide Compound 2F; and (3f) contacting Compound 2F with Compound 2G in the presence of a copper catalyst, a copper catalyst ligand, and a base in a solvent at a temperature sufficient to provide Compound 1.

In some embodiments for step (3a): (i) the chlorinating reagent comprises oxalyl chloride, thionyl chloride, cyanuric chloride, or phosphorus oxychloride; (iii) the solvent comprises a hydrocarbon solvent (e.g., toluene, trifluorotoluene, cyclohexane, n-heptane, xylenes, and benzene), a chlorinated solvent (e.g., dichloromethane, chloroform, dichloroethane, and chlorobenzene), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), or a polar aprotic solvent (e.g., N,N-dimethylformamide); and/or (iv) the temperature is from about 0° C. to about 100° C.

In some embodiments for step (3a), the chlorinating agent comprises oxalyl chloride. In some embodiments for step (3a), the solvent comprises dichloromethane or toluene. In some embodiments for step (3a), the solvent comprises dichloromethane. In some embodiments for step (3a), the solvent comprises toluene. In some embodiments for step (3a), the temperature is from about 10° C. to about 30° C. In some embodiments for step (3a), the temperature is from about 0° C. to about 100° C. In some embodiments for step (3a), the temperature is from about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C. In some embodiments for step (3a), the additive comprises N,N-dimethylformamide.

In some embodiments for step (3b): (i) the organometallic reagent comprises isopropylmagnesium chloride, cyclohexylmagnesium chloride, butylmagnesium chloride, tert-butylmagnesium chloride, isopropylmagnesium chloride lithium chloride complex, sec-butylmagnesium chloride lithium chloride complex, or isopropylmagnesium bromide, ethylmagnesium bromide; (ii) the copper or palladium catalyst comprises a copper catalyst (e.g., copper(I) bromide dimethyl sulfide complex, copper(I) iodide, copper(I) bromide, copper(I) chloride, copper(I) cyanide di(lithium chloride) complex, bromotris(triphenylphosphine) copper(I), copper (I) trifluoromethanesulfonate toluene complex, copper(I) chloride bis(lithium chloride) complex, copper(I) bromide bis(lithium bromide) complex, copper(I) thiocyanate, copper(I) thiophene-2-carboxylate, copper(I) thiophenolate, copper(I) diphenylphosphinate, (1,10-phenanthroline)bis (triphenylphosphine)copper(I) nitrate DCM adduct, copper (I) 3-methylsalicylate, chloro[1,3-bis(2,6-diisopropylphenyl)imidazol-2-ylidene] copper(I), chloro(1,5-cyclooctadiene)copper(I) dimer, copper(II) chloride, copper (II) bromide, and copper(II) acetate), or a palladium(0) precatalyst (e.g., tetrakis(triphenylphosphine)palladium(0), and bis(dibenzylideneacetone)palladium(0)); (iii) the zinc additive, if present, comprises zinc chloride or zinc bromide; (iv) the Lewis base, if present, comprises NN-Dimethylpropyleneurea, hexamethylphosphoramide, 2,6-lutidine, pyridine, diglyme, N-methylmorpholine, diisopropylethylamine, dimethoxyethane, or lithium chloride; (v) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, and diglyme), a hydrocarbon solvent (e.g., n-hexane, toluene, trifluorotoluene, cyclohexane, n-heptane, and xylenes), or a chlorinated solvent (e.g., dichloromethane, chloroform, dichloroethane, and chlorobenzene); and/or (vi) the temperature is from about −80° C. to about 60° C.

In some embodiments for step (3b), the organometallic reagent comprises isopropylmagnesium chloride. In some embodiments for step (3b), the copper or palladium catalyst comprises copper(I) bromide dimethyl sulfide complex. In some embodiments for step (3b), the zinc additive is absent. In some embodiments for step (3b), the Lewis base is absent. In some embodiments for step (3b), the solvent comprises tetrahydrofuran and toluene. In some embodiments for step (3b), the temperature is from about −20° C. to about 0° C. In some embodiments for step (3b), the temperature is from about −80° C. to about 60° C. In some embodiments for step (3b), the temperature is about −80° C., about −75° C., about −70° C., about −65° C., about −60° C., about −55° C., about −50° C., about −45° C., about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., or about 60° C.

In some embodiments for step (3c): (i) the titanium-based or the zirconium-based reagent comprises titanium(IV) ethoxide, titanium(IV) isopropoxide, titanium(IV) butoxide, zirconium(IV) tert-butoxide, or zirconium(IV) ethoxide; (ii) the solvent comprises a hydrocarbon solvent (e.g., toluene, trifluorotoluene, cyclohexane, n-heptane, and xylenes), a chlorinated solvent (e.g., dichloromethane, chloroform, dichloroethane, and chlorobenzene), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), a polar aprotic solvent (e.g., N,N-dimethylformamide, N,N-dimethylacetamide, N-methyl-2-pyrrolidinone, and dimethyl sulfoxide), or a nitrile (e.g., acetonitrile, propionitrile, and butyronitrile); and/or (iii) the temperature is from about 25° C. to about 110° C.

In some embodiments for step (3c), the titanium-based or the zirconium-based reagent comprises titanium(IV) ethoxide. In some embodiments for step (3c), the solvent comprises toluene. In some embodiments for step (3c), the temperature is from about 60° C. to about 75° C. In some embodiments for step (3c), the temperature is from about 25° C. to about 110° C. In some embodiments for step (3c), the temperature is from about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., or about 110° C.

In some embodiments for step (3d): (i) the reducing agent comprises lithium tri-tert-butoxyaluminum hydride, borane dimethylsulfide complex, $NaBH_4/I_2$, an amine·borane complex (e.g., Ammonia Borane, and Diethylphenylamine-borane), a borohydride reagent (e.g., sodium borohydride, lithium borohydride, potassium borohydride, lithium triethylborohydride, and potassium tri-sec-butylborohydride), an aluminum hydride reagent (e.g., Diisobutylaluminum hydride, Sodium bis(2-methoxyethoxy)aluminum hydride, and Lithium tris[(3-ethyl-3-pentyl)oxy]aluminohydride), hydrogen gas, formic acid/triethylamine, or 2-propanol; (ii) the ruthenium, palladium, or platinum catalyst, if present, comprises a Noyori Type Ru catalyst (e.g., RuCl(mesitylene)[(S,S)-Ts-DPEN], and RuCl(p-cymene)[(R,R)-Teth-Ts-DPEN]), or a heterogeneous hydrogenation catalyst (e.g., palladium on carbon, rhodium on alumina, and platinum on carbon); (iii) the solvent comprises an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a chlorinated solvent (e.g., dichloromethane, chloroform, dichloroethane, and chlorobenzene), an alcohol (e.g., methanol, ethanol, isopropanol, tert-butanol, and 1-propanol), a hydrocarbon solvent (e.g., toluene, trifluorotoluene, cyclohexane, n-heptane, and xylenes), or a nitrile (e.g., acetonitrile, propionitrile, and butyronitrile); and/or (iv) the temperature is from about −40° C. to about 100° C. In some embodiments, for step (3d), Compound 3C is produced in at least greater than about 50%, at least greater than about 60%, at least greater than about 70%, at least greater than about 80%, at least greater than about 90%, at least greater than about 95%, or at least greater than about 99% diastereomeric purity.

In some embodiments for step (3d), the reducing agent comprises lithium tri-tert-butoxyaluminum hydride. In some embodiments for step (3d), the ruthenium, palladium, or platinum catalyst is absent. In some embodiments for step (3d), the solvent comprises dichloromethane. In some embodiments for step (3d), the temperature is from about −20° C. to about 0° C. In some embodiments for step (3d), the temperature is from about −40° C. to about 100° C. In some embodiments for step (3d), the temperature is about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C. In some embodiments, for step (3d), Compound 3C is produced in at least greater than about 99% diastereomeric purity.

In some embodiments for step (3e): (i) the acid comprises hydrochloric acid, hydrobromic acid, sulfonic acid (e.g., methanesulfonic acid, p-toluenesulfonic acid, and benzenesulfonic acid), trifluoroacetic acid, phosphoric acid, formic acid, or oxalic acid; (ii) the solvent comprises water, an alcoholic solvent (e.g., methanol, ethanol, isopropanol, and tert-butanol), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or halogenated solvent (e.g., dichloromethane, chloroform, dichloroethane, chlorobenzene, and dibromoethane); and/or (iii) the temperature is from about 0° C. to about 70° C.

In some embodiments for step (3e), the acid comprises hydrochloric acid. In some embodiments for step (3e), the solvent comprises water. In some embodiments for step (3e), the temperature is from about 20° C. to about 50° C. In some embodiments for step (3e), the temperature is from about 0° C. to about 70° C. In some embodiments for step (3e), the temperature is about 0° C., about 5° C., about 10° C., about 15° C., about 20° C., about 25° C., about 30° C., about 35°

C., about 40° C., about 45° C., about 50° C., about 55° C., about 60° C., about 65° C., about 70° C.

In some embodiments for step (3f): (i) the palladium catalyst comprises a palladium(II) catalyst (e.g., XantPhos Pd G2, Pd(acac)$_2$, Pd(OAc)$_2$, Pd(hfac)$_2$, PdCl(allyl), PdCl$_2$, PdSO$_4$·2H$_2$O), palladium pre-catalysts (e.g., Pd(XantPhos)Cl$_2$, XantPhos Pd G3, N-XantPhos Pd G4, tBuXPhos Pd G3, tBuBrettPhos Pd G3, RockPhos Pd G3, JosiPhos-J009 Pd G3, AdBrettPhos Pd G3, and TrixiePhos Pd G3), or palladium(0) catalysts (e.g., Pd$_2$(dba)$_3$, and Pd(PPh$_3$)$_4$); (ii) the base comprises an alkoxide base (e.g., potassium tert-butoxide, sodium tert-butoxide, sodium methoxide, lithium tert-butoxide, potassium tert-pentoxide, sodium tert-pentoxide, potassium propionate, and potassium pivalate), a tertiary amine (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), an aromatic amine (e.g., pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), a hydroxide base (e.g., sodium hydroxide, lithium hydroxide, potassium hydroxide, and ammonium hydroxide), or lithium bis(trimethylsilyl)amide; (iii) the solvent comprises an alcohol (e.g., methanol, ethanol, tert-amyl alcohol, isopropanol, and tert-butanol), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a combination thereof; and/or (iv) the temperature is from about 20° C. to about 120° C.

In some embodiments for step (3f), the palladium catalyst comprises XantPhos Pd G2. In some embodiments for step (3f), the base comprises potassium tert-butoxide. In some embodiments for step (3f), the solvent comprises tetrahydrofuran and toluene. In some embodiments for step (3f), the temperature is from about 60° C. to about 75° C. In some embodiments for step (3f), the temperature is from about 20° C. to about 120° C. In some embodiments for step (3f), the temperature is about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C.

In some embodiments for step (3f): (i) the copper catalyst comprises a copper(II) acetate, copper(I) chloride, copper(I) bromide, copper(I) bromide dimethyl sulfide complex, copper(I) triflate toluene complex, copper(I) iodide, copper(I) iodide tetrabutylammonium iodide complex, tetrakis(acetonitrile)copper(I) hexafluorophosphate, copper(I) iodide triethylphosphite complex, copper(I) bromide triphenylphosphine complex, copper(I) oxide, or copper(II) oxide; (ii) the copper catalyst ligand comprises a diamine (e.g., N,N'-dimethylethane-1,2-diamine, and trans-N,N'-dimethyl-cyclohexane-1,2-diamine), a diol (e.g., ethan-1,2-diol, and propane-1,3-diol), a diketone (e.g., 2-acetylcyclohexanone, and acetoacetonate,2,2,6,6-tetramethylheptane-3, 5-dione), a glycine derivative (e.g., N-methylglycine, and N,N-dimethylglycine), ethyl 2-oxocyclohexanecarboxylate, ethylene glycol, pyridine, 2,2'-bipyridine, 1,10-phenanthroline, neocuproine, 8-hydroxyquinoline, picolinic acid, glyoxal bis(phenylhydrazone), 2,6-dimethylanilino(oxo)acetic acid, 2,6-difluoroanilino(oxo)acetic acid, 2,6-dimethyloxyaniliono(oxo)acetic acid, 2,3,4,5,6-pentafluoroanilino(oxo)acetic acid, 3,5-bis(trifluoromethyl)anilino(oxo)acetic acid, 2-fluoro-6-(piperidine-1-sulfonyl)anilino(oxo)acetic acid, N1,N2-di([1,1'-biphenyl]-2-yl)oxalamide, N1,N2-bis(2-phenoxyphenyl)oxalamide, or thiophene-2-carboxylic acid; (iii) the base comprises an alkoxide base (e.g, sodium tert-butoxide, lithium tert-butoxide, potassium tert-pentoxide, sodium tert-pentoxide, potassium propionate, and potassium pivalate), a tertiary amine (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), an aromatic amine (pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), a hydroxide base (e.g., sodium hydroxide, lithium hydroxide, potassium hydroxide, and ammonium hydroxide), or lithium bis(trimethylsilyl)amide; (iv) the solvent comprises an alcohol (e.g., tert-amyl alcohol, isopropanol, and tert-butanol), an ether (e.g., diethyl ether, 1,4-dioxane, 2-methyltetrahydrofuran, dimethoxyethane, methyl tert-butyl ether, cyclopentyl methyl ether, diphenyl ether, dibutyl ether, and 1,4-dioxane), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a combination thereof; and/or (v) the temperature is from about 0° C. to about 140° C.

In some embodiments for step (3f), the copper catalyst comprises Copper(I) iodide. In some embodiments for step (3f), the copper catalyst ligand comprises 2,6-dimethylanilino(oxo)acetic acid (DMPAO). In some embodiments for step (3f), the base comprises potassium phosphate tribasic. In some embodiments for step (3f), the solvent comprises N-methyl-2-pyrrolidinone. In some embodiments for step (3f), the temperature is from about 100° C. to about 120° C. In some embodiments for step (3f), the temperature is from about 0° C. to about 140° C. In some embodiments, the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., or about 140° C.

Synthesis of Compound 2M

In a non-limiting example, Scheme 5 is a scheme depicting one embodiment of the synthesis of Compound 2A via Compound 2M for Manufacturing Route 3.

In some embodiments, Compound 2M is prepared from a process comprising: (3g) contacting Compound 2H with a chlorinating reagent, optionally an amine catalyst, and optionally an acidic additive in a solvent at a temperature sufficient to provide Compound 2I; (3h) contacting Compound 2I with TsHNNH₂ in a solvent at a temperature sufficient to provide Compound 2J; (3i) contacting Compound 2J with Compound 2K in the presence of a base in a solvent at a temperature sufficient to provide Compound 2L; (3j) contacting Compound 2L with a base in a solvent at a temperature sufficient to provide Compound 2M.

In some embodiments for step (3g): (i) the chlorinating reagent comprises sulfuryl chloride, chlorine gas, or a source of electrophilic chlorine (e.g., acetyl chloride/ceric ammonium nitrate, lithium diisopropylamide/4-toluenesulfonyl chloride, iodosobenzene dichloride, trichloromethanesulfonyl chloride, 1,3-dichloro-5,5-dimethylhydantoin/ammonium chloride, tetrachlorosilane/urea-hydrogen peroxide, N-chlorosuccinimide, trichloroisocyanuric acid, and 3,5-dichloro-2-hydroxy-4,6-s-triazinedione sodium salt); (ii) the amine catalyst, if present, comprises a pyrrolidine type organocatalyst (e.g., L-proline amide, and (2R,5R)-diphenylpyrrolidine); (iii) the acidic additive, if present, comprises Brønsted Acids (e.g., methanesulfonic acid, p-toluenesulfonic acid, and hydrochloric acid); (iv) the solvent comprises a carboxylic acid (e.g., acetic acid, trifluoroacetic acid, and propionic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, and tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (v) the temperature is from about 30° C. to about 70° C.

In some embodiments for step (3g), the chlorinating reagent comprises sulfuryl chloride. In some embodiments for step (3g), the amine catalyst is absent. In some embodiments for step (3g), the acidic additive is absent. In some embodiments for step (3g), the solvent comprises acetic acid. In some embodiments for step (3g), the temperature is from about 35° C. to about 50° C. In some embodiments for step (3g), the temperature is from about 30° C. to about 70° C. In some embodiments for step (3g), the temperature is about 30° C., about 35° C., about 40° C., about 45° C., about 50° C., about 55° C., about 60° C., about 65° C., or about 70° C.

In some embodiments for step (3h): (i) the solvent comprises a carboxylic acid (e.g., acetic acid, trifluoroacetic acid, and propionic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (ii) the temperature is from about 30° C. to about 70° C.

In some embodiments for step (3h), the solvent comprises acetic acid. In some embodiments for step (3h), the temperature is from 35° C. to about 50° C. In some embodiments for step (3h), the temperature is from about 30° C. to about 70° C. In some embodiments for step (3h), the temperature is about 30° C., about 35° C., about 40° C., about 45° C., about 50° C., about 55° C., about 60° C., about 65° C., or about 70° C.

In some embodiments for step (3i): (i) the base comprises a tertiary amine base (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), a hydroxide base (e.g., lithium hydroxide, potassium hydroxide, and sodium hydroxide), a carbonate base (e.g., potassium carbonate, sodium carbonate, and cesium carbonate), a bicarbonate base (e.g., sodium bicarbonate, and potassium bicarbonate), a tetraalkylammonium hydroxide (e.g., tetrabutylammonium hydroxide, benzyltrimethylammonium hydroxide, and choline hydroxide), an alkoxide base (e.g., sodium or potassium methoxide, and sodium or potassium ethoxide), or a phosphate base (e.g., sodium phosphate monobasic, sodium phosphate dibasic, potassium phosphate monobasic, and potassium phosphate dibasic); (ii) the solvent comprises water, a nitrile (e.g., acetonitrile, propionitrile, and butyronitrile), a hydrocarbon solvent (e.g., toluene, 2-methyltetrahydrofuran, trifluorotoluene, cyclohexane, n-heptane, and xylenes), a chlorinated solvent (e.g., dichloromethane, chloroform, dichloroethane, and chlorobenzene), an ether solvent (e.g., diethyl ether, 1,4-dioxane, tetrahydrofuran, dimethoxyethane, methyl tert-butyl ether, cyclopentyl methyl ether, diphenyl ether, and dibutyl ether), an alcohol solvent (e.g., methanol, ethanol, isopropanol, and tert-butanol), or a combination thereof, and/or (iii) the temperature is from about −20° C. to about 60° C.

In some embodiments for step (3i), the base comprises potassium carbonate. In some embodiments for step (3i), the solvent comprises 2-methyltetrahydrofuran and water, or acetonitrile. In some embodiments for step (3i), the temperature is from −20° C. to about 20° C. In some embodiments for step (3i), the temperature is from about −20° C. to about 60° C. In some embodiments for step (3i), the temperature is about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., or about 60° C.

In some embodiments for step (3j): (i) the base comprises a hydroxide base (e.g., sodium hydroxide, lithium hydroxide, and potassium hydroxide); (ii) the solvent comprises water, a nitrile solvent (e.g., acetonitrile, propionitrile, and butyronitrile), a hydrocarbon solvent (e.g., toluene, trifluorotoluene, cyclohexane, n-heptane, and xylenes), a chlorinated solvent (e.g., dichloromethane, chloroform, dichloroethane, and chlorobenzene), an ether solvent (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an alcohol solvent (e.g., methanol, ethanol, isopropanol, and tert-butanol), or a combination thereof; and/or (iii) the temperature is from about −10° C. to about 80° C.

In some embodiments for step (3j), the base comprises sodium hydroxide. In some embodiments for step (3j), the solvent comprises 2-methyltetrahydrofuran and water. In some embodiments for step (3j), the temperature is from about 15° C. to about 25° C. In some embodiments for step (3j), the temperature is about 20° C. In some embodiments for step (3j), the temperature is from about −10° C. to about 80° C. In some embodiments for step (3j), the temperature is about −10° C., about −5° C., about 0° C., about 5° C., about 10° C., about 15° C., about 20° C., about 25° C., about 30° C., about 35° C., about 40° C., about 45° C., about 50°

C., about 55° C., about 60° C., about 65° C., about 70° C., about 75° C., or about 80° C.

Synthesis of Compound 2B

In a non-limiting example, Scheme 6 is a scheme depicting one embodiment of the synthesis of Compound 2B for Manufacturing Routes 3.

In some embodiments, Compound 2B is prepared from a process comprising: (3k) contacting Compound 1E with a copper catalyst, an amine ligand, and an iodide additive in a solvent at a temperature sufficient to provide Compound 2O; (3l) contacting Compound 2O with an alkylating agent in a solvent at a temperature sufficient to provide Compound 2P, wherein X is iodide, chloride, bromide, methylsulfate, sulfate, methylcarbonate, carbonate, methanesulfonate, trifluoromethanesulfonate, toluenesulfonate, or tetrafluoroborate; (3m) contacting Compound 2P with an oxidant and a base in a solvent at a temperature sufficient to provide Compound 2B.

In some embodiments for step (3k): (i) the copper catalyst comprises copper(I) iodide, copper(I) bromide, copper(I) chloride, copper(I) oxide, copper(I) acetate, copper(I) bromide dimethyl sulfide complex, copper(I) triflate, copper(I) iodide tetrabutylammonium iodide complex, tetrakis(acetonitrile)copper(I) hexafluorophosphate, copper(I) iodide triethylphosphite complex, or copper(I) bromide triphenylphosphine complex; (ii) the amine ligand comprises trans-N,N'-dimethylcyclohexane-1,2-diamine, N1,N2-dimethylethane-1,2-diamine, N1,N3-dimethylpropane-1,3-diamine, or N1-(2-aminoethyl)ethane-1,2-diamine; (iii) the iodide additive comprises sodium iodide, lithium iodide, or potassium iodide; (iv) the solvent comprises an ether (e.g., diethylene glycol dimethylether, diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (v) the temperature is from about 50° C. to about 150° C.

In some embodiments for step (3k), the copper catalyst comprises copper(I) iodide. In some embodiments for step (3k), the amine ligand comprises trans-N,N'-dimethylcyclohexane-1,2-diamine. In some embodiments for step (3k), the iodide additive comprises sodium iodide. In some embodiments for step (3k), the solvent comprises diethylene glycol dimethylether. In some embodiments for step (3k), the temperature is from about 80° C. to about 130° C. In some embodiments for step (3k), the temperature is from about 50° C. to about 150° C. In some embodiments for step (3k), the temperature is about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about 150° C.

In some embodiments for step (3l): (i) the alkylating agent comprises iodomethane, trimethylsulfoxonium iodide, diazomethane, dimethylsulfate, 2,2-dimethoxypropane, a carbonate (e.g., dimethylcarbonate, and dimethyldicarbonate), a sulfonate (e.g., methyl fluorosulfonate, and methyl methanesulfonate), chloromethane, bromomethane, or trimethyloxonium tetrafluoroborate; (ii) the solvent comprises an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a chlorinated solvent (e.g., dichloromethane, chloroform, dichloroethane, and chlorobenzene); and/or (iii) the temperature is from about 0° C. to about 100° C.

In some embodiments for step (3l), the alkylating agent comprises iodomethane. In some embodiments for step (3l), the solvent comprises acetonitrile. In some embodiments for step (3l), the temperature is from about 20° C. to about 40° C. In some embodiments for step (3l), the temperature is about 30° C. In some embodiments for step (3l), the temperature is from about 0° C. to about 100° C. In some embodiments for step (3l), the temperature is from about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C. In some embodiments for step (3l), X is iodide.

In some embodiments for step (3m): (i) the oxidant comprises potassium ferricyanide, oxone, lead tetraacetate, peracetic acid, hydrogen peroxide, molecular oxygen, air, sodium hypochlorite, sodium chlorite, sodium periodate, potassium peroxymonosulfate, 2,3-dichloro-5,6-dicyano-1,4-benzoquinone, 1,4-benzoquinone, periodic acid, potassium bromate, meta-chloroperoxybenzoic acid, or magnesium monoperoxypthalate; (ii) the base comprises potassium hydroxide, lithium hydroxide, potassium hydroxide, or ammonium hydroxide; (iii) the solvent comprises hydroxide base (e.g., lithium hydroxide, potassium hydroxide, and ammonium hydroxide); (iii) the solvent comprises water, an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (iv) the temperature is from about 0° C. to about 70° C.

In some embodiments for step (3m), the oxidant comprises potassium ferricyanide. In some embodiments for step (3m), the base comprises potassium hydroxide. In some embodiments for step (3m), the solvent comprises water. In some embodiments for step (3m), the temperature is from about 5° C. to about 20° C. In some embodiments for step (3m), the temperature is from about 0° C. to about 70° C. In some embodiments for step (3m), the temperature is from about 0° C., about 5° C., about 10° C., about 15° C., about 20° C., about 25° C., about 30° C., about 35° C., about 40°

C., about 45° C., about 50° C., about 55° C., about 60° C., about 65° C., or about 70° C.

Synthesis of Compound 2G

In a non-limiting example, Scheme 7 is a scheme depicting one embodiment of the synthesis of Compound 1B via Compound 2G for Manufacturing Route 3.

In some embodiments, Compound 2G is prepared from a process comprising: (3n) contacting Compound 2Q with a brominating agent in a solvent at a temperature sufficient to provide Compound 2R; (3o) contacting Compound 2R with a formamide-based agent in a solvent at a temperature sufficient to provide Compound 2S; (3p) contacting Compound 2S with optionally, a nitrile reagent and a base in a solvent at a temperature sufficient to provide Compound 2T; (3q) contacting Compound 2T with a chlorinating reagent and a base in a solvent at a temperature sufficient to provide Compound 2U; and (3r) contacting Compound 2U with 2,2-dimethylpropan-1-amine and a base in a solvent at a temperature sufficient to provide Compound 2G.

In some embodiments for step (3n): (i) the brominating agent comprises N-bromosuccinimide, 1,3-dibromo-5,5-dimethylhydantoin, pyridinium tribromide, or bromine; (ii) the solvent comprises a polar aprotic solvent (e.g., N,N-dimethylformamide, N,N-dimethylacetamide, N-methyl-2-pyrrolidinone, and dimethyl sulfoxide), or a chlorinated solvent (e.g., dichloromethane, chloroform, dichloroethane, and chlorobenzene); and/or (iii) the temperature is from about 0° C. to about 40° C.

In some embodiments for step (3n), the brominating agent comprises N-bromosuccinimide. In some embodiments for step (3n), the solvent comprises N,N-dimethylformamide. In some embodiments for step (3n), the temperature is from about 15° C. to about 25° C. In some embodiments for step (3n), the temperature is about 20° C. In some embodiments for step (3n), the temperature is from about 0° C. to about 40° C. In some embodiments for step (3n), the temperature is from about 0° C., about 5° C., about 10° C., about 15° C., about 20° C., about 25° C., about 30° C., about 35° C., or about 40° C.

In some embodiments for step (3o): (i) the formamide-based agent comprises N,N-dimethylformamide dimethyl acetal, N,N-dimethylformamide diethyl acetal, or N,N-dimethylformamide diisopropyl acetal; (ii) the solvent comprises a polar aprotic solvent (e.g., N,N-dimethylformamide N,N-dimethylacetamide, N-methyl-2-pyrrolidinone, and dimethyl sulfoxide), N,N-dimethylformamide dimethyl acetal, N,N-dimethylformamide diethyl acetal, or N,N-dimethylformamide diisopropyl acetal; and/or (iii) the temperature is from about 20° C. to about 150° C.

In some embodiments for step (3o), the formamide-based comprises N,N-dimethylformamide dimethyl acetal. In some embodiments for step (3o), the solvent comprises N,N-dimethylformamide. In some embodiments for step (3o), the temperature is from about 100° C. to about 120° C. In some embodiments for step (3o), the temperature is about 110° C. In some embodiments for step (3o), the temperature is about 20° C. to about 150° C. In some embodiments for step (3o), the temperature is about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about 150° C.

In some embodiments for step (3p): (i) the nitrile reagent, if present, comprises acetonitrile; (ii) the base comprises an organolithium reagent (e.g., phenyllithium, mesityllithium, tert-butyllithium, and sec-butyllithium), a Grignard (e.g., isopropylmagnesium chloride, isopropylmagnesium bromide, isopropylmagnesium chloride lithium chloride complex, phenylmagnesium chloride, sec-butylmagnesium chloride, and 2,2,6,6-tetramethylpiperidinylmagnesium chloride lithium chloride complex), an alkoxide base (e.g., potassium tert-butoxide, and potassium tert-amylate), or an amide base (e.g., lithium diisopropylamide, potassium bis(trimethylsilyl)amide, sodium bis(trimethylsilyl)amide, and lithium bis(trimethylsilyl)amide); (iii) the solvent comprises an ether (e.g., tetrahydrofuran, diethyl ether, 1,4-dioxane, 2-methyltetrahydrofuran, dimethoxyethane, methyl tert-butyl ether, cyclopentyl methyl ether, diphenyl ether, and dibutyl ether); and/or (iv) the temperature is from about −80° C. to about 40° C.

In some embodiments for step (3p), the nitrile reagent, if present, comprises acetonitrile. In some embodiments for step (3p), the base comprises lithium bis(trimethylsilyl) amide. In some embodiments for step (3p), the solvent comprises tetrahydrofuran. In some embodiments for step (3p), the temperature is from about −10° C. to about 0° C. In some embodiments for step (3p), the temperature is from about −80° C. to about 40° C. In some embodiments for step (3p), the temperature is from about −80° C., about −75° C., about −70° C., about −65° C., about −60° C., about −55° C., about −50° C., about −45° C., about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., or about 40° C.

In some embodiments for step (3q): (i) the chlorinating reagent comprises oxalyl chloride, phosphorus oxychloride, thionyl chloride, sulfuryl chloride, phosgene, triphosgene, methanesulfonyl chloride, or cyanuric chloride; (ii) the base comprises an amine base (e.g., N,N-Diisopropylethylamine 1-methylimidazole, N-methylmorpholine, tri-n-propylamine, triethylamine, tri-n-butylamine, 1,8-diazabicyclo[5.4.0]undec-7-ene, and 1,4-diazabicyclo[2.2.2]octane), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), or an aromatic amine (e.g., pyridine, 2,6-lutidine, and collidine); (iii) the solvent comprises an ether (e.g., 1,2-dimethoxyethane, diethyl ether, 1,4-dioxane, tetrahydrofuran, 2-methyltetrahydrofuran, methyl tert-butyl ether, cyclopentyl methyl ether, diphenyl ether, and dibutyl ether), an ester solvent (e.g., ethyl acetate, isopropyl acetate, n-propyl acetate, and isobutyl acetate), a hydrocarbon (e.g., toluene, trifluorotoluene, cyclohexane, n-heptane, and xylenes), a chlorinated solvent (e.g., dichloromethane, chloroform, dichloroethane, and chlorobenzene), or a polar aprotic solvent (e.g., N,N-dimethylformamide); and/or (iv) the temperature is from about 20° C. to about 80° C.

In some embodiments for step (3q), the chlorinating reagent comprises oxalyl chloride. In some embodiments for step (3q), the base comprises N,N-Diisopropylethylamine. In some embodiments for step (3q), the solvent comprises 1,2-dimethoxyethane. In some embodiments for step (3q), the temperature is from about 55° C. to about 65° C. In some embodiments for step (3q), the temperature is about 60° C.

In some embodiments for step (3q), the temperature is from about 20° C. to about 80° C. In some embodiments for step (3q), the temperature is about 20° C., about 25° C., about 30° C., about 35° C., about 40° C., about 45° C., about 50° C., about 55° C., about 60° C., about 65° C., about 70° C., about 75° C., or about 80° C.

In some embodiments for step (3r): (i) the base comprises an amine base (e.g., N,N-Diisopropylethylamine 1-methyl-imidazole, N-methylmorpholine, tri-n-propylamine, triethylamine, tri-n-butylamine, 1,8-diazabicyclo[5.4.0]undec-7-ene, and 1,4-diazabicyclo[2.2.2]octane), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), or an aromatic amine (e.g., pyridine, 2,6-lutidine, and collidine); (ii) the solvent comprises an alcohol (e.g., methanol, ethanol, tert-butanol, sec-butanol, and isopropanol), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), a hydrocarbon (e.g., toluene, trifluorotoluene, cyclohexane, n-heptane, and xylenes), a polar aprotic solvent (e.g., N,N-dimethylformamide, N,N-dimethylacetamide, N-methyl-2-pyrrolidinone, and dimethyl sulfoxide), or a nitrile (e.g., acetonitrile, propionitrile, and butyronitrile); and/or (iii) the temperature is from about 20° C. to about 100° C.

In some embodiments for step (3r), the base comprises N,N-Diisopropylethylamine. In some embodiments for step (3r), the solvent comprises isopropanol. In some embodiments for step (3r), the temperature is from about 70° C. to about 80° C. In some embodiments for step (3r), the temperature is about 75° C. In some embodiments for step (3r), the temperature is from about 20° C. to about 100° C. In some embodiments for step (3r), the temperature is about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

Compound 1 Manufacturing Route 4

In a non-limiting example, Scheme 9 is a scheme depicting one embodiment of the alternate synthesis of Compound 2E for Manufacturing Route 4. In a non-limiting example, Schemes 9, 10, 5 and 7 depict one embodiment of a synthesis of Compound 1.

Scheme 9

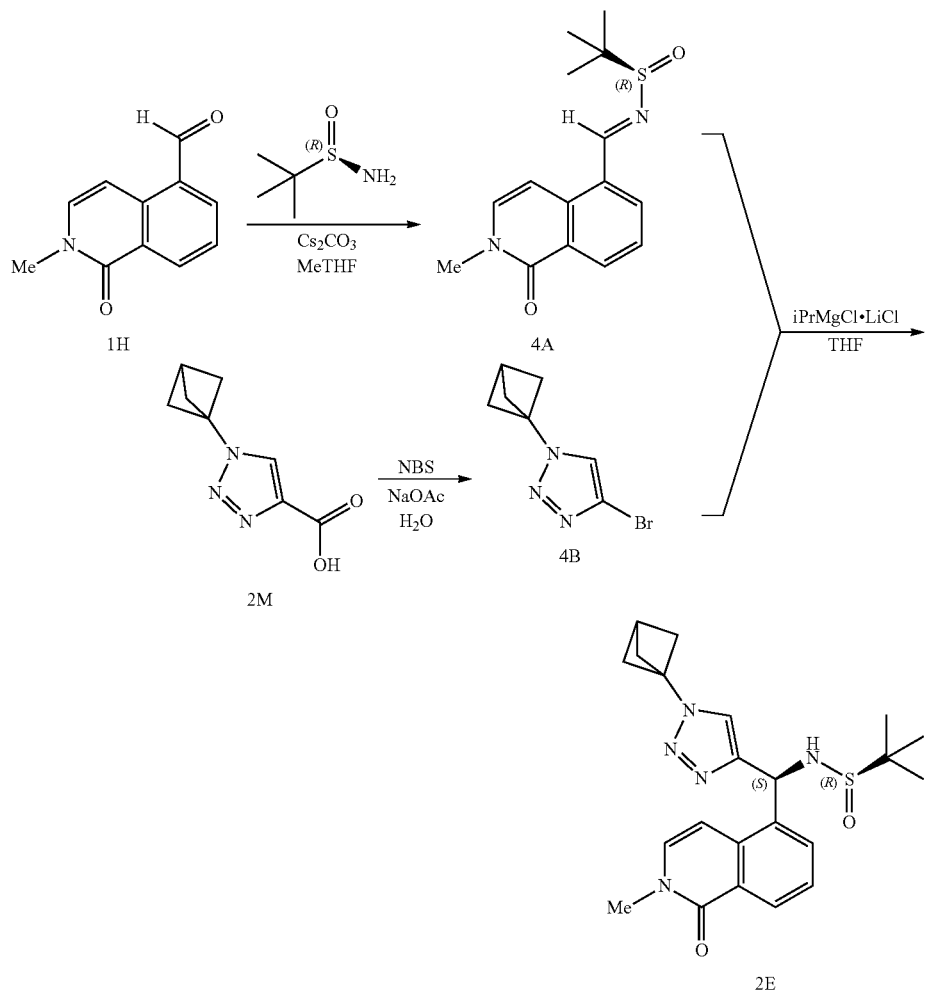

In a non-limiting example, Scheme 9A is a scheme depicting one embodiment of the alternate synthesis of Compound 4A from Compound 1H for Manufacturing Route 4. In a non-limiting example, Schemes 9, 9a, 10, 5 and 7 depict one embodiment of a synthesis of Compound 1.

Scheme 9A

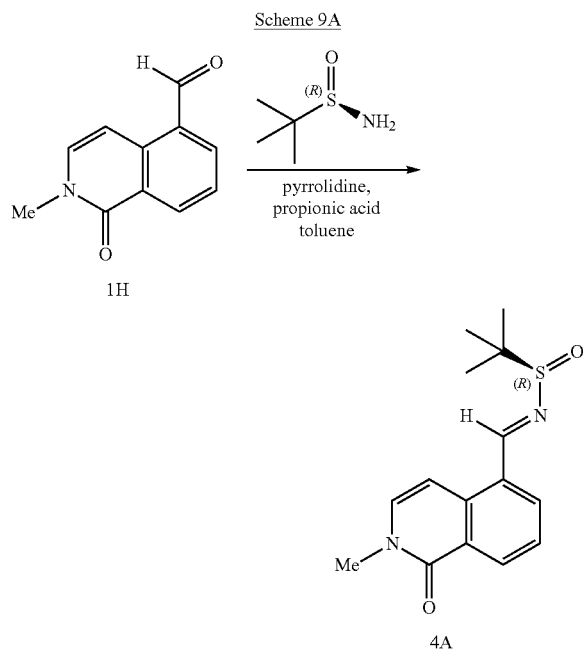

4A

One method for the synthesis of Compound 1 is a process comprising: (4a) contacting Compound 1H in the presence of

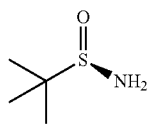

in the presence of a catalyst in a solvent at a temperature sufficient to provide Compound 4A; (4b) contacting Compound 4A with Compound 4B in the presence of a base, followed by optionally, a copper catalyst, optionally, a Lewis base additive, and optionally, a zinc additive in a solvent at a temperature sufficient to provide Compound 2E; (4c) contacting Compound 2E with an acid in a solvent at a temperature sufficient to provide Compound 2F; and (4d) contacting Compound 2F with Compound 2G in the presence of a palladium catalyst and a base in a solvent at a temperature sufficient to provide Compound 1.

One method for the synthesis of Compound 1 is a process comprising: (4a) contacting Compound 1H in the presence of

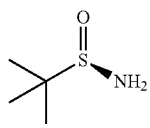

in the presence of a catalyst in a solvent at a temperature sufficient to provide Compound 4A; (4b) contacting Compound 4A with Compound 4B in the presence of a base, followed by optionally, a copper catalyst, optionally, a Lewis base additive, and optionally, a zinc additive in a solvent at a temperature sufficient to provide Compound 2E; (4c) contacting Compound 2E with an acid in a solvent at a temperature sufficient to provide Compound 2F; and (4d) contacting Compound 2F with Compound 2G in the presence of a copper catalyst, a copper catalyst ligand, and a base in a solvent at a temperature sufficient to provide Compound 1.

In some embodiments for step (4a): (i) the catalyst comprises an inorganic catalyst (e.g., magnesium sulfate, carbonate bases (e.g., potassium carbonate, sodium carbonate, and cesium carbonate), hydroxides bases (e.g., potassium hydroxide, lithium hydroxide, and sodium hydroxide), and titanium(IV) isopropoxide), an organic catalyst (e.g., secondary amines (e.g., pyrrolidine, piperidine, proline, diisopropylamine, and dibutylamine), organic acid (e.g., acetic acid, trifluoroacetic acid, benzoic acid, 4-nitrobenzoic acid, methoxyacetic acid, propionic acid, isobutyric acid, pivalic acid, decanoic acid, hexanoic acid, and phenyl boronic acid), or a combination thereof; (ii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a hydrocarbon solvent (e.g., n-hexane, toluene, trifluorotoluene, cyclohexane, n-heptane, and xylenes), a chlorinated solvent (e.g., dichloromethane, chloroform, dichloroethane, and chlorobenzene), a nitrile (e.g., acetonitrile, propionitrile, and butyronitrile), or ester (e.g., ethyl acetate, isopropyl acetate, n-propyl acetate, and isobutyl acetate); and/or (iii) the temperature is from about −20° C. to about 65° C.

In some embodiments for step (4a): (i) the catalyst comprises cesium carbonate, magnesium sulfate, potassium carbonate, sodium carbonate, a hydroxides base (potassium hydroxide, lithium hydroxide, and sodium hydroxide), titanium(IV) isopropoxide, pyrrolidine or piperidine; (ii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a hydrocarbon solvent (e.g., n-hexane, toluene, trifluorotoluene, cyclohexane, n-heptane, and xylenes), a chlorinated solvent (e.g., dichloromethane, chloroform, dichloroethane, and chlorobenzene), a nitrile (e.g., acetonitrile, propionitrile, and butyronitrile), or ester (e.g., ethyl acetate, isopropyl acetate, n-propyl acetate, and isobutyl acetate); and/or (iii) the temperature is from about −20° C. to about 65° C.

In some embodiments for step (4a), the catalyst comprises cesium carbonate. In some embodiments for step (4a), the solvent comprises 2-methyltetrahydrofuran. In some embodiments for step (4a), the temperature is from about to 20° C. to about 30° C. In some embodiments for step (4a), the temperature is about 25° C. In some embodiments for step (4a), the temperature is from about −20° C. to about 65° C. In some embodiments for step (4a), the temperature is from about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., or 65° C.

In some embodiments for step (4a), the catalyst comprises a combination of pyrrolidine and propionic acid. In some embodiments for step (4a), the solvent comprises toluene. In some embodiments for step (4a), the temperature is about 50° C. In some embodiments for step (4a), the temperature is from about −20° C. to about 65° C. In some embodiments for step (4a), the temperature is from about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., or 65° C.

In some embodiments for step (4b), (i) the base comprises a Grignard (e.g., isopropylmagnesium chloride lithium chloride complex, isopropylmagnesium chloride, cyclohexylmagnesium chloride, butylmagnesium chloride, tert-butylmagnesium chloride, sec-butylmagnesium chloride lithium chloride complex, isopropylmagnesium bromide, and ethylmagnesium bromide), or a organolithium reagent (e.g., n-hexyllithium, phenyllithium, mesityllithium, n-butyllithium, tert-butyllithium, and sec-butyllithium); (ii) the copper catalyst, if present, comprises a copper catalyst (e.g., copper(I) iodide, copper(I) bromide, copper(I) chloride, copper(I) cyanide di(lithium chloride) complex, bromotris(triphenylphosphine) copper(I), copper(I) trifluoromethanesulfonate toluene complex, copper(I) chloride bis(lithium chloride) complex, copper(I) bromide bis(lithium bromide) complex, copper(I) thiocyanate, copper(I) thiophene-2-carboxylate, copper(I) thiophenolate, copper(I) diphenylphosphinate, (1,10-phenanthroline)bis(triphenylphosphine)copper(I) nitrate DCM adduct, copper(I) 3-methylsalicylate, chloro[1,3-bis(2,6-diisopropylphenyl)imidazol-2-ylidene] copper(I), chloro(1,5-cyclooctadiene)copper(I) dimer, copper(II) chloride, copper(II) bromide, and copper(II) acetate); (iii) the zinc additive, if present, comprises zinc chloride, zinc bromide; (iv) the Lewis base additive, if present, comprises N,N'-Dimethylpropyleneurea, hexamethylphosphoramide, 2,6-lutidine, pyridine, diglyme, N-methylmorpholine, N,N-diisopropylethylamine, dimethoxyethane, or lithium chloride; (v) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, and diglyme), a hydrocarbon solvent (e.g., n-hexane, toluene, trifluorotoluene, cyclohexane, n-heptane, and xylenes), or chlorinated solvent (e.g., dichloromethane, chloroform, dichloroethane, and chlorobenzene); and/or (iv) the temperature is from about −80° C. to about 60° C. In some embodiments, for step (4b), Compound 2E is produced in at least greater than about 50%, at least greater than about 60%, at least greater than about 70%, at least greater than about 80%, at least greater than about 90%, at least greater than about 95%, or at least greater than about 99% diastereomeric purity.

In some embodiments for step (4b), the base comprises isopropylmagnesium chloride lithium chloride complex. In some embodiments for step (4b), the copper catalyst is absent. In some embodiments for step (4b), the zinc additive, is absent. In some embodiments for step (4b), the Lewis base additive is absent. In some embodiments for step (4b), the solvent comprises tetrahydrofuran. In some embodiments for step (4b), the temperature is from about 0° C. to about 25° C. In some embodiments for step (4b), the temperature is from about −80° C. to about 60° C. In some embodiments for step (4b), the temperature is about −80° C., about −75° C., about −70° C., about −65° C., about −60° C., about −55° C., about −50° C., about −45° C., about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C. C., about 55° C., or about 60° C. In some embodiments, for step (4b), Compound 2E is produced in at least greater than about 99% diastereomeric purity.

In some embodiments for step (4c): (i) the acid comprises hydrochloric acid, hydrobromic acid, a sulfonic acid (e.g., methanesulfonic acid, p-toluenesulfonic acid, and benzenesulfonic acid), a trifluoroacetic acid, phosphoric acid, formic acid, or oxalic acid; (ii) the solvent comprises water, an ester (e.g., ethyl acetate, isopropyl acetate, n-propyl acetate, and isobutyl acetate), an alcohol (e.g., ethanol, ethylene glycol, propylene glycol, methanol, isopropanol, and tert-butanol), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (iii) the temperature is from about 0° C. to about 70° C.

In some embodiments for step (4c), the acid comprises hydrochloric acid. In some embodiments for step (4c), the solvent comprises water. In some embodiments for step (4c), the temperature is from about 20° C. to about 50° C. In some embodiments for step (4c), the temperature is from about 0° C. to about 70° C. In some embodiments for step (4c), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., or about 70° C.

In some embodiments for step (4d): (i) the palladium catalyst comprises a palladium(II) catalyst (e.g., XantPhos Pd G2, Pd(acac)$_2$, Pd(OAc)$_2$, Pd(hfac)$_2$, PdCl(allyl), PdCl$_2$, and PdSO$_4$·2H$_2$O), a palladium pre-catalyst (e.g., Pd(XantPhos)Cl$_2$, XantPhos Pd G3, N-XantPhos Pd G4, tBuXPhos Pd G3, tBuBrettPhos Pd G3, RockPhos Pd G3, JosiPhos-J009 Pd G3, AdBrettPhos Pd G3, and TrixiePhos Pd G3), or a palladium(0) catalyst (e.g., Pd$_2$(dba)$_3$, and Pd(PPh$_3$)$_4$); (ii) the base comprises an alkoxide base (e.g., potassium tert-butoxide, sodium tert-butoxide, sodium methoxide, lithium tert-butoxide, potassium tert-pentoxide, sodium tert-pentoxide, potassium propionate, and potassium pivalate), a tertiary amine (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), an aromatic amine (e.g., pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), a hydroxide base (e.g., sodium hydroxide, lithium hydroxide, potassium hydroxide, and ammonium hydroxide), or lithium bis(trimethylsilyl)amide; (iii) the solvent comprises an alcohol (e.g., methanol, ethanol, tert-amyl alcohol, isopropanol, and tert-butanol), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a combination thereof; and/or (iv) the temperature is from about 20° C. to about 120° C.

In some embodiments for step (4d), the palladium catalyst comprises chloro[(4,5-bis(diphenylphosphino)-9,9-dimethylxanthene)-2-(2'-amino-1,1'-biphenyl)]palladium(II) (XantPhos Pd G2). In some embodiments for step (4d), the base comprises potassium tert-butoxide. In some embodiments for step (4d), the solvent comprises tetrahydrofuran and toluene. In some embodiments for step (4d), the temperature is from about 60° C. to about 75° C. In some embodiments for step (4d), the temperature is from about 20° C. to about 120° C. In some embodiments for step (4d), the temperature is from about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C.

In some embodiments for step (4d): (i) the copper catalyst comprises a copper(II) acetate, copper(I) chloride, copper(I) bromide, copper(I) bromide dimethyl sulfide complex, copper(I) triflate toluene complex, copper(I) iodide, copper(I) iodide tetrabutylammonium iodide complex, tetrakis(acetonitrile)copper(I) hexafluorophosphate, copper(I) iodide triethylphosphite complex, copper(I) bromide triphenylphosphine complex, copper(I) oxide, or copper(II) oxide; (ii) the copper catalyst ligand comprises a diamine (e.g., N,N'-dimethylethane-1,2-diamine, and trans-N,N'-dimethyl-cyclohexane-1,2-diamine), a diol (e.g., ethan-1,2-diol, and propane-1,3-diol), a diketone (e.g., 2-acetylcyclohexanone, and acetoacetonate,2,2,6,6-tetramethylheptane-3,5-dione), a glycine derivative (e.g., N-methylglycine, and N,N-dimethylglycine), ethyl 2-oxocyclohexanecarboxylate, ethylene glycol, pyridine, 2,2'-bipyridine, 1,10-phenanthroline, neocuproine, 8-hydroxyquinoline, picolinic acid, glyoxal bis(phenylhydrazone), 2,6-dimethylanilino(oxo)acetic acid, 2,6-difluoroanilino(oxo)acetic acid, 2,6-dimethyloxyaniliono(oxo)acetic acid, 2,3,4,5,6-pentafluoroanilino(oxo) acetic acid, 3,5-bis(trifluoromethyl)anilino(oxo)acetic acid, 2-fluoro-6-(piperidine-1-sulfonyl)anilino(oxo)acetic acid, N1,N2-di([1,1'-biphenyl]-2-yl)oxalamide, N1,N2-bis(2-phenoxyphenyl)oxalamide, or thiophene-2-carboxylic acid; (iii) the base comprises an alkoxide base (e.g, sodium tert-butoxide, lithium tert-butoxide, potassium tert-pentoxide, sodium tert-pentoxide, potassium propionate, and potassium pivalate), a tertiary amine (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), an aromatic amine (pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), a hydroxide base (e.g., sodium hydroxide, lithium hydroxide, potassium hydroxide, and ammonium hydroxide), or lithium bis(trimethylsilyl) amide; (iv) the solvent comprises an alcohol (e.g., tert-amyl alcohol, isopropanol, and tert-butanol), an ether (e.g., diethyl ether, 1,4-dioxane, 2-methyltetrahydrofuran, dimethoxyethane, methyl tert-butyl ether, cyclopentyl methyl ether, diphenyl ether, dibutyl ether, and 1,4-dioxane), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a combination thereof; and/or (v) the temperature is from about 0° C. to about 140° C.

In some embodiments for step (4d), the copper catalyst comprises Copper(I) iodide. In some embodiments for step (4d), the copper catalyst ligand comprises 2,6-dimethylanilino(oxo)acetic acid (DMPAO). In some embodiments for step (4d), the base comprises potassium phosphate tribasic. In some embodiments for step (4d), the solvent comprises N-methyl-2-pyrrolidinone. In some embodiments for step (4d), the temperature is from about 100° C. to about 120° C. In some embodiments for step (4d), the temperature is from about 0° C. to about 140° C. In some embodiments, the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., or about 140° C.

Synthesis of Compound 4B

In a non-limiting example, Scheme 9 is a scheme depicting one embodiment of the synthesis of Compound 4B for Manufacturing Route 4.

In some embodiments, Compound 4B is prepared from a process comprising: (4e) contacting Compound 2M in the presence of a brominating reagent with a base in a solvent at a temperature sufficient to provide Compound 4B.

In some embodiments for step (4e): (i) the brominating reagent comprises N-bromosuccinimide, potassium bromide/hypochlorous acid, pyridinium tribromide, 1,3-dibromo-5,5-dimethylhydantoin, dibromoisocyanuric acid, or bromine; (ii) the base comprises sodium acetate, potassium hydroxide, lithium hydroxide, sodium hydroxide, tetrabutylammonium hydroxide, lithium carbonate, sodium carbonate, potassium carbonate, cesium carbonate, lithium acetate, potassium acetate, or potassium phosphate; (iii) the solvent comprises water, an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a hydrocarbon (e.g., toluene, trifluorotoluene, cyclohexane, n-heptane, and xylenes), or a chlorinated solvent (e.g., dichloromethane, chloroform, dichloroethane, and chlorobenzene); and/or (iv) the temperature is from about 0° C. to about 100° C.

In some embodiments for step (4e), the brominating reagent comprises N-bromosuccinimide. In some embodiments for step (4e), the base comprises sodium acetate. In some embodiments for step (4e), the solvent comprises water. In some embodiments for step (4e), the temperature is from about 70° C. to about 90° C. In some embodiments for step (4e), the temperature is from about 0° C. to about 100° C. In some embodiments for step (4e), the temperature is from about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

Alternate Synthesis of Compound 1H for Manufacturing Route 4

In a non-limiting example, Scheme 10 is a scheme depicting one embodiment of the alternate synthesis of Compound 1H for Manufacturing Route 4.

Scheme 10

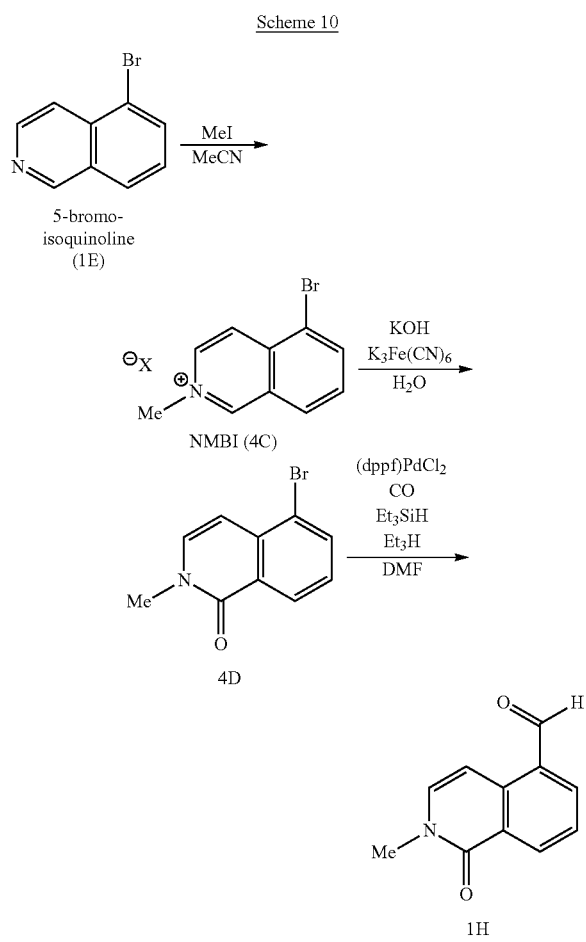

In some embodiments, Compound 1H is prepared from a process comprising: (4f) contacting Compound 1E with an alkylating agent in a solvent at a temperature sufficient to provide Compound 4C, wherein X is iodide, chloride, bromide, methylsulfate, sulfate, methylcarbonate, carbonate, methanesulfonate, trifluoromethanesulfonate, toluenesulfonate, or tetrafluoroborate; (4g) contacting Compound 4C with an oxidant and a hydroxide base in a solvent at a temperature sufficient to provide Compound 4D; (4h) contacting Compound 4D with a palladium or copper catalyst, a carbonyl source, a hydride source, and a base in a solvent at a temperature sufficient to provide Compound 1H.

In some embodiments for step (4f): (i) the alkylating agent comprises iodomethane, bromomethane, chloromethane, trimethylsulfoxonium iodide, diazomethane, dimethylsulfate, 2,2-dimethoxypropane, a carbonate (e.g., dimethylcarbonate, and dimethyldicarbonate), a sulfonate (e.g., methyl fluorosulfonate, and methyl methanesulfonate), or trimethyloxonium tetrafluoroborate; (ii) the solvent comprises an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a chlorinated solvent (e.g., dichloromethane, chloroform, dichloroethane, and chlorobenzene); and/or (iii) the temperature is from about −20° C. to about 45° C.

In some embodiments for step (4f), the alkylating agent comprises iodomethane. In some embodiments for step (4f), the solvent comprises acetonitrile. In some embodiments for step (4f), the temperature is from about 0° C. to about 35° C. In some embodiments for step (4f), the temperature is from about −20° C. to about 45° C. In some embodiments for step (4f), the temperature is from about −20° C., about −15° C., about −10° C., about −5° C., about 0° C., about 5° C., about 10° C., about 15° C., about 20° C., about 25° C., about 30° C., about 40° C., or about 45° C. In some embodiments for step (4f), X is iodide.

In some embodiments for step (4g): (i) the oxidant comprises potassium ferricyanide, oxone, lead tetraacetate, peracetic acid, hydrogen peroxide, molecular oxygen, air, sodium hypochlorite, sodium chlorite, sodium periodate, potassium peroxymonosulfate, 2,3-dichloro-5,6-dicyano-1,4-benzoquinone, 1,4-benzoquinone, periodic acid, potassium bromate, meta-chloroperoxybenzoic acid, or magnesium monoperoxypthalate; (ii) the hydroxide base comprises a hydroxide base (e.g., potassium hydroxide, lithium hydroxide, sodium hydroxide, and ammonium hydroxide); (iii) the solvent comprises water, an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (iv) the temperature is from about −5° C. to about 70° C.

In some embodiments for step (4g), the oxidant comprises potassium ferricyanide. In some embodiments for step (4g), the hydroxide base comprises potassium hydroxide. In some embodiments for step (4g), the solvent comprises water. In some embodiments for step (4g), the temperature is from about 0° C. to about 20° C. In some embodiments for step (4g), the temperature is from about −5° C. to about 70° C. In some embodiments for step (4g), the temperature is from about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., or about 70° C.

In some embodiments for step (4h): (i) the palladium or copper catalyst comprises a palladium catalyst (e.g., 1,1'-bis(diphenylphosphino)ferrocene)palladium(II) chloride, palladium(II) acetate, palladium dichloride bis(acetonitrile), bis(triphenylphosphine)palladium chloride, tris(dibenzylideneacetone)dipalladium(0)-chloroform adduct, [1,1'-Bis(di-tert-butylphosphino)ferrocene]dichloropalladium (II), dichlorobis(tricyclohexylphosphine)palladium(II), bis(benzonitrile)palladium dichloride, palladium(II) acetylacetonate, [1,3-Bis(2,6-Diisopropylphenyl)imidazol-2-ylidene](3-chloropyridyl)palladium(II) dichloride, tris(dibenzylideneacetone)dipalladium(0) in combination with a tertiary phosphine (e.g., triphenylphosphine, tributylphosphine, tri(2-furyl)phosphine, tri(p-tolyl)phosphine, and tri(o-tolyl)phosphine)), or a copper catalyst (e.g., copper(I) iodide, copper(II) acetate with a tertiary phosphine (e.g., triphenylphosphine, tributylphosphine, tri(2-furyl)phosphine, tri(p-tolyl)phosphine, and tri(o-tolyl)phosphine)); (ii) the carbonyl source comprises carbon monoxide, iron pentacarbonyl, dicobalt octacarbonyl, N-formylsaccharine, paraformaldehyde, or formic acid; (iii) the hydride source comprises a silane (e.g., triethylsilane methyldiethoxysilane, trichlorosilane, polymethylhydrosiloxane, dimethyl(phenyl) silane, 1,1,2,2-tetramethyldisilane, and diphenylsilane), or hydrogen gas; (iv) the base comprises a tertiary amine (e.g., triethylamine, N-methylmorpholine, tri-n-propylamine, N,N-diisopropylethylamine, tri-n-butylamine, 1,8-diazabicyclo[5.4.0]undec-7-ene, 1,4-diazabicyclo[2.2.2]octane, and tetramethylethylenediamine), an aromatic amine (e.g., pyridine, 2,6-lutidine, and collidine), or an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate); (v) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a hydrocarbon solvent (e.g., toluene, trifluorotoluene, cyclohexane, n-heptane, and xylenes), or a polar aprotic solvent (e.g., N,N-dimethylformamide, N,N-dimethylacetamide, N-methyl-2-pyrrolidinone, and dimethyl sulfoxide); and/or (vi) the temperature is from about 0° C. to about 100° C.

In some embodiments for step (4h), the palladium or copper catalyst comprises 1,1'-bis(diphenylphosphino)ferrocene)palladium(II) chloride. In some embodiments for step (4h), the carbonyl source comprises carbon monoxide. In some embodiments for step (4h), the hydride source comprises triethylsilane. In some embodiments for step (4h), the base comprises triethylamine. In some embodiments for step (4h), the solvent comprises N,N-dimethylformamide. In some embodiments for step (4h), the temperature is about 80° C. In some embodiments for step (4h), the temperature is from about 0° C. to about 100° C. In some embodiments for step (4h), the temperature is about 0° C., about 5° C., about 10° C., about 15° C., about 20° C., about 25° C., about 30° C., about 35° C., about 40° C., about 45° C., about 50° C., about 55° C., about 60, about 65, about 70° C., about 75° C., about 80° C., about 85° C., about 90° C., about 95° C., or about 100° C.

Synthesis of Compound 2M

In a non-limiting example, Scheme 5 is a scheme depicting one embodiment of the synthesis of Compound 2A via Compound 2M for Manufacturing Route 4.

In some embodiments, Compound 2M is prepared from a process comprising: (4i) contacting Compound 2H with a chlorinating reagent, optionally an amine catalyst, and optionally an acidic additive in a solvent at a temperature sufficient to provide Compound 2I; (4j) contacting Compound 2I with TsHNNH$_2$ in a solvent at a temperature sufficient to provide Compound 2J; (4k) contacting Compound 2J with Compound 2K in the presence of a base in a solvent at a temperature sufficient to provide Compound 2L; (4l) contacting Compound 2L with a base in a solvent at a temperature sufficient to provide Compound 2M.

In some embodiments for step (4i): (i) the chlorinating comprises sulfuryl chloride, chlorine gas, or a source of electrophilic chlorine (e.g., acetyl chloride/ceric ammonium nitrate, lithium diisopropylamide/4-toluenesulfonyl chloride, iodosobenzene dichloride, trichloromethanesulfonyl chloride, 1,3-dichloro-5,5-dimethylhydantoin/ammonium chloride, tetrachlorosilane/urea-hydrogen peroxide, N-chlorosuccinimide, trichloroisocyanuric acid, and 3,5-dichloro-2-hydroxy-4,6-s-triazinedione sodium salt); (ii) the amine catalyst, if present, comprises a pyrrolidine type organocatalyst (e.g., L-proline amide, and (2R,5R)-diphenylpyrrolidine); (iii) the acidic additive, if present, comprises a Brønsted Acid (e.g., methanesulfonic acid, p-toluenesulfonic acid, and hydrochloric acid); (iv) the solvent comprises a carboxylic acid (e.g., acetic acid, trifluoroacetic acid, and propionic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, and tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (v) the temperature is from about 30° C. to about 70° C.

In some embodiments for step (4i), the chlorinating agent comprises sulfuryl chloride. In some embodiments for step (4i), the amine catalyst is absent. In some embodiments for step (4i), the acidic additive is absent. In some embodiments for step (4i), the solvent comprises acetic acid. In some embodiments for step (4i), the temperature is from about 35° C. to about 50° C. In some embodiments for step (4i), the temperature is from about 30° C. to about 70° C. In some embodiments for step (4i), the temperature is about 30° C., about 35° C., about 40° C., about 45° C., about 50° C., about 55° C., about 60° C., about 65° C., or about 70° C.

In some embodiments for step (4j): (i) the solvent comprises a carboxylic acid (e.g., acetic acid, trifluoroacetic acid, and propionic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, and tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (ii) the temperature is from about 30° C. to about 70° C.

In some embodiments for step (4j), the solvent comprises acetic acid. In some embodiments for step (4j), the temperature is from about 35° C. to about 50° C. In some embodiments for step (4j), the temperature is from about 30° C. to about 70° C. In some embodiments for step (4j), the temperature is about 30° C., about 35° C., about 40° C., about 45° C., about 50° C., about 55° C., about 60° C., about 65° C., or about 70° C.

In some embodiments for step (4k): (i) the base comprises a tertiary amine base (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), a hydroxide base (e.g., lithium hydroxide, potassium hydroxide, and sodium hydroxide), a carbonate base (e.g., potassium carbonate, sodium carbonate, and cesium carbonate), a bicarbonate base (e.g., sodium bicarbonate, and potassium bicarbonate), a tetraalkylammonium hydroxide (e.g., tetrabutylammonium hydroxide, benzyltrimethylammonium hydroxide, and choline hydroxide), an alkoxide base (e.g., sodium or potassium methoxide, and sodium or potassium ethoxide), or a phosphate base (e.g., sodium phosphate monobasic, sodium phosphate dibasic, potassium phosphate monobasic, and potassium phosphate dibasic); (ii) the solvent comprises water, a nitrile (e.g., acetonitrile, propionitrile, and butyronitrile), a hydrocarbon solvent (e.g., toluene, 2-methyltetrahydrofuran, trifluorotoluene, cyclohexane, n-heptane, and xylenes), a chlorinated solvent (e.g., dichloromethane, chloroform, dichloroethane, and chlorobenzene), an ether solvent (e.g., diethyl ether, 1,4-dioxane, tetrahydrofuran, dimethoxyethane, methyl tert-butyl ether, cyclopentyl methyl ether, diphenyl ether, and dibutyl ether), an alcohol solvent (e.g., methanol, ethanol, isopropanol, and tert-butanol), or a combination thereof; and/or (iii) the temperature is from about −20° C. to about 60° C.

In some embodiments for step (4k), the base comprises potassium carbonate. In some embodiments for step (4k), the solvent comprises 2-methyltetrahydrofuran and water, or acetonitrile. In some embodiments for step (4k), the temperature is from about −20° C. to about 20° C. In some embodiments for step (4k), the temperature is from about −20° C. to about 60° C. In some embodiments for step (4k), the temperature is about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., or about 60° C.

In some embodiments for step (4l): (i) the base comprises a hydroxide base (e.g., sodium hydroxide, lithium hydroxide, and potassium hydroxide); (ii) the solvent comprises water, a nitrile solvent (e.g., acetonitrile, propionitrile, and butyronitrile), a hydrocarbon solvent (e.g., toluene, trifluorotoluene, cyclohexane, n-heptane, and xylenes), a chlorinated solvent (e.g., dichloromethane, chloroform, dichloroethane, and chlorobenzene), an ether solvent (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an alcohol solvent (e.g., methanol, ethanol, isopropanol, and tert-butanol), or a combination thereof; and/or (iii) the temperature is from about −10° C. to about 80° C.

In some embodiments for step (4l), the base comprises sodium hydroxide. In some embodiments for step (4l), the solvent comprises 2-methyltetrahydrofuran and water. In some embodiments for step (4l), the temperature is from about 15° C. to about 25° C. In some embodiments for step (4l), the temperature is about 20° C. In some embodiments for step (4l), the temperature is from about −10° C. to about 80° C. In some embodiments for step (4l), the temperature is about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., or about 80° C.

Synthesis of Compound 2G

In a non-limiting example, Scheme 7 is a scheme depicting one embodiment of the synthesis of Compound 1B via Compound 2G for Manufacturing Route 4.

In some embodiments, Compound 2G is prepared from a process comprising: (4m) contacting Compound 2Q with a brominating agent in a solvent at a temperature sufficient to provide Compound 2R; (4n) contacting Compound 2R with a formamide-based agent in a solvent at a temperature sufficient to provide Compound 2S; (4o) contacting Compound 2S with optionally, a nitrile reagent and a base in a solvent at a temperature sufficient to provide Compound 2T; (4p) contacting Compound 2T with a chlorinating reagent and a base in a solvent at a temperature sufficient to provide Compound 2U; and (4q) contacting Compound 2U with 2,2-dimethylpropan-1-amine and a base in a solvent at a temperature sufficient to provide Compound 2G.

In some embodiments for step (4m): (i) the brominating agent comprises N-bromosuccinimide, 1,3-dibromo-5,5-dimethylhydantoin, pyridinium tribromide, or bromine; (ii) the solvent comprises a polar aprotic solvent (e.g., N,N-dimethylformamide, N,N-dimethylacetamide, N-methyl-2-pyrrolidinone, and dimethyl sulfoxide), or a chlorinated solvent (e.g., dichloromethane, chloroform, dichloroethane, and chlorobenzene); and/or (iii) the temperature is from about 0° C. to about 40° C.

In some embodiments for step (4m), the brominating agent comprises N-bromosuccinimide. In some embodiments for step (4m), the solvent comprises N,N-dimethylformamide. In some embodiments for step (4m), the temperature is from about to 15° C. to about 25° C. In some embodiments for step (4m), the temperature is about 20° C. In some embodiments for step (4m), the temperature is from about 0° C. to about 40° C. In some embodiments for step (4m), the temperature is from about 0° C., about 5° C., about 10° C., about 15° C., about 20° C., about 25° C., about 30° C., about 35° C., or about 40° C.

In some embodiments for step (4n): (i) the formamide-based agent comprises N,N-dimethylformamide dimethyl acetal, N,N-dimethylformamide diethyl acetal, or N,N-dimethylformamide diisopropyl acetal; (ii) the solvent comprises a polar aprotic solvent (e.g., N,N-dimethylformamide N,N-dimethylacetamide, N-methyl-2-pyrrolidinone, and dimethyl sulfoxide), N,N-dimethylformamide dimethyl acetal, N,N-dimethylformamide diethyl acetal, or N,N-dimethylformamide diisopropyl acetal; and/or (iii) the temperature is from about 20° C. to about 150° C.

In some embodiments for step (4n), the formamide-based agent comprises N,N-dimethylformamide dimethyl acetal. In some embodiments for step (4n), the solvent comprises N,N-dimethylformamide. In some embodiments for step (4n), the temperature is from about 100° C. to about 120° C. In some embodiments for step (4n), the temperature is about 110° C. In some embodiments for step (4n), the temperature is from about 20° C. to about 150° C. In some embodiments for step (4n), the temperature is from about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about 150° C.

In some embodiments for step (4o): (i) the nitrile reagent, if present, comprises acetonitrile; (ii) the base comprises an organolithium reagent (e.g., phenyllithium, mesityllithium, tert-butyllithium, and sec-butyllithium), a Grignard (e.g., isopropylmagnesium chloride, isopropylmagnesium bromide, isopropylmagnesium chloride lithium chloride complex, phenylmagnesium chloride, sec-butylmagnesium chloride, and 2,2,6,6-tetramethylpiperidinylmagnesium chloride lithium chloride complex), an alkoxide base (e.g., potassium tert-butoxide, and potassium tert-amylate), or an amide base (e.g., lithium diisopropylamide, potassium bis(trimethylsilyl)amide, sodium bis(trimethylsilyl)amide, and lithium bis(trimethylsilyl)amide); (iii) the solvent comprises an ether (e.g., tetrahydrofuran, diethyl ether, 1,4-dioxane, 2-methyltetrahydrofuran, dimethoxyethane, methyl tert-butyl ether, cyclopentyl methyl ether, diphenyl ether, and dibutyl ether); and/or (iv) the temperature is from about −80° C. to about 40° C.

In some embodiments for step (4o), the nitrile reagent, if present, comprises acetonitrile. In some embodiments for step (4o), the base comprises lithium bis(trimethylsilyl)amide. In some embodiments for step (4o), the solvent comprises tetrahydrofuran. In some embodiments for step (4o), the temperature is from about −10° C. to about 0° C. In some embodiments for step (4o), the temperature is from about −80° C. to about 40° C. In some embodiments for step (4o), the temperature is about −80° C., about −75° C., about −70° C., about −65° C., about 60° C., about −55° C., about −50° C., about −45° C., about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., or about 40° C.

In some embodiments for step (4p): (i) the chlorinating reagent comprises oxalyl chloride, phosphorus oxychloride, thionyl chloride, sulfuryl chloride, phosgene, triphosgene, methanesulfonyl chloride, or cyanuric chloride; (ii) the base comprises an amine base (e.g., N,N-Diisopropylethylamine, 1-methylimidazole, N-methylmorpholine, tri-n-propylamine, triethylamine, tri-n-butylamine, 1,8-diazabicyclo[5.4.0]undec-7-ene, and 1,4-diazabicyclo[2.2.2]octane), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), or an aromatic amine (e.g., pyridine, 2,6-lutidine, and collidine); (iii) the solvent comprises an ether (e.g., 1,2-dimethoxyethane, diethyl ether, 1,4-dioxane, tetrahydrofuran, 2-methyltetrahydrofuran, methyl tert-butyl ether, cyclopentyl methyl ether, diphenyl ether, and dibutyl ether), an ester solvent (e.g., ethyl acetate, isopropyl acetate, n-propyl acetate, and isobutyl acetate), a hydrocarbon (e.g., toluene, trifluorotoluene, cyclohexane, n-heptane, and xylenes), a chlorinated solvent (e.g., dichloromethane, chloroform, dichloroethane, and chlorobenzene), or a polar aprotic solvent (e.g., N,N-dimethylformamide); and/or (iv) the temperature is from about 20° C. to about 80° C.

In some embodiments for step (4p), the chlorinating reagent comprises oxalyl chloride. In some embodiments for step (4p), the base comprises N,N-Diisopropylethylamine. In some embodiments for step (4p), the solvent comprises 1,2-dimethoxyethane. In some embodiments for step (4p), the temperature is from about 55° C. to about 65° C. In some embodiments for step (4p), the temperature is about 60° C. In some embodiments for step (4p), the temperature is from about 20° C. to about 80° C. In some embodiments for step (4p), the temperature is from about 20° C., about 25° C., about 30° C., about 35° C., about 40° C., about 45° C., about 50° C., about 55° C., about 60° C., about 65° C., about 70° C., about 75° C., or about 80° C.

In some embodiments for step (4q): (i) the base comprises an amine base (e.g., N,N-Diisopropylethylamine, 1-methylimidazole, N-methylmorpholine, tri-n-propylamine, triethylamine, tri-n-butylamine, 1,8-diazabicyclo[5.4.0]undec-7-ene, and 1,4-diazabicyclo[2.2.2]octane), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), or an aromatic amine (e.g., pyridine, 2,6-lutidine, and collidine); (ii) the solvent comprises an alcohol (e.g., methanol, ethanol, tert-butanol, sec-butanol, and isopropanol), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), a hydrocarbon (e.g., toluene, trifluorotoluene, cyclohexane, n-heptane, and xylenes), a polar aprotic solvent (e.g., N,N-dimethylformamide, N,N-dimethylacetamide, N-methyl-2-pyrrolidinone, and dimethyl sulfoxide), or a nitrile (e.g., acetonitrile, propionitrile, butyronitrile); and/or (iii) the temperature is from about 20° C. to about 100° C.

In some embodiments for step (4q), the base comprises N,N-Diisopropylethylamine. In some embodiments for step (4q), the solvent comprises isopropanol. In some embodiments for step (4q), the temperature is from about 70° C. to about 80° C. In some embodiments for step (4q), the temperature is about 75° C. In some embodiments for step (4q), the temperature is from about 20° C. to about 100° C. In some embodiments for step (4q), the temperature is from about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

Synthesis of Compound 2M

In a non-limiting example, Scheme 5 illustrates one embodiment of preparing Compound 2M. In one aspect, Compound 2M is prepared from a process comprising: (5a) contacting Compound 2H with a chlorinating reagent, optionally an amine catalyst, and optionally an acidic additive in a solvent at a temperature sufficient to provide Compound 2I; (5b) contacting Compound 2I with TsHNNH$_2$ in a solvent at a temperature sufficient to provide Compound 2J; (5c) contacting Compound 2J with Compound 2K in the presence of a base in a solvent at a temperature sufficient to provide Compound 2L; (5d) contacting Compound 2L with a base in a solvent at a temperature sufficient to provide Compound 2M.

In some embodiments for step (5a): (i) the chlorinating reagent comprises sulfuryl chloride, chlorine gas, or a source of electrophilic chlorine (e.g., acetyl chloride/ceric ammonium nitrate, lithium diisopropylamide/4-toluenesulfonyl chloride, iodosobenzene dichloride, trichloromethanesulfonyl chloride, 1,3-dichloro-5,5-dimethylhydantoin/ammonium chloride, tetrachlorosilane/urea-hydrogen peroxide, N-chlorosuccinimide, trichloroisocyanuric acid, and 3,5-dichloro-2-hydroxy-4,6-s-triazinedione sodium salt); (ii) the amine catalyst, if present, comprises a pyrrolidine type organocatalyst (e.g., L-proline amide, and (2R,5R)-diphenylpyrrolidine); (iii) the acidic additive, if present, comprises a Brønsted Acid (e.g., methanesulfonic acid, p-toluenesulfonic acid, and hydrochloric acid); (iv) the solvent comprises a carboxylic acid (e.g., acetic acid, trifluoroacetic acid, and propionic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, and tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (v) the temperature is from about 30° C. to about 70° C.

In some embodiments for step (5a), the chlorinating reagent comprises sulfuryl chloride. In some embodiments for step (5a), the amine catalyst is absent. In some embodiments for step (5a), the acidic additive is absent. In some embodiments for step (5a), the solvent comprises acetic acid. In some embodiments for step (5a), the temperature is from about 35° C. to about 50° C. In some embodiments for step (5a), the temperature is from about 30° C. to about 70° C. In some embodiments for step (5a), the temperature is about 30° C., about 35° C., about 40° C., about 45° C., about 50° C., about 55° C., about 60° C., about 65° C., or about 70° C.

In some embodiments for step (5b): (i) the solvent comprises a carboxylic acid (e.g., acetic acid, trifluoroacetic acid, propionic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, and tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (ii) the temperature is from about 30° C. to about 70° C.

In some embodiments for step (5b), the solvent comprises acetic acid. In some embodiments for step (5b), the temperature is from about 35° C. to about 50° C. In some embodiments for step (5b), the temperature is from about 30° C. to about 70° C. In some embodiments for step (5b), the temperature is about 30° C., about 35° C., about 40° C., about 45° C., about 50° C., about 55° C., about 60° C., about 65° C., or about 70° C.

In some embodiments for step (5c): (i) the base comprises a tertiary amine base (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), a hydroxide base (e.g., lithium hydroxide, potassium hydroxide, and sodium hydroxide), a carbonate base (e.g., potassium carbonate, sodium carbonate, and cesium carbonate), a bicarbonate base (e.g., sodium bicarbonate, and potassium bicarbonate), a tetraalkylammonium hydroxide (e.g., tetrabutylammonium hydroxide, benzyltrimethylammonium hydroxide, and choline hydroxide), an alkoxide base (e.g., sodium or potassium methoxide, and sodium or potassium ethoxide), or a phosphate base (e.g., sodium phosphate monobasic, sodium phosphate dibasic, potassium phosphate monobasic, and potassium phosphate dibasic); (ii) the solvent comprises water, a nitrile (e.g., acetonitrile, propionitrile, and butyronitrile), a hydrocarbon solvent (e.g., toluene, 2-methyltetrahydrofuran, trifluorotoluene, cyclohexane, n-heptane, and xylenes), a chlorinated solvent (e.g., dichloromethane, chloroform, dichloroethane, and chlorobenzene), an ether solvent (e.g., diethyl ether, 1,4-dioxane, tetrahydrofuran, dimethoxyethane, methyl tert-butyl ether, cyclopentyl methyl ether, diphenyl ether, and dibutyl ether), an alcohol solvent (e.g., methanol, ethanol, isopropanol, and tert-butanol), or a combination thereof, and/or (iii) the temperature is from about −20° C. to about 60° C.

In some embodiments for step (5c), (i) the base comprises potassium carbonate. In some embodiments for step (5c), the solvent comprises 2-methyltetrahydrofuran and water, or acetonitrile. In some embodiments for step (5c), the temperature is from about −20° C. to about 20° C. In some embodiments for step (5c), the temperature is from about −20° C. to about 60° C. In some embodiments for step (5c), the temperature is about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., or about 60° C.

In some embodiments for step (5d): (i) the base comprises a hydroxide base (e.g., sodium hydroxide, lithium hydroxide, and potassium hydroxide); (ii) the solvent comprises water, a nitrile solvent (e.g., acetonitrile, propionitrile, and butyronitrile), a hydrocarbon solvent (e.g., toluene, trifluorotoluene, cyclohexane, n-heptane, and xylenes), a chlorinated solvent (e.g., dichloromethane, chloroform, dichloroethane, and chlorobenzene), an ether solvent (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an alcohol solvent (e.g., methanol, ethanol, isopropanol, and tert-butanol), or a combination thereof, and/or (iii) the temperature is from about −10° C. to about 80° C.

In some embodiments for step (5d), the base comprises sodium hydroxide. In some embodiments for step (5d), the solvent comprises 2-methyltetrahydrofuran and water. In some embodiments for step (5d), the temperature is from about 15° C. to about 25° C. In some embodiments for step (5d), the temperature is about 20° C. In some embodiments for step (5d), the temperature is from about −10° C. to about 80° C. In some embodiments for step (5d), the temperature is about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., or about 80° C.

Synthesis of Compound 2B

In a non-limiting example, Scheme 6 illustrates one embodiment of preparing Compound 2B. In one aspect, Compound 2B is prepared from a process comprising: (6a) contacting Compound 1E with a copper catalyst, an amine ligand, and an iodide additive in a solvent at a temperature sufficient to provide Compound 2O; (6b) contacting Compound 2O with an alkylating agent in a solvent at a temperature sufficient to provide Compound 2P, wherein X is iodide, chloride, bromide, methylsulfate, sulfate, methylcarbonate, carbonate, methanesulfonate, trifluoromethanesulfonate, toluenesulfonate, or tetrafluoroborate; (6c) contacting Compound 2P with an oxidant and a base in a solvent at a temperature sufficient to provide Compound 2B.

In some embodiments for step (6a): (i) the copper catalyst comprises copper(I) iodide, copper(I) bromide, copper(I) chloride, copper(I) oxide, copper(I) acetate, copper(I) bromide dimethyl sulfide complex, copper(I) triflate, copper(I) iodide tetrabutylammonium iodide complex, tetrakis(acetonitrile)copper(I) hexafluorophosphate, copper(I) iodide triethylphosphite complex, or copper(I) bromide triphenylphosphine complex; (ii) the amine ligand comprises trans-N,N'-dimethylcyclohexane-1,2-diamine, N1,N2-dimethylethane-1,2-diamine, N1,N3-dimethylpropane-1,3-diamine, or N1-(2-aminoethyl)ethane-1,2-diamine; (iii) the iodide additive comprises sodium iodide, lithium iodide, or potassium iodide; (iv) the solvent comprises an ether (e.g., diethylene glycol dimethylether, diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (v) the temperature is from about 50° C. to about 150° C.

In some embodiments for step (6a), the copper catalyst comprises copper(I) iodide. In some embodiments for step (6a), the amine ligand comprises trans-N,N'-dimethylcyclohexane-1,2-diamine. In some embodiments for step (6a), the iodide additive comprises sodium iodide. In some embodiments for step (6a), the solvent comprises diethylene glycol dimethylether. In some embodiments for step (6a), the temperature is from about 80° C. to about 130° C. In some embodiments for step (6a), the temperature is from about 50° C. to about 150° C. In some embodiments for step (6a), the temperature is from about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about 150° C.

In some embodiments for step (6b): (i) the alkylating agent comprises iodomethane, trimethylsulfoxonium iodide, diazomethane, dimethylsulfate, 2,2-dimethoxypropane, a carbonate (e.g., dimethylcarbonate, and dimethyldicarbonate), a sulfonate (e.g., methyl fluorosulfonate, and methyl methanesulfonate), chloromethane, bromomethane, or trimethyloxonium tetrafluoroborate; (ii) the solvent comprises an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a chlorinated solvent (e.g., dichloromethane, chloroform, dichloroethane, and chlorobenzene); and/or (iii) the temperature is from about 0° C. to about 100° C.

In some embodiments for step (6b), the alkylating agent comprises iodomethane. In some embodiments for step (6b), the solvent comprises acetonitrile. In some embodiments for step (6b), the temperature is from about 20° C. to about 40° C. In some embodiments for step (6b), the temperature is about 30° C. In some embodiments for step (6b), the temperature is from about 0° C. to about 100° C. In some embodiments for step (6b), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C. In some embodiments for step (6b), X is iodide.

In some embodiments for step (6c): (i) the oxidant comprises potassium ferricyanide, oxone, lead tetraacetate, peracetic acid, hydrogen peroxide, molecular oxygen, air, sodium hypochlorite, sodium chlorite, sodium periodate, potassium peroxymonosulfate, 2,3-dichloro-5,6-dicyano-1,4-benzoquinone, 1,4-benzoquinone, periodic acid, potassium bromate, meta-chloroperoxybenzoic acid, or magnesium monoperoxyphthalate; (ii) the base comprises a hydroxide base (e.g., lithium hydroxide, potassium hydroxide, and ammonium hydroxide); (iii) the solvent comprises water, an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (iv) the temperature is from about 0° C. to about 70° C.

In some embodiments for step (6c), the oxidant comprises potassium ferricyanide. In some embodiments for step (6c), the base comprises potassium hydroxide. In some embodiments for step (6c), the solvent comprises water. In some embodiments for step (6c), the temperature is from about 5° C. to about 20° C. In some embodiments for step (6c), the temperature is from about 0° C. to about 70° C. In some embodiments for step (6c), the temperature is from about 0° C., about 5° C., about 10° C., about 15° C., about 20° C., about 25° C., about 30° C., about 35° C., about 40° C., about 45° C., about 50° C., about 55° C., about 60° C., about 65° C., or about 70° C.

Compound 1 Alternate Route 1

In a non-limiting example, Scheme 23 is a scheme depicting one embodiment of the alternate synthesis 1 of Compound 1.

Scheme 23

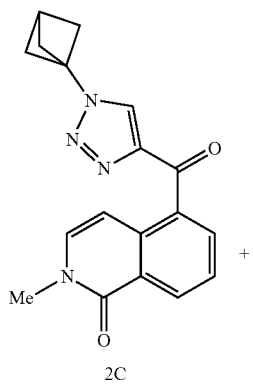

2C

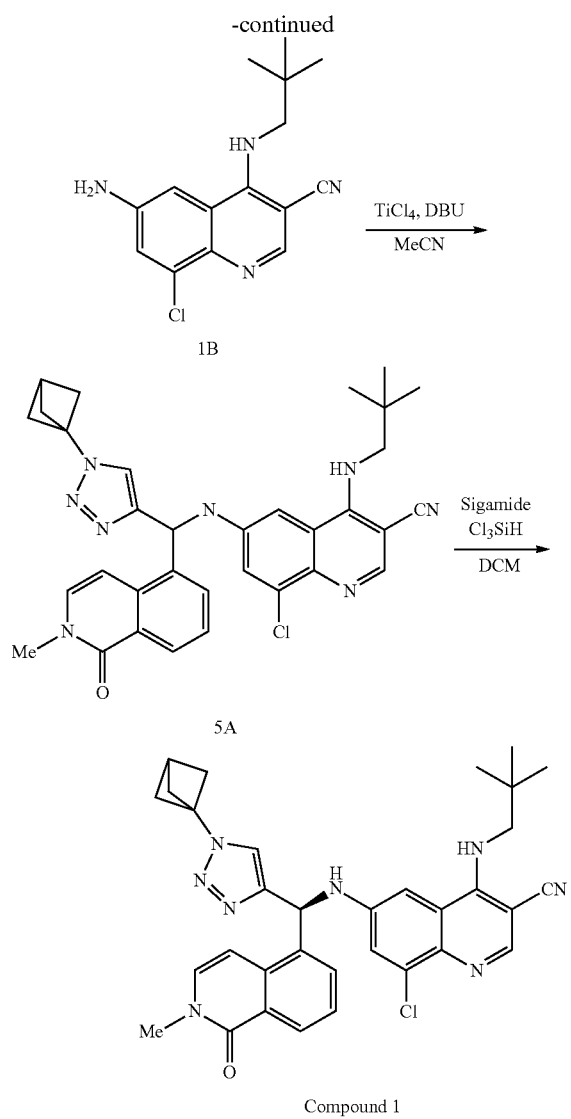

Compound 1

One method for the synthesis of Compound 1 is a process comprising: (7a) contacting Compound 2C with Compound 1B in the presence of a titanium catalyst and a base in a solvent at an temperature sufficient to provide Compound 5A; and (7b) contacting Compound 5A in the presence of a catalyst and a reagent in a solvent at a temperature sufficient to provide Compound 1.

In some embodiments for step (7a): (i) the titanium catalyst comprises a titanium Lewis Acid (e.g., titanium(IV) tetrachloride titanium(IV) ethoxide, titanium(IV) isopropoxide); (ii) the base comprises a tertiary amine (e.g., 1,8-Diazabicyclo[5.4.0]undec-7-ene (DBU)N-methylmorpholine, tri-n-propylamine, N,N-diisopropylethylamine, triethylamine, tri-n-butylamine, and 1,4-diazabicyclo[2.2.2]octane); (iii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a chlorinated solvent (e.g., dichloromethane, chloroform, dichloroethane, and chlorobenzene), a hydrocarbon solvent (e.g., toluene, trifluorotoluene, cyclohexane, n-heptane, and xylenes), or a nitrile (e.g., acetonitrile, propionitrile, and butyronitrile); and/or (iv) the temperature is from about −10° C. to about 120° C.

In some embodiments for step (7a), the titanium catalyst comprises titanium(IV) tetrachloride. In some embodiments for step (7a), the base comprises 1,8-diazabicyclo[5.4.0]undec-7-ene (DBU). In some embodiments for step (7a), the solvent comprises acetonitrile. In some embodiments for step (7a), the temperature is from about 40° C. to about 60° C. In some embodiments for step (7a), the temperature is about 50° C. In some embodiments for step (7a), the temperature is from about −10° C. to about 120° C. In some embodiments for step (7a), the temperature is from about −10° C., about −5° C., about 0° C., about 5° C., about 10° C., about 15° C., about 20° C., about 25° C., about 30° C., about 35° C., about 40° C., about 45° C., about 50° C., about 55° C., about 60° C.

In some embodiments for step (7b): (i) the catalyst comprises Sigamide ((S)—N-(3,5-Di-tert-butylphenyl)-3-methyl-2-(N-formyl-N-methylamino)butanamide), a Noyori Type Ru or Rh catalyst (e.g., RuCl(mesitylene)[(S,S)-Ts-DPEN], and RuCl(p-cymene)[(R,R)-Teth-Ts-DPEN]), a CBS type catalyst, a copper hydride-bisoxazoline complexes with stoichiometric reductants, a chiral phosphine ligands with transitions metals such as Pd, Ru, Rh, or Ir (e.g., BINAP, DIPAMP, Segphos, Phanephos, Norphos, Me-DuPhos, PPhos, Josiphos, MeBoPhoz, and Chenphos), or a chiral formamide catalysts; (ii) the reagent comprises trichlorosilane, hydrogen gas or hydrogen equivalents (e.g., Ammonium formate, iPrOH, and Formic Acid-Triethylamine), a chiral borane reagent (e.g., Alpine Borane, and ipc-borane), a chiral borohydride reagent (e.g., Alpine-Hydride), a borane or amine·borane reagent with a chiral CBS-type catalyst (e.g., Borane·THF, Borane·DMS, Ammonia Borane, and Diethylphenylamine-borane), a silane with chiral DMF or a chiral copper catalyst (e.g., Triethoxysilane, Triphenylsilane, and Triethylsilane); (iii) the solvent comprises an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a chlorinated solvent (e.g., chloroform, dichloromethane, dichloroethane, and chlorobenzene), an alcohol (e.g., methanol, ethanol, isopropanol, tert-butanol, and 1-propanol), a hydrocarbon solvent (e.g., toluene, trifluorotoluene, cyclohexane, n-heptane, and xylenes); and/or (iv) the temperature is from about −40° C. to about 120° C.

In some embodiments for step (7b), the catalyst comprises Sigamide ((S)—N-(3,5-Di-tert-butylphenyl)-3-methyl-2-(N-formyl-N-methylamino)butanamide). In some embodiments for step (7b), the reagent comprises trichlorosilane. In some embodiments for step (7b), the solvent comprises dichloromethane. In some embodiments for step (7b), the temperature is from about 20° C. to about 40° C. In some embodiments for step (7b), the temperature is about 30° C. In some embodiments for step (7b), the temperature is from about −40° C. to about 120° C. In some embodiments for step (7b), the temperature is about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C.

Compound 1 Alternate Route 2

In a non-limiting example, Scheme 24 is a scheme depicting one embodiment of the alternate synthesis 2 of Compound 1.

Scheme 24

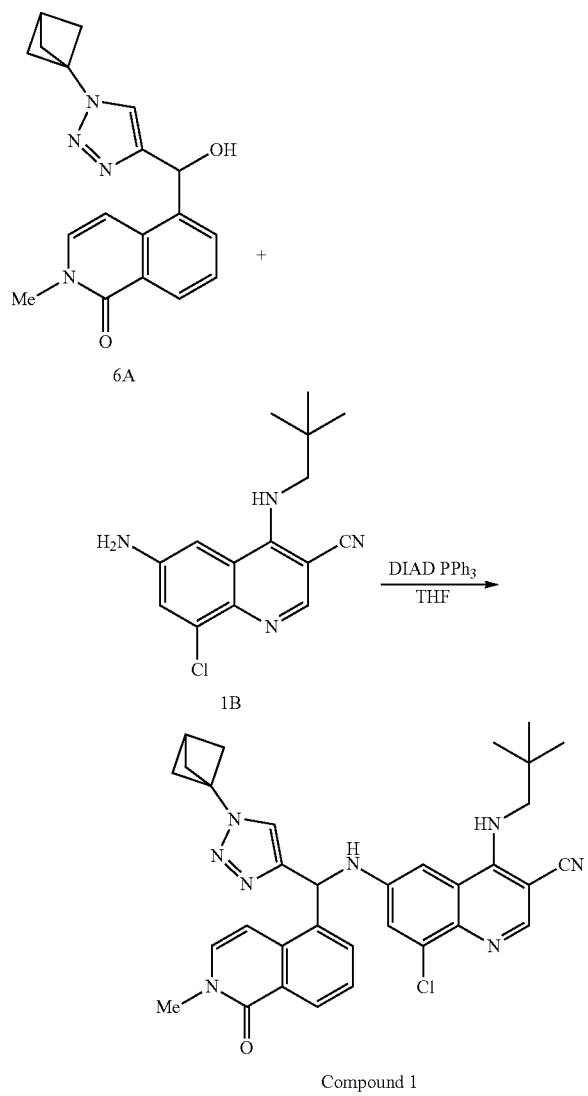

Compound 1

One method for the synthesis of Compound 1 is a process comprising: (8a) contacting Compound 6A with Compound 1B in the presence of a reagent, and optionally an additive, in a solvent at a temperature sufficient to provide Compound 1.

In some embodiments for step (8a): (i) the reagent comprises a tertiary phosphine (e.g., triphenylphosphine, tributylphosphine, tri(2-furyl)phosphine, tri(p-tolyl)phosphine, and tri(o-tolyl)phosphine) with a coupling reagent (e.g., diisopropyl azodicarboxylate, dicyclohexylcarbodiimide, diisopropylcarbodiimide, and 1-ethyl-3-(3-dimethylaminopropyl)carbodiimide), carbonyl diimidazole, isobutyl chloroformate, 3-[Bis(dimethylamino)methyliumyl]-3H-benzotriazol-1-oxide hexafluorophosphate, 1-[Bis(dimethylamino)methylene]-1H-1,2,3-triazolo[4,5-b]pyridinium 3-oxide hexafluorophosphate, N-[(7-Aza-1H-benzotriazol-1-yl)(dimethylamino)methylene]-N-methylmethanaminium tetrafluoroborate N-oxide, 2-(1H-Benzotriazole-1-yl)-1,1,3,3-tetramethylaminium tetrafluoroborate, 0-(1H-6-Chlorobenzotriazole-1-yl)-1,1,3,3-tetramethyluronium hexafluorophosphate, (Benzotriazol-1-yloxy)tris(dimethylamino)phosphonium hexafluorophosphate, (Benzotriazol-1-yloxy)tripyrrolidinophosphonium hexafluorophosphate, (1-Cyano-2-ethoxy-2-oxoethylidenaminooxy)dimethylamino-morpholino-carbenium hexafluorophosphate, oxalyl chloride, thionyl chloride; (ii) the additive, if present, comprises 4-dimethylaminopyridine, hydroxybenzotriazole, or 1-Hydroxy-7-azabenzotriazole; (iii) the solvent comprises an ether (e.g., diethyl ether, tetrahydrofuran, 1,4-dioxane, 2-methyltetrahydrofuran, dimethoxyethane, methyl tert-butyl ether, cyclopentyl methyl ether, diphenyl ether, and dibutyl ether), a hydrocarbon solvent (e.g., toluene, trifluorotoluene, cyclohexane, n-heptane, and xylenes), an ester (e.g., ethyl acetate, isopropyl acetate, n-propyl acetate, and isobutyl acetate), a polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, and butyronitrile), or a chlorinated solvent (e.g., dichloromethane, chloroform, dichloroethane, and chlorobenzene); and/or (iv) the temperature is from about 0° C. to about 100° C.

In some embodiments for step (8a), the reagent comprises diisopropyl azodicarboxylate and triphenylphosphine. In some embodiments for step (8a), the additive is not present. In some embodiments for step (8a), the solvent comprises tetrahydrofuran. In some embodiments for step (8a), the temperature is from about 20° C. to about 30° C. In some embodiments for step (8a), the temperature is about 25° C. In some embodiments for step (8a), the temperature is from about 0° C. to about 100° C. In some embodiments for step (8a), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

Compound 1 Alternate Route 3

In a non-limiting example, Scheme 25 is a scheme depicting one embodiment of the alternate synthesis 3 of Compound 1.

Scheme 25

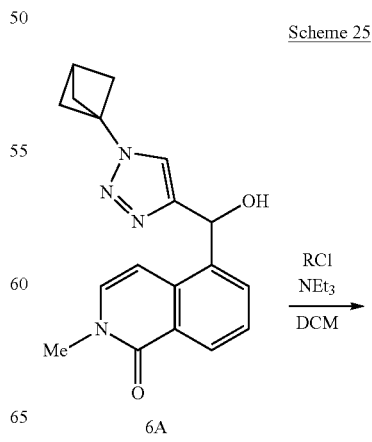

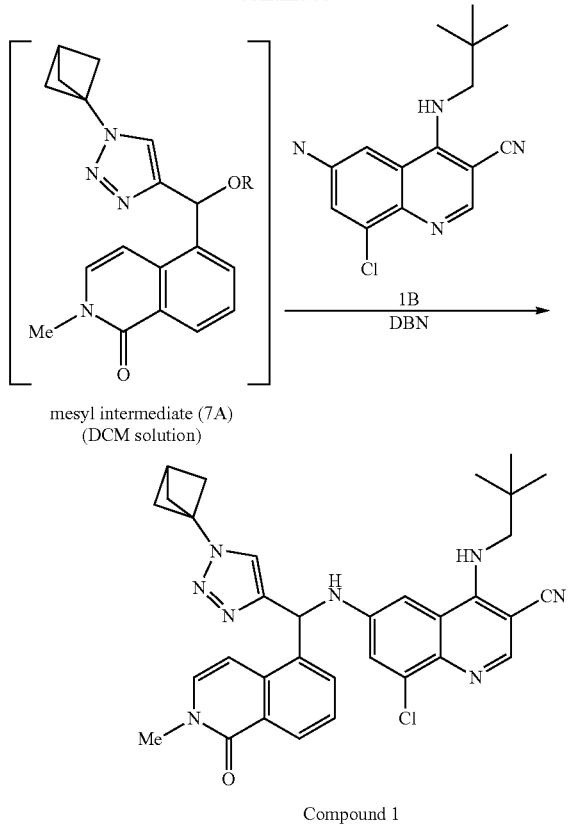

mesyl intermediate (7A)
(DCM solution)

Compound 1

One method for the synthesis of Compound 1 is a process comprising: (9a) contacting Compound 6A with an activating reagent and a base in a solvent at a temperature sufficient to provide Compound 7A, wherein R is methylsulfonyl, ethylsulfonyl, toluenesulfonyl, phenylsulfonyl, 4-chlorobenzenesulfonyl, or 4-nitrobenzenesulfonyl; and (9b) contacting Compound 7A with Compound 1B in the presence of a base in a solvent at a temperature sufficient to provide Compound 1.

In some embodiments for step (9a): (i) the activating reagent comprises methanesulfonic anhydride, or a sulfonyl chloride (e.g., methanesulfonyl chloride, ethylsulfonyl chloride, toluenesulfonyl chloride, phenylsulfonyl chloride, 4-chlorobenzenesulfonyl chloride, and 4-nitrobenzenesulfonyl chloride); (ii) the base comprises a tertiary amine (e.g., triethylamine, N-methylmorpholine, tri-n-propylamine, N,N-diisopropylethylamine, tri-n-butylamine, 1,8-diazabicyclo[5.4.0]undec-7-ene, and 1,4-diazabicyclo[2.2.2]octane), an aromatic amine (e.g., pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, cesium carbonate, and sodium hydride), an alkoxide base (e.g., potassium tert-butoxide, and sodium tert-butoxide), or a hydroxide base (e.g., sodium hydroxide, lithium hydroxide, potassium hydroxide, and ammonium hydroxide); (iii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a hydrocarbon solvent (e.g., toluene, trifluorotoluene, cyclohexane, n-heptane, and xylenes), an ester (e.g., ethyl acetate, isopropyl acetate, n-propyl acetate, and isobutyl acetate), a polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, and butyronitrile), a chlorinated solvent (e.g., dichloromethane, chloroform, dichloroethane, and chlorobenzene); and/or (iv) the temperature is from about 0° C. to about 100° C.

In some embodiments for step (9a), the activating reagent comprises methanesulfonyl chloride. In some embodiments for step (9a), the base comprises triethylamine. In some embodiments for step (9a), the solvent comprises dichloromethane. In some embodiments for step (9a), the temperature is from about 0° C. to about 25° C. In some embodiments for step (9a), the temperature is from about 0° C. to about 100° C. In some embodiments for step (9a), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C. In some embodiments for step (9a), R is methylsulfonyl.

In some embodiments for step (9b), (i) the base comprises a tertiary amine (e.g., 1,5-diazabicyclo[4.3.0]non-5-ene (DBN), N-methylmorpholine, tri-n-propylamine, triethylamine, N,N-diisopropylethylamine, tri-n-butylamine, 1,8-diazabicyclo[5.4.0]undec-7-ene, and 1,4-diazabicyclo[2.2.2]octane), an aromatic amine (e.g., pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, cesium carbonate, and sodium hydride), an alkoxide base (e.g., potassium tert-butoxide, and sodium tert-butoxide), or a hydroxide base (e.g., sodium hydroxide, lithium hydroxide, potassium hydroxide, and ammonium hydroxide); (ii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a hydrocarbon solvent (e.g., toluene, trifluorotoluene, cyclohexane, n-heptane, and xylenes), an ester (e.g., ethyl acetate, isopropyl acetate, n-propyl acetate, and isobutyl acetate), a polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, and butyronitrile), a chlorinated solvent (e.g., dichloromethane, chloroform, dichloroethane, and chlorobenzene); and/or (iii) the temperature is from about 0° C. to about 100° C.

In some embodiments for step (9b), the base comprises 1,5-diazabicyclo[4.3.0]non-5-ene (DBN). In some embodiments for step (9b), the solvent comprises dichloromethane. In some embodiments for step (9b), the temperature is from about 20° C. to about 30° C. In some embodiments for step (9b), the temperature is about 25° C. In some embodiments for step (9b), the temperature is from about 0° C. to about 100° C. In some embodiments for step (9b), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100 CC.

Alternate Synthesis of Compound 2M from Ethyl Pyruvate

In a non-limiting example, Scheme 11 is a scheme depicting one embodiment of the alternate synthesis of Compound 2M from ethyl pyruvate.

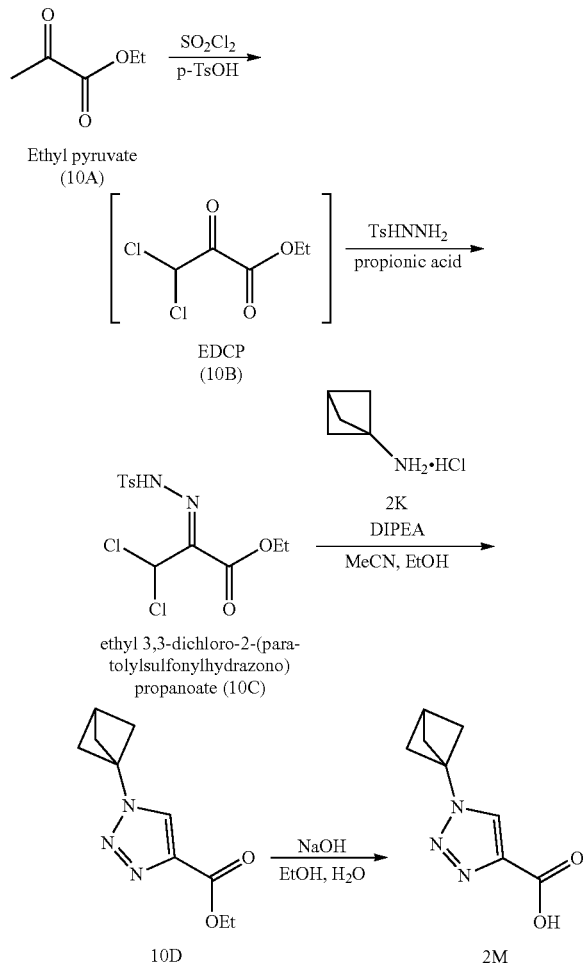

Scheme 11

In some embodiments, Compound 2M is prepared from a process comprising: (10a) contacting Compound 10A with a chlorinating reagent, optionally an amine catalyst, and optionally an acidic additive in an optional solvent at a temperature sufficient to provide Compound 10B; (10b) contacting Compound 10B with TsHNNH₂ in a solvent at a temperature sufficient to provide Compound 10C; (10c) contacting Compound 10C with Compound 2K in the presence of a base in a solvent at a temperature sufficient to provide Compound 10D; (10d) contacting Compound 10D with a base in a solvent at a temperature sufficient to provide Compound 2M.

In some embodiments for step (10a): (i) the chlorinating reagent comprises sulfuryl chloride, chlorine gas, or a source of electrophilic chlorine (e.g., acetyl chloride/ceric ammonium nitrate, lithium diisopropylamide/4-toluenesulfonyl chloride, iodosobenzene dichloride, trichloromethanesulfonyl chloride, 1,3-dichloro-5,5-dimethylhydantoin/ammonium chloride, tetrachlorosilane/urea-hydrogen peroxide, N-chlorosuccinimide, trichloroisocyanuric acid, and sodium dichloroisocyanurate); (ii) the amine catalyst, if present, comprises a pyrrolidine type organocatalyst (e.g., L-proline amide, and (2R,5R)-diphenylpyrrolidine); (iii) the acidic additive, if present, comprise p-toluenesulfonic acid or a Brønsted Acid (e.g., hydrochloric acid, and methanesulfonic acid); (iv) the solvent, if present, comprises a carboxylic acid (e.g., trifluoroacetic acid, acetic acid, formic acid, and propionic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, tert-butanol), a nitrile (e.g., acetonitrile, propionitrile, and butyronitrile), or a hydrocarbon solvent (e.g., toluene, trifluorotoluene, cyclohexane, n-heptane, and xylenes); and/or (v) the temperature is from about 40° C. to about 80° C.

In some embodiments for step (10a), the chlorinating reagent comprises sulfuryl chloride. In some embodiments for step (10a), the amine catalyst is absent. In some embodiments for step (10a), the acidic additive comprises p-toluenesulfonic acid. In some embodiments for step (10a), the solvent is absent. In some embodiments for step (10a), the temperature is from about 65° C. to about 75° C. In some embodiments for step (10a), the temperature is from about 40° C. to about 80° C. In some embodiments for step (10a), the temperature is about 40° C., about 45° C., about 50° C., about 55° C., about 60° C., about 65° C., about 70° C., about 75° C., or about 80° C.

In some embodiments for step (10b): (i) the solvent comprises a carboxylic acid (e.g., propionic acid, trifluoroacetic acid, acetic acid, and formic acid), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, and diphenyl ether), a chlorinated solvent (e.g., dichloromethane, chloroform, dichloroethane, and chlorobenzene), an alcohol (e.g., methanol, ethanol, isopropanol, and tert-butanol), nitriles (e.g., acetonitrile, propionitrile, and butyronitrile), a hydrocarbon solvent (e.g., toluene, trifluorotoluene, cyclohexane, n-heptane, and xylenes); and/or (ii) the temperature is from about 20° C. to about 60° C.

In some embodiments for step (10b), the solvent comprises propionic acid. In some embodiments for step (10b), the temperature is about 25° C. In some embodiments for step (10b), the temperature is from about 20° C. to about 60° C. In some embodiments for step (10b), the temperature is about 20° C., about 25° C., about 30° C., about 35° C., about 40° C., about 45° C., about 50° C., about 55° C., or about 60° C.

In some embodiments for step (10c): (i) the base comprises a tertiary amine (e.g., N,N-diisopropylethylamine, N-methylmorpholine, tri-n-propylamine, triethylamine, tri-n-butylamine, 1,8-diazabicyclo[5.4.0]undec-7-ene, and 1,4-diazabicyclo[2.2.2]octane), an aromatic amine (e.g., pyridine, 2,6-lutidine, and collidine), or an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate); (ii) the solvent comprises an alcohol (e.g., methanol, isopropanol, tert-butanol, ethanol, and 1-propanol), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a hydrocarbon solvent (e.g., benzene, toluene, trifluorotoluene, cyclohexane, n-heptane, and xylenes), a chlorinated solvent (e.g., dichloromethane, chloroform, dichloroethane, and chlorobenzene), a nitrile (e.g., acetonitrile, propionitrile, and butyronitrile), a polar aprotic solvent (e.g., N,N-dimethylformamide, N,N-dimethylacetamide, N-methyl-2-pyrrolidinone, and dimethyl sulfoxide), or a combination thereof; and/or (iii) the temperature is from about −20° C. to about 60° C.

In some embodiments for step (10c), the base comprises N,N-diisopropylethylamine. In some embodiments for step (10c), the solvent comprises acetonitrile and ethanol. In some embodiments for step (10c), the temperature is from about 0° C. to about 20° C. In some embodiments for step (10c), the temperature is from about −20° C. to about 60° C. In some embodiments for step (10c), the temperature is about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., or about 60° C.

In some embodiments for step (10d): (i) the base comprises a hydroxide base (e.g., sodium hydroxide, lithium hydroxide, and potassium hydroxide), or potassium trimethylsilanoate; (ii) the solvent comprises water, an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an alcohol (e.g., methanol, ethanol, isopropanol, tert-butanol, and 1-propanol), a hydrocarbon solvent (e.g., benzene, toluene, trifluorotoluene, cyclohexane, n-heptane, and xylenes), a nitrile (e.g., acetonitrile, propionitrile, and butyronitrile), chlorinated solvents (e.g., dichloromethane, chloroform, dichloroethane, and chlorobenzene), or a combination thereof; and/or (iii) the temperature is from about 0° C. to about 100° C.

In some embodiments for step (10d), the base comprises sodium hydroxide. In some embodiments for step (10d), the solvent comprises ethanol and water. In some embodiments for step (10d), the temperature is from about 10° C. to about 70° C. In some embodiments for step (10d), temperature is from about 0° C. to about 100° C. In some embodiments for step (10d), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

Alternate Synthesis of Compound 2L from Click Chemistry

In a non-limiting example, Scheme 12 is a scheme depicting one embodiment of the alternate synthesis of Compound 2L via click chemistry.

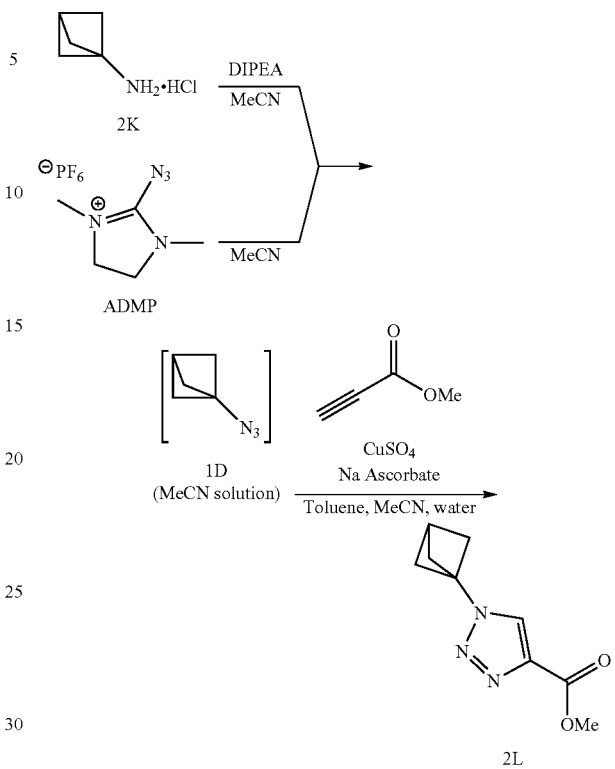

Scheme 12

In some embodiments, Compound 2L is prepared from a process comprising: (11a) contacting Compound 2K with an azide reagent and base in a solvent at a temperature sufficient to provide Compound 1D; (11b) contacting Compound 1D with

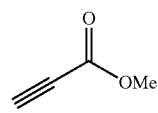

a copper reagent, and optionally, a reagent in a solvent at a temperature sufficient to provide Compound 2L.

In some embodiments for step (11a): (i) the azide reagent comprises 2-azido-1,3-dimethylimidazolinium hexafluorophosphate (ADMP), imidazole-1-sulfonyl azide hydrochloric acid salt, imidazole-1-sulfonyl azide sulfuric acid salt, imidazole-1-sulfonyl azide tetrafluoroboric acid salt, or para-toluenesulfonylazide; (ii) the base comprises a tertiary amine (e.g., N,N-diisopropylethylamine N-methylmorpholine, tri-n-propylamine, triethylamine, tri-n-butylamine, 1,8-diazabicyclo[5.4.0]undec-7-ene, and 1,4-diazabicyclo[2.2.2]octane), diethylamine, or dibutylamine; (iii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), an alcohol (e.g., methanol, ethanol, isopropanol, and tert-butanol), a polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, and butyronitrile), or hydrocarbon solvents (e.g., trifluorotoluene, toluene, cyclohexane, n-heptane, and xylenes); and/or (iv) the temperature is from about 0° C. to about 50° C.

In some embodiments for step (11a), the azide reagent comprises 2-azido-1,3-dimethylimidazolinium hexafluorophosphate (ADMP). In some embodiments for step (11a), the base comprises N,N-diisopropylethylamine. In some embodiments for step (11a), the solvent comprises acetonitrile. In some embodiments for step (11a), the temperature is about 20° C. In some embodiments for step (11a), the temperature is from about 0° C. to about 50° C. In some embodiments for step (11a), the temperature is about 0° C., about 5° C., about 10° C., about 15° C., about 20° C., about 25° C., about 30° C., about 35° C., about 40° C., about 45° C., or about 50° C.

In some embodiments, step (11a) is performed in a batch mode. In some embodiments, contacting Compound 2K with an azide reagent and a base in a solvent at a temperature provides a stoichiometric amount of Compound 1D. In some embodiments, producing a stoichiometric amount of Compound 1D comprises simultaneously adding Compound 2K, the azide reagent, the base and the solvent into a batch reactor. In some embodiments, the stoichiometric amount of Compound 1D is contacted with

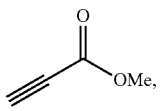

a copper reagent, and optionally, a reagent in a solvent at a temperature sufficient to provide Compound 2L.

In some embodiments step (11a) is performed in a continuous flow process. In some embodiments, Compound 2K, the azide reagent, the base and the solvent are added into a continuous flow reactor to produce Compound 1D. In some embodiments, Compound 1D is contacted with

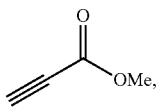

a copper reagent, and optionally, a reagent in a batch reactor in a solvent at a temperature sufficient to provide Compound 2L. In some embodiments, Compound 1D produced into the continuous flow reactor is continuously fed to a batch reactor containing methyl propiolate, the copper reagent, sodium ascorbate, solvent, and optionally, the reagent to provide Compound 2L.

In some embodiments, step (11a) is performed in the following manner to provide Compound 2L in a continuous flow process. In some embodiments, a reactor is charged with methyl propiolate, copper sulfate, sodium ascorbate, toluene, and water. In some embodiments, Compound 2K, diisopropylethylamine and acetonitrile are combined in a second vessel. In some embodiments, 2-azido-1,3-dimethylimidazolinium hexafluorophosphate (ADMP) and acetonitrile are combined in a third vessel. In some embodiments, the mixtures containing Compound 2K and ADMP in the second and third vessels, respectively, are combined in a tube or continuous flow reactor to form Compound 1D, and the resulting mixture containing Compound 2L is collected in the first reactor containing methyl propiolate.

Alternate Synthesis of Compound 2A from Ethyl 1-(bicyclo[1.1.1]pentan-1-yl)-1H-1,2,3-triazole-4-carboxylate In a non-limiting example, Scheme 13 is a scheme depicting one embodiment of the alternate synthesis of Compound 2A from ethyl 1-(bicyclo[1.1.1]pentan-1-yl)-1H-1,2,3-triazole-4-carboxylate (Compound 10D).

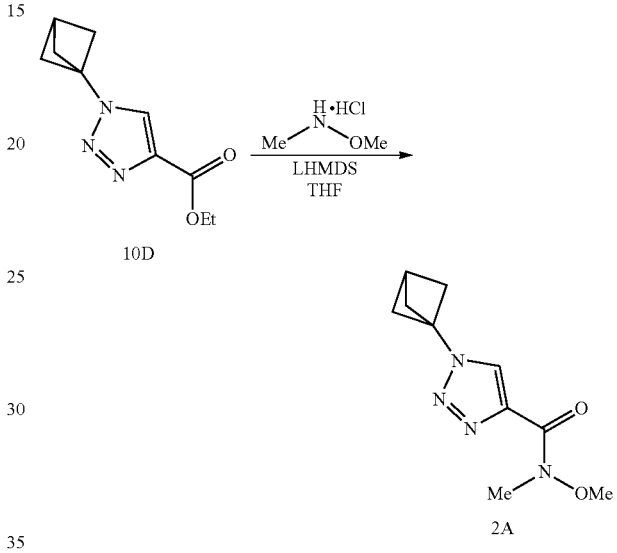

In some embodiments, Compound 2A is prepared from a process comprising: (12a) contacting Compound 10D with MeNHOMe·HCl and a base in a solvent at a temperature sufficient to provide Compound 2A.

In some embodiments for step (12a): (i) the base comprises an organomagnesium reagent (e.g., isopropylmagnesium chloride, tert-butylmagnesium chloride, isopropylmagnesium bromide, isopropylmagnesium chloride lithium chloride complex, and 2,2,6,6-tetramethylpiperidinylmagnesium chloride lithium chloride complex), an organolithium reagent (e.g., phenyllithium, mesityllithium, tert-butyllithium, and sec-butyllithium), or an amide base (e.g., lithium bis(trimethylsilyl)amide, lithium diisopropylamide, potassium bis(trimethylsilyl)amide, and sodium bis(trimethylsilyl)amide); (ii) the solvent comprises an ether (e.g., tetrahydrofuran, diethyl ether, 1,4-dioxane, 2-methyltetrahydrofuran, dimethoxyethane, methyl tert-butyl ether, cyclopentyl methyl ether, diphenyl ether, and dibutyl ether), or a hydrocarbon (e.g., toluene, trifluorotoluene, cyclohexane, n-heptane, and xylenes); and/or (iii) the temperature is from about −40° C. to about 60° C.

In some embodiments for step (12a), the base comprises lithium bis(trimethylsilyl)amide. In some embodiments for step (12a), the solvent comprises tetrahydrofuran. In some embodiments for step (12a), temperature is from about −10° C. to about 10° C. In some embodiments for step (12a), temperature is from about −40° C. to about 60° C. In some embodiments for step (12a), the temperature is about −40° C., about −35° C., about −30° C., about −35° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., or about 60° C.

Alternate Synthesis of Ethyl 1-(Bicyclo[1.1.1]pentan-1-yl)-1H-1, 2, 3-Triazole-4-Carboxylate (Compound 10D)

In a non-limiting example, Scheme 14 is a scheme depicting one embodiment of the alternate synthesis of ethyl 1-(bicyclo[1.1.1]pentan-1-yl)-1H-1,2,3-triazole-4-carboxylate (Compound 10D).

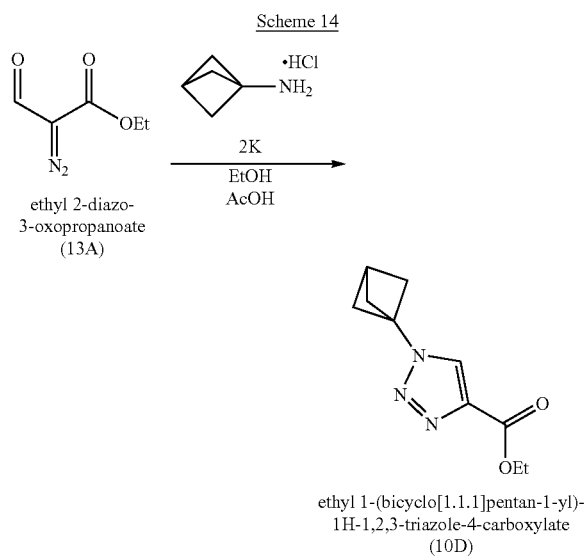

In some embodiments, Compound 10D is prepared from a process comprising: (13a) contacting Compound 13A with Compound 2K with an acid in a solvent at a temperature sufficient to provide Compound 10D.

In some embodiments for step (13a): (i) the acid comprises acetic acid, trifluoroacetic acid, benzoic acid, pivalic acid, hydrochloric acid, sulfuric acid, phosphoric acid, methanesulfonic acid, para-toluenesulfonic acid, propionic acid; (ii) the solvent comprises an alcohol (e.g., methanol, ethanol, isopropanol, and tert-butanol), a nitrile (e.g., acetonitrile, propionitrile, and butyronitrile), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), or a polar aprotic solvent (e.g., N,N-dimethylformamide, N,N-dimethylacetamide, N-methyl-2-pyrrolidinone, and dimethyl sulfoxide); and/or (iii) the temperature is from about 0° C. to about 60° C.

In some embodiments for step (13a), the acid comprises acetic acid. In some embodiments for step (13a), the solvent comprises ethanol. In some embodiments for step (13a), the temperature is about 35° C. In some embodiments for step (13a), the temperature is from about 0° C. to about 60° C. In some embodiments for step (13a), temperature is from about −40° C. to about 60° C. In some embodiments for step (12a), the temperature is about 0° C., about 5° C., about 10° C., about 15° C., about 20° C., about 25° C., about 30° C., about 35° C., about 40° C., about 45° C., about 50° C., about 55° C., or about 60° C.

Alternate Synthesis of 5-Iodoisoquinoline (Compound 2O)

In a non-limiting example, Scheme 15 is a scheme depicting one embodiment of the alternate synthesis of 5-iodoisoquinoline (Compound 2O).

Scheme 15 isoquinoline (14A) → NIS, TfOH → 5-iodo-isoquinoline (IIQ, 2O)

In some embodiments, Compound 2O is prepared from a process comprising: (14a) contacting Compound 14A with an iodide reagent in a solvent at a temperature sufficient to provide Compound 2O.

In some embodiments for step (14a): (i) the iodide reagent comprises N-iodosuccinimide, iodine, iodine with iodic acid, bis(pyridine)iodonium(I) tetrafluoroborate, sodium iodide with bleach, sodium iodide with oxidant (e.g., oxone, sodium periodate, and periodic acid), 1,3-diiodo-5,5-dimethylhydantoin, iodine monochloride, pyridine iodine monochloride; (ii) the solvent comprises trifluoromethanesulfonic acid, sulfuric acid, trifluoroacetic acid, acetic acid, methanesulfonic acid, acid in combination with water, dimethylformamide, methanol, acetonitrile, dichloromethane, tetrahydrofuran, or toluene; and/or (iii) the temperature is from about −30° C. to about 60° C.

In some embodiments for step (14a), the iodide reagent comprises N-iodosuccinimide. In some embodiments for step (14a), the solvent comprises trifluoromethanesulfonic acid. In some embodiments for step (14a), the temperature is from about −20° C. to about 0° C. In some embodiments for step (14a), the temperature is from about −30° C. to about 60° C. In some embodiments for step (14a), the temperature is about −30° C., about −25° C., about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., or about 60° C.

Alternate Synthesis of Compound 2B

Scheme 16 is a scheme depicting one embodiment of the alternate synthesis of Compound 2B.

Scheme 16

4D → MeHN, NHMe, CuI, NaI, diglyme →

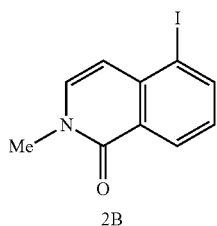

2B

In some embodiments, Compound 2B is prepared from a process comprising: (15a) contacting Compound 4D with a copper catalyst, an amine ligand, and an iodide additive in a solvent at a temperature sufficient to provide Compound 2B.

In some embodiments for step (15a): (i) the copper catalyst comprises copper(I) iodide, copper(I) bromide, copper(I) chloride, copper(I) oxide, copper acetate, copper(I) bromide dimethyl sulfide complex, copper(I) triflate, copper (I) iodide tetrabutylammonium iodide complex, tetrakis (acetonitrile)copper(I) hexafluorophosphate, copper(I) iodide triethylphosphite complex, or copper(I) bromide triphenylphosphine complex; (ii) the amine ligand comprises trans-N,N'-dimethylcyclohexane-1,2-diamine, N,N'-dimethylethane-1,2-diamine, N,N'-dimethylpropane-1,3-diamine, or N1-(2-aminoethyl)ethane-1,2-diamine; (iii) the iodide additive comprises sodium iodide, lithium iodide, or potassium iodide; (iv) the solvent comprises an ether (e.g., diethylene glycol dimethylether, diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (v) the temperature is from about 50° C. to about 150° C.

In some embodiments for step (15a), the copper catalyst comprises copper(I) iodide. In some embodiments for step (15a), the amine ligand comprises trans-N,N'-dimethylcyclohexane-1,2-diamine. In some embodiments for step (15a), the iodide additive comprises sodium iodide. In some embodiments for step (15a), the solvent comprises diethylene glycol dimethylether. In some embodiments for step (15a), the temperature is from about 80° C. to about 130° C. In some embodiments for step (15a), the temperature is from about 50° C. to about 150° C. In some embodiments for step (15a), the temperature is from about 50° C., about 55° C., about 60° C., about 65° C., about 70° C., about 75° C., about 80° C., about 85° C., about 90° C., about 95° C., about 100° C., about 105° C., about 110° C., about 115° C., about 120° C., about 125° C., about 130° C., about 135° C., about 140° C., about 145° C., or about 150° C.

Alternate Synthesis of Compound 2C

In a non-limiting example, Scheme 17 is a scheme depicting one embodiment of the alternate synthesis of Compound 2C.

Scheme 17

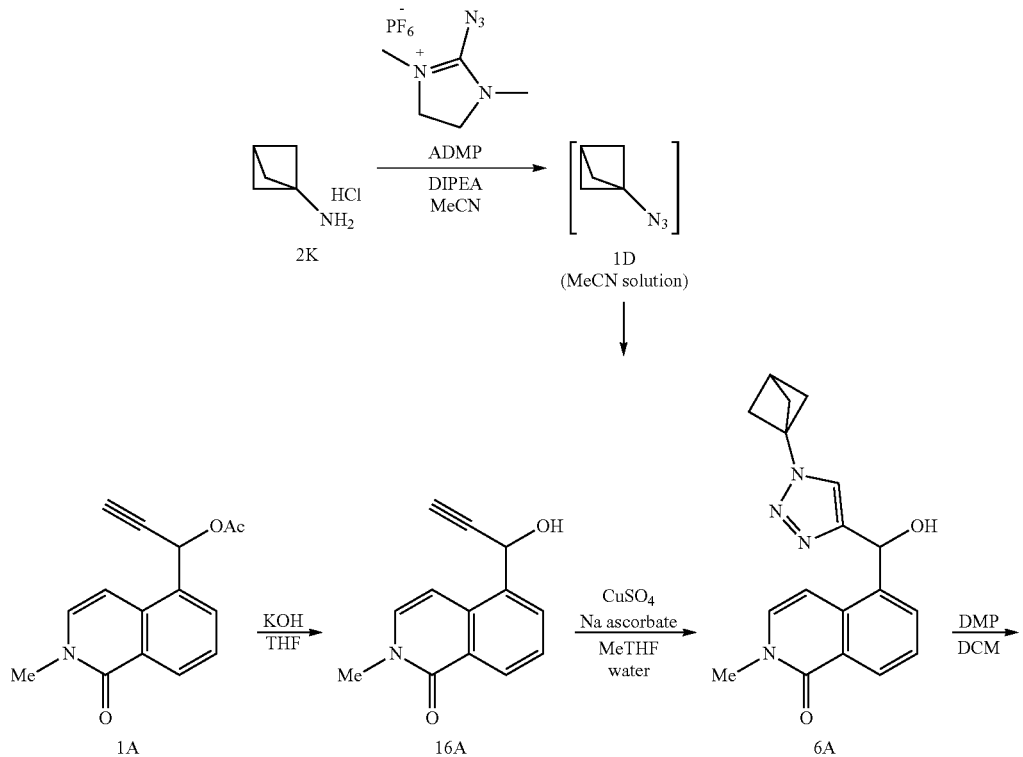

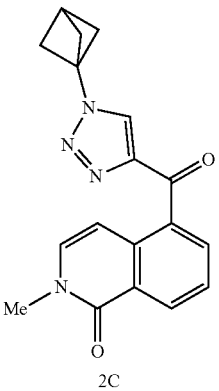

2C

In some embodiments, Compound 2C is prepared from a process comprising (16a) contacting Compound 1A with base in a solvent at a temperature sufficient to provide Compound 16A; (16b) contacting Compound 16A with a Compound 1D in the presence of a copper catalyst, and optionally, a reagent in a solvent at a temperature sufficient to provide Compound 6A; (16c) contacting Compound 6A in the presence of an oxidant, and optionally, a base in a solvent at a temperature sufficient to provide Compound 2C.

In some embodiments for step (16a): (i) the base comprises a hydroxide base (e.g., potassium hydroxide, lithium hydroxide, sodium hydroxide, and ammonium hydroxide), or a carbonate base (e.g., sodium carbonate, potassium carbonate, and cesium carbonate); (ii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an alcohol (e.g., ethylene glycol, propylene glycol, methanol, ethanol, isopropanol, and tert-butanol), a chlorinated solvent (e.g., dichloromethane, chloroform, dichloroethane, and chlorobenzene), or a polar aprotic solvent (e.g., N,N-dimethylformamide, N,N-dimethylacetamide, N-methyl-2-pyrrolidinone, and dimethyl sulfoxide); and/or (iii) the temperature is from about 0° C. to about 50° C.

In some embodiments for step (16a), the base comprises potassium hydroxide. In some embodiments for step (16a), the solvent comprises tetrahydrofuran. In some embodiments for step (16a), the temperature is from about 15° C. to about 30° C. In some embodiments for step (16a), the temperature is from about 0° C. to about 50° C. In some embodiments for step (16a), the temperature is from about 0° C., about 5° C., about 10° C., about 15° C., about 20° C., about 25° C., about 30° C., about 35° C., about 40° C., about 45° C., or about 50° C.

In some embodiments for step (16b), (i) the copper catalyst comprises copper(II) sulfate, copper(II) acetate, copper(I) chloride, copper(I) bromide, copper (I) bromide dimethyl sulfide complex, copper(I) triflate toluene complex, copper(I) iodide tetrabutylammonium iodide complex, tetrakis(acetonitrile)copper(I) hexafluorophosphate, copper (I) iodide triethylphosphite complex, copper(I) bromide triphenylphosphine complex; (ii) the reagent, if present, comprises sodium ascorbate; (iii) the solvent comprises water, an ether (e.g., 2-methyltetrahydrofuran, diethyl ether, 1,4-dioxane, tetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), alcohols (e.g., methanol, ethanol, isopropanol, and tert-butanol), a polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, and butyronitrile), or hydrocarbon solvent (e.g., toluene, trifluorotoluene, cyclohexane, n-heptane, and xylenes); and/or (iv) the temperature is from about 0° C. to about 50° C.

In some embodiments for step (16b), the copper catalyst comprises copper(II) sulfate. In some embodiments for step (16b), the reagent, if present, comprises sodium ascorbate. In some embodiments for step (16b), the solvent comprises 2-methyltetrahydrofuran, acetonitrile, and/or water. In some embodiments for step (16b), the temperature is about 20° C. In some embodiments for step (16b), the temperature is from about 0° C. to about 50° C. In some embodiments for step (16b), the temperature is from about 0° C., about 5° C., about 10° C., about 15° C., about 20° C., about 25° C., about 30° C., about 35° C., about 40° C., about 45° C., or about 50° C.

In some embodiments for step (16c), (i) the oxidant comprises Dess-Martin periodinane (DMP), dimethyl sulfoxide with an activating agent (e.g., oxalyl chloride, cyanuric chloride, N,N'-dicyclohexylcarbodiimide, N,N'-diisopropylcarbodiimide, N-chlorosuccinimide, benzoic anhydride, methanesulfonic anhydride, tosic anhydride, triflic anhydride, methyl chloroglyoxylate, thionyl chloride, diphosgene, triphosgene, methanesulfonyl chloride, tosyl chloride, benzenesulfonyl chloride, trichloroacetonitrile, 2-chloro-1,2-dimethylimidazolinium chloride, polyphosphoric acid, phosphorus trichloride, phosphorus pentoxide, triphenylphosphine dichloride, triphenylphosphine dibromide, phosphorus oxychloride, acetyl chloride, benzoyl chloride, acetyl bromide, phenyl dichlorophosphate, diphenyl chlorophosphate, diethyl chlorophosphate, and ethoxyacetylene), TEMPO/bleach, chromium trioxide, or 2-iodoxybenzoic acid; (ii) the base, if present, comprises a tertiary amine (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), an aromatic amine (e.g., pyridine, 2,6-lutidine, and collidine), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), or a hydroxide base (e.g., sodium hydroxide, lithium hydroxide, potassium hydroxide, and ammonium hydroxide); (iii) the solvent comprises an alcoholic solvent (e.g., methanol, ethanol, isopropanol, and tert-butanol), an ester (e.g., ethyl acetate, isopropyl acetate, n-propyl acetate, and isobutyl acetate), a ketone (e.g., acetone, and methyl ethyl ketone), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or halogenated solvent (e.g., dichloromethane, chloroform, dichloroethane, chlorobenzene, and dibromoethane); and/or (iv) the temperature is from about −20° C. to about 100° C.

In some embodiments for step (16c), the oxidant comprises Dess-Martin periodinane. In some embodiments for step (16c), the base is not present. In some embodiments for step (16c), the solvent comprises dichloromethane. In some embodiments for step (16c), the temperature is from about 25° C. In some embodiments for step (16c), the temperature is from about −20° C. to about 100° C. In some embodiments for step (16c), the temperature is from about −20° C., about −15° C., about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

In some embodiments, Compound 1D is prepared from a process comprising; (16d) contacting Compound 2K with an azide reagent and base in a solvent at a temperature sufficient to provide Compound 1D.

In some embodiments for step (16d): (i) the azide reagent comprises 2-azido-1,3-dimethylimidazolinium hexafluorophosphate (ADMP), imidazole-1-sulfonyl azide hydrochloric acid salt, imidazole-1-sulfonyl azide sulfuric acid salt, imidazole-1-sulfonyl azide tetrafluoroboric acid salt, or para-toluenesulfonylazide; (ii) the base comprises a tertiary amine (e.g., N,N-diisopropylethylamine, N-methylmorpholine, tri-n-propylamine, triethylamine, tri-n-butylamine, 1,8-diazabicyclo[5.4.0]undec-7-ene, and 1,4-diazabicyclo[2.2.2]octane), diethylamine, or dibutylamine; (iii) the solvent comprises an ether (e.g., diethyl ether, 1,4-dioxane, 2-methyltetrahydrofuran, tetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), an alcohol (e.g., methanol, ethanol, isopropanol, and tert-butanol), a polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, and butyronitrile), or a hydrocarbon solvent (e.g., toluene, trifluorotoluene, cyclohexane, n-heptane, and xylenes); and/or (iv) the temperature is from about 0° C. to about 50° C.

In some embodiments for step (16d), the azide reagent comprises 2-azido-1,3-dimethylimidazolinium hexafluorophosphate (ADMP). In some embodiments for step (16d), the base comprises N,N-diisopropylethylamine. In some embodiments for step (16d), the solvent comprises acetonitrile. In some embodiments for step (16d), the temperature is about 20° C. In some embodiments for step (16d), the temperature is from about 0° C. to about 50° C. In some embodiments for step (16d), the temperature is about 0° C., about 5° C., about 10° C., about 15° C., about 20° C., about 25° C., about 30° C., about 35° C., about 40° C., about 45° C., or about 50° C.

In some embodiments, steps (16d) and (16b) are performed in a batch mode. In some embodiments, contacting Compound 2K with an azide reagent and a base in a solvent at a temperature provides a stoichiometric amount of Compound 1D. In some embodiments, producing a stoichiometric amount of Compound 1D comprises simultaneously adding Compound 2K, the azide reagent, the base and the solvent into a batch reactor. In some embodiments, the stoichiometric amount of Compound 1D is contacted with Compound 16A, a copper catalyst, and optionally, a reagent in a solvent at a temperature sufficient to provide Compound 6A.

In some embodiments steps, (16d) and (16b) are performed in a continuous flow process. In some embodiments, Compound 2K, the azide reagent, the base and the solvent are added into a continuous flow reactor to produce Compound 1D. In some embodiments, Compound 1D is contacted with Compound 16A, a copper catalyst, and optionally, a reagent in a batch reactor in a solvent at a temperature sufficient to provide Compound 6A. In some embodiments, Compound 1D produced into the continuous flow reactor is continuously fed to a batch reactor containing Compound 16A, the copper catalyst, sodium ascorbate, solvent, and optionally, the reagent to provide Compound 6A.

Alternate Synthesis 1 of Compound 6A

In a non-limiting example, Scheme 18 is a scheme depicting one embodiment of the alternate synthesis 1 of Compound 6A.

Scheme 18

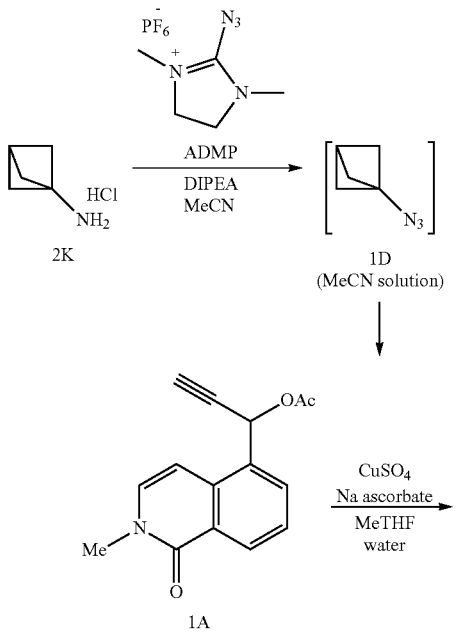

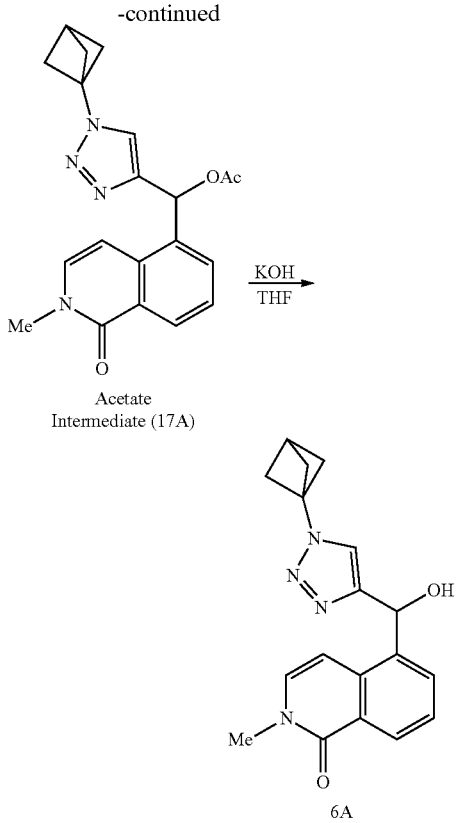

Acetate Intermediate (17A)

6A

In some embodiments, Compound 6A is prepared from a process comprising: (17a) contacting Compound 1A with a Compound 1D in the presence of a copper catalyst, and optionally, a reagent in a solvent at a temperature sufficient to provide Compound 17A; (17b) contacting Compound 17A in the presence of a base in a solvent at a temperature sufficient to provide Compound 6A.

In some embodiments for step (17a), (i) the copper catalyst comprises copper(II) sulfate, copper(II) acetate, copper(I) chloride, copper(I) bromide, copper (I) bromide dimethyl sulfide complex, copper(I) triflate toluene complex, copper(I) iodide, copper(I) iodide tetrabutylammonium iodide complex, tetrakis(acetonitrile)copper(I) hexafluorophosphate, copper(I) iodide triethylphosphite complex, or copper(I) bromide triphenylphosphine complex; (ii) the reagent, if present, comprises sodium ascorbate; (iii) the solvent comprises water, an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), an alcohol (e.g., methanol, ethanol, isopropanol, and tert-butanol), polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, and butyronitrile), a hydrocarbon solvent (e.g., toluene, trifluorotoluene, cyclohexane, n-heptane, and xylenes), or a combination thereof; and/or (iv) the temperature is from about 0° C. to about 50° C.

In some embodiments for step (17a), the copper catalyst comprises copper(II) sulfate. In some embodiments for step (17a), the reagent, if present, comprises sodium ascorbate. In some embodiments for step (17a), the solvent comprises 2-methyltetrahydrofuran, acetonitrile, and/or water. In some embodiments for step (17a), the temperature is about 20° C. In some embodiments for step (17a), the temperature is from about 0° C. to about 50° C. In some embodiments for step (17a), the temperature is from about 0° C., about 5° C., about 10° C., about 15° C., about 20° C., about 25° C., about 30° C., about 35° C., about 40° C., about 45° C., or about 50° C.

In some embodiments for step (17b), (i) the base comprises a hydroxide base (e.g., potassium hydroxide, lithium hydroxide, sodium hydroxide, and ammonium hydroxide), or a carbonate base (e.g., sodium carbonate, potassium carbonate, and cesium carbonate); (ii) the solvent comprises an ether (e.g., tetrahydrofuran, diethyl ether, 1,4-dioxane, 2-methyltetrahydrofuran, dimethoxyethane, methyl tert-butyl ether, cyclopentyl methyl ether, diphenyl ether, and dibutyl ether), an alcohol (e.g., ethylene glycol, propylene glycol, methanol, ethanol, isopropanol, and tert-butanol), a chlorinated solvent (e.g., dichloromethane, chloroform, dichloroethane, and chlorobenzene), or a polar aprotic solvent (e.g., N,N-dimethylformamide, N,N-dimethylacetamide, N-methyl-2-pyrrolidinone, and dimethyl sulfoxide); and/or (iii) the temperature is from about 0° C. to about 50° C.

In some embodiments for step (17b), the base comprises potassium hydroxide. In some embodiments for step (17b), the solvent comprises tetrahydrofuran. In some embodiments for step (17b), the temperature is from about 10° C. to about 30° C. In some embodiments for step (17b), the temperature is from about 0° C. to about 50° C. In some embodiments for step (17b), the temperature is from about 0° C., about 5° C., about 10° C., about 15° C., about 20° C., about 25° C., about 30° C., about 35° C., about 40° C., about 45° C., or about 50° C.

In some embodiments, Compound 1D is prepared from a process comprising: (17c) contacting Compound 2K with an azide reagent and base in a solvent at a temperature sufficient to provide Compound 1D.

In some embodiments for step (17c): (i) the azide reagent comprises 2-azido-1,3-dimethylimidazolinium hexafluorophosphate (ADMP), imidazole-1-sulfonyl azide hydrochloric acid salt, imidazole-1-sulfonyl azide sulfuric acid salt, imidazole-1-sulfonyl azide tetrafluoroboric acid salt, or para-toluenesulfonylazide; (ii) the base comprises a tertiary amine (e.g., N,N-diisopropylethylamine, N-methylmorpholine, tri-n-propylamine, triethylamine, tri-n-butylamine, 1,8-diazabicyclo[5.4.0]undec-7-ene, and 1,4-diazabicyclo[2.2.2]octane), diethylamine, or dibutylamine; (iii) the solvent comprises an ether (e.g., diethyl ether, 1,4-dioxane, 2-methyltetrahydrofuran, tetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), an alcohol (e.g., methanol, ethanol, isopropanol, and tert-butanol), a polar aprotic solvent (e.g., N,N-dimethylformamide, N,N-dimethylacetamide, N-methyl-2-pyrrolidinone, and dimethyl sulfoxide), a nitrile (e.g., acetonitrile, propionitrile, and butyronitrile), or a hydrocarbon solvent (e.g., toluene, trifluorotoluene, cyclohexane, n-heptane, and xylenes); and/or (iv) the temperature is from about 0° C. to about 50° C.

In some embodiments for step (17c), the azide reagent comprises 2-azido-1,3-dimethylimidazolinium hexafluorophosphate (ADMP). In some embodiments for step (17c), the base comprises N,N-diisopropylethylamine. In some embodiments for step (17c), the solvent comprises acetonitrile. In some embodiments for step (17c), the temperature is about 20° C. In some embodiments for step (17c), the temperature is from about 0° C. to about 50° C. In some embodiments for step (17c), the temperature is about 0° C., about 5° C., about 10° C., about 15° C., about 20° C., about 25° C., about 30° C., about 35° C., about 40° C., about 45° C., or about 50° C.

In some embodiments, steps (17c) and (17a) are performed in a batch mode. In some embodiments, contacting Compound 2K with an azide reagent and a base in a solvent at a temperature provides a stoichiometric amount of Compound 1D. In some embodiments, producing a stoichiometric amount of Compound 1D comprises simultaneously adding Compound 2K, the azide reagent, the base and the solvent into a batch reactor. In some embodiments, the stoichiometric amount of Compound 1D is contacted with Compound 1A, a copper catalyst, and optionally, a reagent in a solvent at a temperature sufficient to provide Compound 17A.

In some embodiments steps (17c) and (17a) are performed in a continuous flow process. In some embodiments, Compound 2K, the azide reagent, the base and the solvent are added into a continuous flow reactor to produce Compound 1D. In some embodiments, Compound 1D is contacted with Compound 1A, a copper catalyst, and optionally, a reagent in a batch reactor in a solvent at a temperature sufficient to provide Compound 17A. In some embodiments, Compound 1D produced into the continuous flow reactor is continuously fed to a batch reactor containing Compound 1A, the copper catalyst, sodium ascorbate, solvent, and optionally, the reagent to provide Compound 17A.

Alternate Synthesis 2 of Compound 6A

In a non-limiting example, Scheme 19 is a scheme depicting one embodiment of the alternate synthesis 2 of Compound 6A.

Scheme 19

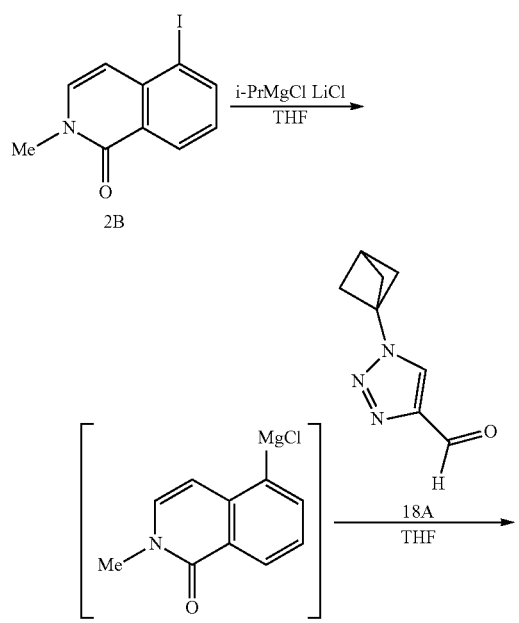

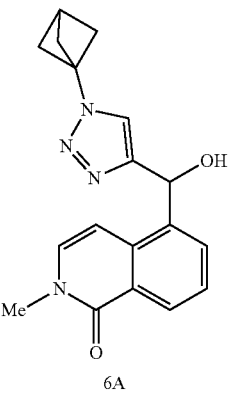

6A

In some embodiments, Compound 6A is prepared from a process comprising: (18a) contacting Compound 2B with Compound 18A in the presence of an organometallic reagent in a solvent at temperature sufficient to provide Compound 6A.

In some embodiments for step (18a): (i) the organometallic reagent comprises an organomagnesium reagent (e.g., isopropylmagnesium chloride lithium chloride complex cyclohexylmagnesium chloride, butylmagnesium chloride, tert-butylmagnesium chloride, isopropylmagnesium chloride, sec-butylmagnesium chloride lithium chloride complex, isopropylmagnesium bromide, and ethylmagnesium bromide); (ii) the solvent comprises an ether (e.g., diethyl ether, 1,4-dioxane, 2-methyltetrahydrofuran, tetrahydrofuran, dimethoxyethane, methyl tert-butyl ether, cyclopentyl methyl ether, diphenyl ether, and dibutyl ether), a hydrocarbon (e.g., toluene, trifluorotoluene, cyclohexane, n-heptane, and xylenes), or a chlorinated solvent (e.g., dichloromethane, chloroform, dichloroethane, and chlorobenzene); and/or (iii) the temperature is from about −20° C. to about 50° C.

In some embodiments for step (18a), the organometallic reagent comprises isopropylmagnesium chloride lithium chloride complex. In some embodiments for step (18a), the solvent comprises tetrahydrofuran. In some embodiments for step (18a), the temperature is from about 0° C. to about 50° C. In some embodiments for step (18a), the temperature is from about −20° C. to about 50° C. In some embodiments for step (18a), the temperature is about −20° C., about −15° C., about −10° C., about −5° C., about 0° C., about 5° C., about 10° C., about 15° C., about 20° C., about 25° C., about 30° C., about 35° C., about 40° C., about 45° C., or about 50° C.

Alternate Synthesis 3 of Compound 6A

In a non-limiting example, Scheme 20 is a scheme depicting one embodiment of the alternate synthesis 3 of Compound 6A.

Scheme 20

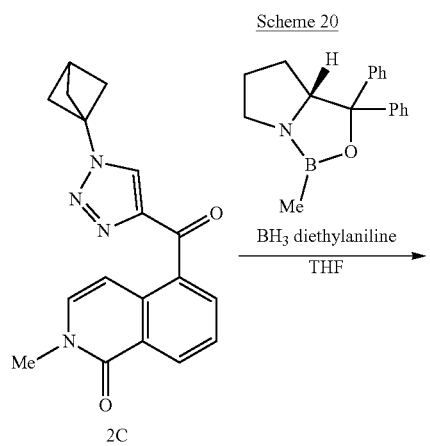

2C

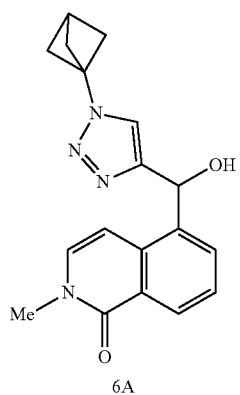

6A

In some embodiments, Compound 6A is prepared from a process comprising: (19a) contacting Compound 2C with a catalyst and a hydride source in a solvent at temperature sufficient to provide Compound 6A.

In some embodiments for step (19a): (i) the catalyst comprises (R)-(−)-2-methyl-CBS-oxazoborolidine, (R)-(+)-o-tolyl-CBS-oxazaborolidine, (R)-(+)-2-butyl-CBS-oxazaborolidine, trans-RuCl$_2$[(R)-xylbinap]-[(R)-diapen], RuBr$_2$[(R)-BINAP], [RuCl(PhH)(R)-BINAP)]Cl, RuCl(p-cymene)[(S,S)-Ts-DPEN], RuCl(mesitylene)[(S,S)-Ts-DPEN], RuBF$_4$(p-cymene)[(S,S)-Ts-DPEN], RuCl(p-cymene)[(S,S)-Fs-DPEN], or RuCl(p-cymene)[(R,R)-Teth-Ts-DPEN]; (ii) the hydride source comprises borane N,N-diethylaniline complex, borane dimethylsulfide complex, borane tetrahydrofuran complex, borane trimethylamine complex, borane triethylamine complex, catecholborane, hydrogen gas, formic acid/triethylamine, or 2-propanol; (iii) the solvent comprises an ether (e.g., tetrahydrofuran, diethyl ether, 1,4-dioxane, 2-methyltetrahydrofuran, dimethoxyethane, methyl tert-butyl ether, cyclopentyl methyl ether, diphenyl ether, and dibutyl ether), a hydrocarbon solvent (e.g., n-hexane, toluene, trifluorotoluene, cyclohexane, n-heptane, and xylenes), an ester (e.g., ethyl acetate, isopropyl acetate, n-propyl acetate, and isobutyl acetate), a chlorinated solvent (e.g., dichloromethane, chloroform, dichloroethane, chlorobenzene), or a nitrile (e.g., acetonitrile, propionitrile, and butyronitrile); and/or (iv) the temperature is from about −20° C. to about 50° C.

In some embodiments for step (19a), the catalyst comprises (R)-(−)-2-methyl-CBS-oxazoborolidine. In some embodiments for step (19a), the hydride source comprises borane N,N-diethylaniline complex. In some embodiments for step (19a), the solvent comprises tetrahydrofuran. In some embodiments for step (19a), the temperature is from about 0° C. to about 20° C. In some embodiments for step (19a), the temperature is from about −20° C. to about 50° C. In some embodiments for step (19a), the temperature is about −20° C., about −15° C., about −10° C., about −5° C., about 0° C., about 5° C., about 10° C., about 15° C., about 20° C., about 25° C., about 30° C., about 35° C., about 40° C., about 45° C., or about 50° C.

Alternate Synthesis of Compound 2E

In a non-limiting example, Scheme 21A is a scheme depicting one embodiment of the alternate synthesis of Compound 2E.

Scheme 21A

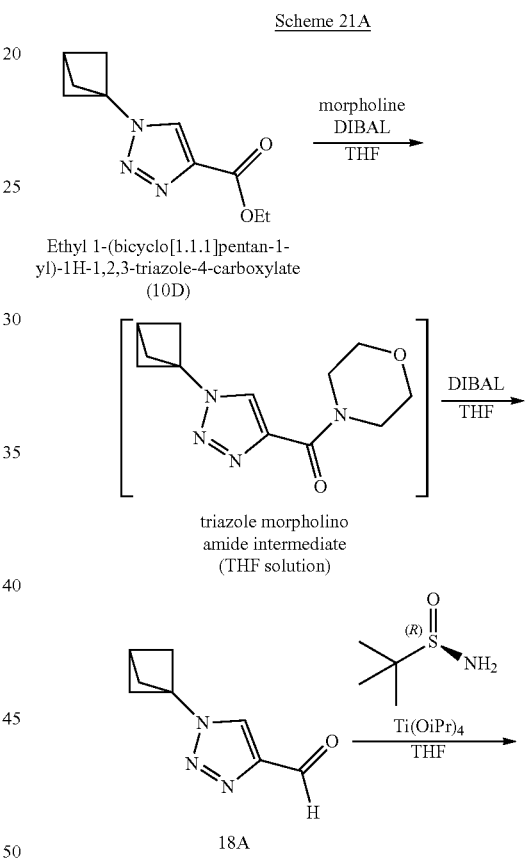

Ethyl 1-(bicyclo[1.1.1]pentan-1-yl)-1H-1,2,3-triazole-4-carboxylate
(10D)

triazole morpholino amide intermediate
(THF solution)

18A

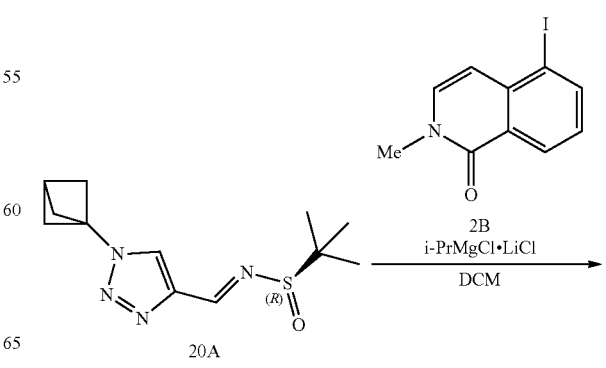

20A 2B
i-PrMgCl·LiCl
DCM

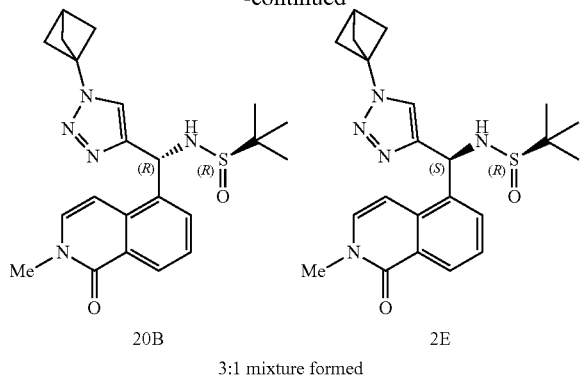

20B          2E

3:1 mixture formed

In some embodiments, Compound 2E is prepared from a process comprising: (20a) contacting Compound 10D with morpholine and a reducing agent in a solvent at temperature sufficient to provide Compound 18A; (20b) contacting Compound 18A with

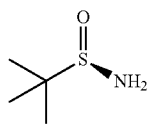

in the presence of a catalyst in a solvent at a temperature sufficient to provide Compound 20A; (20c) contacting Compound 20A with Compound 2B in the presence of an organometallic reagent in a solvent at temperature sufficient to provide Compound 20B and Compound 2E.

In some embodiments for step (20a): (i) the reducing agent comprises borane dimethylsulfide complex, $NaBH_4$/$I_2$, an amine·borane complex (e.g., ammonia borane, and diethylphenylamine-borane), a borohydride reagent (e.g., sodium borohydride, lithium borohydride, potassium borohydride, lithium triethylborohydride, and potassium tri-sec-butylborohydride), an aluminum hydride reagent (e.g., diisobutylaluminum hydride, sodium bis(2-methoxyethoxy) aluminum hydride, lithium tri-tert-butoxyaluminum hydride, and lithium tris[(3-ethyl-3-pentyl)oxy]aluminohydride), hydrogen gas, formic acid/triethylamine, 2-propanol; (ii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a chlorinated solvent (e.g., dichloromethane, chloroform, dichloroethane, and chlorobenzene), or a hydrocarbon (e.g., toluene, trifluorotoluene, cyclohexane, n-heptane, and xylenes); and/or (iii) the temperature is from about −20° C. to about 30° C.

In some embodiments for step (20a), the reducing agent comprises diisobutylaluminum hydride. In some embodiments for step (20a), the solvent comprises tetrahydrofuran. In some embodiments for step (20a), the temperature is from about 0° C. to about 20° C. In some embodiments for step (20a), the temperature is from about −20° C. to about 30° C. In some embodiments for step (20a), the temperature is about −20° C., about −15° C., about −10° C., about −5° C., about 0° C., about 5° C., about 10° C., about 15° C., about 20° C., about 25° C., or about 30° C.

In some embodiments for step (20b): (i) the catalyst comprises titanium(IV) isopropoxide, magnesium sulfate, cesium carbonate, potassium carbonate, sodium carbonate, or a hydroxide base (e.g., potassium hydroxide, lithium hydroxide, and sodium hydroxide); (ii) the solvent comprises an ether (e.g., diethyl ether, 1,4-dioxane, 2-methyltetrahydrofuran, tetrahydrofuran, dimethoxyethane, methyl tert-butyl ether, cyclopentyl methyl ether, diphenyl ether, and dibutyl ether), a chlorinated solvent (e.g., dichloromethane, chloroform, dichloroethane, and chlorobenzene), or a hydrocarbon (e.g., toluene, trifluorotoluene, cyclohexane, n-heptane, and xylenes); and/or (iii) the temperature is from about 0° C. to about 30° C.

In some embodiments for step (20b), the catalyst comprises titanium(IV) isopropoxide. In some embodiments for step (20b), the solvent comprises tetrahydrofuran. In some embodiments for step (20b), the temperature is about 20° C. In some embodiments for step (20b), the temperature is from about 0° C. to about 30° C. In some embodiments for step (20b), the temperature is about 0° C., about 5° C., about 10° C., about 15° C., about 20° C., about 25° C., or about 30° C.

In some embodiments for step (20c): (i) the organometallic reagent comprises an organomagnesium reagent (e.g., isopropylmagnesium chloride lithium chloride complex, cyclohexylmagnesium chloride, butylmagnesium chloride, tert-butylmagnesium chloride, sec-butylmagnesium chloride lithium chloride complex, and isopropylmagnesium chloride, isopropylmagnesium bromide, ethylmagnesium bromide); (ii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a chlorinated solvent (e.g., chloroform, dichloromethane, dichloroethane, and chlorobenzene), or a hydrocarbon (e.g., toluene, trifluorotoluene, cyclohexane, n-heptane, and xylenes); and/or (iii) the temperature is from about −78° C. to about 40° C.

In some embodiments for step (20c), the organometallic reagent comprises isopropylmagnesium chloride lithium chloride complex. In some embodiments for step (20c), the solvent comprises dichloromethane. In some embodiments for step (20c), the temperature is from about 0° C. to about 20° C. In some embodiments for step (20c), the temperature is from about −78° C. to about 40° C. In some embodiments for step (20c), the temperature is about −78° C., about −75° C., about −70° C., about −65° C., about −60° C., about −55° C., about −50° C., about −45° C., about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., or about 40° C.

In a non-limiting example, Scheme 21B is a scheme depicting one embodiment of the alternate synthesis of Compound 3C.

Scheme 21B

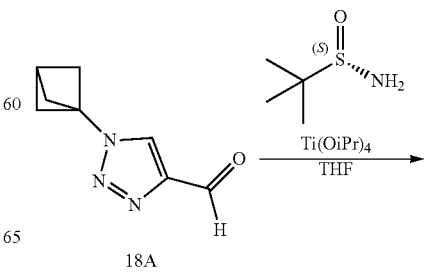

18A

-continued

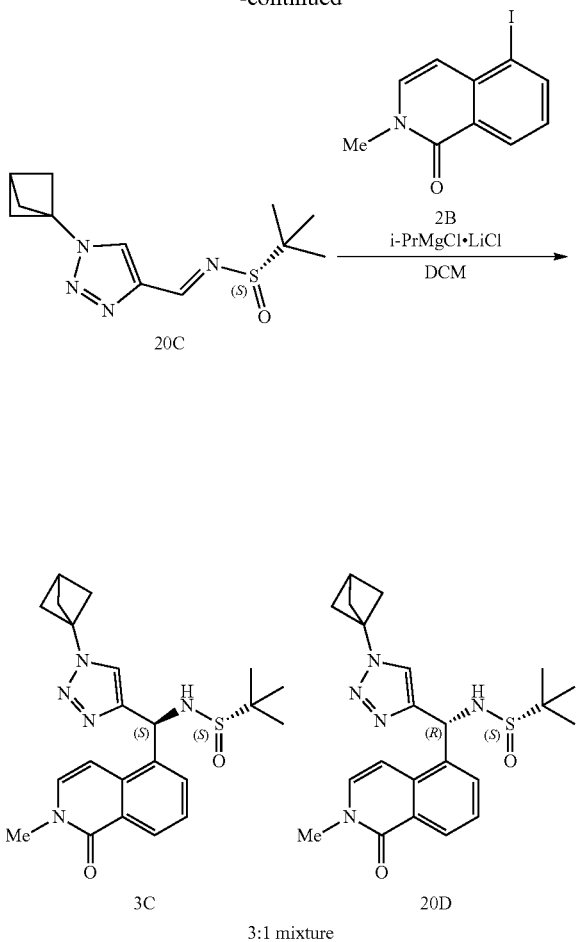

3:1 mixture

In some embodiments, Compound 3C is prepared from a process comprising: (20d) contacting Compound 18A with

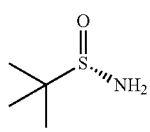

in the presence of a catalyst in a solvent at a temperature sufficient to provide Compound 20C; (20e) contacting Compound 20C with Compound 2B in the presence of an organometallic reagent in a solvent at temperature sufficient to provide Compound 3C and Compound 20D.

In some embodiments for step (20d): (i) the catalyst comprises titanium(IV) isopropoxide, magnesium sulfate, cesium carbonate, potassium carbonate, sodium carbonate, or a hydroxide base (e.g., potassium hydroxide, lithium hydroxide, and sodium hydroxide); (ii) the solvent comprises an ether (e.g., diethyl ether, 1,4-dioxane, 2-methyltetrahydrofuran, tetrahydrofuran, dimethoxyethane, methyl tert-butyl ether, cyclopentyl methyl ether, diphenyl ether, and dibutyl ether), a chlorinated solvent (e.g., dichloromethane, chloroform, dichloroethane, and chlorobenzene), or a hydrocarbon (e.g., toluene, trifluorotoluene, cyclohexane, n-heptane, and xylenes); and/or (iii) the temperature is from about 0° C. to about 30° C.

In some embodiments for step (20d), the catalyst comprises titanium(IV) isopropoxide. In some embodiments for step (20d), the solvent comprises tetrahydrofuran. In some embodiments for step (20d), the temperature is about 20° C. In some embodiments for step (20d), the temperature is from about 0° C. to about 30° C. In some embodiments for step (20d), the temperature is about 0° C., about 5° C., about 10° C., about 15° C., about 20° C., about 25° C., or about 30° C.

In some embodiments for step (20e): (i) the organometallic reagent comprises an organomagnesium reagent (e.g., isopropylmagnesium chloride lithium chloride complex, cyclohexylmagnesium chloride, butylmagnesium chloride, tert-butylmagnesium chloride, sec-butylmagnesium chloride lithium chloride complex, isopropylmagnesium chloride, isopropylmagnesium bromide, and ethylmagnesium bromide); (ii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a chlorinated solvent (e.g., chloroform, dichloromethane, dichloroethane, and chlorobenzene), or a hydrocarbon (e.g., toluene, trifluorotoluene, cyclohexane, n-heptane, and xylenes); and/or (iii) the temperature is from about −78° C. to about 40° C.

In some embodiments for step (20e), the organometallic reagent comprises isopropylmagnesium chloride lithium chloride complex. In some embodiments for step (20e), the solvent comprises dichloromethane. In some embodiments for step (20e), the temperature is from about 0° C. to about 20° C. In some embodiments for step (20e), the temperature is from about −78° C. to about 40° C. In some embodiments for step (20e), the temperature is about −78, about −75° C., about −70° C., about −65° C., about −60° C., about −55° C., about −50° C., about −45° C., about −40° C., about −35° C., about −30° C., about −25° C., about −20° C., about −15° C., about −10° C., about −5° C., about 0° C., about 5° C., about 10° C., about 15° C., about 20° C., about 25° C., about 30° C., about 35° C., or about 40° C.

Alternate Synthesis of Compound 2F Salt

In a non-limiting example, Scheme 22 is a scheme depicting one embodiment of the alternate synthesis of Compound 2F (in salt form).

Scheme 22

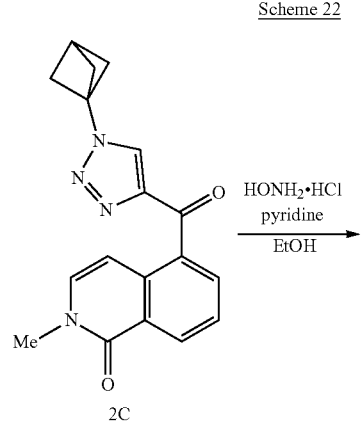

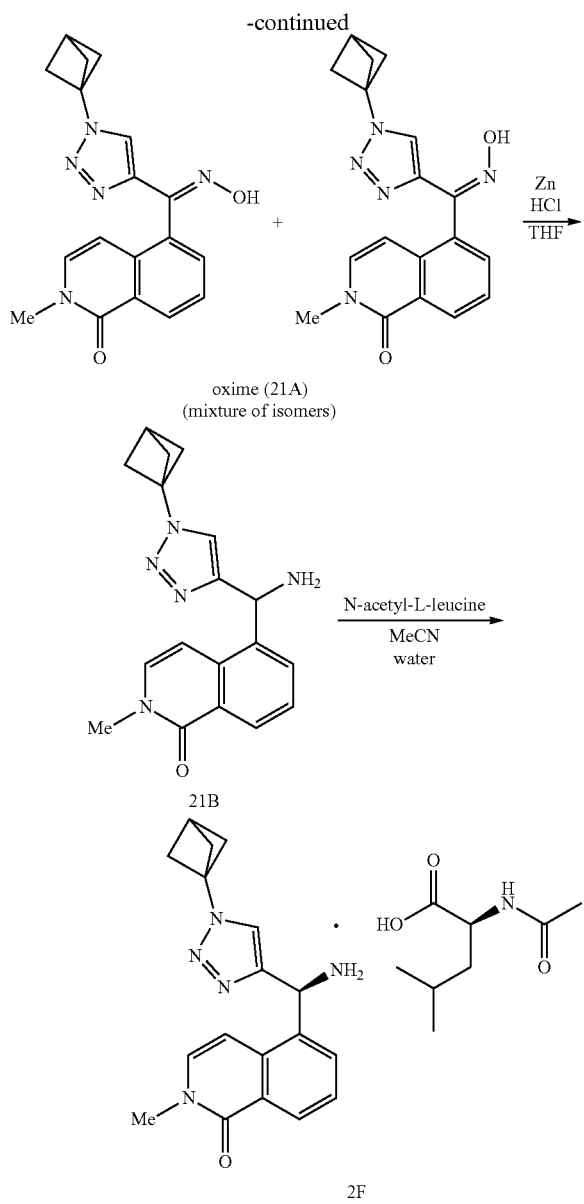

oxime (21A)
(mixture of isomers)

21B

2F

In some embodiments, Compound 2F is prepared from a process comprising: (21a) contacting Compound 2C with HONH$_2$·HCl in the presence of a base in a solvent at a temperature sufficient to provide Compound 21A; (21b) contacting Compound 21A with a reagent in a solvent at a temperature sufficient to provide Compound 21B; (21c) contacting Compound 21B with a chiral acid in a solvent at a temperature sufficient to provide salt of Compound 2F.

In some embodiments for step (21a): (i) the base comprises a tertiary amine (e.g., N-methylmorpholine, tri-n-propylamine, N,N-diisopropylethylamine, triethylamine, tri-n-butylamine, 1,8-diazabicyclo[5.4.0]undec-7-ene, and 1,4-diazabicyclo[2.2.2]octane), an inorganic base (e.g., sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, and cesium carbonate), an alkoxide base (e.g., potassium tert-butoxide, sodium tert-butoxide, sodium methoxide, sodium ethoxide, potassium methoxide, and potassium ethoxide), an hydroxide base (e.g., sodium hydroxide, lithium hydroxide, potassium hydroxide, and ammonium hydroxide), or an aromatic amine (e.g., pyridine, 2,6-lutidine, and collidine); (ii) the solvent comprises an alcoholic solvent (e.g., methanol, ethanol, isopropanol, and tert-butanol), an ester (e.g., ethyl acetate, isopropyl acetate, n-propyl acetate, and isobutyl acetate), an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a polar aprotic solvent (e.g., N,N-dimethylformamide, N,N-dimethylacetamide, N-methyl-2-pyrrolidinone, and dimethyl sulfoxide), a hydrocarbon solvent (e.g., toluene, trifluorotoluene, cyclohexane, n-heptane, and xylenes), a nitrile (e.g., acetonitrile, propionitrile, and butyronitrile), or a halogenated solvent (e.g., dichloromethane, chloroform, dichloroethane, chlorobenzene, and dibromoethane); and/or (iii) the temperature is from about 0° C. to about 120° C.

In some embodiments for step (21a), the base comprises pyridine. In some embodiments for step (21a), the solvent comprises ethanol. In some embodiments for step (21a), the temperature is about 80° C. In some embodiments for step (21a), the temperature is from about 0° C. to about 120° C. In some embodiments for step (21a), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 105° C., about 110° C., about 115° C., or about 120° C.

In some embodiments for step (21b): (i) the reagent comprises a Lewis Acid (e.g., zirconium tetrachloride, zirconium tetrachloride/alumina, titanium tetrachloride) with a borohydride (e.g., sodium cyanoborohydride, and sodium borohydride), a hydride (e.g., lithium aluminum hydride), borane with lithium chloride and Amberlyst 15, a metal (e.g., zinc, magnesium, sodium) with acid (e.g., hydrochloric acid, acetic acid, Amberlyst 15, ammonium formate), a metal (e.g., zinc) with base (e.g., sodium hydroxide, and ammonia), samarium(II) iodide with base (e.g., potassium hydroxide), or a palladium catalyst (e.g., palladium on carbon) with a proton source (e.g., hydrogen gas, hydrochloric acid, acetic acid, and ammonium formate); (ii) the solvent comprises an alcohol (e.g., methanol, ethanol, isopropanol, and tert-butanol), water, an ether (e.g., tetrahydrofuran, diethyl ether, 1,4-dioxane, 2-methyltetrahydrofuran, dimethoxyethane, methyl tert-butyl ether, cyclopentyl methyl ether, diphenyl ether, and dibutyl ether), an ester (e.g., ethyl acetate, isopropyl acetate, n-propyl acetate, and isobutyl acetate), a ketone (e.g., acetone, and methyl ethyl ketone), a polar aprotic solvent (e.g., N,N-dimethylformamide, N,N-dimethylacetamide, N-methyl-2-pyrrolidinone, and dimethyl sulfoxide), a hydrocarbon (e.g., toluene, trifluorotoluene, cyclohexane, n-heptane, and xylenes), or a chlorinated solvent (e.g., dichloromethane, chloroform, dichloroethane, and chlorobenzene); and/or (iii) the temperature is from about 0° C. to about 100° C.

In some embodiments for step (21b), the reagent comprises zinc with hydrochloric acid. In some embodiments for step (21b), the solvent comprises tetrahydrofuran. In some embodiments for step (21b), the temperature is about 60° C. In some embodiments for step (21b), the temperature is from about 0° C. to about 100° C. In some embodiments for step (21b), the temperature is about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

In some embodiments for step (21c): (i) the chiral acid comprises N-acetyl-L-leucine, (R)-mandelic acid, lactic acid, L-(+)-tartaric acid, L-aspartic acid, L-glutamic acid, L-(−)-malic acid, D-glucoronic acid, (1R,3S)-(+)-camphoric acid, (1S)-(+)-camphor-10-sulfonic acid, (R)-(+)-N-(1-phenylethyl)succinamic acid, carbobenzyloxy-L-proline, dibenzoyl-L-tartaric acid, (R)-(+)-3-methyladipic acid, (+)-menthyloxyacetic acid, (−)-pyroglutamic acid, N-Boc-D-leucine, N-(+)-Boc-phenylalanine, (−)-quinic acid, (+)-n-acetyl-L-phenylalanine, (+)-N-Boc-isoleucine, L-(−)-acetyl glutamic acid, or (−)-acetyl mandelic acid; (ii) the solvent comprises an ether (e.g., diethyl ether, 1,4-dioxane, tetrahydrofuran, 2-methyltetrahydrofuran, dimethoxyethane, methyl tert-butyl ether, cyclopentyl methyl ether, diphenyl ether, and dibutyl ether), a hydrocarbon solvent (e.g., benzene, toluene, trifluorotoluene, cyclohexane, n-heptane, and xylenes), a chlorinated solvent (e.g., dichloromethane, chloroform, dichloroethane, and chlorobenzene), an alcohol (e.g., methanol, ethanol, isopropanol, and tert-butanol), a ketone (e.g., acetone, methyl ethyl ketone, and methylisobutylketone), a nitrile (e.g., acetonitrile, propionitrile, and butyronitrile), water, or mixtures thereof; and/or (iii) the temperature is from about 10° C. to about 70° C. In some embodiments, for step (21c), Compound 2F is produced in at least greater than about 50%, at least greater than about 60%, at least greater than about 70%, at least greater than about 80%, at least greater than about 90%, at least greater than about 95%, or at least greater than about 99% chiral purity.

In some embodiments for step (21c), the chiral acid comprises N-acetyl-L-leucine. In some embodiments for step (21c), the solvent comprises acetonitrile and water. In some embodiments for step (21c), the temperature is from about 40° C. to about 60° C. In some embodiments for step (21c), the temperature is from about 10° C. to about 70° C. In some embodiments for step (21b), the temperature is about 10° C., about 15° C., about 20° C., about 25° C., about 30° C., about 35° C., about 40° C., about 45° C., about 50° C., about 55° C., about 60° C., about 65° C., or about 70° C. In some embodiments, for step (21c), Compound 2F is produced in at least greater than about 95% chiral purity.

In a non-limiting example, Scheme 26 is a scheme depicting one embodiment of the alternate synthesis of Compound 2F. In a non-limiting example, Scheme 26 depicts one embodiment of a synthesis of Compound 1.

Scheme 26

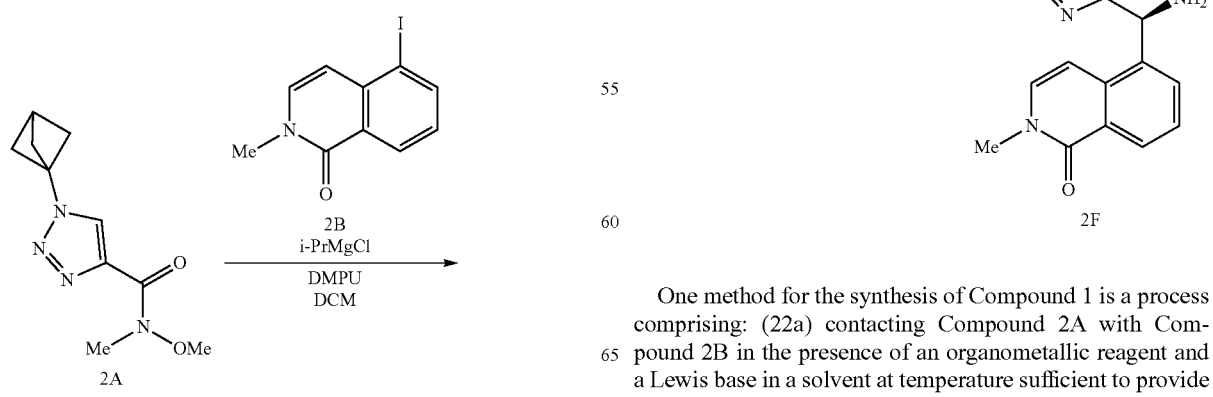

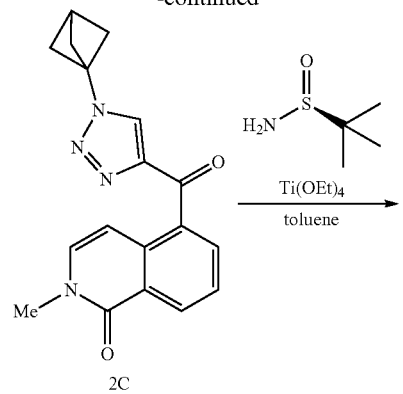

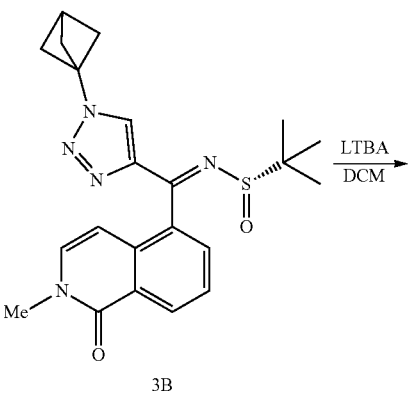

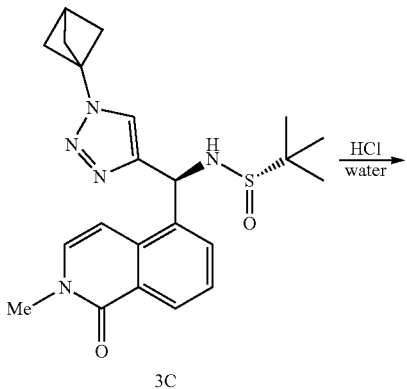

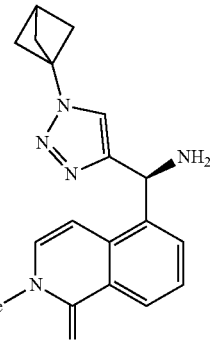

One method for the synthesis of Compound 1 is a process comprising: (22a) contacting Compound 2A with Compound 2B in the presence of an organometallic reagent and a Lewis base in a solvent at temperature sufficient to provide Compound 2C; (22b) contacting Compound 2C with

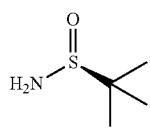

in the presence of a titanium-based or zirconium-based reagent in a solvent at a temperature sufficient to provide Compound 3B; (22c) contacting Compound 3B with a reducing agent, and optionally a ruthenium, palladium, or platinum catalyst in a solvent at a temperature sufficient to provide Compound 3C; (22d) contacting Compound 3C with an acid in a solvent at a temperature sufficient to provide Compound 2F; and (22e) contacting Compound 2F with Compound 2G in the presence of a palladium catalyst and a base in a solvent at a temperature sufficient to provide Compound 1.

One method for the synthesis of Compound 1 is a process comprising: (22a) contacting Compound 2A with Compound 2B in the presence of an organometallic reagent and a Lewis base in a solvent at temperature sufficient to provide Compound 2C; (22b) contacting Compound 2C with

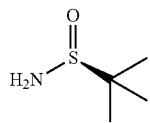

in the presence of a titanium-based or zirconium-based reagent in a solvent at a temperature sufficient to provide Compound 3B; (22c) contacting Compound 3B with a reducing agent, and optionally a ruthenium, palladium, or platinum catalyst in a solvent at a temperature sufficient to provide Compound 3C; (22d) contacting Compound 3C with an acid in a solvent at a temperature sufficient to provide Compound 2F; and (22e) contacting Compound 2F with Compound 2G in the presence of a copper catalyst, a copper catalyst ligand, and a base in a solvent at a temperature sufficient to provide Compound 1.

In a non-limiting example, Scheme 27 is a scheme depicting one embodiment of the alternate synthesis of Compound 2F. In a non-limiting example, Scheme 27 depicts one embodiment of a synthesis of Compound 1.

Scheme 27

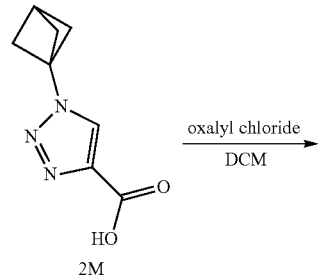

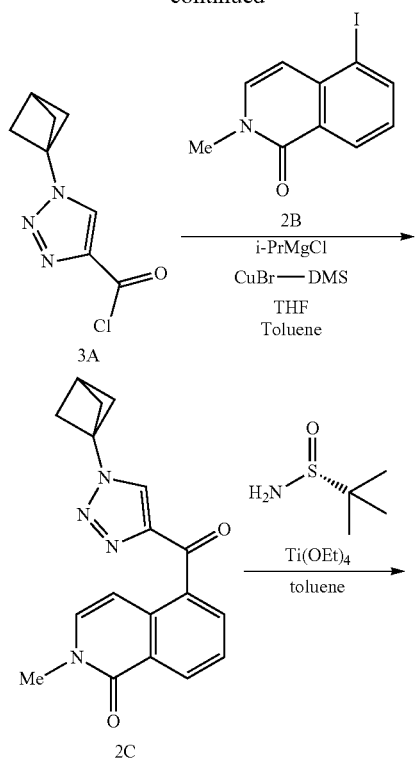

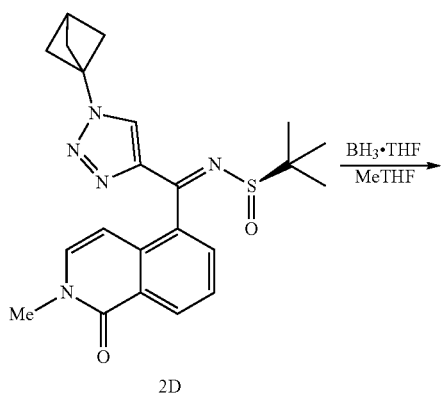

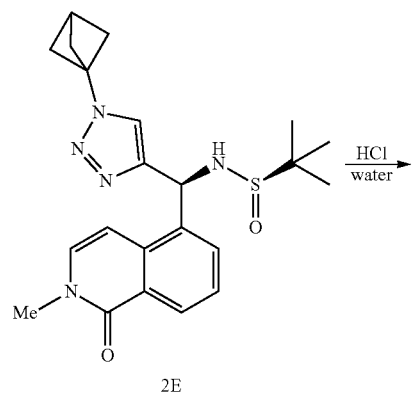

-continued

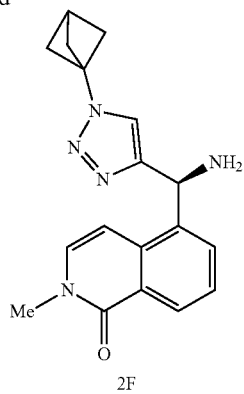

2F

One method for the synthesis of Compound 1 is a process comprising (23a) contacting Compound 2M with a chlorinating reagent and an additive in a solvent at a temperature sufficient to provide Compound 3A; (23b) contacting Compound 3A with Compound 2B in the presence of an organometallic reagent, then followed by the addition of a copper or palladium catalyst, optionally, a zinc additive, and optionally, a Lewis base in a solvent at a temperature sufficient to provide Compound 2C; (23c) contacting Compound 2C with

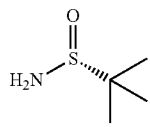

in the presence of a titanium or zirconium based reagent in a solvent at a temperature sufficient to provide Compound 2D; (23d) contacting Compound 2D with a reducing agent and optionally, a ruthenium, palladium, rhodium, or platinum catalyst in a solvent at a temperature sufficient to provide Compound 2E; (23e) contacting Compound 2E with an acid in a solvent at a temperature sufficient to provide Compound 2F; and (23f) contacting Compound 2F with Compound 2G in the presence of a palladium catalyst and a base in a solvent at a temperature sufficient to provide Compound 1.

One method for the synthesis of Compound 1 is a process comprising (23a) contacting Compound 2M with a chlorinating reagent and an additive in a solvent at a temperature sufficient to provide Compound 3A; (23b) contacting Compound 3A with Compound 2B in the presence of an organometallic reagent, then followed by the addition of a copper or palladium catalyst, optionally, a zinc additive, and optionally, a Lewis base in a solvent at a temperature sufficient to provide Compound 2C; (23c) contacting Compound 2C with

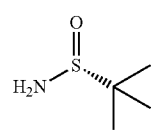

in the presence of a titanium or zirconium based reagent in a solvent at a temperature sufficient to provide Compound 2D; (23d) contacting Compound 2D with a reducing agent and optionally, a ruthenium, palladium, rhodium, or platinum catalyst in a solvent at a temperature sufficient to provide Compound 2E; (23e) contacting Compound 2E with an acid in a solvent at a temperature sufficient to provide Compound 2F; and (23f) contacting Compound 2F with Compound 2G in the presence of a copper catalyst, a copper catalyst ligand, and a base in a solvent at a temperature sufficient to provide Compound 1.

The present invention, thus generally described, will be understood more readily by reference to the following examples, which are provided by way of illustration and are not intended to be limiting of the present invention.

EXAMPLES

Example 1: Compound 1 Manufacturing Route 1

Propargylic Amination of Compound 1A and Compound 1B to Compound 1C

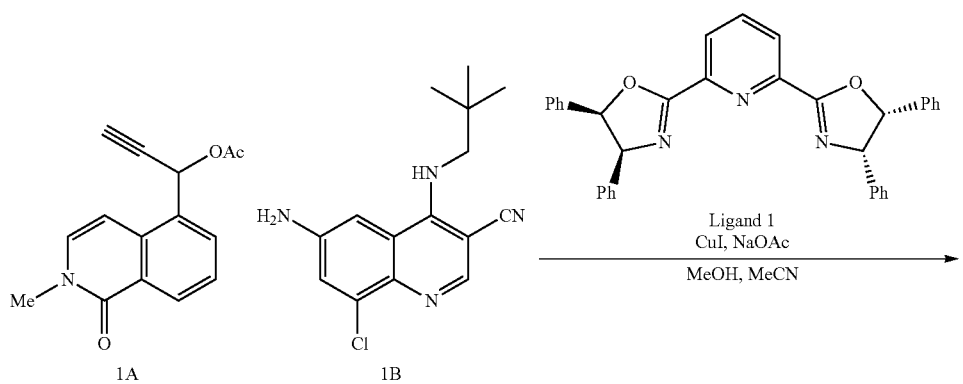

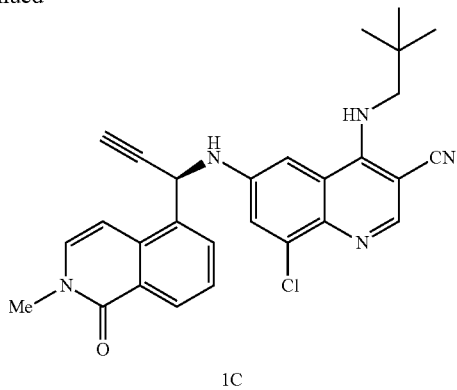

1C

A reactor was charged with copper iodide (0.0024 equiv), Ligand 1 (0.003 equiv), and 1:1 v/v acetonitrile:methanol (7.5 volumes). To a separate reactor, Compound 1B (1.0 equiv, scaling factor), Compound 1A (1.1 equiv), sodium acetate (1.25 equiv), and 1:1 v/v acetonitrile:methanol (7.5 volumes) were charged and the mixture was cooled to about 0° C. The catalyst mixture in the first reactor was charged to the second reactor, and the reaction was agitated for about 20 hours. An aqueous solution of 5 wt % ammonium chloride (10 volumes) was charged and the slurry was warmed to about 20° C. and filtered. The cake was rinsed with water (5 volumes) and MTBE (5 volumes). The wet cake was combined with acetone (20 volumes) at about 50° C., then cooled to about 20° C. and filtered. The filtrate was concentrated to about 8 volumes, then water (8 volumes) was charged at about 50° C. The slurry was cooled to about 20° C., filtered, and the solids were rinsed with water (5 volumes). The cake was dried at about 50° C. to afford Compound 1C. $^1$H NMR (400 MHz, DMSO): δ 8.31 ppm (s, 1H), 8.28 (dd, J=8.2, 0.8 Hz, 1H), 8.08 (dd, J=7.5, 1.2 Hz, 1H), 7.56 (d, J=7.8 Hz, 1H), 7.55 (m, 1H), 7.52 (d, J=2.2 Hz, 1H), 7.36 (d, J=2.0 Hz, 2H), 7.12 (d, J=8.2 Hz, 1H), 6.68 (d, J=7.7 Hz, 1H), 6.15 (dd, J=8.1, 2.0 Hz, 1H), 3.80 (dd, J=13.9, 7.0 Hz, 1H), 3.63 (dd, J=13.9, 6.5 Hz, 1H), 3.56 (d, J=2.2 Hz, 1H), 3.51 (s, 3H), 0.92 (s, 9H).

Click Reaction of Compound 1C and Compound 1D to Compound 1

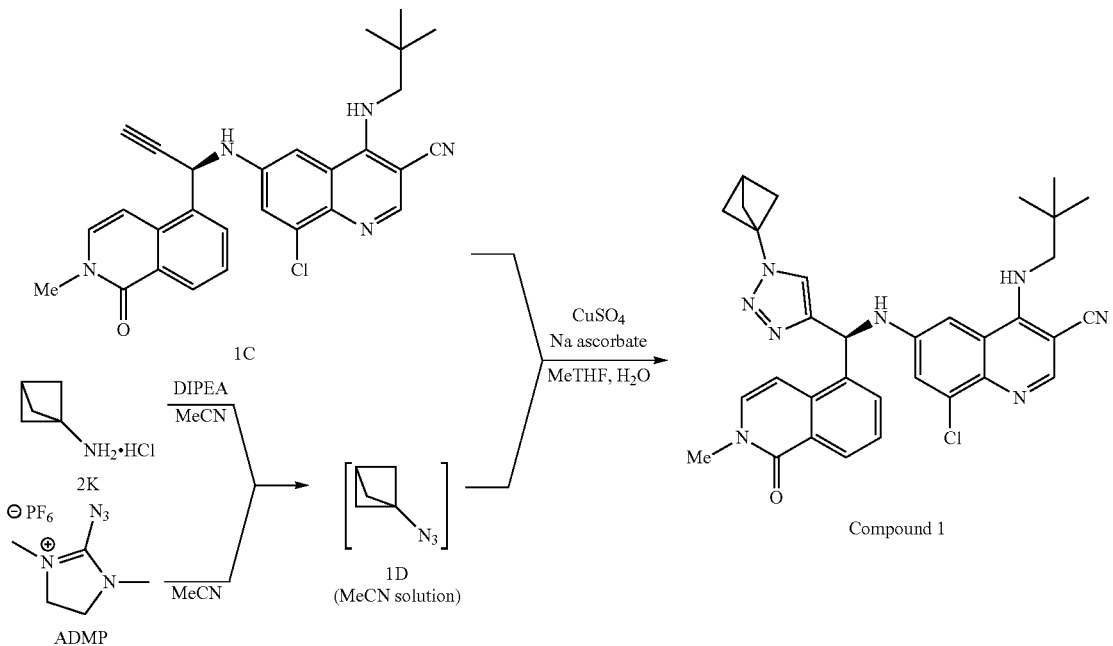

A reactor was charged with 2-azido-1,3-dimethylimidazolium hexafluorophosphate (ADMP, 1.37 equiv) and acetonitrile (2.4 volumes) at about 20° C. A second reactor was charged with Compound 2K (1.26 equiv), acetonitrile (1.8 volumes), and diisopropylethylamine (2.33 equiv) at about 20° C. A third reactor was charged with copper sulfate (0.1 equiv), sodium ascorbate (0.3 equiv) Compound 1C (scaling factor, 1.0 equiv), 2-methyltetrahydrofuran (5 volumes) and water (0.7 volumes) at about 20° C. The ADMP and Compound 2K mixtures in the first and second reactors were combined in a tube reactor to form Compound 1D, and the resulting mixture was collected in the first reactor containing Compound 1C. The combined reaction mixture was agitated for about 4 hours at about 20° C., and then MTBE (4 volumes) was added. The mixture was cooled to about 0° C. and the resulting slurry was filtered. The solids were rinsed with MTBE (3 volumes), water (3 volumes), and MTBE (3 volumes). The solids were deliquored and then combined with DMF (7 volumes) and heated to about 50° C. Water (1 volume) and Compound 1 seed crystals were charged, and the mixture was agitated at about 50° C. Additional water (2.5 volumes) was charged over about 2 hours and the resulting slurry was held at about 50° C. for about 16 hours, then cooled to about 20° C. over about 3 hours. The slurry was filtered and the solids were rinsed with a mixture of 1:1 v/v DMF/water (2 volumes), followed by water (4 volumes) and MTBE (2 volumes). The cake was dried at about 50° C. to provide Compound 1. $^1$H NMR (400 MHz, DMSO-$d_6$): δ 8.24 (s, 1H), 8.18 (d, J=7.2 Hz, 1H), 7.95 (s, 1H), 7.68 (dd, J=7.6, 1.2 Hz, 1H), 7.57 (d, J=2.0 Hz, 1H), 7.50 (d, J=8.0 Hz, 1H), 7.43 (at, J=7.8 Hz, 1H), 7.36 (d, J=6.8 Hz, 1H), 6.95 (at, J=6.4 Hz, 1H), 6.89 (d, J=2.0 Hz, 1H), 6.79 (d, J=7.6 Hz, 1H), 6.62 (d, J=6.8 Hz, 1H), 3.66 (dd, J=13.6, 7.2 Hz, 1H), 3.49 (s, 3H), 3.43 (dd, J=13.8, 5.4 Hz, 1H), 2.65 (s, 1H), 2.29 (s, 6H), 0.68 (s, 9H).

Example 2: Synthesis of Compound 1A

Formylation of 5-bromoisoquinoline (Compound 1E) to Compound 1F

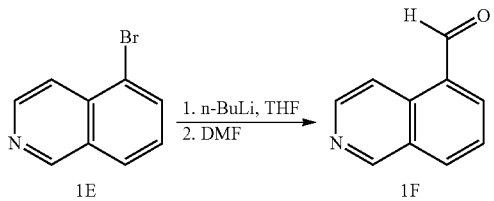

A reactor was charged with 5-bromoisoquinoline (Compound 1E) (scaling factor, 1.0 equiv) and tetrahydrofuran (4 volumes). A second reactor was charged with tetrahydrofuran (6 volumes) and cooled to about −60° C., after which n-butyllithium (1M in tetrahydrofuran, 1.2 equiv) was charged and the mixture was cooled further to about −80° C. The mixture of 5-bromoisoquinoline in tetrahydrofuran was charged to the second reactor and the combined reaction mixture was agitated at about −80° C. for about 2 hours. N,N-Dimethylformamide (2.0 equiv) was charged and the mixture was then agitated at about −80° C. until reaction was deemed complete. The reaction mixture was warmed to about 8° C. and then aqueous hydrochloric acid (0.8 M, 16 volumes) was charged. The mixture was adjusted to about 20° C. and then charged with ethyl acetate (5 volumes). The phases were separated, the aqueous phase was diluted with 8 wt % aqueous NaHCO$_3$ (2.5 volumes), and then extracted with ethyl acetate (3 volumes) twice. The organic phases were combined and washed with 12 wt % aqueous NaCl (5 volumes). The phases were separated and the organic phase was concentrated to remove ethyl acetate and exchanged into n-heptane (about 5 volumes) to obtain a slurry. The slurry was adjusted to about 10° C. and then filtered. The filter cake was rinsed with 10:1 v/v ethyl acetate:n-heptane (4.4 volumes) and then twice with n-heptane (2 volumes). The cake was dried at about 40° C. to afford Compound 1F.

$^1$H NMR (400 MHz, CDCl$_3$): δ 10.38 (d, J=0.8 Hz, 1H), 9.42 (d, J=1.1 Hz, 1H), 8.84 (dp, J=6.0, 1.0 Hz, 1H), 8.65 (dd, J=6.0, 0.8 Hz, 1H), 8.45-8.40 (m, 2H), 7.88 (ddd, J=8.1, 7.2, 0.9 Hz, 1H).

Methylation of Compound 1F to Compound 1G

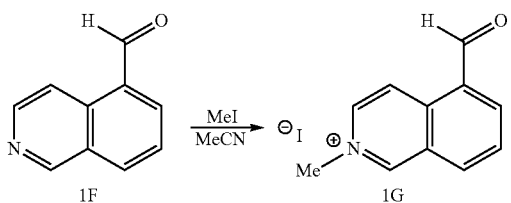 [SMILES: "MeI" ; "MeCN" ; O=Cc1cccc2cnccc12 ; [I-] ; C[n+]1ccc2c(C=O)cccc2c1]

A reactor was charged with Compound 1F (scaling factor, 1.0 equiv) and acetonitrile (8 volumes), and then adjusted to about 30° C. Iodomethane (2 equiv) was charged and the reaction mixture was agitated for about 6 hours. Toluene (5 volumes) was charged and the slurry was cooled to about 5° C. The slurry was filtered and the cake was rinsed with toluene (3 volumes), and then dried at about 30° C. to afford Compound 1G. $^1$H NMR (400 MHz, DMSO): δ 10.50 ppm (s, 1H), 10.16 (s, 1H), 9.41 (d, J=7.1 Hz, 1H), 8.86 (ddd, J=12.1, 7.1, 1.4 Hz, 2H), 8.75 (d, J=8.34 Hz, 1H), 8.28 (dd, J=8.3, 7.2 Hz, 1H) 4.52 (s, 3H).

Oxidation of Compound 1G to Compound H

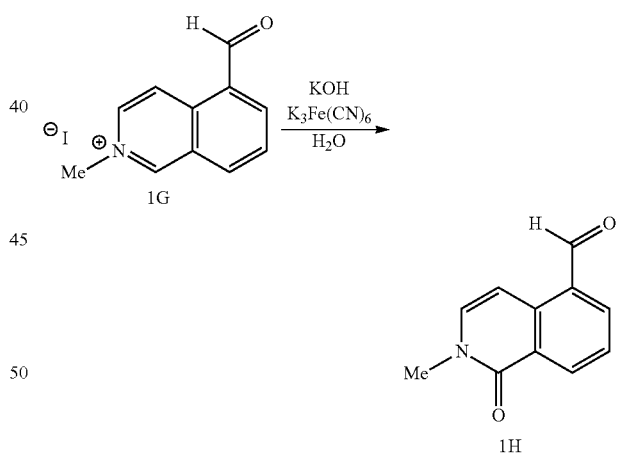

Compound 1G (scaling factor, 1.0 equiv) and potassium ferricyanide (2 equiv) were charged to a reactor. Water (20 volumes) was charged to the reactor and the temperature was adjusted to about 5° C. A mixture of potassium hydroxide (4 equiv) in water (3 volumes) was prepared and then charged to the reactor over about 2 hours. The reaction mixture was agitated for about 3 hours and then filtered. The filter cake was rinsed with water (3 volumes) three times. The cake was dried at about 50° C. to afford Compound 1H. $^1$H NMR (400 MHz, DMSO-$d_6$) δ 10.26 (s, 1H), 8.46 (dd, J=8.0, 1.5 Hz, 1H), 8.20 (dd, J=7.4, 1.5 Hz, 1H), 7.62 (t, J=7.7 Hz, 1H), 7.59 (s, 2H), 3.47 (s, 3H).

Ethynylation/Acetylation of Compound 1H to Compound 1A

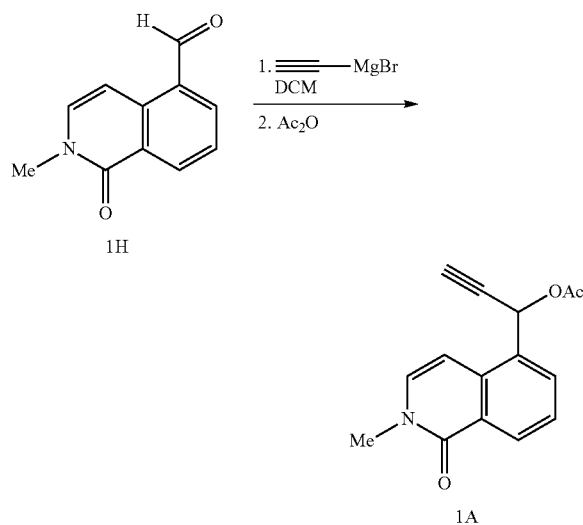

To a reactor was charged Compound 1H (scaling factor, 1.0 equiv) and dichloromethane (10 volumes). Ethynylmagnesium bromide (0.5M in tetrahydrofuran, 1.6 equiv) was then charged to the reactor maintaining the internal temperature below about 25° C. The reaction was then agitated for about 2 hours, after which acetic anhydride (1.8 equiv) was charged and the mixture was agitated at about 25° C. for about 3 hours. Aqueous hydrochloric acid (1M, 2 volumes) was charged and the mixture was concentrated to about 5 volumes to obtain a slurry. The slurry was diluted with water (8 volumes), agitated for about 1 hour and then filtered. The filtered cake was rinsed with water (5 volumes) three times and then the solids were transferred back into a reactor. Isopropanol (3 volumes) was charged to the reactor and the mixture was heated to about 75° C. The mixture was cooled to about 25° C. over about 6 hours and aged for about 3 hours. The slurry was then filtered and rinsed with isopropanol (0.5 volumes) twice. The resulting filter cake was dried at about 40° C. to obtain Compound 1A. $^1$H NMR (400 MHz, DMSO-d$_6$): δ 8.29 (ddd, J=8.1, 1.2, 0.7 Hz, 1H), 7.93 (ddd, J=7.5, 1.3, 0.3 Hz, 1H), 7.57 (d, J=7.7 Hz, 1H), 7.53 (dd, J=7.8, 7.6 Hz, 1H), 6.79 (d, J=2.3 Hz, 1H), 6.74 (dd, J=7.7, 0.6 Hz, 1H), 3.87 (d, J=2.3 Hz, 1H), 3.52 (s, 3H), 2.09 (s, 3H).

Example 3: Synthesis of Compound 1B

Coupling of 2-chloro-4-nitroaniline (Compound 1I) and ethyl 2-cyano-3-ethoxyacrylate (Compound 1J) to Compound 1K

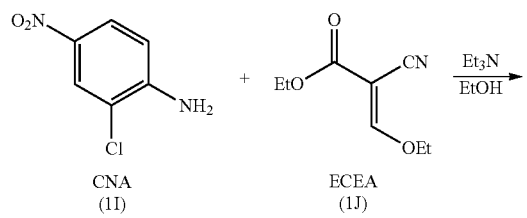

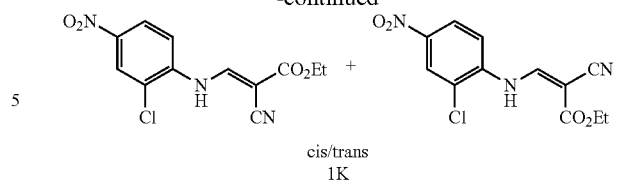

To a reactor was charged 2-chloro-4-nitroaniline (Compound 1I) (scaling factor, 1.0 equiv) and ethyl (ethoxymethylene)cyanoacetate (Compound 1J) (1.3 equiv). Ethanol (10 volumes) was charged and the reaction mixture was heated to about 30° C., and then triethylamine (2.0 equiv) was charged while maintaining the temperature below about 40° C. The reaction mixture was heated to about 75° C. for about 24 hours. When the reaction was deemed complete, ethanol (5 volumes) was charged and the mixture was cooled to about 20° C. The resulting slurry was aged for about 3 hours and then filtered. The solids were washed with ethanol (3 volumes) twice and then dried at about 50° C. to afford a mixture of cis/trans Compound 1K (approximately 95:5). $^1$H NMR (Compound 1K cis, 400 MHz, CDCl$_3$): δ 11.48 (d, J=12.7 Hz, 1H), 8.38 (d, J=2.5 Hz, 1H), 8.24 (ddd, J=9.1, 2.5, 0.5 Hz, 1H), 7.95 (dd, J=12.7, 0.5 Hz, 1H), 7.36 (d, J=9.1 Hz, 1H), 4.37 (q, J=7.2 Hz, 2H), 1.40 (t, J=7.2 Hz, 3H).

Cyclization of Compound 1K to Compound 1L

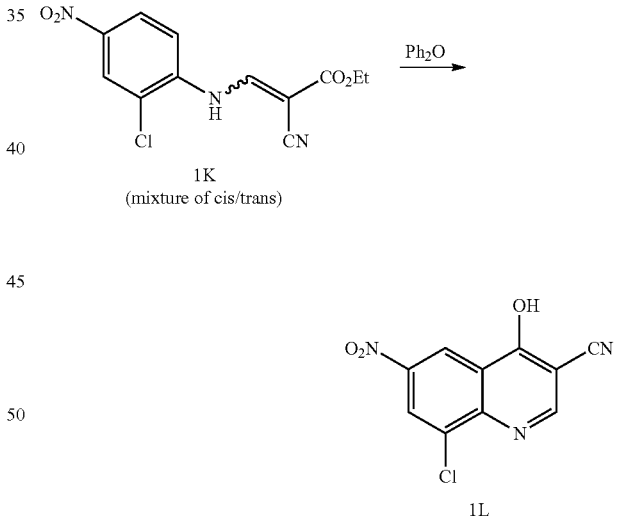

A mixture of Compound 1K (scaling factor, 1.0 equiv) and diphenyl ether (15 volumes, pre-melted at about 50° C.) were charged to a reactor. The reaction was heated to about 260° C. for about 10 hours, then cooled to about 50° C. and aged for about 16 hours. Isopropyl acetate (3 volumes) and n-heptane (6 volumes) were charged and the resulting slurry was filtered. The solids were rinsed with isopropyl acetate (3 volumes) and twice with n-heptane (3 volumes), and then dried at about 50° C. to afford Compound 1L. $^1$H NMR (400 MHz, CDCl$_3$): δ 12.85 (broad s, 1H), 8.74 (d, J=2.6 Hz, 1H), 8.73 (s, 1H), 8.72 (d, J=2.6 Hz, 1H).

Amination of Compound 1L to Compound 1N

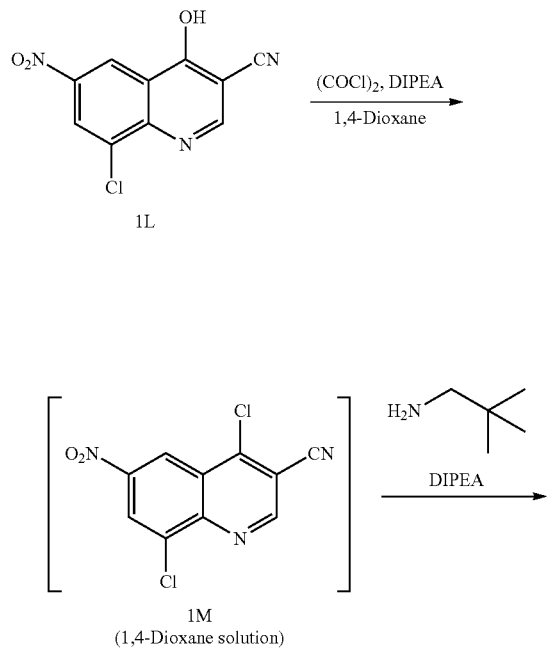

Reduction of Compound 1N to Compound 1B

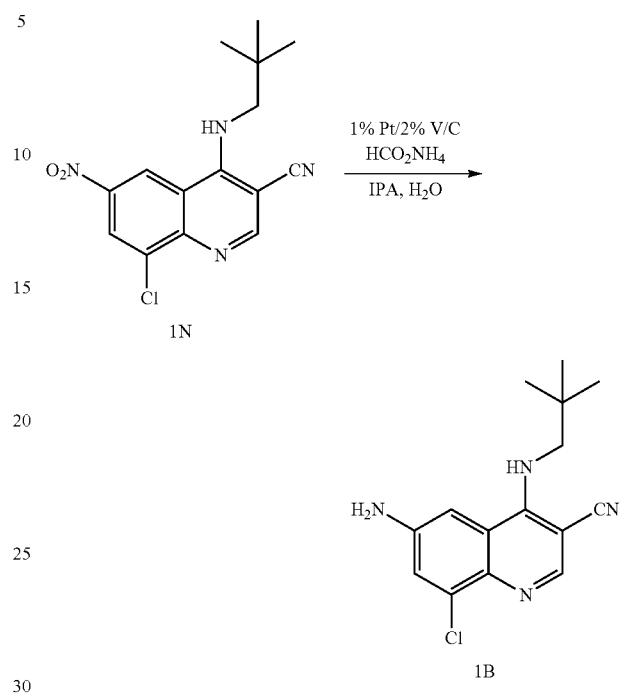

Compound 1L (scaling factor, 1.0 equiv), 1,4-dioxane (8 volumes) and DIPEA (1.2 equiv) were charged to a reactor. The temperature was adjusted to about 40° C. and oxalyl chloride (2.0 equiv) was slowly charged. The reaction was heated to about 60° C. and agitated for about 5 hours until the reaction was deemed complete. The reaction was cooled to about 10° C. and DIPEA (2.5 equiv) was charged, followed by IPA (3.0 equiv) while maintaining the temperature below about 20° C. The reaction was warmed to about 20° C. and DIPEA (1.1 equiv) was charged, followed by neopentylamine (1.15 equiv). The reaction was agitated at about 20° C. for about 16 hours. Water (10 volumes) was charged over about 1 hour and the resulting slurry was filtered. The cake was washed with water (4 volumes), methanol (4 volumes), and MTBE (6 volumes), and then dried at about 50° C. to afford Compound 1N. $^1$H NMR (400 MHz, CDCl$_3$): δ 8.80 (s, 1H), 8.72 (s, 1H), 8.65 (s, 1H), 3.84 (s, 2H), 1.15 (s, 9H).

To a reactor was charged Compound 1N (scaling factor, 1.0 equiv), ammonium formate (6 equiv), and platinum/vanadium on carbon (0.0025 equiv). Isopropanol (13 volumes) and water (2 volumes) were charged and the slurry was agitated at about 60° C. for about 5 hours. The slurry was cooled to about 20° C. and tetrahydrofuran (15 volumes) was charged. The slurry was filtered and rinsed forward with tetrahydrofuran (5 volumes). The filtrate was concentrated to about 8 volumes, water (7 volumes) was charged, and the slurry was filtered. The solids were rinsed with water (5 volumes) and MTBE (5 volumes) then dried at about 40° C. to afford Compound 1B. $^1$H NMR (400 MHz, DMSO): δ 8.22 ppm (s, 1H), 7.35 (d, J=2.2 Hz, 1H), 7.25 (dd, J=6.7, 6.7 Hz, 1H), 7.21 (d, J=2.3 Hz, 1H), 5.74 (broad s, 2H), 3.68 (d, J=6.7, 2H), 0.97 (s, 9H).

Example 4: Compound 1 Manufacturing Route 2

Coupling of Compound 2A and Compound 2B to Compound 2C

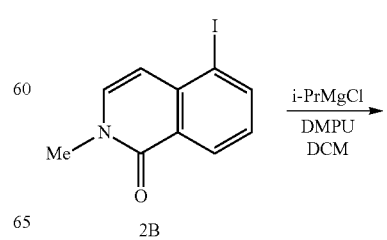

Condensation of Compound 2C to Compound 2D

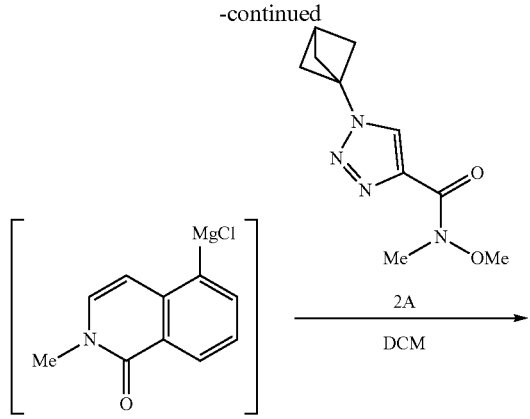

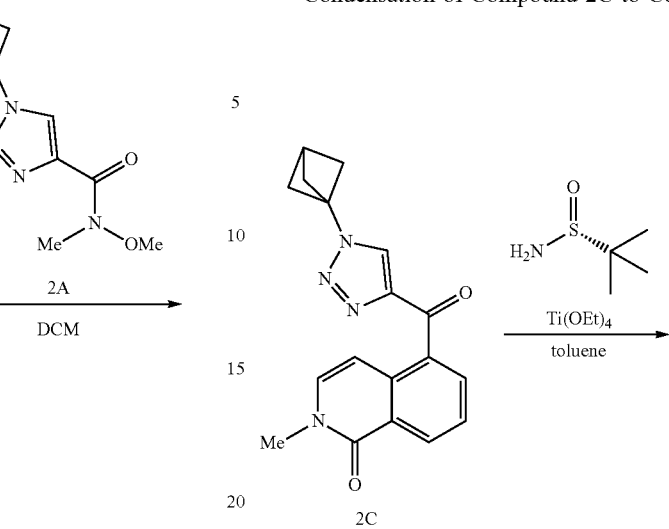

To a reactor was charged Compound 2B (1.2 equiv), DCM (10 volumes) and DMPU (2.4 equiv). The mixture was cooled to about −5° C. and a solution of i-PrMgCl (1.25 equiv, 2M in tetrahydrofuran) was then charged over about 1 hour. The mixture was agitated until the magnesiation reaction was deemed complete, and then a solution of Compound 2A (scaling factor, 1.0 equiv) in DCM (5 volumes) was charged to the reactor. The mixture was then adjusted to about 20° C. and agitated until the reaction was deemed complete. A 10 wt % aqueous citric acid solution (7 volumes) was charged and the biphasic mixture was agitated for about 15 minutes. The layers were separated and the organic layer was washed with water (5 volumes). The organic layer was then solvent exchanged to ethanol and the volume was adjusted to about 9 volumes. The resulting slurry was then adjusted to about 75° C. and agitated for about 1 hour, then cooled to about 0° C. The slurry was filtered, the cake was rinsed with ethanol (2 volumes) twice, and then dried at about 40° C. to give Compound 2C. $^1$H NMR (400 MHz, CDCl$_3$) δ 8.63 (ddd, J=7.9, 1.1, 0.5 Hz, 1H), 8.26 (d, J=7.5, 1.4 Hz, 1H), 8.21 (s, 1H), 7.53 (dd, J=7.9, 7.8 Hz, 1H), 7.09 (d, J=7.7 Hz, 1H), 7.04 (d, J=7.7 Hz, 1H), 3.57 (s, 3H), 2.74 (s, 1H), 2.43 (s, 6H).

Compound 2C (scaling factor, 1.0 equiv), (R)-2-methylpropane-2-sulfinamide (1.1 equiv) and toluene (15 volumes) was charged to a reactor, followed by Ti(OEt)$_4$ (2.2 equiv). The temperature was adjusted to about 70° C. The mixture was then either sparged with a continuous flow of nitrogen or placed under vacuum at about 150-250 mbar, and the volume was maintained at about 15 volumes by charging additional toluene. The mixture was agitated for about 12 hours and then cooled to about 25° C. and aged for about 3 hours. The slurry was filtered, and then the cake was rinsed with toluene (5 volumes) and dried at about 45° C. to afford Compound 2D. $^1$H NMR (400 MHz, CDCl$_3$): δ 8.55 (d, J=8.5 Hz, 1H), 7.90 (s, 1H), 7.65 (d, J=6.9 Hz, 1H), 7.54 (dd, J=7.6, 7.6 Hz, 1H), 7.04 (d, J=7.5, 1H), 6.17 (d, J=7.0 Hz, 1H), 3.56 (s, 3H), 2.74 (s, 1H), 2.41 (s, 6H), 1.27 (s, 9H).

Reduction of Compound 2D to Compound 2E

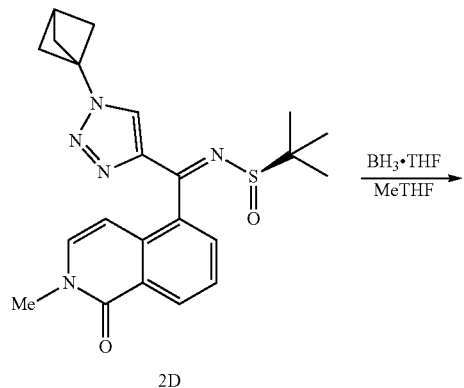

2D

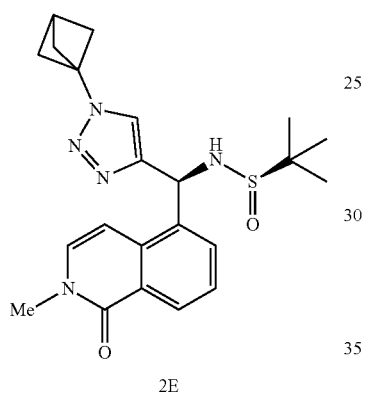

2E

To a reactor was charged 2-methyltetrahydrofuran (10V) and BH$_3$·THF (1M in tetrahydrofuran, 2.5 equiv), and the temperature was adjusted to about −10° C. Compound 2D (scaling factor, 1.0 equiv) was charged followed by 2-methyltetrahydrofuran (2.8 volumes). The reaction was agitated at about 0° C. until deemed complete. The mixture was then adjusted to about −10° C. and a solution of 20 wt % aqueous KHCO$_3$ (12.5 volumes) was slowly added while maintaining the reaction mixture below about 5° C. The mixture was then heated to about 50° C. for about 4 hours and then cooled to about 20° C. The organic layer was separated and washed with a solution of 15 wt % aqueous NaCl (10 volumes) and then solvent exchanged to DMF and the volume was adjusted to about 3.5 volumes. The reaction mixture was adjusted to about 50° C. and MTBE (10 volumes) was charged while maintaining the temperature above about 40° C. Compound 2E (0.005 equiv) was charged and the mixture was agitated for about 1 hour at about 50° C. MTBE (10 volumes) was charged over about 2 hours and the slurry was cooled to about 10° C. over about 4 hours and aged for about 16 hours. The slurry was then filtered and the wet cake was rinsed with MTBE (3 volumes) twice. The resulting solids were dried at about 50° C. to yield Compound 2E in 99.0% diastereomeric purity. $^1$H NMR (400 MHz, DMSO): δ 8.19 (dd, J=8.0, 1.1 Hz, 1H), 8.01 (s, 1H), 7.83 (dd, J=7.8, 1.1 Hz, 1H), 7.50 (t, J=8.0 Hz, 1H), 7.48 (d, J=7.7 Hz, 1H), 6.78 (d, J=7.7 Hz, 1H), 6.26 (d, J=5.9 Hz, 1H), 6.15 (d, J=5.9 Hz, 1H), 3.44 (s, 3H), 2.62 (s, 1H), 2.25 (s, 6H), 1.04 (s, 9H).

Cleavage of Compound 2E to Compound 2F

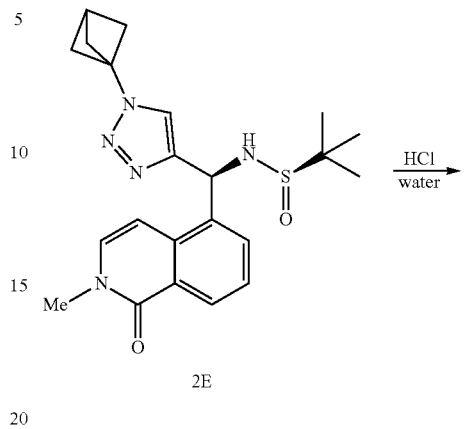

2E

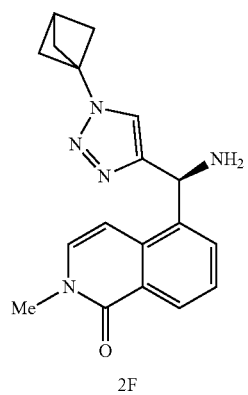

2F

To a reactor was charged Compound 2E (scaling factor, 1.0 equiv) and water (5 volumes). Concentrated hydrochloric acid (approx. 37 wt %, 1.6 equiv) was charged and the reaction mixture was adjusted to about 50° C. for about 20 hours. The solution was diluted with water (1 volume), cooled to about 20° C., and then washed with dichloromethane (2 volumes). The layers were separated and a solution of sodium hydroxide (3.2 equivs) in water (2 volumes) was charged to the aqueous layer over about 1 hour. The slurry was aged at about 50° C. for about 4 hours, then cooled to about 15° C. and filtered. The cake was rinsed with water (3 volumes) twice, followed by MTBE (4 volumes), and the solids were dried at about 60° C. to afford Compound 2F. $^1$H NMR (400 MHz, DMSO): δ 8.16 ppm (ddd, J=7.9, 1.2, 0.6 Hz, 1H), 7.89 (ddd, J=7.4, 1.4, 0.4 Hz, 1H), 7.88 (s, 1H), 7.48 (dd, J=7.8, 7.8 Hz, 1H), 7.44 (d, J=7.7 Hz, 1H), 6.84 (dd, J=7.9, 0.4 Hz, 1H), 5.71 (s, 1H), 3.48 (s, 3H), 2.65 (s, 1H), 2.41 (broad s, 2H), 2.28 (s, 6H).

Coupling of Compound 2F and Compound 2G to Compound 1

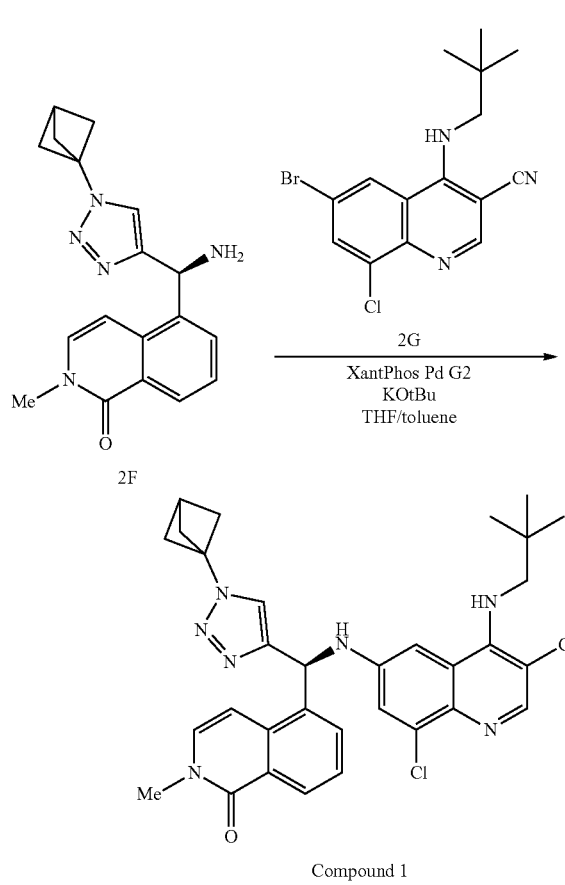

2F

Alternative Coupling of Compound 2F and Compound 2G to Compound 1

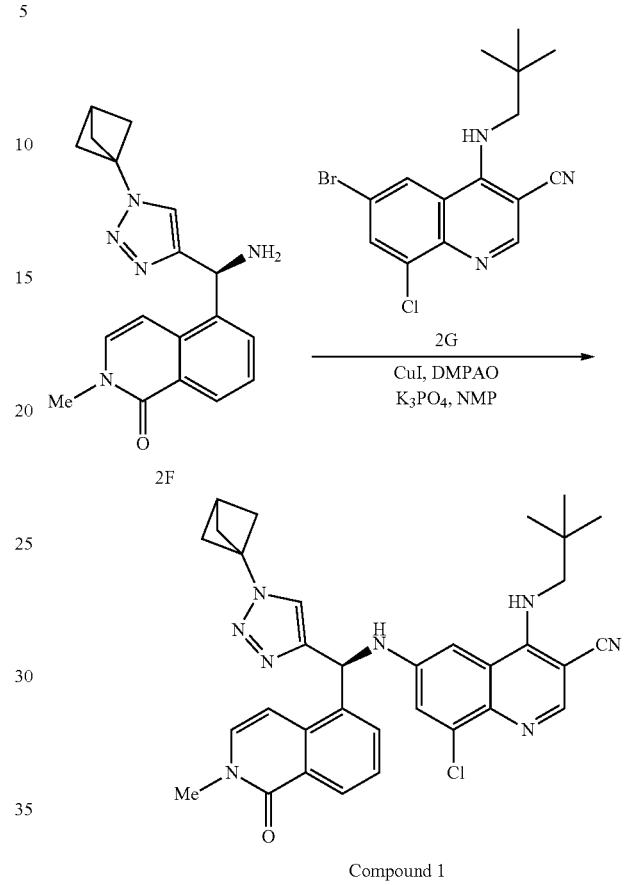

To a reactor was charged Compound 2F (scaling factor, 1.0 equiv), Compound 2G (1.1 equiv), (XantPhos)Pd-G2 (0.05 equiv), toluene (5 volumes), and tetrahydrofuran (3 volumes), and then the reaction mixture was heated to about 70° C. Potassium tert-butoxide (1M in tetrahydrofuran, 1.2 equiv) was charged over about 1 hour and the reaction was agitated at about 70° C. until the deemed complete. The mixture was then adjusted to about 50° C. over about 2 hours, after which the slurry was filtered. The filtered cake was rinsed sequentially with toluene (3 volumes), water (3 volumes), and MTBE (3 volumes), and then dried at about 50° C. for about 16 hours. The dried solids were then combined in a reactor with DMF (7.5 volumes) and heated to about 50° C. A solution of 4 wt % aqueous N-acetyl-L-cysteine (2.5 volumes) was charged over about 4 hours and the resulting slurry was aged for about 16 hours. The slurry was then cooled to about 22° C. over about 3 hours and then filtered. The filtered cake was rinsed sequentially with 1:1 v/v DMF/water (2 volumes), water (4 volumes), and MTBE (2 volumes), and then dried at about 50° C. to provide Compound 1. $^1$H NMR (400 MHz, DMSO-$d_6$): δ 8.24 (s, 1H), 8.18 (d, J=7.2 Hz, 1H), 7.95 (s, 1H), 7.68 (dd, J=7.6, 1.2 Hz, 1H), 7.57 (d, J=2.0 Hz, 1H), 7.50 (d, J=8.0 Hz, 1H), 7.43 (at, J=7.8 Hz, 1H), 7.36 (d, J=6.8 Hz, 1H), 6.95 (at, J=6.4 Hz, 1H), 6.89 (d, J=2.0 Hz, 1H), 6.79 (d, J=7.6 Hz, 1H), 6.62 (d, J=6.8 Hz, 1H), 3.66 (dd, J=13.6, 7.2 Hz, 1H), 3.49 (s, 3H), 3.43 (dd, J=13.8, 5.4 Hz, 1H), 2.65 (s, 1H), 2.29 (s, 6H), 0.68 (s, 9H).

To a reactor was charged Compound 2F (scaling factor, 1.0 equiv), Compound 2G (1.5 equiv), copper (I) iodide (0.10 equiv), 2,6-dimethylanilino(oxo)acetic acid (0.10 equiv), tribasic potassium phosphate (3.0 equiv), and methyl-2-pyrrolidinone (16 volumes). The mixture was heated to about 105° C. and agitated for about 21 hours. The mixture was cooled to about 50° C., diluted with water (4 volumes). The mixture was cooled to about 22° C. and diluted with water (2 volumes). Additional water (2 volumes) and dichloromethane (6 volumes) were charged and the layers were separated. The aqueous layer was extracted with dichloromethane (10 volumes) and the combined organic layers were concentrated under vacuum. The concentrated mixture was filtered through a pad of silica gel and the silica gel pad was rinsed with dichloromethane (10 volumes). The combined filtrate was concentrated under vacuum and the residue was purified by flash column chromatography to provide Compound 1. $^1$H NMR (400 MHz, DMSO-$d_6$): δ 8.24 (s, 1H), 8.18 (d, J=7.2 Hz, 1H), 7.95 (s, 1H), 7.68 (dd, J=7.6, 1.2 Hz, 1H), 7.57 (d, J=2.0 Hz, 1H), 7.50 (d, J=8.0 Hz, 1H), 7.43 (at, J=7.8 Hz, 1H), 7.36 (d, J=6.8 Hz, 1H), 6.95 (at, J=6.4 Hz, 1H), 6.89 (d, J=2.0 Hz, 1H), 6.79 (d, J=7.6 Hz, 1H), 6.62 (d, J=6.8 Hz, 1H), 3.66 (dd, J=13.6, 7.2 Hz, 1H), 3.49 (s, 3H), 3.43 (dd, J=13.8, 5.4 Hz, 1H), 2.65 (s, 1H), 2.29 (s, 6H), 0.68 (s, 9H).

Example 5: Synthesis of Compound 2a Via Compound 2M (for Manufacturing Routes 2-4)

Formation of Compound 2J from Methyl Pyruvate (Compound 2H)

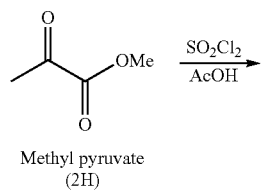

Methyl pyruvate
(2H)

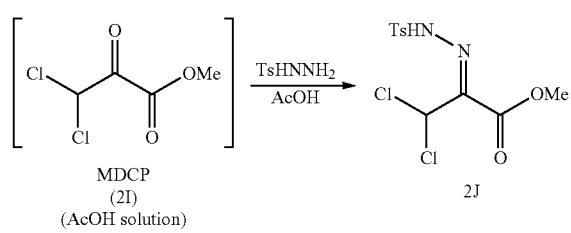

To a reactor was charged methyl pyruvate (Compound 2H) (1.2 equiv) and acetic acid (2 volumes) followed by sulfuryl chloride (3 equiv). The reaction mixture was heated to about 50° C. and agitated until the reaction was deemed complete. The reaction mixture was cooled to about 40° C. and concentrated to about 2 volumes. The mixture was then cooled to about 20° C. and tosyl hydrazide (scaling factor, 1.0 equiv) was charged over about 30 minutes while maintaining the temperature below about 30° C. The mixture was heated to about 30° C. and agitated until the reaction was deemed complete. The reaction was cooled to about 10° C. over about 2 hours and agitated for about 3 hours. The resulting slurry was filtered and the cake was rinsed with 2:1 w/w heptane:acetic acid (2 volumes) followed by heptane (2 volumes). The solids were dried at about 40° C. to afford Compound 2J. $^1$H NMR (400 MHz, CDCl$_3$): δ 11.91 (s, 1H), 7.85 (d, J=8.4 Hz, 2H), 7.34 (d, J=8.4 Hz, 2H), 6.45 (s, 1H), 3.92 (s, 3H), 2.44 (s, 3H).

Cyclization Hydrolysis of Compound 2J to Compound 2M

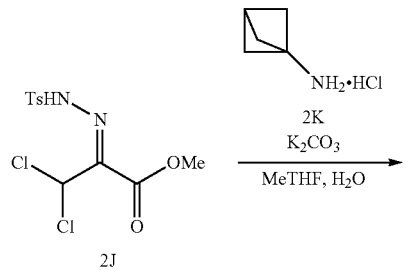

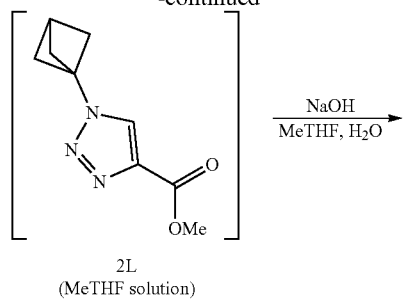

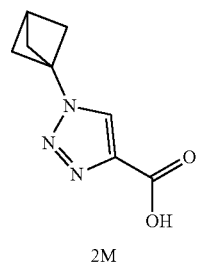

2M

To a reactor was charged potassium carbonate (2.2 equiv) and water (9 volumes). The temperature was adjusted to about 20° C. and then Compound 2K (scaling factor, 1.0 equiv) was charged, followed by 2-methyltetrahydrofuran (10 volumes). The mixture was then cooled to about −10° C. To a separate reactor was charged Compound 2J (1.1 equiv) and 2-methyltetrahydrofuran (13.3 volumes), and then the resulting mixture was charged to the reactor containing Compound 2K over about 1 hour. Additional 2-methyltetrahydrofuran (2.3 volumes) was charged and the resulting slurry was warmed to about 20° C. over about 30 minutes. The mixture was agitated at about 20° C. until the reaction was deemed complete. The layers were separated and the aqueous layer was extracted with 2-methyltetrahydrofuran (3.5 volumes). The combined organic layers containing Compound 2L were then carried into the Compound 2M step.

Compound 2M Synthesis

To the Compound 2L solution in 2-methyltetrahydrofuran was charged 2M aqueous sodium hydroxide (1.9 equiv) and agitated at about 20° C. for about 1 hour. The layers were separated and the aqueous layer was washed with 2-methyltetrahydrofuran (3.5 volumes). The layers were separated, charged with water (1 volume) to the aqueous layer, and then concentrated to remove about 1 volume of distillate. To the aqueous layer was charged 5M hydrochloric acid (2.5 equiv) over about 2 hours while maintaining the temperature at about 20° C. The resulting slurry was cooled to about 2° C. and aged for about 3 hours. The slurry was filtered and rinsed the wet cake with water (4 volumes). The cake was dried at about 45° C. to obtain Compound 2M. $^1$H NMR (400 MHz, CDCl$_3$): δ 11.06 (s, 1H), 8.16 (s, 1H), 2.76 (s, 1H), 2.44 (s, 6H).

Amidation of Compound 2M to Compound 2A

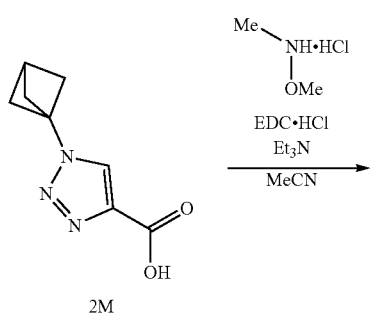

To a reactor was charged Compound 2M (scaling factor, 1.0 equiv), N,O-dimethylhydroxylamine hydrochloride (1.4 equiv) and acetonitrile (10 volumes). The mixture was cooled to about 0° C., and 1-(3-dimethylaminopropyl)-3-ethylcarbodiimide hydrochloride (1.2 equiv) was charged while maintaining the temperature below about 5° C. Triethylamine (1.5 equiv) was then charged. The mixture was adjusted to about 20° C. and agitated until the reaction was deemed complete, after which it was concentrated to about 6 volumes. A 10 wt % aqueous citric acid solution (3 volumes) was then charged to the reactor and the resulting mixture was concentrated to about 5 volumes. The contents were adjusted to about 20° C. and then isopropyl acetate (8 volumes) was charged. The layers were separated and the aqueous layer was extracted with isopropyl acetate (4 volumes) twice. The combined organic layers were washed with a solution of 20 wt % aqueous potassium bicarbonate (2 volumes) and then concentrated to about 4 volumes. The resulting slurry was warmed to about 60° C., cooled to about 25° C. and then n-heptane (8 volumes) was charged over about 4 hours. The slurry was then cooled to about 5° C. over about 2 hours. The solids were filtered, rinsed with n-heptane (3 volumes) and dried at about 50° C. to give Compound 2A. $^1$H NMR (400 MHz, DMSO-d$_6$): δ 8.59 (s, 1H), 3.73 (s, 3H), 3.31 (s, 3H), 2.72 (s, 1H), 2.38 (s, 6H).

Example 6: Synthesis of Compound 2B (for Manufacturing Routes 2-3)

Iodination of 5-bromoisoquinoline (Compound 1E) to 5-iodoisoquinoline (Compound 2O)

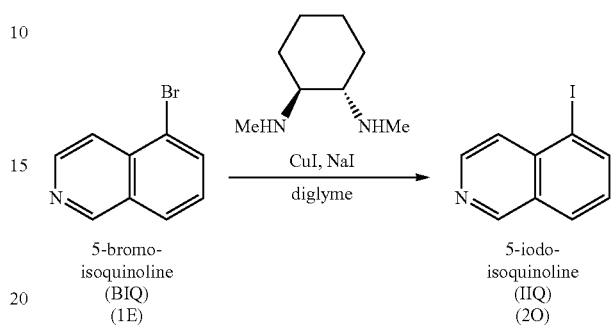

To a reactor was charged diethylene glycol dimethyl ether (diglyme, 4 volumes), 5-bromoisoquinoline (Compound 1E) (scaling factor, 1.0 equiv), sodium iodide (4 equiv), copper iodide (0.1 equiv) and trans-N1,N2-dimethylcyclohexane-1,2-diamine (0.2 equiv). The slurry was heated to about 130° C. for about 40 hours, and then cooled to about 20° C. 30 wt % aqueous ammonium hydroxide (10 volumes) and water (10 volumes) were charged, and then the slurry was filtered and rinsed twice with water (2 volumes). The solids were dried at about 60° C. to afford 5-iodoisoquinoline (Compound 2O). $^1$H NMR (400 MHz, Chloroform-d) δ 9.12 (d, J=1.0 Hz, 1H), 8.62 (d, J=6.0 Hz, 1H), 8.25 (dt, J=7.3, 1.0 Hz, 1H), 7.96 (dt, J=8.2, 1.0 Hz, 1H), 7.82 (dt, J=6.1, 1.0 Hz, 1H), 7.33 (dd, J=8.2, 7.3 Hz, 1H).

Methylation of 5-iodoisoquinoline (Compound 2O) to Compound 2P

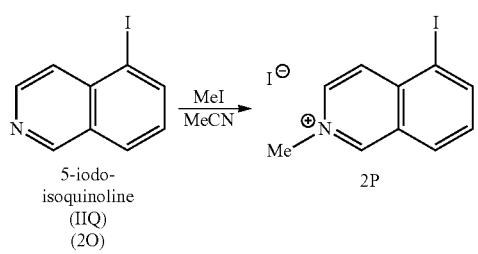 [SMILES: "MeI" ; "MeCN" ; Ic1cccc2cnccc12 ; [I-] ; C[n+]1ccc2c(I)cccc2c1]

To a reactor was charged 5-iodoisoquinoline (Compound 2O) (scaling factor, 1.0 equiv) and acetonitrile (8 volumes). The reactor contents were heated to about 30° C., iodomethane (1.5 equiv) was charged, and the reaction was aged for about 16 hours until deemed complete. The reactor contents were then cooled to about 25° C. and toluene (5 volumes) was charged. The reactor contents were further cooled to about 0° C. and aged for about 2 hours. The resulting slurry was then filtered and the cake was washed with toluene (2 volumes). The solids were dried at about 40° C. to provide Compound 2P. $^1$H NMR (400 MHz, DMSO-d$_6$): δ 10.01 (s, 1H), 8.85-8.72 (m, 2H), 8.48 (dd, J=15.8, 7.6 Hz, 2H), 7.85-7.76 (m, 1H), 4.50 (s, 3H).

Oxidation of Compound 2P to Compound 2B

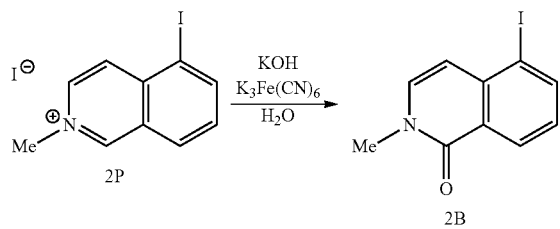

Compound 2P (scaling factor, 1.0 equiv) and potassium ferricyanide (2.5 equiv) were charged to a reactor. Water (15 volumes) was charged to the reactor and the temperature was adjusted to about 5° C. A solution of potassium hydroxide (4 equiv) in water (3 volumes) was then charged to the reactor over about 2 hours. The reaction mixture was agitated for about 3 hours, and then filtered. The filter cake was rinsed with water (3 volumes) three times. The cake was dried at about 80° C. to afford Compound 2B. $^1$H NMR (400 MHz, DMSO): δ 8.24 ppm (ddd, J=8.0, 1.3, 0.7 Hz, 1H), 8.21 (dd, J=7.6, 1.2 Hz, 1H), 7.59 (d, J=7.6 Hz, 1H), 7.23 (dd, J=7.9, 7.6 Hz, 1H), 6.57 (dd, J=7.7, 0.8 Hz, 1H), 3.51 (s, 3H).

Example 7: Synthesis of Compound 1B Via Compound 2G (for Manufacturing Routes 2-4)

Bromination of CAA (Compound 2Q) to Compound 2R

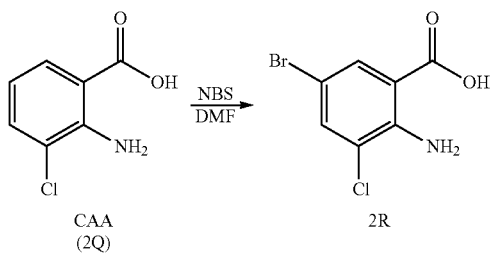

3-chloroanthranilic acid (Compound 2Q) (scaling factor, 1.0 equiv) and N,N-dimethylformamide (5 volumes) were charged to a reactor and agitated for about 30 minutes at about 25° C. The contents were adjusted to about 10° C. and N-bromosuccinimide (1.02 equiv) was slowly charged while maintaining the temperature below about 25° C. The contents were adjusted to about 20° C. and agitated until the reaction was deemed complete. Water (15 volumes) was charged at about 20° C. and the slurry was agitated at about 20° C. for about 2 hours. The slurry was filtered and the cake was washed with water (4 volumes) three times, and then dried at about 50° C. to produce Compound 2R. $^1$H NMR (400 MHz, DMSO-d6): δ 13.4 (broad s, 1H), 7.81 (s, 1H), 7.71 (d, J=2.4 Hz, 1H), 6.93 (broad s, 1H).

Condensation Cyclization of Compound 2R to Compound 2T

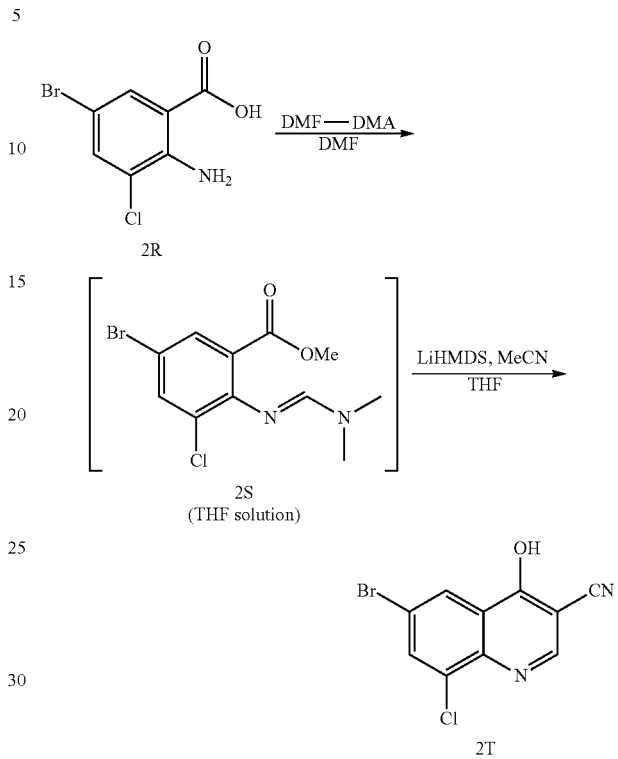

Compound 2R (scaling factor, 1.0 equiv) and N,N-dimethylformamide (5 volumes) were charged to a reactor. The contents were agitated at about 20° C. and then N,N-dimethylformamide dimethyl acetal (2.5 equiv) was charged. The contents were heated to about 110° C. and agitated until the reaction was deemed complete. The mixture was cooled to about 20° C. and methyl tert-butyl ether (15 volumes) and water (10 volumes) were charged. The aqueous layer was separated and extracted with methyl tert-butyl ether (5 volumes). The combined organic layers were washed with water (5 volumes) twice. The organic layer was dried over anhydrous magnesium sulfate, filtered and washed with methyl tert-butyl ether (3 volumes). The filtrate was concentrated and the solvent was exchanged to tetrahydrofuran (32 volumes). Acetonitrile (1.35 equiv) was charged and the contents were cooled to about −10° C. LiHMDS (1.0M in tetrahydrofuran, 2.0 equiv) was charged and the reaction was agitated at about −10° C. until deemed complete. Acetic acid (8.0 equiv) was slowly charged while maintaining the internal temperature below about 10° C. The slurry was adjusted to about 20° C. and agitated for about 2 hours, then filtered and the solids were washed with tetrahydrofuran (7.5 volumes) twice. The wet cake and water (23 volumes) were charged to a reactor and the mixture was adjusted to about pH 4 by charging acetic acid (11 equiv) and agitating at about 20° C. for about 2 hours. The slurry was filtered and the solids were washed with water (5 volumes) three times and then dried at about 50° C. to afford Compound 2T. $^1$H NMR (400 MHz, DMSO-d6): δ 12.56 (s, 1H), 8.63 (s, 1H), 8.25 (d, J=2.0 Hz, 1H), 8.17 (d, J=2.0 Hz, 1H).

Chlorination of Compound 2T to Compound 2U

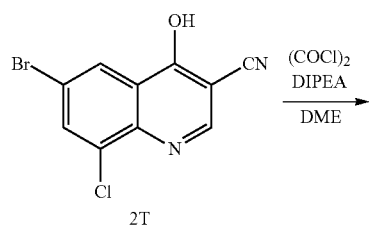

Compound 2T (scaling factor, 1.0 equiv), 1,2-dimethoxyethane (8 volumes) and DIPEA (1.1 equiv) were charged to a reactor. The reaction mixture was adjusted to about 40° C. and oxalyl chloride (2.0 equiv) was charged to the reactor. The reaction was heated to about 60° C. and agitated until reaction was deemed complete. A solution of 10 wt % aqueous $KHCO_3$ (16 volumes) was slowly charged maintaining the temperature below about 20° C. The slurry was then adjusted to about 10° C. and agitated for about 1 hour and then filtered. The solids were washed with water (5 volumes) twice, and then dried at about 50° C. to afford Compound 2U. $^1$H NMR (400 MHz, DMSO-d6): δ 9.34 (s, 1H), 8.52 (d, J=2.0 Hz, 1H), 8.45 (d, J=2.0 Hz, 1H).

Amination of Compound 2U to Compound 2G

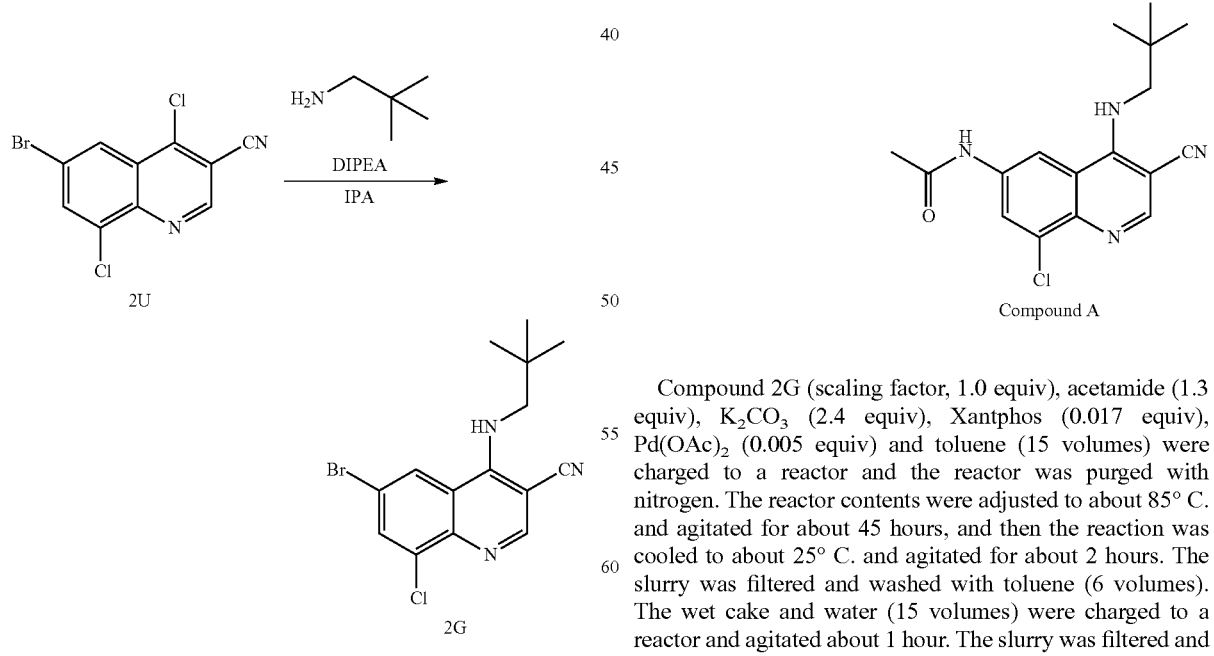

Compound 2U (scaling factor, 1.0 equiv), IPA (15 volumes) and DIPEA (1.2 equiv) were charged to a reactor. The reactor contents were heated to about 75° C. and agitated for about 5 hours until reaction was deemed complete. The contents were then cooled to about 5° C. and agitated for about 1 hour. The resulting slurry was filtered and washed twice with IPA (2.5 volumes) pre-cooled to about 5° C. The wet cake was dried at about 50° C. to afford Compound 2G. $^1$H NMR (400 MHz, $CDCl_3$): δ 8.68 (s, 1H), 7.98 (d, J=1.6 Hz, 1H), 7.81 (d, J=1.6 Hz, 1H), 5.57 (broad s, 1H), 3.77 (d, J=5.6 Hz, 2H), 1.12 (s, 9H).

Amidation of Compound 2G to Acetamide Intermediate

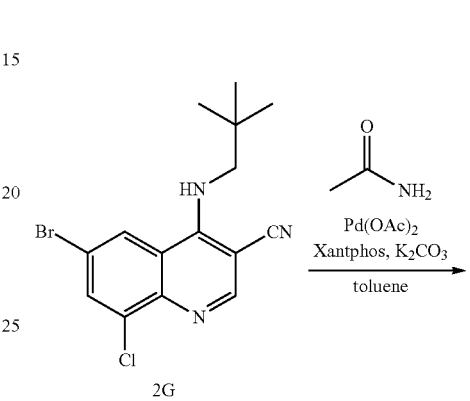

Compound 2G (scaling factor, 1.0 equiv), acetamide (1.3 equiv), $K_2CO_3$ (2.4 equiv), Xantphos (0.017 equiv), Pd(OAc)$_2$ (0.005 equiv) and toluene (15 volumes) were charged to a reactor and the reactor was purged with nitrogen. The reactor contents were adjusted to about 85° C. and agitated for about 45 hours, and then the reaction was cooled to about 25° C. and agitated for about 2 hours. The slurry was filtered and washed with toluene (6 volumes). The wet cake and water (15 volumes) were charged to a reactor and agitated about 1 hour. The slurry was filtered and washed with water (15 volumes), and the solids were dried at about 50° C. to afford Compound A. $^1$H NMR (400 MHz, DMSO-d6): δ 10.34 (s, 1H), 8.48 (s, 1H), 8.42 (s, 1H), 8.13 (s, 1H), 7.67 (s, 1H), 3.71 (s, 2H), 2.11 (s, 3H), 0.99 (s, 9H).

Cleavage of Acetamide Intermediate to Compound 1B

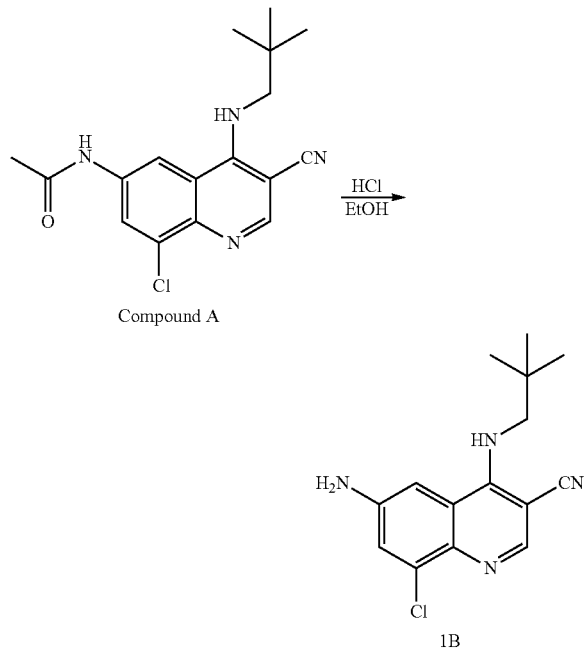

Compound A (scaling factor, 1.0 equiv) and ethanol (10 volumes) were charged to a reactor and agitated at about 20° C. Concentrated hydrochloric acid (8.0 equiv) was slowly charged while maintaining the temperature below about 30° C. The reaction was adjusted to about 60° C. and agitated for about 4 hours until reaction was deemed complete. The reaction was cooled to about 15° C. and then water (5 volumes) was charged. The pH was adjusted to about 8-9 by charging 10 wt % aqueous NaOH. The resulting slurry was filtered and washed with water (5 volumes), and the solids were dried at about 50° C. to afford Compound 1B. $^1$H NMR (400 MHz, DMSO-d6): δ 8.21 (s, 1H), 7.35 (d, J=2.0 Hz, 1H), 7.28 (dd, J=6.4 Hz, 1H), 7.21 (d, J=2.0 Hz, 1H), 5.75 (broad s, 2H), 3.68 (d, J=8.8 Hz, 2H), 0.97 (s, 9H).

Example 8: Alternate Synthesis of Compound 2F (for Manufacturing Route 3)

Chlorination of Compound 2M to Compound 3A

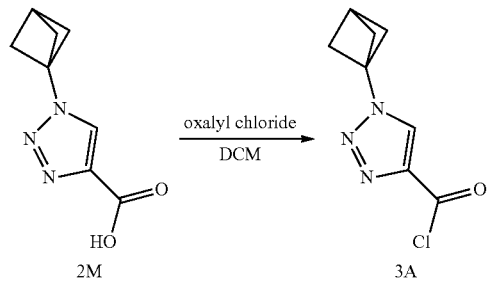 [SMILES: O=C(O)c1cn(C23CC(C2)C3)nn1 ; O=C(Cl)c1cn(C23CC(C2)C3)nn1]

Oxalyl chloride (1.1 equiv) was slowly charged to a reactor containing Compound 2M (scaling factor, 1.0 equiv), DCM (6 volumes) and DMF (0.005 equiv). The resulting mixture was agitated at about 20° C. until the reaction was deemed complete. n-Heptane (10 volumes) was then charged and the solution was concentrated to remove dichloromethane. The resulting slurry was filtered, rinsed with n-heptane (10 volumes), and dried at about 40° C. to give Compound 3A. $^1$H NMR (400 MHz, CDCl$_3$) δ 8.19 (s, 1H), 2.79 (s, 1H), 2.46 (s, 6H).

Coupling of Compound 3A and Compound 2B to Compound 2C

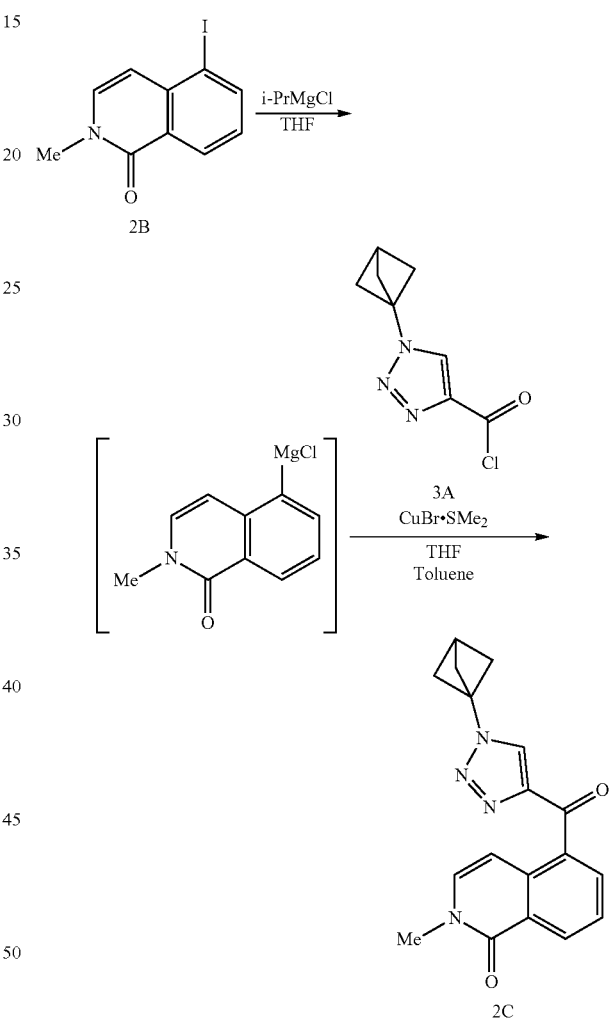

Compound 2B (1.2 equiv) and tetrahydrofuran (20 volumes) were charged to a reactor and the mixture was cooled to about −15° C. A solution of isopropylmagnesium chloride (1.3 equiv, 2M in tetrahydrofuran) was then charged to the reactor over about 30 minutes and the resulting mixture was agitated until the magnesiation reaction was deemed complete. To a second reactor was charged Compound 3A (scaling factor, 1.0 equiv), tetrahydrofuran (2 volumes), toluene (2.5 volumes), and CuBr dimethylsulfide complex (0.05 equiv). The resulting slurry was cooled to about −15° C., and then the aryl Grignard mixture was charged to the reactor containing Compound 3A over about 30 minutes followed by a rinse of tetrahydrofuran (2 volumes). The reaction mixture was agitated until deemed complete, and then quenched with a solution of 1N aqueous hydrochloric acid containing 10 wt % sodium chloride (7 volumes). The temperature was adjusted to about 20° C. and the layers were separated. The organic layer was concentrated and solvent exchanged to ethanol and the volume was adjusted to about 10 volumes. The resulting slurry was heated to about 75° C., and then water (10 volumes) was charged and the mixture was cooled to about 0° C. over about 8 hours. The resulting slurry was filtered, the cake was rinsed sequentially with water (5 volumes) and ethanol (4 volumes), and the solids were dried at about 50° C. to give Compound 2C. $^1$H NMR (400 MHz, CDCl$_3$) δ 8.63 (ddd, J=7.9, 1.1, 0.5 Hz, 1H), 8.26 (d, J=7.5, 1.4 Hz, 1H), 8.21 (s, 1H), 7.53 (dd, J=7.9, 7.8 Hz, 1H), 7.09 (d, J=7.7 Hz, 1H), 7.04 (d, J=7.7 Hz, 1H), 3.57 (s, 3H), 2.74 (s, 1H), 2.43 (s, 6H).

Condensation of Compound 2C to Compound 3B

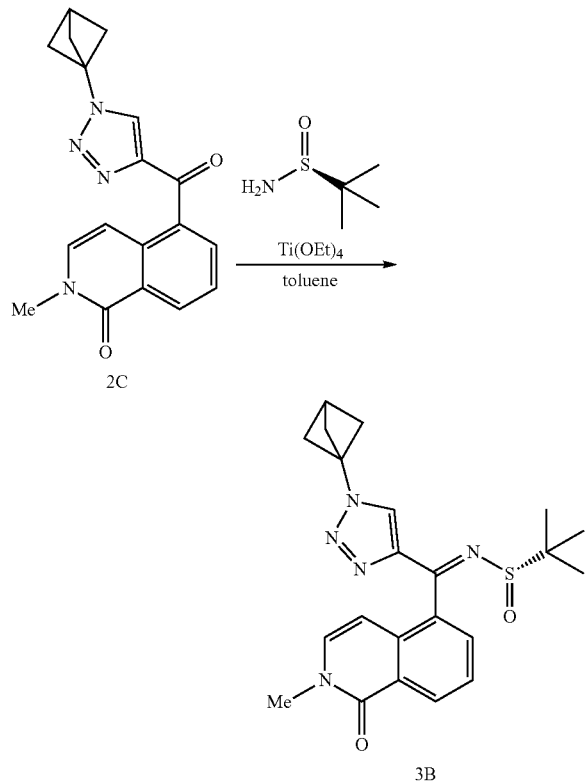

2C

Compound 2C (scaling factor, 1.0 equiv), (S)-2-methyl-propane-2-sulfinamide (1.1 equiv) and toluene (15 volumes) were charged to a reactor, followed by Ti(OEt)$_4$ (2.2 equiv). The temperature was adjusted to about 70° C. The mixture was then either sparged with a continuous flow of nitrogen or placed under vacuum at about 150-250 mbar, and the volume was maintained at about 15 volumes by charging additional toluene. The mixture was agitated for about 12 hours and then cooled to about 25° C. and aged for about 3 hours. The slurry was filtered, and then the cake was rinsed with toluene (5 volumes) and dried at about 45° C. to afford Compound 3B. $^1$H NMR (400 MHz, CDCl$_3$): δ 8.55 (d, J=8.5 Hz, 1H), 7.90 (s, 1H), 7.65 (d, J=6.9 Hz, 1H), 7.54 (dd, J=7.6, 7.6 Hz, 1H), 7.04 (d, J=7.5, 1H), 6.17 (d, J=7.0 Hz, 1H), 3.56 (s, 3H), 2.74 (s, 1H), 2.41 (s, 6H), 1.27 (s, 9H).

Reduction of Compound 3B to Compound 3C

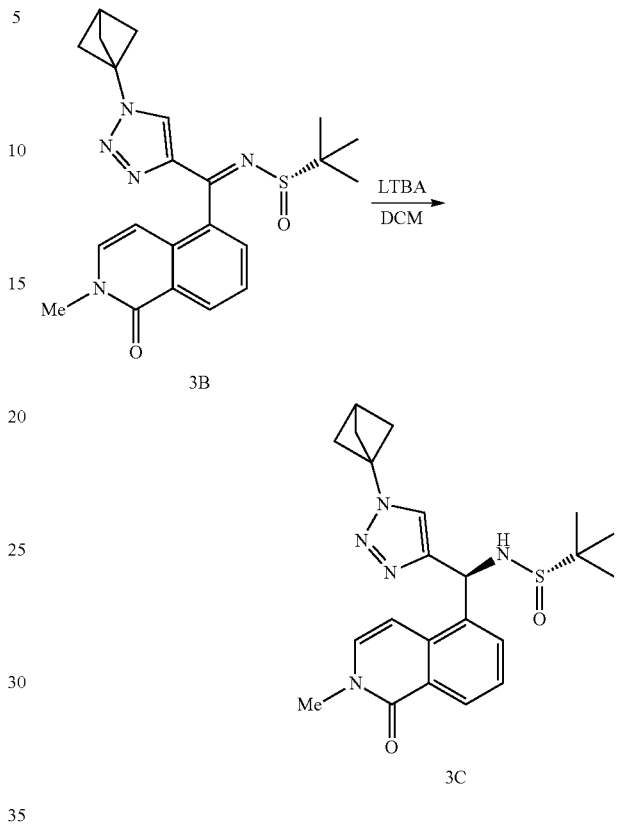

A reactor was charged with Compound 3B (scaling factor, 1.0 equiv) and dichloromethane (10 volumes), and the mixture was cooled to about −15° C. Lithium tri-tert-butoxyaluminum hydride (1 M in tetrahydrofuran, 1.5 equiv) was charged over about 3 hours. The reaction mixture was agitated at about −10° C. for about 4 hours and then quenched with a solution of 14 wt % aqueous tartaric acid (12 volumes) while maintaining the temperature below about 0° C. The mixture was warmed to about 25° C. and the layers were separated. The aqueous layer was extracted with dichloromethane (5 volumes) twice. The organic layers were combined and concentrated to about 5 volumes. Dichloromethane (7.5 volumes) was charged and the solution was concentrated to about 5 volumes, and then additional dichloromethane (7.5 volumes) was charged and the solution was concentrated again to about 5 volumes. The solution was adjusted to about 25° C. and methyl tert-butyl ether (8 volumes) was charged over about 2 hours. The resulting slurry was agitated for about 1 hour, and then additional methyl tert-butyl ether (11 volumes) was charged over about 2 hours. The slurry was then cooled to about 0° C. over about 4 hours and aged for about 16 hours. The mixture was filtered and the cake was rinsed with methyl tert-butyl ether (7 volumes). The solids were dried at about 50° C. to afford Compound 3C in 99.8% diastereomeric purity. $^1$H NMR (400 MHz, DMSO): δ 8.19 (dd, J=7.8, 1.5 Hz, 1H), 8.00 (s, 1H), 7.82 (dd, J=7.4 Hz, 1.5 Hz, 1H), 7.49 (t, J=7.6 Hz, 1H), 7.46 (d, J=7.7 Hz, 1H), 6.78 (d, J=7.7 Hz, 1H), 6.12 (d, J=6.0 Hz, 1H), 5.99 (d, J=6.0 Hz, 1H), 3.48 (s, 3H), 2.68 (s, 1H), 2.31 (s, 6H), 1.12 (s, 9H).

Cleavage of Compound 3C to Compound 2F

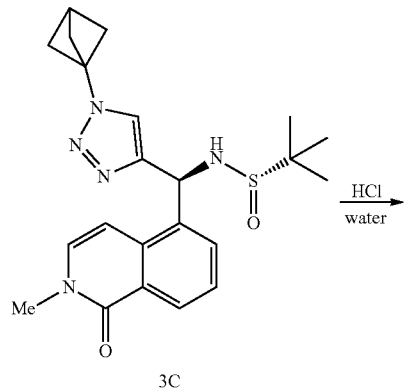

3C

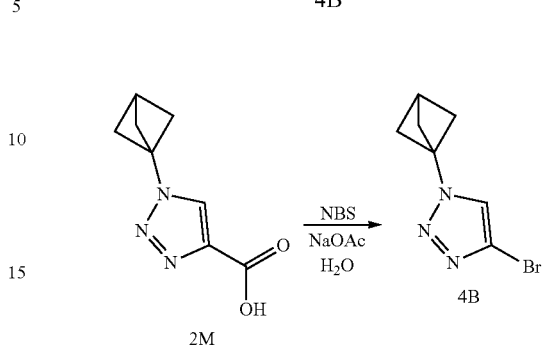

To a reactor was charged Compound 3C (scaling factor, 1.0 equiv), water (5 volumes), and concentrated hydrochloric acid (approximately 37 wt %, 1.6 equiv). The reaction mixture was heated to about 50° C. and agitated for about 20 hours. The solution was diluted with water (1 volume), then cooled to about 20° C., and washed with dichloromethane (2 volumes). The acidic aqueous mixture was charged to a solution of sodium hydroxide (3.2 equivs) in water (2 volumes) over about 1 hour. The resulting slurry was aged at about 50° C. for about 4 hours, then cooled to about 15° C. and filtered. The cake was rinsed with water (3 volumes) twice, then with MTBE (4 volumes). The solids were dried at about 60° C. to afford Compound 2F. $^1$H NMR (400 MHz, DMSO): δ 8.16 ppm (ddd, J=7.9, 1.2, 0.6 Hz, 1H), 7.89 (ddd, J=7.4, 1.4, 0.4 Hz, 1H), 7.88 (s, 1H), 7.48 (dd, J=7.8, 7.8 Hz, 1H), 7.44 (d, J=7.7 Hz, 1H), 6.84 (dd, J=7.9, 0.4 Hz, 1H), 5.71 (s, 1H), 3.48 (s, 3H), 2.65 (s, 1H), 2.41 (broad s, 2H), 2.28 (s, 6H).

Example 9: Alternate Synthesis of Compound 2E (for Manufacturing Route 4)

Bromination of Compound 2M to Give Compound 4B

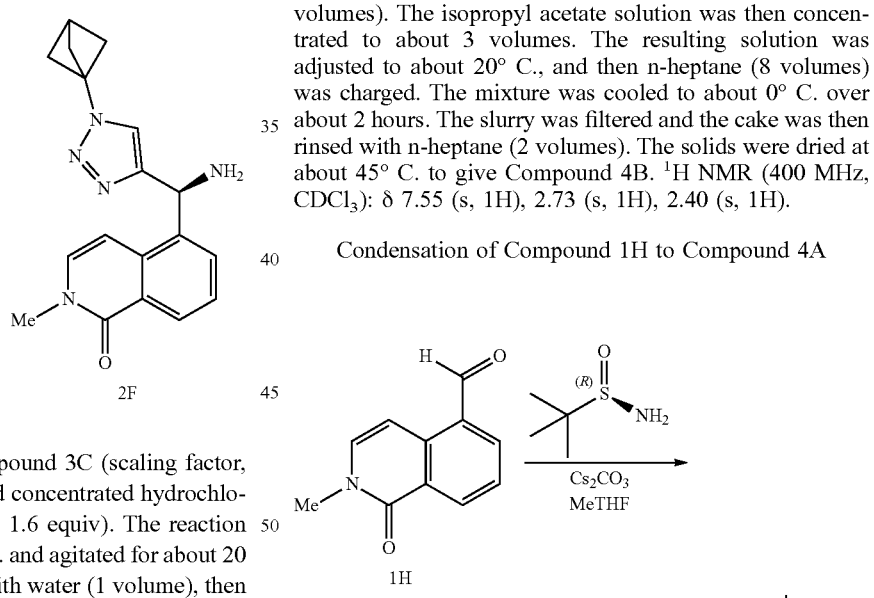

To a reactor was charged Compound 2M (scaling factor, 1.0 equiv), sodium acetate (1.1 equiv), N-bromosuccinimide (2.5 equiv) and water (10 volumes). The mixture was heated to about 75° C. for about 21 hours. Isopropyl acetate (6 volumes) was then charged to the reactor and the resulting biphasic solution was cooled to about 20° C. The layers were separated and the aqueous layer was extracted once with isopropyl acetate (6 volumes). The combined organic layers were then washed with a 10 wt % sodium thiosulfate solution (8 volumes), followed by a 15 wt % potassium bicarbonate solution (6 volumes), followed by water (6 volumes). The isopropyl acetate solution was then concentrated to about 3 volumes. The resulting solution was adjusted to about 20° C., and then n-heptane (8 volumes) was charged. The mixture was cooled to about 0° C. over about 2 hours. The slurry was filtered and the cake was then rinsed with n-heptane (2 volumes). The solids were dried at about 45° C. to give Compound 4B. $^1$H NMR (400 MHz, CDCl$_3$): δ 7.55 (s, 1H), 2.73 (s, 1H), 2.40 (s, 1H).

Condensation of Compound 1H to Compound 4A

Compound 1H (scaling factor, 1.0 equiv), (R)-(+)-2-methyl-2-propanesulfinamide (1.2 equiv), cesium carbonate (1.0 equiv) and 2-methyltetrahydrofuran (10 volumes) were charged to a reactor. The mixture was agitated for about 49 hours at about 25° C. Additional cesium carbonate (1.5 equiv) and dichloromethane (5 volumes) were charged and the mixture was agitated for about 25 hours at about 25° C. The mixture was then filtered and the filtrate was concentrated to dryness. The residue was suspended in isopropyl acetate (5 volumes) and then filtered. The isolated solids were dried at about 50° C. to afford Compound 4A. $^1$H NMR (400 MHz, CDCl$_3$): δ 8.99 (s, 1H), 8.65 (d, J=8.0 Hz, 1H), 8.18 (dd, J=7.8, 1.5 Hz, 1H), 7.58 (t, J=7.8 Hz, 1H), 7.52 (d, J=7.8 Hz, 1H), 7.21 (d, J=7.8 Hz, 1H), 3.64 (s, 3H), 1.30 (s, 9H).

Alternative Condensation of Compound 1H to Compound 4A

Compound 1H (scaling factor, 1.0 equiv), (S)-(−)2-methyl-2-propanesulfinamide (1.1 equiv), and tetrahydrofuran (15 volumes) were charged to a reactor. To the mixture was charged titanium(IV) isopropoxide (2.0 equiv) at about 20° C. The reaction was agitated for about 16 hours at about 20° C. and then quenched with 15 wt % aqueous sodium chloride (15 volumes). The resulting slurry was filtered and the cake was washed with ethyl acetate (15 volumes) twice. The filtrate was dried over magnesium sulfate, filtered, and concentrated. The residue was purified by silica gel chromatography to afford the enantiomer of Compound 4A. (It should be understood that the use of the (R)-(+) enantiomer of 2-methyl-2-propanesulfinamide would afford Compound 4A using otherwise identical reaction conditions.) $^1$H NMR (400 MHz, CDCl$_3$): δ 8.99 (s, 1H), 8.65 (d, J=8.0 Hz, 1H), 8.18 (dd, J=7.8, 1.5 Hz, 1H), 7.58 (t, J=7.8 Hz, 1H), 7.52 (d, J=7.8 Hz, 1H), 7.21 (d, J=7.8 Hz, 1H), 3.64 (s, 3H), 1.30 (s, 9H).

Note: It should be readily apparent to one skilled in the art of organic synthesis that use of the (R)-(+) enantiomer of 2-methyl-2-propanesulfinamide will afford Compound 4A using otherwise identical reaction conditions.

Alternative Condensation of Compound 1H to Compound 4A

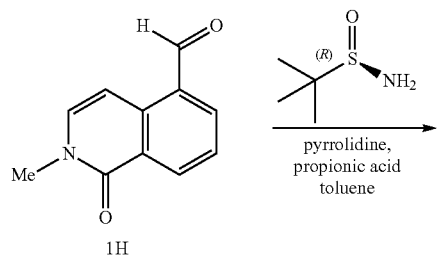

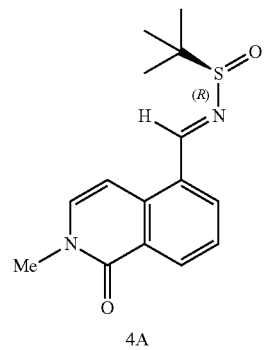

Compound 1H (scaling factor, 1.0 equiv), (R)-(+)-2-methyl-2-propanesulfinamide (1.2 equiv), pyrrolidine (0.2 equiv), propionic acid (0.2 equiv) and toluene (10 volumes) were charged to a reactor. The mixture was heated to about 50° C. and agitated for about 46 hours at about 50° C. The mixture was cooled to about 20° C. and 2-methyltetrahydrofuran (10 volumes) and aqueous potassium bicarbonate (10 wt % solution, 5 volumes) were charged. The mixture was warmed to about 35° C., agitated and the layers were separated. The aqueous layer was extracted with 2-methyltetrahydrofuran (5 volumes) and the combined organic layers were filtered through an activated carbon cartridge. The cartridge was rinsed with additional 2-methyltetrahydrofuran (2×3 volumes) and the combined filtrate and rinse was concentrated under vacuum. The concentrate was diluted with 2-methyltetrahydrofuran (4 volumes), heated to about 50° C. and heptane (2 volumes) was charged, followed by seed crystals. The mixture was cooled to about 20° C. over about 3 hours, and additional heptane (10 volumes) was charged. The mixture was agitated, filtered, and the solids were rinsed with heptane (2×3 volumes). The isolated solids were dried at about 50° C. to afford Compound 4A. $^1$H NMR (400 MHz, CDCl$_3$): δ 8.99 (s, 1H), 8.65 (d, J=8.0 Hz, 1H), 8.18 (dd, J=7.8, 1.5 Hz, 1H), 7.58 (t, J=7.8 Hz, 1H), 7.52 (d, J=7.8 Hz, 1H), 7.21 (d, J=7.8 Hz, 1H), 3.64 (s, 3H), 1.30 (s, 9H).

Coupling of Compound 4B and Compound 4A to Give Compound 2E

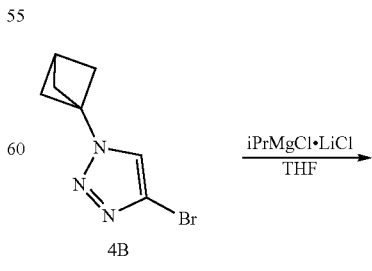

-continued

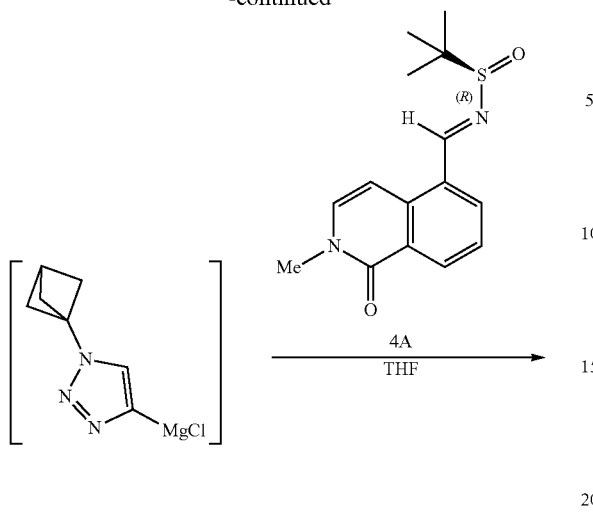

4A
THF

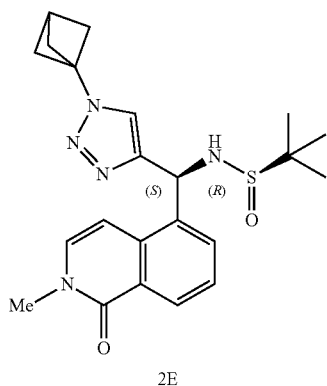

2E

A reactor was charged with Compound 4B (scaling factor, 1.0 equiv) and tetrahydrofuran (10 volumes). The resulting solution was cooled to about 0° C. and charged with isopropylmagnesium chloride-lithium chloride complex (1.4 equiv), and the mixture was aged until the magnesiation reaction was deemed complete. A solution of Compound 4A (1.1 equiv) in tetrahydrofuran (5 volumes) was then added to the Grignard mixture at about 0° C. over about 6 minutes. The resulting mixture was then agitated at about 0° C. for about 17 hours. The reaction mixture was quenched with 15 wt % ammonium chloride solution (8 volumes) and then adjusted to about 20° C. The layers were separated and the organic layer was then concentrated to about 10 volumes. Methyl tert-butyl ether (10 volumes) was then added to the mixture and the resulting slurry was adjusted to about 0° C. over about 2 hours. The slurry was filtered, and the solids were washed with methyl tert-butyl ether (4 volumes) and dried at about 40° C. to afford Compound 2E in 99.3% diastereomeric purity. $^1$H NMR (400 MHz, DMSO): δ 8.19 (dd, J=8.0, 1.1 Hz, 1H), 8.01 (s, 1H), 7.83 (dd, J=7.8, 1.1 Hz, 1H), 7.50 (t, J=8.0 Hz, 1H), 7.48 (d, J=7.7 Hz, 1H), 6.78 (d, J=7.7 Hz, 1H), 6.26 (d, J=5.9 Hz, 1H), 6.15 (d, J=5.9 Hz, 1H), 3.44 (s, 3H), 2.62 (s, 1H), 2.25 (s, 6H), 1.04 (s, 9H).

Example 10: Alternate Synthesis of Compound 1H (for Manufacturing Route 4)

Methylation of 5-bromoisoquinoline (Compound 1E) to N-methyl bromoisoquinolinium iodide (Compound 4C)

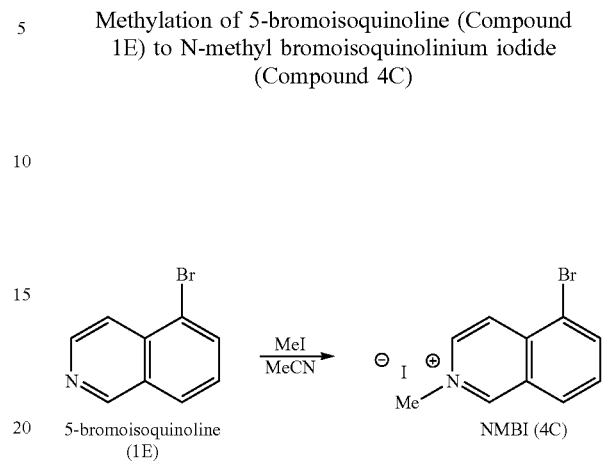

To a reactor were charged 5-bromoisoquinoline (Compound 1E) (scaling factor, 1.0 equiv) and acetonitrile (8 volumes) and the temperature was adjusted to about 30° C. Iodomethane (2.0 equiv) was charged and the slurry was agitated for about 3 hours. Toluene (5 volumes) was charged and the slurry was cooled to about 5° C. The slurry was filtered, rinsed with toluene (2 volumes), and dried at about 30° C. to afford NMBI (Compound 4C). $^1$H NMR (400 MHz, CD$_3$CN): δ 9.67 ppm (s, 1H), 8.62 (d, J=7.1 Hz, 1H), 8.52 (dd, J=7.6, 1.0 Hz, 1H), 8.50 (dd, J=7.6, 1.0 Hz, 1H), 8.45 (d, J=8.3 Hz, 1H), 7.94 (t, J=7.6 Hz, 1H), 4.48 (s, 3H).

Oxidation of N-methyl bromoisoquinolinium iodide (Compound 4C) to Compound 4D

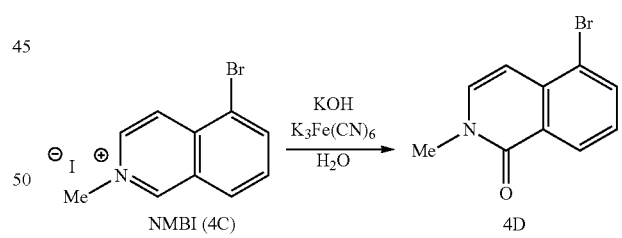

NMBI (Compound 4C) (scaling factor, 1.0 equiv) and potassium ferricyanide (2.5 equiv) were charged to a reactor. Water (15 volumes) was charged to the reactor and the temperature was adjusted to about 5° C. A solution of potassium hydroxide (4.0 equiv) in water (3 volumes) was prepared. The potassium hydroxide solution was charged to the reactor over about 2 hours. The reaction mixture was agitated for about 3 hours, then filtered. The filter cake was rinsed with water (3 volumes) three times and then dried at about 80° C. to afford Compound 4D. $^1$H NMR (400 MHz, DMSO): δ 8.23 ppm (ddd, J=8.1, 1.1, 0.8 Hz, 1H), 7.99 (dd, J=7.7, 1.2 Hz, 1H), 7.61 (d, J=7.6 Hz, 1H), 7.40 (dd, J=7.9, 7.9 Hz, 1H), 6.67 (dd, J=7.6, 0.8 Hz, 1H), 3.51 (s, 3H).

Formylation of Compound 4D to Compound 1H

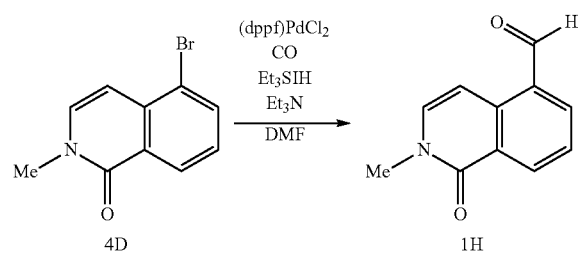

Compound 4D (scaling factor, 1.0 equiv), [1,1'-bis(diphenylphosphino)ferrocene]palladium(II) dichloride (0.025 equiv), triethylamine (1.0 equiv), triethylsilane (2.0 equiv), and N,N-dimethylformamide (10 volumes) were charged to a reactor, and then the reactor was sparged with carbon monoxide. The reaction mixture was heated to about 80° C. until the reaction was deemed complete to provide Compound 1H. $^1$H NMR (400 MHz, DMSO-$d_6$): δ 10.34 (d, J=1.2 Hz, 3H), 8.54 (dt, J=8.0, 1.4 Hz, 1H), 8.29 (dt, J=7.5, 1.5 Hz, 1H), 7.73-7.66 (m, 3H), 3.54 (d, J=1.3 Hz, 3H).

Example 11: Alternate Synthesis of Compound 2M from Ethyl Pyruvate (Compound 10A)

Chlorination Condensation of Ethyl Pyruvate (Compound 10A)

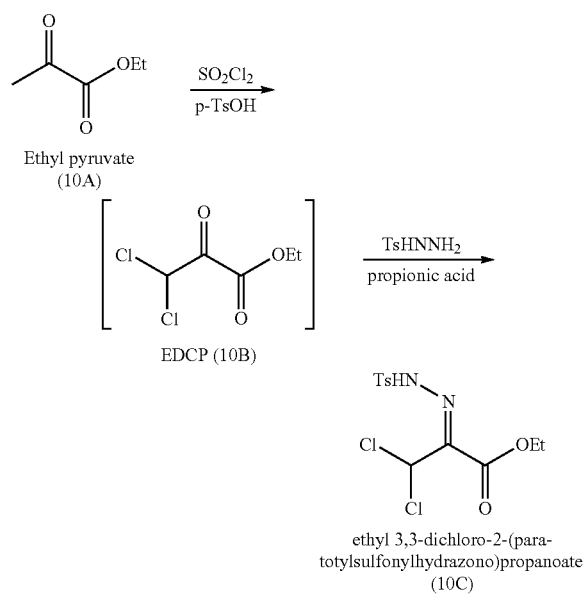

Ethyl pyruvate (Compound 10A) (scaling factor, 1.0 equiv), para-toluenesulfonic acid (0.10 equiv) and sulfuryl chloride (4 volumes) were charged to a reactor and heated to reflux for about 16 hours. The reaction mixture was concentrated to remove sulfuryl chloride, diluted with MTBE (3 volumes), and washed with water (2 volumes). The layers were separated and the aqueous layer was extracted with MTBE (2 volumes). The combined organic layers were washed sequentially with water (2 volumes) and 10 wt % aqueous sodium chloride (2 volumes), and then concentrated under vacuum to remove organic solvent. To the residue was charged propionic acid (5 volumes) and para-toluenesulfonyl hydrazide (0.91 equiv). The reaction was agitated at about 25° C. for about 16 hours. The resulting slurry was filtered, and the solids were rinsed with n-heptane (3 volumes) and then dried at about 50° C. to afford ethyl 3,3-dichloro-2-(para-tolylsulfonylhydrazono)propanoate (Compound 10C). $^1$H NMR (400 MHz, CDCl$_3$): δ 11.96 (s, 1H), 7.86 (d, J=8 Hz, 2H), 7.34 (d, J=8 Hz, 2H), 6.45 (s, 1H), 4.38 (q, J=4, 8 Hz, 2H), 3.17 (s, 3H), 1.38 (t, J=8 Hz, 3H).

Cyclization to ethyl 1-(bicyclo[1.1.1]pentan-1-yl)-1H-1,2,3-triazole-4-carboxylate (Compound 10D)

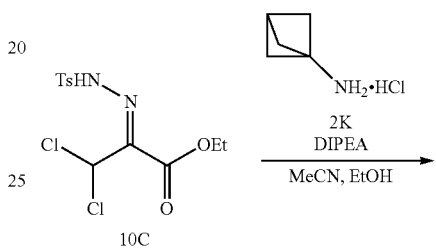

To a reactor containing Compound 2K (1.1 equiv) and ethanol (8 volumes) was added DIPEA (3.2 equiv). The resulting solution was then cooled to about 0° C. A solution of ethyl 3,3-dichloro-2-(para-tolylsulfonylhydrazono)propanoate (Compound 10C) (scaling factor, 1.0 equiv) in acetonitrile (10 volumes) was added to the Compound 2K solution while maintaining the temperature below about 13° C., and the mixture was rinsed forward with acetonitrile (1 volume) and ethanol (1 volume). The resulting solution was adjusted to about 20° C. and agitated until the reaction was deemed complete. The solution was then concentrated to remove solvent, and ethyl acetate (11 volumes) was charged to the residue. The organic solution was washed with 1N aqueous NaOH (4 volumes) twice, followed by 10 wt % aqueous ammonium chloride solution (7 volumes) and saturated aqueous sodium chloride (7 volumes). The organic layers were combined and concentrated to remove solvent. The residue was purified by silica gel chromatography eluting with ethyl acetate and heptane to yield ethyl 1-(bicyclo[1.1.1]pentan-1-yl)-1H-1,2,3-triazole-4-carboxylate (Compound 10D). $^1$H NMR (400 MHz, CDCl$_3$) δ 8.04 (s, 1H), 4.40 (q, J=7.1 Hz, 2H), 2.73 (s, 1H), 2.42 (s, 6H), 1.39 (t, J=7.1 Hz, 3H).

Hydrolysis to Compound 2M

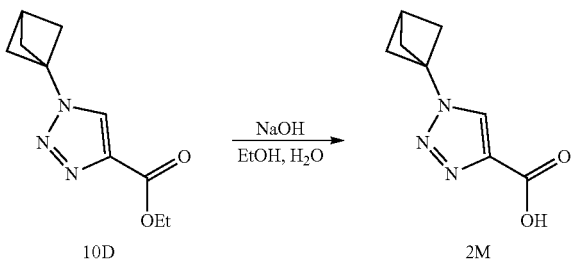 [SMILES: CCOC(=O)c1cn(C23CC(C2)C3)nn1 ; "NaOH" ; O=C(O)c1cn(C23CC(C2)C3)nn1]

To a reactor was charged ethyl 1-(3-bicyclo[1.1.1]pentanyl)triazole-4-carboxylate (Compound 10D) (scaling factor, 1.0 equiv) and ethanol (4 volumes), and the mixture was heated to about 50° C. A solution of 2M aqueous sodium hydroxide (1.1 equiv) was then added and the resulting mixture was agitated until the reaction was deemed complete. The solution was cooled to about 20° C. and then 15 wt % aqueous hydrochloric acid (2 volumes) was charged. The solution was then concentrated to remove ethanol and water (4 volumes) was added. The resulting slurry was filtered, and the wet cake was rinsed with water (2 volumes) and dried at about 50° C. to give Compound 2M. $^1$H NMR (400 MHz, CDCl$_3$) δ 11.06 (s, 1H), 8.16 (s, 1H), 2.76 (s, 1H), 2.44 (s, 6H).

Example 12: Alternate Synthesis of Compound 2L Via Click Chemistry

Click Reaction of Compound 1D and Methyl Propiolate to Compound 2L

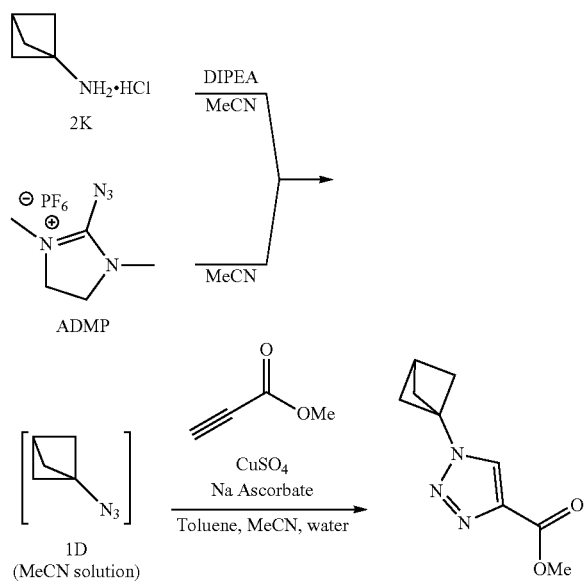

Methyl propiolate (1.5 equiv), copper sulfate (0.1 equiv), sodium ascorbate (0.25 equiv), toluene (15 volumes), and water (2 volumes) were charged to a reactor and mixed at about 22° C. In a second vessel, Compound 2K (scaling factor, 1.0 equiv), diisopropylethylamine (2.2 equiv) and acetonitrile (4.2 volumes) were combined. In a third vessel, 2-azido-1,3-dimethylimidazolium hexafluorophosphate (ADMP, 1.2 equiv) and acetonitrile (5.3 volumes) were combined. The mixtures containing Compound 2K and ADMP in the second and third vessels, respectively, were combined in a tube reactor to form Compound 1D, and the resulting mixture was collected in the first reactor containing methyl propiolate over about 3 hours. The combined mixture was aged for about 16 hours, and then washed with 5 wt % aqueous potassium bicarbonate (5 volumes) twice. The organic layer was then concentrated and the residue was then extracted with toluene (20 volumes) three times. The combined toluene extracts were then concentrated to afford Compound 2L. $^1$H NMR (400 MHz, CDCl$_3$) δ 8.06 (s, 1H), 3.94 (s, 3H), 2.75 (s, 1H), 2.43 (s, 6H).

Example 13: Alternate Synthesis of Compound 2A from ethyl 1-(bicyclo[1.1.1]pentan-1-yl)-1H-1,2,3-triazole-4-carboxylate (Compound 10D)

Amidation of ethyl 1-(bicyclo[1.1.1]pentan-1-yl)-1H-1,2,3-triazole-4-carboxylate (Compound 10D) to Give Compound 2A

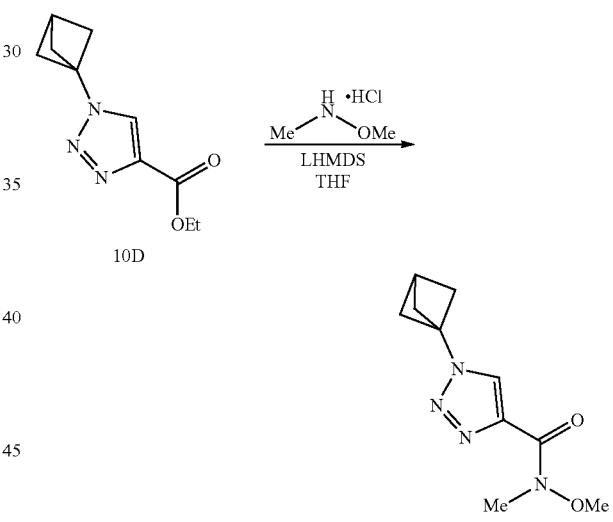

To a reactor was charged ethyl 1-(3-bicyclo[1.1.1]pentanyl)triazole-4-carboxylate (Compound 10D) (scaling factor, 1.0 equiv), N,O-dimethylhydroxylamine hydrochloride (1.3 equiv), and tetrahydrofuran (10 volumes). The resulting slurry was cooled to about 0° C. and charged with lithium bis(trimethylsilyl)amide (2.5 equiv, 1M in tetrahydrofuran). The resulting solution was then adjusted to about 20° C. and agitated until the reaction was deemed complete. A 10 wt % aqueous ammonium chloride solution (10 volumes) was then charged. The layers were separated and the aqueous layer was extracted with 2-methyltetrahydrofuran (20 volumes) twice. The combined organic layers were washed with water (20 volumes), the layers were separated, and the aqueous layer was extracted with 2-methyltetrahydrofuran (20 volumes) twice. The organic layers were combined, concentrated to remove solvent, and the residue was purified by silica gel chromatography eluting with ethyl acetate and n-heptane to give Compound 2A. $^1$H NMR (400 MHz, DMSO-d$_6$) δ 8.59 (s, 1H), 3.73 (s, 3H), 3.31 (s, 3H), 2.72 (s, 1H), 2.38 (s, 6H).

Example 14: Alternate Synthesis of ethyl 1-(bicyclo[1.1.1]pentan-1-yl)-1H-1,2,3-triazole-4-carboxylate (Compound 10D)

Cyclization of ethyl 2-diazo-3-oxopropanoate (Compound 13A) and Compound 2K to ethyl 1-(bicyclo[1.1.1]pentan-1-yl)-1H-1,2,3-triazole-4-carboxylate (Compound 10D)

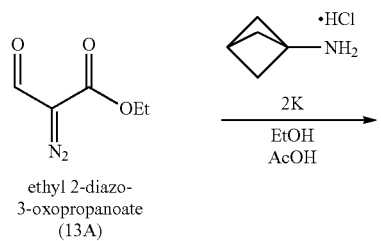

Example 15: Alternate Synthesis of 5-iodoisoquinoline (Compound 2O)

Iodination of Isoquinoline (Compound 14A) to 5-iodoisoquinoline (Compound 2O)

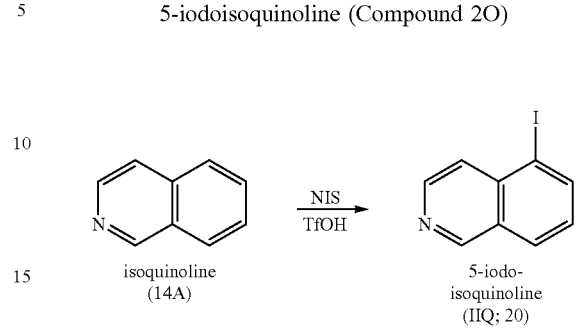

Isoquinoline (Compound 14A) (scaling factor, 1.0 equiv) and triflic acid (3 volumes) were charged to a reactor. The temperature was adjusted to about −20° C., then N-iodosuccinimide (1.25 equiv) was charged. The reaction mixture was agitated for about 48 hours, and then the temperature was adjusted to about 0° C. Water (6 volumes) and 10 wt % aqueous sodium bisulfite (5 volumes) were charged, then the slurry was filtered and the solids were rinsed with water (2 volumes). The solids were dried at about 50° C. to obtain 5-iodoisoquinoline (Compound 2O). $^1$H NMR (400 MHz, Chloroform-d) δ 9.12 (d, J=1.0 Hz, 1H), 8.62 (d, J=6.0 Hz, 1H), 8.25 (dt, J=7.3, 1.0 Hz, 1H), 7.96 (dt, J=8.2, 1.0 Hz, 1H), 7.82 (dt, J=6.1, 1.0 Hz, 1H), 7.33 (dd, J=8.2, 7.3 Hz, 1H).

Example 16: Alternate Synthesis of Compound 2B

Iodination of Compound 4D to Compound 2B

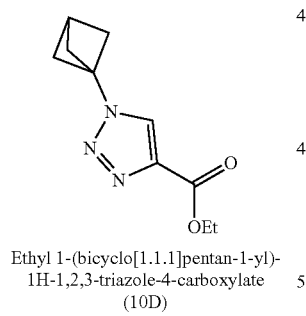

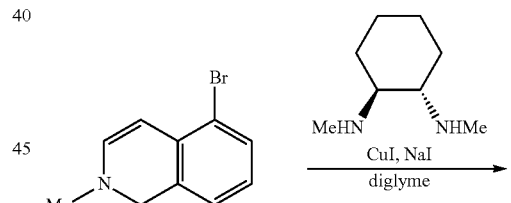

Ethyl 2-diazo-3-oxopropanoate (Compound 13A) (scaling factor, 1.0 equiv), Compound 2K (1.1 equiv) and ethanol (12.5 volumes) were charged to a reactor. Acetic acid (1.4 volumes) was then charged and the mixture was heated to about 35° C. and agitated for about 6 days. The reaction mixture was concentrated to remove solvent and the residue was suspended in dichloromethane (6 volumes). The resulting slurry was filtered to remove solids, and the cake was rinsed with dichloromethane (2 volumes). The filtrate was concentrated and the residue was purified by silica gel chromatography to yield ethyl 1-(bicyclo[1.1.1]pentan-1-yl)-1H-1,2,3-triazole-4-carboxylate (Compound 10D). $^1$H NMR (400 MHz, CDCl$_3$) δ 8.05 (s, 1H), 4.42 (q, J=4 Hz, 2H), 2.75 (s, 1H), 2.43 (s, 6H), 1.40 (t, J=4 Hz, 3H).

To a reactor was charged diethylene glycol dimethyl ether (diglyme, 4 volumes), Compound 4D (scaling factor, 1.0 equiv), sodium iodide (4 equiv), copper iodide (0.1 equiv) and trans-N1,N2-dimethylcyclohexane-1,2-diamine (0.2 equiv). The mixture was heated to about 130° C. for about 40 hours. The reactor contents were then adjusted to about 20° C. and ammonium hydroxide (10 volumes) was charged.

The layers were separated and water (10 volumes) was then added to the organic stream. The resulting mixture was agitated for about 2 hours after which a slurry was obtained. The slurry was then filtered and rinsed with water (5 volumes). The solids were then dried at about 50° C. to obtain Compound 2B. ¹H NMR (400 MHz, DMSO): δ 8.24 ppm (ddd, J=8.0, 1.3, 0.7 Hz, 1H), 8.21 (dd, J=7.6, 1.2 Hz, 1H), 7.59 (d, J=7.6 Hz, 1H), 7.23 (dd, J=7.9, 7.6 Hz, 1H), 6.57 (dd, J=7.7, 0.8 Hz, 1H), 3.51 (s, 3H).

Example 17: Alternate Synthesis of Compound 2C

Hydrolysis of Compound 1A to Compound 16A

Compound 1A (scaling factor, 1.0 equiv) and tetrahydrofuran (10 volumes) were charged to a reactor. A solution of potassium hydroxide (2 equiv) in water (4 volumes) was charged to the reactor. The reaction was agitated at about 20° C. for about 16 hours. An aqueous solution of 1M hydrochloric acid (4 volumes) was charged and the mixture was extracted with DCM (7 volumes). The organic layer was separated and washed with saturated aqueous sodium chloride (3 volumes). The organic layer was concentrated to afford Compound 16A. ¹H NMR (400 MHz, DMSO-d₆) δ 8.15 (dt, J=7.8, 1.1 Hz, 1H), 7.82 (dt, J=7.4, 1.0 Hz, 1H), 7.47-7.37 (m, 2H), 6.83 (dd, J=7.7, 0.8 Hz, 1H), 6.17 (dd, J=5.6, 1.2 Hz, 1H), 5.72 (dd, J=5.6, 2.3 Hz, 1H), 3.45 (s, 3H).

Click Reaction of Compound 16A and Compound 1D to Compound 6A

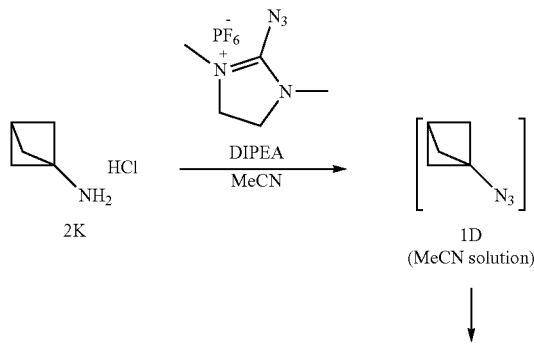

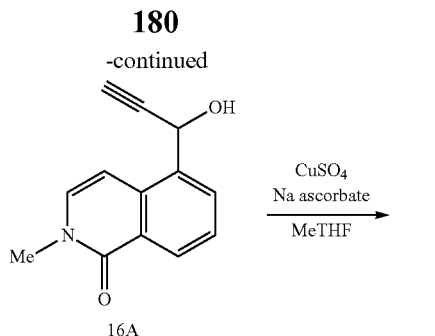

Compound 16A (scaling factor, 1.0 equiv), copper sulfate (0.1 equiv), sodium ascorbate (0.5 equiv) and 2-methyltetrahydrofuran (8 volumes) were charged to a reactor at about 20° C. In a second vessel was charged with Compound 2K (1.15 equiv), diisopropylethylamine (2.2 equiv) and acetonitrile (4.2 volumes). A third vessel was charged with 2-azido-1,3-dimethylimidazolium hexafluorophosphate (ADMP, 1.25 equiv) and acetonitrile (5.3 volumes). The mixtures containing Compound 2K and ADMP in the second and third vessels, respectively, were combined in a tube reactor to form Compound 1D, and the resulting mixture was collected in the first reactor containing Compound 16A over about 3 hours. After about 16 hours, 1M aqueous hydrochloric acid (8 volumes) and 2-methyltetrahydrofuran (8 volumes) were charged. The layers were separated and the organic layer was washed with 10 wt % aqueous sodium bicarbonate (10 volumes) and then concentrated to afford Compound 6A. ¹H NMR (400 MHz, DMSO): δ 8.19 ppm (d, J=7.6 Hz, 1H), 7.93 (s, 1H), 7.92 (d, J=7.6 Hz, 1H), 7.51 (dd, J=7.7, 7.7 Hz, 1H), 7.42 (d, J=7.7 Hz, 1H), 6.74 (d, J=7.6 Hz, 1H), 6.30 (d, J=4.6 Hz, 1H), 6.18 (d, J=4.6 Hz, 1H), 3.47 (s, 3H), 2.64 (s, 1H), 2.28 (s, 6H).

Oxidation of Compound 6A to Compound 2C

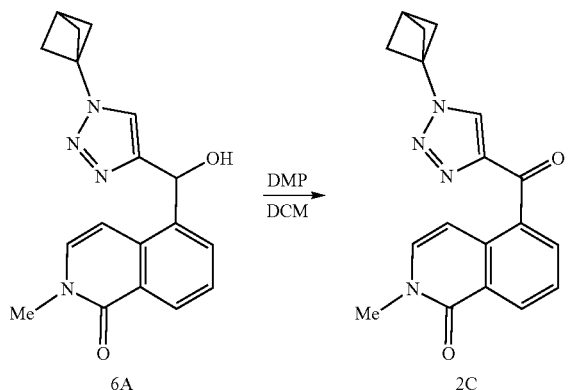 [SMILES: Cn1ccc2c(C(O)c3cn(C45CC(C4)C5)nn3)cccc2c1=O ; Cn1ccc2c(C(=O)c3cn(C45CC(C4)C5)nn3)cccc2c1=O]

To a reactor was charged Compound 6A (scaling factor, 1.0 equiv) and dichloromethane (10 volumes). Dess-Martin periodinane (1.2 equiv) was then charged to the reactor in portions. The reaction mixture was agitated at about 25° C. for about 3 hours until the reaction was deemed complete, and then a solution of 1M aqueous sodium hydroxide (8 volumes) was charged. The layers were separated and the organic layer was washed with a solution of 10 wt % aqueous sodium chloride (8 volumes). The layers were separated, and the organic layer was solvent exchanged into isopropanol (15 volumes). The mixture was heated to about 80° C. and then cooled to about 10° C. over about 6 hours and aged for about 6 hours. The resulting slurry was then filtered, the filter cake was rinsed with isopropanol (2 volumes) and n-heptane (2 volumes), and the cake was dried at about 20° C. to provide Compound 2C. $^1$H NMR (400 MHz, CDCl$_3$): δ 8.63 (ddd, J=7.9, 1.1, 0.5 Hz, 1H), 8.26 (d, J=7.5, 1.4 Hz, 1H), 8.21 (s, 1H), 7.53 (dd, J=7.9, 7.8 Hz, 1H), 7.09 (d, J=7.7 Hz, 1H), 7.04 (d, J=7.7 Hz, 1H), 3.57 (s, 3H), 2.74 (s, 1H), 2.43 (s, 6H).

Example 18: Alternate Synthesis #1 of Compound 6A

Click Reaction of Compound 1D and Compound 1A

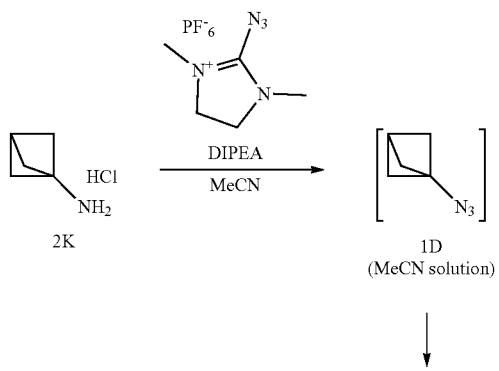

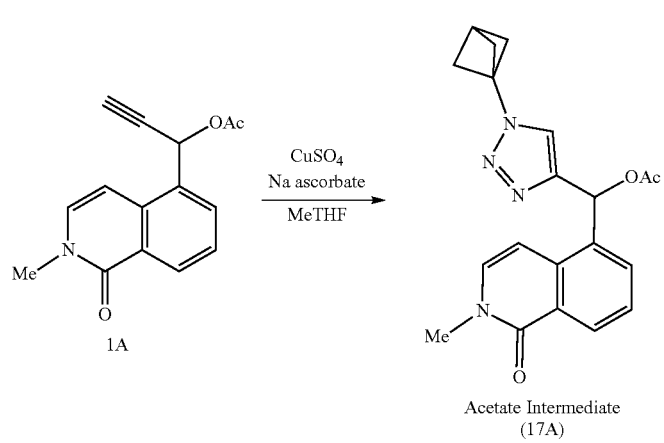

Compound 1A (scaling factor, 1.0 equiv), copper sulfate (0.1 equiv), sodium ascorbate (0.5 equiv), and 2-methyltetrahydrofuran (8 volumes) were charged to a reactor at about 20° C. To a second vessel was charged Compound 2K (1.15 equiv), diisopropylethylamine (2.2 equiv), and acetonitrile (4.2 volumes). To a third vessel was charged 2-azido-1,3-dimethylimidazolium hexafluorophosphate (ADMP, 1.25 equiv) and acetonitrile (5.3 volumes). The mixtures containing Compound 2K and ADMP in the second and third vessels, respectively, were combined in a tube reactor to form Compound 1D, and the resulting mixture was collected in the first reactor containing Compound 1A over about 3 hours. After about 16 hours, 1M aqueous hydrochloric acid (8 volumes) and 2-methyltetrahydrofuran (8 volumes) were charged. The layers were separated and the organic layer was washed with 10 wt % aqueous sodium bicarbonate (10 volumes) and then concentrated to afford acetate intermediate (Compound 17A). $^1$H NMR (400 MHz, Chloroform-d) δ 8.43 (d, J=7.7 Hz, 1H), 7.79 (d, J=7.5 Hz, 1H), 7.47 (t, J=7.7 Hz, 1H), 7.42 (s, 1H), 7.19 (s, 1H), 7.03 (dd, J=7.6, 1.0 Hz, 1H), 6.67 (d, J=7.7 Hz, 1H), 3.54 (s, 3H), 2.64 (s, 1H), 2.30 (s, 6H), 2.13 (s, 3H).

Hydrolysis of Acetate Intermediate (Compound 17A) to Compound 6A

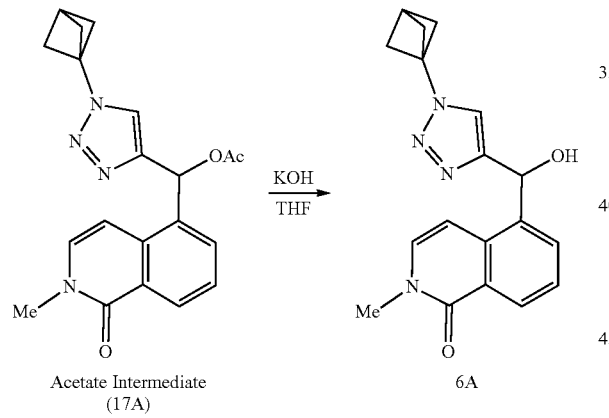

Acetate Intermediate (17A)

Acetate Intermediate (Compound 17A) (scaling factor, 1.0 equiv) and tetrahydrofuran (10 volumes) were charged to a reactor followed by a solution of potassium hydroxide (2 equiv) in water (4 volumes). The reaction was agitated at about 20° C. for about 16 hours. The reaction was quenched with a solution of 1M aqueous hydrochloric acid (4 volumes) and extracted with dichloromethane (7 volumes). The organic layer was washed with saturated aqueous sodium chloride (3 volumes) and concentrated to afford Compound 6A. $^1$H NMR (400 MHz, DMSO): δ 8.19 ppm (d, J=7.6 Hz, 1H), 7.93 (s, 1H), 7.92 (d, J=7.6 Hz, 1H), 7.51 (dd, J=7.7, 7.7 Hz, 1H), 7.42 (d, J=7.7 Hz, 1H), 6.74 (d, J=7.6 Hz, 1H), 6.30 (d, J=4.6 Hz, 1H), 6.18 (d, J=4.6 Hz, 1H), 3.47 (s, 3H), 2.64 (s, 1H), 2.28 (s, 6H).

Example 19: Alternate Synthesis #2 of Compound 6A

Coupling of Compound 18A and Compound 2B to Give Compound 6A

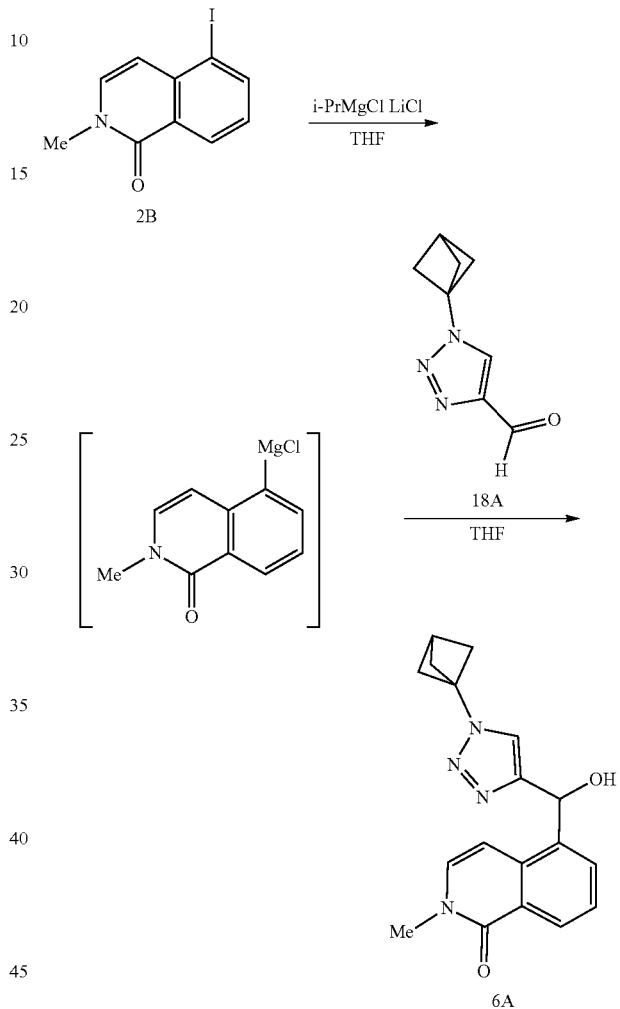

Compound 2B (1.1 equiv) and tetrahydrofuran (15 volumes) were charged to a reactor. The mixture was cooled to about 0° C. and charged with isopropylmagnesium chloride lithium chloride complex (1.2 equiv). A solution of Compound 18A (scaling factor, 1.0 equiv) in tetrahydrofuran (10 volumes) was charged at about 0° C. and the reaction was heated to about 50° C. and agitated for about 2 hours. The mixture was cooled to about 20° C. and quenched with 10 wt % aqueous ammonium chloride (40 volumes). Ethyl acetate (40 volumes) was charged and the layers were separated. The aqueous layer was extracted with ethyl acetate (40 volumes) twice. The combined organic layers were washed with 15 wt % aqueous sodium chloride (40 volumes), dried over magnesium sulfate, filtered, and concentrated. The residue was purified by silica gel chromatography to afford Compound 6A. $^1$H NMR (400 MHz, CDCl$_3$): δ 8.47 (d, J=8 Hz, 1H), 7.53 (t, J=8 Hz, 1H), 7.05 (d, J=8 Hz, 2H), 6.63 (d, J=8 Hz, 1H), 6.50 (s, 1H), 3.59 (s, 2H), 2.68 (s, 1H), 2.33 (s, 6H).

Example 20: Alternate Synthesis #3 of Compound 6A

Reduction of Compound 2C to Compound 6A

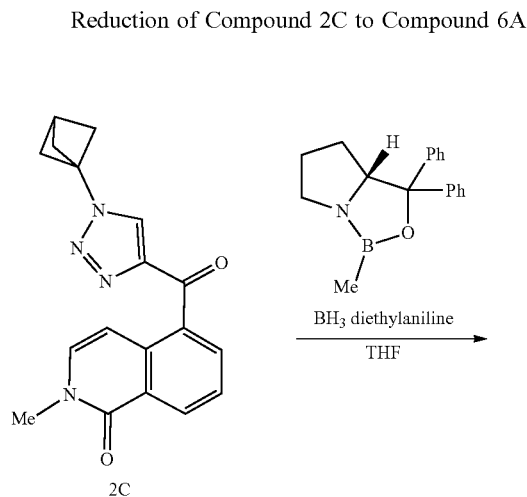

Compound 2C (scaling factor, 1.0 equiv) and (R)-(−)-2-methyl-CBS-oxazoborolidine (0.25 equiv) were charged to a reactor. Tetrahydrofuran (20 volumes) and borane N,N-diethylaniline (1.0 equiv) were charged and the reaction was agitated at about 20° C. for about 16 hours. Methanol (20 volumes) was charged followed by ethyl acetate (20 volumes), and the mixture was washed with 0.2M aqueous hydrochloric acid (20 volumes). The layers were separated and the organic layer was washed with saturated aqueous sodium chloride (20 volumes). The organic layer was concentrated and the residue was purified by silica gel chromatography eluting with ethyl acetate and n-heptane to afford Compound 6A. $^1$H NMR (400 MHz, DMSO): δ 8.19 ppm (d, J=7.6 Hz, 1H), 7.93 (s, 1H), 7.92 (d, J=7.6 Hz, 1H), 7.51 (dd, J=7.7, 7.7 Hz, 1H), 7.42 (d, J=7.7 Hz, 1H), 6.74 (d, J=7.6 Hz, 1H), 6.30 (d, J=4.6 Hz, 1H), 6.18 (d, J=4.6 Hz, 1H), 3.47 (s, 3H), 2.64 (s, 1H), 2.28 (s, 6H).

Example 21: Alternate Synthesis of Compound 2E/Compound 3C

Reduction of ethyl 1-(bicyclo[1.1.1]pentan-1-yl)-1H-1,2,3-triazole-4-carboxylate (Compound 10D) to Compound 18A Tetrahydrofuran (10 volumes) and morpholine (2.1 equiv) were charged to a reactor and the solution was cooled to about 0° C. A solution of diisobutylaluminum hydride (2.0 equiv, 1.0M in heptane) was charged at about 0° C. and the mixture was aged for about 3 hours. A solution of triazole ethyl ester (Compound 10D) (scaling factor, 1.0 equiv) in tetrahydrofuran (10 volumes) was charged at about 0° C. and then the temperature was adjusted to about 20° C. and the reaction was aged for about 18 hours. The mixture was then cooled to about 0° C. and a solution of diisobutylaluminum hydride (1.25 equiv, 1.0M in heptane) was charged. After the reaction was deemed complete, a solution of 2M aqueous hydrochloric acid (7.5 volumes) was charged. The temperature was adjusted to about 20° C. and the layers were separated. The aqueous layer was extracted with ethyl acetate (5 volumes) three times. The combined organic layers were dried over magnesium sulfate, filtered, and concentrated, and the residue was dried at about 40° C. to afford Compound 18A. $^1$H NMR (400 MHz, CDCl$_3$): δ 10.15 (s, 1H), 8.07 (s, 1H), 2.77 (s, 1H), 2.44 (s, 6H).

Condensation of Compound 18A to Compound 20A

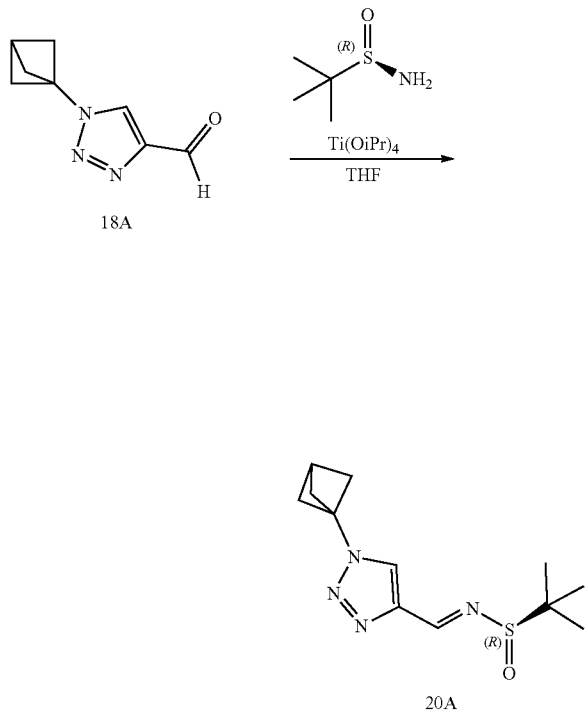

Compound 18A (scaling factor, 1.0 equiv), (R)-(+)-2-methyl-2-propanesulfinamide (1.05 equiv) and anhydrous tetrahydrofuran (15 volumes) were charged to a reactor. This solution was charged with titanium(IV) isopropoxide (2.0 equiv). The resulting solution was agitated at about 20° C. until the reaction was deemed complete. The solution was diluted with 15 wt % aqueous NaCl (10 volumes) and ethyl acetate (8 volumes). The resulting suspension was filtered through a pad of diatomaceous earth and rinsed forward with ethyl acetate. The organic layer was separated washed with water (8 volumes), and then concentrated. The residue was purified by silica gel chromatography to afford Compound 20A. ¹H NMR (400 MHz, CDCl₃): δ 8.79 (s, 1H), 8.02 (s, 1H), 2.77 (s, 1H), 2.45 (s, 6H), 1.25 (s, 9H).

Coupling of Compound 20A and Compound 2B to Compound 2E

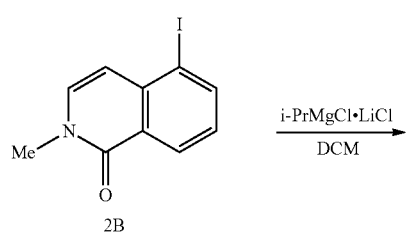

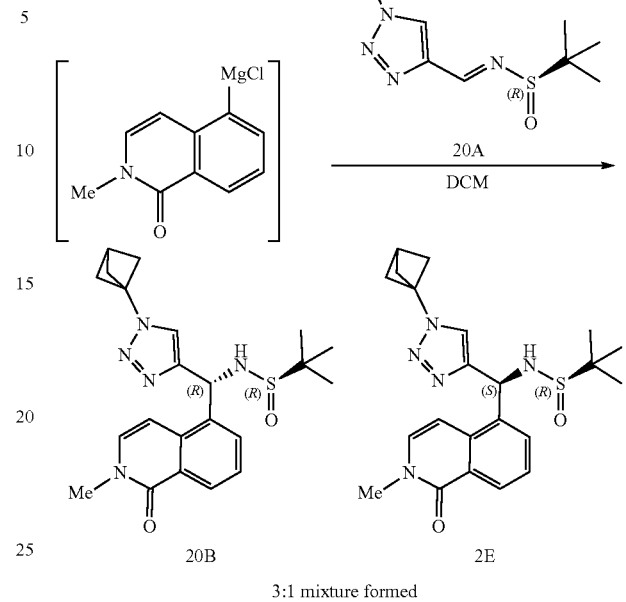

3:1 mixture formed

To a reactor was charged Compound 2B (1.5 equiv) and dichloromethane (20 volumes). The mixture was cooled to about 0° C. and charged with isopropylmagnesium chloride-lithium chloride complex (1.65 equiv, 1.3M in tetrahydrofuran), and the mixture was aged until the magnesiation reaction was deemed complete. A solution of Compound 20A (scaling factor, 1.0 equiv) in dichloromethane (20 volumes) was then charged at about 0° C. The resulting slurry was then adjusted to about 20° C. and agitated for about 19 hours to achieve 94% conversion to a mixture of Compound 20B and Compound 2E (3:1).

Note: It should be clear to one skilled in the art that using the (S)-enantiomer of Compound 20A (i.e., Compound 20C) will afford the opposite enantiomers of the products shown (i.e., a 3:1 mixture of Compound 3C and Compound 20D).

Example 22: Alternate Synthesis of Compound 2F

Oxime Formation from Compound 2C

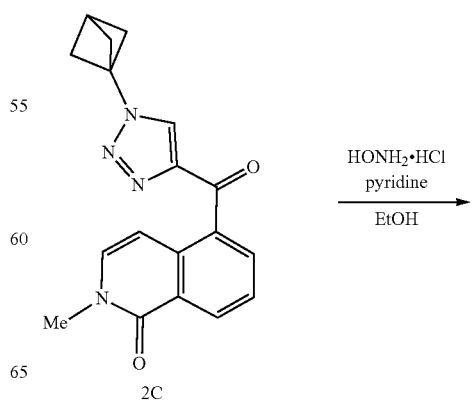

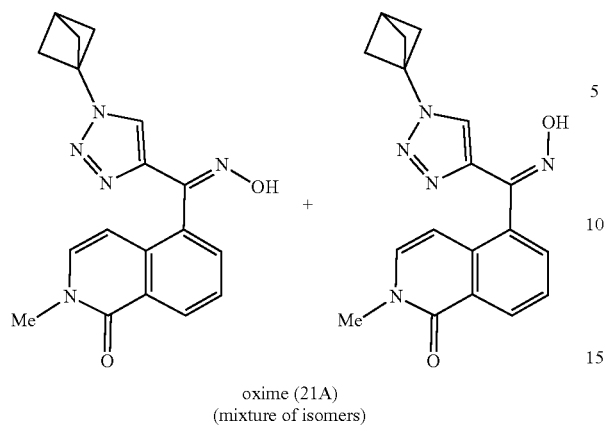

oxime (21A)
(mixture of isomers)

To a reactor were charged Compound 2C (scaling factor, 1.0 equiv), hydroxylamine hydrochloride (1.2 equiv) and ethanol (10 volumes). The mixture was agitated at about 20° C. and pyridine (3.0 equiv) was then charged. The reactor contents were heated to about 80° C. for about 16 hours until the reaction was deemed complete. The mixture was then cooled to about 25° C. and quenched with water (10 volumes). The mixture was diluted with ethyl acetate (10 volumes) and the layers were separated. The aqueous layer was extracted with ethyl acetate (5 volumes) twice and the combined organic layers were washed with 10 wt % aqueous sodium chloride (10 volumes). The organic layer was dried over magnesium sulfate and filtered. The resulting filtrate was concentrated and the residue was purified by silica gel chromatography eluting with methanol and dichloromethane to provide oxime (Compound 21A) (approximate 3:2 mixture of isomers). $^1$H NMR (400 MHz, DMSO-d$_6$): δ 12.29 (s, 0.6H), 11.46 (s, 0.4H), 8.88 (s, 0.6H), 8.35-8.27 (m, 1.4H), 7.64-7.62 (m, 0.6H), 7.56-7.53 (m, 1.6H), 7.39-7.33 (m, 1.4H), 6.18-6.11 (m, 1H), 3.48-3.47 (m, 3H), 2.71-2.67 (m, 1H), 2.38-2.32 (m, 6H).

Reduction of Oxime (Compound 21A) to Compound 21B

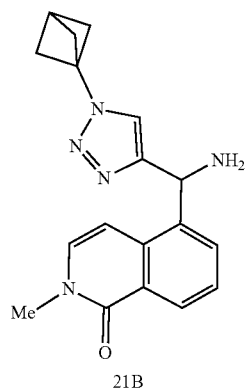

21B

To a reactor was charged oxime (Compound 21A) (scaling factor, 1.0 equiv), zinc dust (10 equiv), and tetrahydrofuran (8 volumes). A solution of 2M aqueous hydrochloric acid (5.0 equiv) was then charged to the reactor while maintaining the temperature below about 30° C. The reaction mixture was heated to about 60° C. for about 1 hour. When the reaction was deemed complete, the mixture was cooled to about 25° C. and filtered over diatomaceous earth. The filtrate was quenched with 1N aqueous sodium hydroxide. The organic layer was separated, and washed sequentially with water (8 volumes) and 10 wt % aqueous sodium chloride (8 volumes). The organic layer was dried over magnesium sulfate, filtered, and concentrated. The residue was purified by silica gel chromatography eluting with methanol and dichloromethane to afford Compound 21B. $^1$H NMR (400 MHz, DMSO-d$_6$): δ 8.16 (ddd, J=7.9, 1.2, 0.6 Hz, 1H), 7.89 (ddd, J=7.4, 1.4, 0.4 Hz, 1H), 7.88 (s, 1H), 7.48 (dd, J=7.8, 7.8 Hz, 1H), 7.44 (d, J=7.7 Hz, 1H), 6.84 (dd, J=7.9, 0.4 Hz, 1H), 5.71 (s, 1H), 3.48 (s, 3H), 2.65 (s, 1H), 2.41 (br s, 2H), 2.28 (s, 6H).

Conversion of Compound 21B to Compound 2F Salt

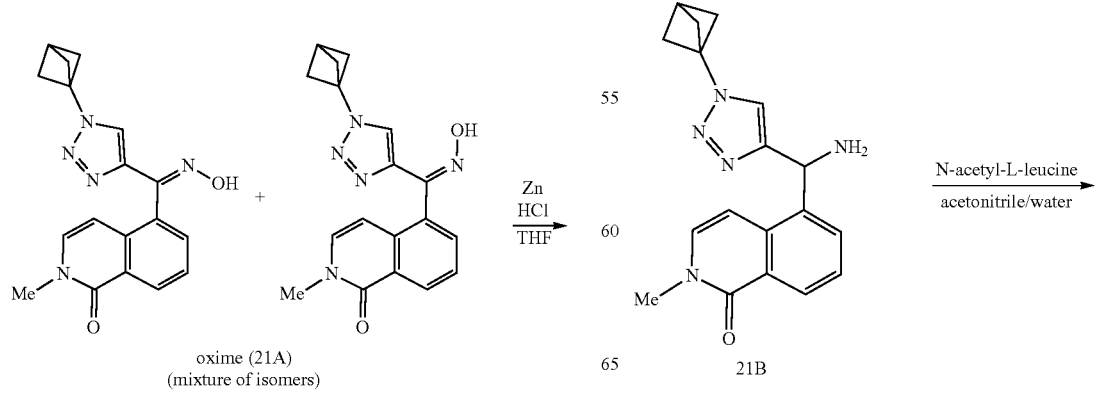

oxime (21A)
(mixture of isomers)

21B

-continued

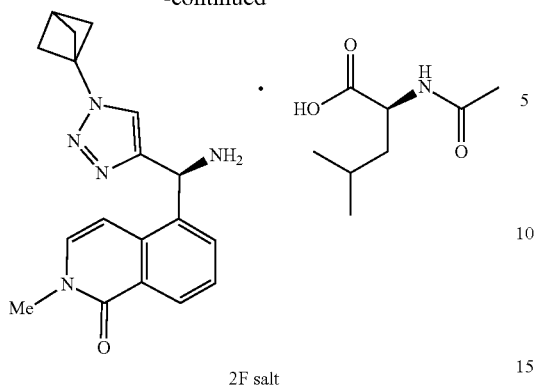

2F salt

To a reaction vessel were charged Compound 21B (scaling factor, 1.0 equiv), N-acetyl-L-leucine (1 equiv), acetonitrile (18 volumes) and water (2 volumes). The slurry was heated to about 50° C. and agitated for about 1 hour, then cooled to about 20° C. and filtered. The solids were rinsed with a mixture of acetonitrile (4.5 volumes) and water (0.5 volumes), and then dried at about 50° C. to afford Compound 2F·N-acetyl-L-leucine complex in 97.0% chiral purity. $^1$H NMR (400 MHz, DMSO-d$_6$) δ 8.15 (d, J=7.7 Hz, 1H), 8.02 (d, J=8.0 Hz, 1H), 7.86 (t, J=7.4 Hz 2H), 7.51-7.40 (m, 2H), 6.82 (d, J=7.7 Hz, 1H), 5.71 (s, 1H), 4.16 (td, J=8.1, 6.4 Hz, 1H), 3.47 (s, 3H), 2.64 (s, 1H), 2.26 (s, 5H), 1.81 (s, 3H), 1.66-1.53 (m, 1H), 1.46 (ddd, J=7.8, 5.9, 1.3 Hz, 2H), 0.84 (dd, J=19.0, 6.6 Hz, 6H).

Example 23: Alternate Synthesis #1 of Compound 1

Condensation of Compound 2C and Compound 1B to Compound 5A

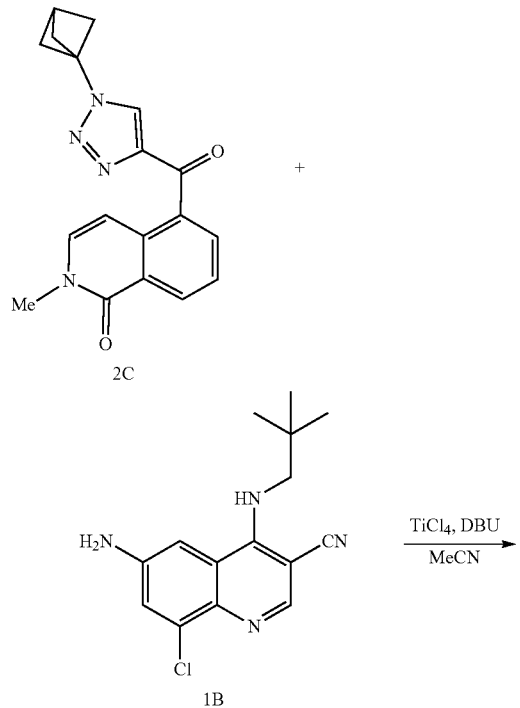

-continued

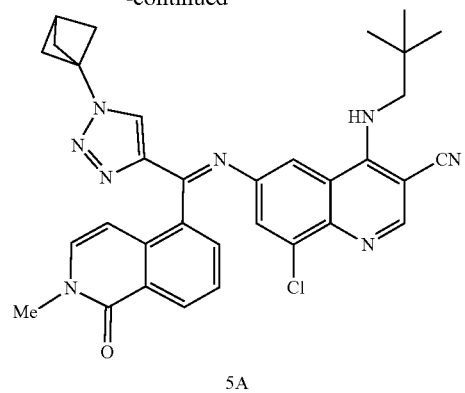

5A

To a reactor was charged Compound 2C (scaling factor, 1.0 equiv), Compound 1B (1.05 equiv), and acetonitrile (20 volumes). The mixture was cooled to about 0° C. and 1,8-diazabicyclo[5.4.0]undec-7-ene (DBU, 2.5 equiv) was charged. Titanium(IV) chloride (2.5 equiv) was charged while maintaining the temperature below about 10° C. The mixture was heated to about 50° C. and agitated for about 20 hours. The reaction mixture was then transferred to a solution of 10 wt % aqueous potassium carbonate (20 volumes) pre-cooled to 0° C. The resulting slurry was agitated for about 30 minutes, and then filtered through a pad of diatomaceous earth. The layers of the filtrate were separated and the aqueous layer was extracted with dichloromethane (5 volumes) three times. The organic layers were combined and concentrated to remove solvent. The residue was purified by silica gel chromatography eluting with ethyl acetate and n-heptane. The fractions containing Compound 5A were combined and concentrated, and the residue suspended in dichloromethane (5 volumes) and agitated for about 16 hours. The resulting slurry was filtered and the cake was rinsed with dichloromethane (3 volumes). The solids were dried at about 30° C. to afford Compound 5A. $^1$H NMR (400 MHz, DMSO-d$_6$): δ 8.84 (s, 1H), 8.38 (s, 1H), 8.17 (ddd, J=8.2, 1.1, 0.6 Hz, 1H), 7.73 (d, J=2.0 Hz, 1H), 7.70 (dd, J=7.4, 1.3 Hz, 1H), 7.64 (t, J=6.3 Hz, 1H), 7.46 (d, J=2.0 Hz, 1H), 7.43 (dd, J=7.9, 7.6 Hz, 1H), 7.36 (d, J=7.5 Hz, 1H), 6.28 (dd, J=7.5, 0.4 Hz, 1H), 3.70 (dd, J=13.9, 6.6 Hz), 3.60 (dd, J=dd, 13.9, 6.2), 3.42 (s, 3H), 2.72 (s, 1H), 2.38 (s, 6H), 0.87 (s, 9H).

Reduction of Compound 5A to Compound 1

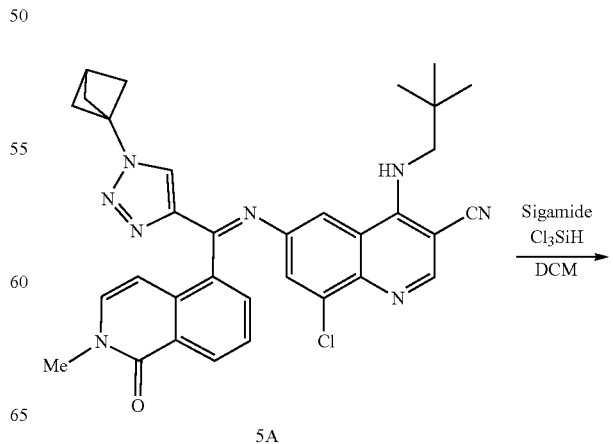

-continued

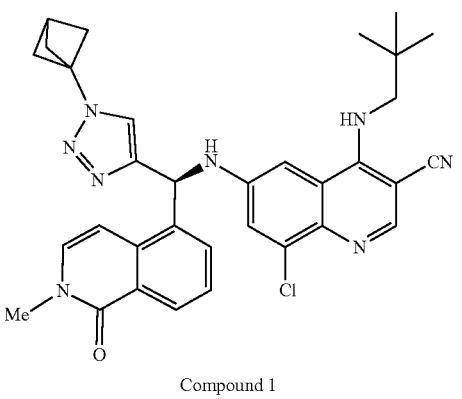

Compound 1

To a reactor was charged (S)—N-(3,5-Di-tert-butylphenyl)-3-methyl-2-(N-formyl-N-methylamino)butanamide (Sigamide, 0.34 equiv), trichlorosilane (4.0 equiv) and dichloromethane (10 volumes). The mixture was heated to about 30° C. and was then transferred to another reactor containing a solution of Compound 5A (scaling factor, 1.0 equiv) in dichloromethane (10 volumes). The resulting mixture was heated at about 30° C. for about 2 hours to achieve complete conversion to Compound 1 (3:2 mixture of enantiomers) by high pressure liquid chromatography.

Example 24: Alternate Synthesis #2 of Compound 1

Coupling of Compound 6A and Compound 1B to Compound 1

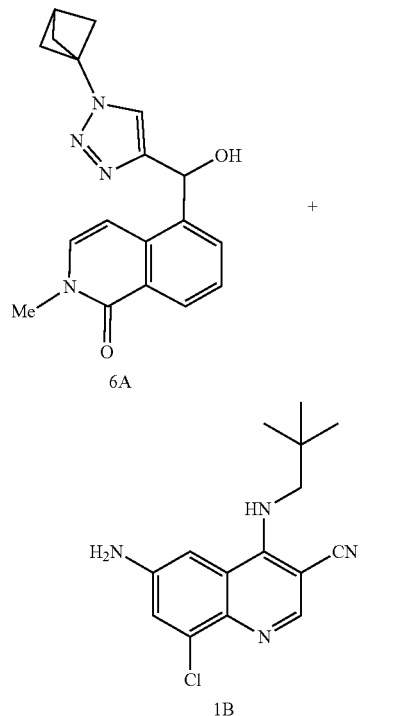

-continued

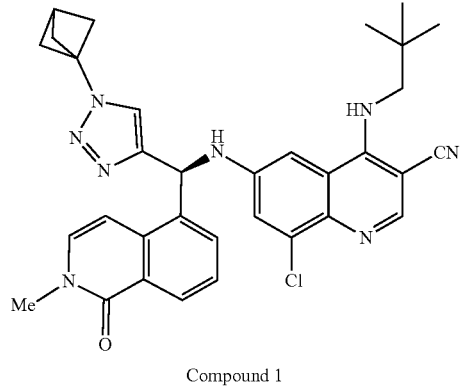

Compound 1

To a reactor was charged Compound 6A (scaling factor, 1.0 equiv), Compound 1B (1.0 equiv), triphenylphosphine (1.2 equiv), and tetrahydrofuran (10 volumes). To the mixture was then charged diisopropylazodicarboxylate (DIAD, 1.2 equiv) while maintaining the temperature below about 30° C. The reaction was agitated at about 20° C. for about 24 hours to obtain about 62% conversion to Compound 1 by high pressure liquid chromatography.

Example 25: Alternate Synthesis #3 of Compound 1

Activation of Compound 6A Displacement with Compound 1B to Compound 1

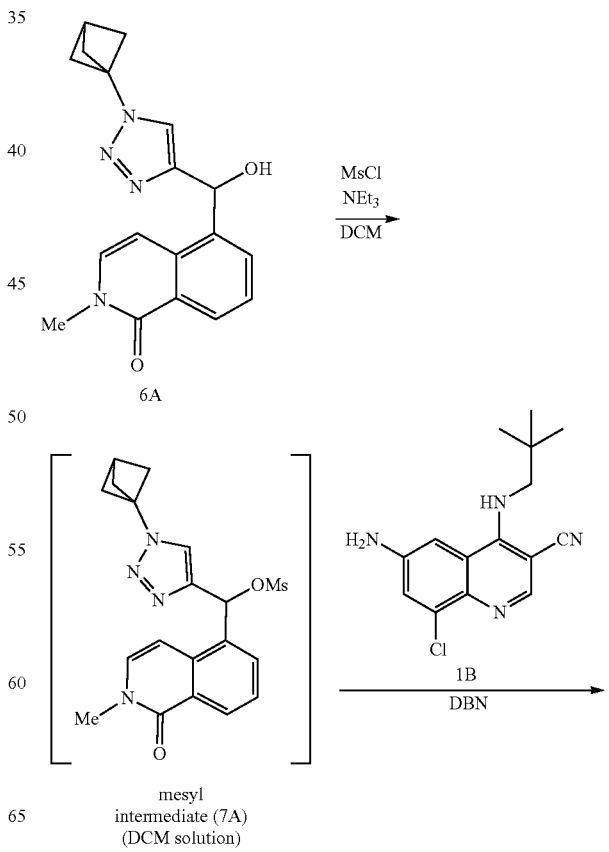

-continued

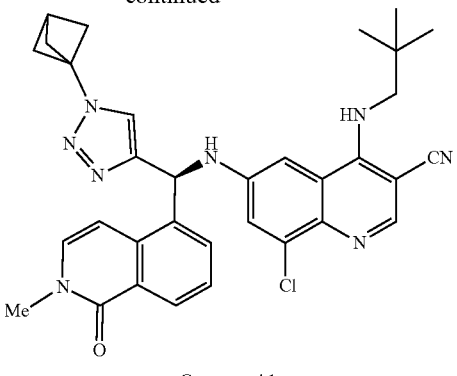

Compound 1

To a reactor were charged Compound 6A (scaling factor, 1.0 equiv), dichloromethane (10 volumes), and triethylamine (1.3 equiv). The mixture was cooled to about 0° C. and methanesulfonyl chloride (1.1 equiv) was charged. The reaction mixture was warmed to about 20° C. and agitated for about 4 hours, and then Compound 1B (1.0 equiv) and 1,5-diazabicyclo[4.3.0]non-5-ene (DBN, 1.2 equiv) were charged. The reaction mixture was agitated for about 18 hours, and then the mixture was diluted with ethyl acetate (8 volumes) and water (10 volumes). The layers were separated and the organic layer was washed with 10 wt % aqueous sodium chloride (8 volumes). The organic layer was dried over magnesium sulfate, filtered, and concentrated. The residue was purified by silica gel chromatography eluting with methanol and dichloromethane to provide Compound 1. $^1$H NMR (400 MHz, DMSO-$d_6$): δ 8.24 (s, 1H), 8.18 (d, J=7.2 Hz, 1H), 7.95 (s, 1H), 7.68 (dd, J=7.6, 1.2 Hz, 1H), 7.57 (d, J=2.0 Hz, 1H), 7.50 (d, J=8.0 Hz, 1H), 7.43 (at, J=7.8 Hz, 1H), 7.36 (d, J=6.8 Hz, 1H), 6.95 (at, J=6.4 Hz, 1H), 6.89 (d, J=2.0 Hz, 1H), 6.79 (d, J=7.6 Hz, 1H), 6.62 (d, J=6.8 Hz, 1H), 3.66 (dd, J=13.6, 7.2 Hz, 1H), 3.49 (s, 3H), 3.43 (dd, J=13.8, 5.4 Hz, 1H), 2.65 (s, 1H), 2.29 (s, 6H), 0.68 (s, 9H).

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A process for preparing Compound 2B, the process comprising:

(6a) contacting Compound 1E:

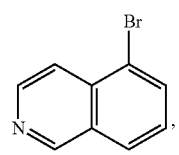

1E with a copper catalyst, an amine ligand, and an iodide additive in a solvent at a temperature sufficient to provide Compound 2O:

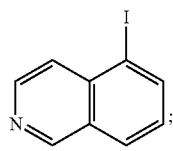

(6b) contacting Compound 2O with an alkylating agent in a solvent at a temperature sufficient to provide Compound 2P:

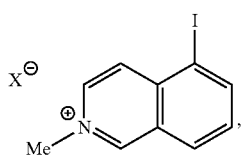

wherein X is iodide, chloride, bromide, methylsulfate, sulfate, methylcarbonate, carbonate, methanesulfonate, trifluoromethanesulfonate, toluenesulfonate, or tetrafluoroborate;

(6c) contacting Compound 2P with an oxidant and a base in a solvent at a temperature sufficient to provide Compound 2B:

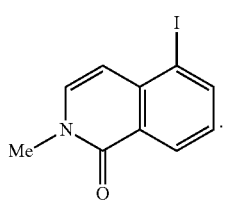

2. The process of claim 1, wherein for step (6a):
(i) the copper catalyst comprises copper (I) iodide, copper (I) bromide, copper (I) chloride, copper (I) oxide, copper (I) acetate, copper (I) bromide dimethyl sulfide complex, copper (I) triflate, copper (I) iodide tetrabutylammonium iodide complex, tetrakis (acetonitrile) copper (I) hexafluorophosphate, copper (I) iodide triethylphosphite complex, or copper (I) bromide triphenylphosphine complex;
(ii) the amine ligand comprises trans-N,N'-dimethylcyclohexane-1,2-diamine, N1,N2-dimethylethane-1,2-diamine, N1,N3-dimethylpropane-1,3-diamine, or N1-(2-aminoethyl) ethane-1,2-diamine;
(iii) the iodide additive comprises sodium iodide, lithium iodide, or potassium iodide;
(iv) the solvent comprises diethylene glycol dimethylether, diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, N,N-dimethylformamide, N,N-dimethylacetamide, N-methyl-2-pyrrolidinone, dimethyl sulfoxide, toluene, trifluorotoluene, cyclohexane, n-heptane, xylenes, acetonitrile, propionitrile, butyronitrile, dichloromethane, chloroform, dichloroethane, chlorobenzene, or dibromoethane; and/or
(v) the temperature is from about 50° C. to about 150° C.

3. The process of claim 1, wherein for step (6a):
(i) the copper catalyst comprises copper (I) iodide;
(ii) the amine ligand comprises trans-N,N'-dimethylcyclohexane-1,2-diamine;
(iii) the iodide additive comprises sodium iodide;
(iv) the solvent comprises diethylene glycol dimethylether; and/or
(v) the temperature is from about 80° C. to about 130° C.

4. The process of claim 1, wherein for step (6b):
(i) the alkylating agent comprises iodomethane, trimethylsulfoxonium iodide, diazomethane, dimethylsulfate, 2,2-dimethoxypropane, dimethylcarbonate, dimethyldicarbonate, methyl fluorosulfonate, methyl methanesulfonate, chloromethane, bromomethane, or trimethyloxonium tetrafluoroborate;
(ii) the solvent comprises acetonitrile, methanol, ethanol, isopropanol, tert-butanol, ethyl acetate, isopropyl acetate, n-propyl acetate, isobutyl acetate, acetone, methyl ethyl ketone, diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, N,N-dimethylformamide, N,N-dimethylacetamide, N-methyl-2-pyrrolidinone, dimethyl sulfoxide, toluene, trifluorotoluene, cyclohexane, n-heptane, xylenes, propionitrile, butyronitrile, dichloromethane, chloroform, dichloroethane, or chlorobenzene; and/or
(iii) the temperature is from about 0° C. to about 100° C.

5. The process of claim 1, wherein for step (6b):
(i) the alkylating agent comprises iodomethane;
(ii) the solvent comprises acetonitrile; and/or
(iii) the temperature is from about 20° C. to about 40° C.; and/or
(iv) X is iodide.

6. The process of claim 1, wherein for step (6c):
(i) the oxidant comprises potassium ferricyanide, oxone, lead tetraacetate, peracetic acid, hydrogen peroxide, molecular oxygen, air, sodium hypochlorite, sodium chlorite, sodium periodate, potassium peroxymonosulfate, 2,3-dichloro-5,6-dicyano-1,4-benzoquinone, 1,4-benzoquinone, periodic acid, potassium bromate, metachloroperoxybenzoic acid, or magnesium monoperoxypthalate;
(ii) the base comprises potassium hydroxide, lithium hydroxide, potassium hydroxide, or ammonium hydroxide;
(iii) the solvent comprises water, methanol, ethanol, isopropanol, tert-butanol, ethyl acetate, isopropyl acetate, n-propyl acetate, isobutyl acetate, acetone, methyl ethyl ketone, diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, N,N-dimethylformamide, N,N-dimethylacetamide, N-methyl-2-pyrrolidinone, dimethyl sulfoxide, toluene, trifluorotoluene, cyclohexane, n-heptane, xylenes, acetonitrile, propionitrile, butyronitrile, dichloromethane, chloroform, dichloroethane, chlorobenzene, or dibromoethane; and/or
(iv) the temperature is from about 0° C. to about 70° C.

7. The process of claim 1, wherein for step (6c):
(i) the oxidant comprises potassium ferricyanide;
(ii) the base comprises potassium hydroxide;
(iii) the solvent comprises water; and/or
(iv) the temperature is from about 5° C. to about 20° C.

8. A process for preparing Compound 1, the process comprising:

(3s) contacting Compound 10A:

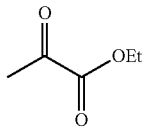
10A with a chlorinating reagent, optionally an amine catalyst, and optionally an acidic additive in an optional solvent at a temperature sufficient to provide Compound 10B:

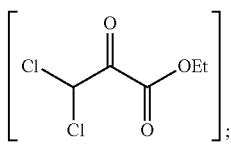
10B (3t) contacting Compound 10B with TsHNNH$_2$ in a solvent at a temperature sufficient to provide Compound 10C:

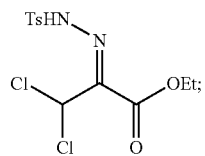
10C (3u) contacting Compound 10C with Compound 2K:

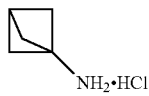
2K in the presence of a base in a solvent at a temperature sufficient to provide Compound 10D:

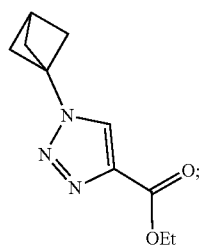
10D (3v) contacting Compound 10D with a base in a solvent at a temperature sufficient to provide Compound 2M:

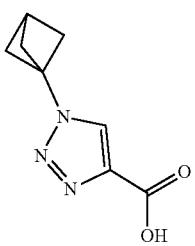
2M (3a) contacting Compound 2M with a chlorinating reagent and an additive in a solvent at a temperature sufficient to provide Compound 3A:

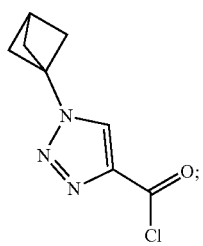
3A (3b) contacting Compound 3A with Compound 2B:

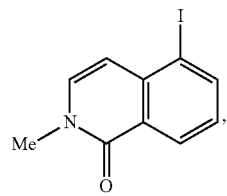
2B in the presence of an organometallic reagent, then followed by the addition of a copper or palladium catalyst, optionally, a zinc additive, and optionally, a Lewis base in a solvent at a temperature sufficient to provide Compound 2C:

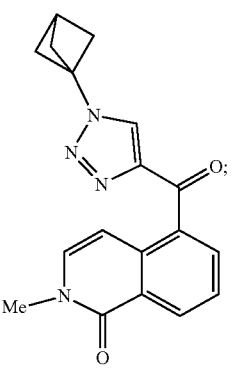
2C (3c) contacting Compound 2C with

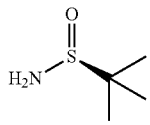

in the presence of a titanium-based or zirconium-based reagent in a solvent at a temperature sufficient to provide Compound 3B:

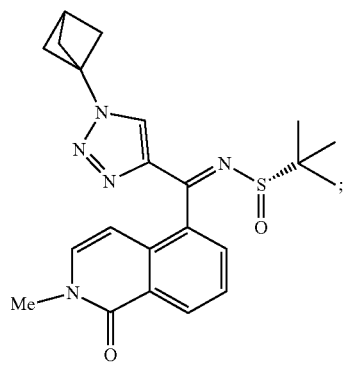

3B (3d) contacting Compound 3B with a reducing agent, and optionally a ruthenium, palladium, or platinum catalyst in a solvent at a temperature sufficient to provide Compound 3C:

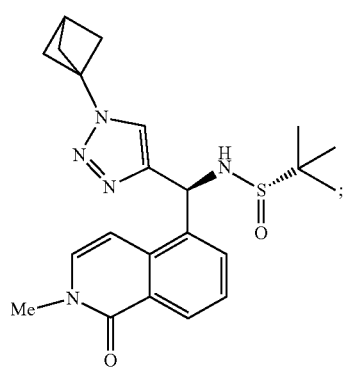

3C (3e) contacting Compound 3C with an acid in a solvent at a temperature sufficient to provide Compound 2F:

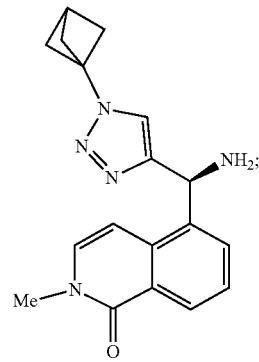

2F and (3f) contacting Compound 2F with Compound 2G:

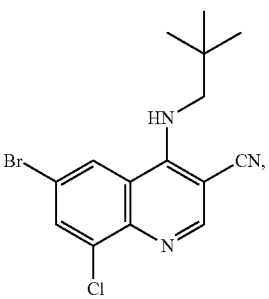

2G in the presence of a palladium catalyst and a base in a solvent at a temperature sufficient to provide Compound 1:

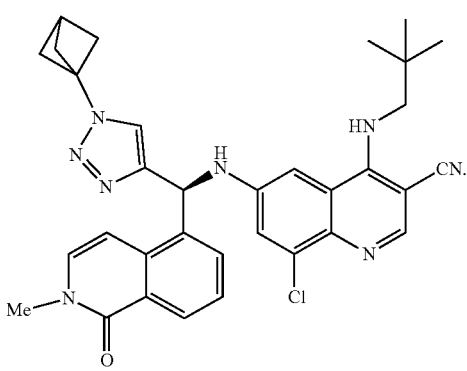

Compound 1

9. The process of claim 8, wherein for step (3s):

(i) the chlorinating reagent comprises sulfuryl chloride, chlorine gas, acetyl chloride/ceric ammonium nitrate, lithium diisopropylamide/4-toluenesulfonyl chloride, iodosobenzene dichloride, trichloromethanesulfonyl chloride, 1,3-dichloro-5,5-dimethylhydantoin/ammonium chloride, tetrachlorosilane/urea-hydrogen peroxide, N-chlorosuccinimide, trichloroisocyanuric acid, or sodium dichloroisocyanurate;

(ii) the amine catalyst, if present, comprises a L-proline amide or (2R,5R)-diphenylpyrrolidine;

(iii) the acidic additive, if present, comprise p-toluenesulfonic acid, hydrochloric acid, or methanesulfonic acid;
(iv) the solvent, if present, comprises trifluoroacetic acid, acetic acid, formic acid, propionic acid, ethyl acetate, isopropyl acetate, n-propyl acetate, isobutyl acetate, diethyl ether, 1,4-dioxane, tetrahydrofuran, 2-methyltetrahydrofuran, dimethoxyethane, methyl tert-butyl ether, cyclopentyl methyl ether, diphenyl ether, dichloromethane, chloroform, dichloroethane, chlorobenzene, methanol, ethanol, isopropanol, tert-butanol, acetonitrile, propionitrile, butyronitrile, toluene, trifluorotoluene, cyclohexane, n-heptane, or xylenes; and/or
(v) the temperature is from about 40° C. to about 80° C.

10. The process of claim 8, wherein for step (3s):
(i) the chlorinating reagent comprises sulfuryl chloride;
(ii) the amine catalyst is absent;
(iii) the acidic additive comprises p-toluenesulfonic acid;
(iv) the solvent is absent; and/or
(v) the temperature is from about 65° C. to about 75° C.

11. The process of claim 8, wherein for step (3t):
(i) the solvent comprises propionic acid, trifluoroacetic acid, acetic acid, formic acid, ethyl acetate, isopropyl acetate, n-propyl acetate, isobutyl acetate, diethyl ether, 1,4-dioxane, tetrahydrofuran, 2-methyltetrahydrofuran, dimethoxyethane, methyl tert-butyl ether, cyclopentyl methyl ether, diphenyl ether, dichloromethane, chloroform, dichloroethane, chlorobenzene, methanol, ethanol, isopropanol, tert-butanol, acetonitrile, propionitrile, butyronitrile, toluene, trifluorotoluene, cyclohexane, n-heptane, or xylenes; and/or
(ii) the temperature is from about 20° C. to about 60° C.

12. The process of claim 8, wherein for step (3t):
(i) the solvent comprises propionic acid; and/or
(ii) the temperature is about 25° C.

13. The process of claim 8, wherein for step (3u):
(i) the base comprises N,N-diisopropylethylamine, N-methylmorpholine, tri-n-propylamine, triethylamine, tri-n-butylamine, 1,8-diazabicyclo [5.4.0] undec-7-ene, 1,4-diazabicyclo [2.2.2] octane, pyridine, 2,6-lutidine, collidine, sodium bicarbonate, sodium carbonate, sodium phosphate monobasic, sodium phosphate dibasic, sodium phosphate tribasic, sodium acetate, potassium bicarbonate, potassium carbonate, potassium phosphate monobasic, potassium phosphate dibasic, potassium phosphate tribasic, potassium acetate, potassium fluoride, lithium carbonate, lithium acetate, or cesium carbonate;
(ii) the solvent comprises methanol, isopropanol, tert-butanol, ethanol, 1-propanol, diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, benzene, toluene, trifluorotoluene, cyclohexane, n-heptane, xylenes, dichloromethane, chloroform, dichloroethane, chlorobenzene, acetonitrile, propionitrile, butyronitrile, N,N-dimethylformamide, N,N-dimethylacetamide, N-methyl-2-pyrrolidinone, dimethyl sulfoxide, or a combination thereof; and/or
(iii) the temperature is from about −20° C. to about 60° C.

14. The process of claim 8, wherein for step (3u):
(i) the base comprises N,N-diisopropylethylamine;
(ii) the solvent comprises acetonitrile and ethanol; and/or
(iii) the temperature is from about 0° C. to about 20° C.

15. The process of claim 8, wherein for step (3v):
(i) the base comprises sodium hydroxide, lithium hydroxide, potassium hydroxide, or potassium trimethylsilanoate;
(ii) the solvent comprises water, diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, methanol, ethanol, isopropanol, tert-butanol, 1-propanol, benzene, toluene, trifluorotoluene, cyclohexane, n-heptane, xylenes, acetonitrile, propionitrile, butyronitrile, dichloromethane, chloroform, dichloroethane, chlorobenzene, or a combination thereof; and/or
(iii) the temperature is from about 0° C. to about 100° C.

16. The process of claim 8, wherein for step (3v):
(i) the base comprises sodium hydroxide;
(ii) the solvent comprises ethanol and water; and/or
(iii) the temperature is from about 10° C. to about 70° C.

17. The process of claim 8, wherein Compound 2B is prepared from a process comprising:
(3k) contacting Compound 1E:

[Structure 1E: 5-bromoisoquinoline]

with a copper catalyst, an amine ligand, and an iodide additive in a solvent at a temperature sufficient to provide Compound 2O:

[Structure 2O: 5-iodoisoquinoline]

(3l) contacting Compound 2O with an alkylating agent in a solvent at a temperature sufficient to provide Compound 2P:

[Structure 2P: N-methyl-5-iodoisoquinolinium X⁻]

wherein X is iodide, chloride, bromide, methylsulfate, sulfate, methylcarbonate, carbonate, methanesulfonate, trifluoromethanesulfonate, toluenesulfonate, or tetrafluoroborate;

(3m) contacting Compound 2P with an oxidant and a base in a solvent at a temperature sufficient to provide Compound 2B:

2B

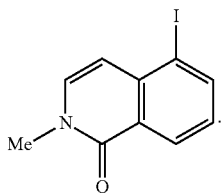

18. The process of claim 17, wherein for step (3k):
(i) the copper catalyst comprises copper (I) iodide, copper (I) bromide, copper (I) chloride, copper (I) oxide, copper (I) acetate, copper (I) bromide dimethyl sulfide complex, copper (I) triflate, copper (I) iodide tetrabutylammonium iodide complex, tetrakis (acetonitrile) copper (I) hexafluorophosphate, copper (I) iodide triethylphosphite complex, or copper (I) bromide triphenylphosphine complex;
(ii) the amine ligand comprises trans-N,N'-dimethylcyclohexane-1,2-diamine, N1,N2-dimethylethane-1,2-diamine, N1,N3-dimethylpropane-1,3-diamine, or N1-(2-aminoethyl) ethane-1,2-diamine;
(iii) the iodide additive comprises sodium iodide, lithium iodide, or potassium iodide;
(iv) the solvent comprises diethylene glycol dimethylether, diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, N,N-dimethylformamide, N,N-dimethylacetamide, N-methyl-2-pyrrolidinone, dimethyl sulfoxide, toluene, trifluorotoluene, cyclohexane, n-heptane, xylenes, acetonitrile, propionitrile, butyronitrile, dichloromethane, chloroform, dichloroethane, chlorobenzene, or dibromoethane; and/or
(v) the temperature is from about 50° C. to about 150° C.

19. The process of claim 17, wherein for step (3l):
(i) the alkylating agent comprises iodomethane, trimethylsulfoxonium iodide, diazomethane, dimethylsulfate, 2,2-dimethoxypropane, dimethylcarbonate, dimethyldicarbonate, methyl fluorosulfonate, methyl methanesulfonate, chloromethane, bromomethane, or trimethyloxonium tetrafluoroborate;
(ii) the solvent comprises acetonitrile, methanol, ethanol, isopropanol, tert-butanol, ethyl acetate, isopropyl acetate, n-propyl acetate, isobutyl acetate, acetone, methyl ethyl ketone, diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, N,N-dimethylformamide, N,N-dimethylacetamide, N-methyl-2-pyrrolidinone, dimethyl sulfoxide, toluene, trifluorotoluene, cyclohexane, n-heptane, xylenes, propionitrile, butyronitrile, dichloromethane, chloroform, dichloroethane, or chlorobenzene; and/or
(iii) the temperature is from about 0° C. to about 100° C.

20. The process of claim 17, wherein for step (3m):
(i) the oxidant comprises potassium ferricyanide, oxone, lead tetraacetate, peracetic acid, hydrogen peroxide, molecular oxygen, air, sodium hypochlorite, sodium chlorite, sodium periodate, potassium peroxymonosulfate, 2,3-dichloro-5,6-dicyano-1,4-benzoquinone, 1,4-benzoquinone, periodic acid, potassium bromate, metachloroperoxybenzoic acid, or magnesium monoperoxypthalate;
(ii) the base comprises potassium hydroxide, lithium hydroxide, potassium hydroxide, or ammonium hydroxide;
(iii) the solvent comprises water, methanol, ethanol, isopropanol, tert-butanol, ethyl acetate, isopropyl acetate, n-propyl acetate, isobutyl acetate, acetone, methyl ethyl ketone, diethyl ether, 1,4-dioxane, tetrahydrofuran, 2-methyltetrahydrofuran, dimethoxyethane, methyl tert-butyl ether, cyclopentyl methyl ether, diphenyl ether, dibutyl ether, N,N-dimethylformamide, N,N-dimethylacetamide, N-methyl-2-pyrrolidinone, dimethyl sulfoxide, toluene, trifluorotoluene, cyclohexane, n-heptane, xylenes, acetonitrile, propionitrile, butyronitrile, dichloromethane, chloroform, dichloroethane, chlorobenzene, or dibromoethane; and/or
(iv) the temperature is from about 0° C. to about 70° C.

* * * * *

UNITED STATES PATENT AND TRADEMARK OFFICE
CERTIFICATE OF CORRECTION

PATENT NO. : 12,365,666 B2
APPLICATION NO. : 18/386675
DATED : July 22, 2025
INVENTOR(S) : Kevin M. Allan et al.

It is certified that error appears in the above-identified patent and that said Letters Patent is hereby corrected as shown below:

In the Claims

Column 197, Line 42, Claim 2, delete "copper (I)" and insert -- copper(I) --.

Column 197, Lines 42-43, Claim 2, delete "copper (I)" and insert -- copper(I) --.

Column 197, Line 43, Claim 2, first occurrence, delete "copper (I)" and insert -- copper(I) --.

Column 197, Line 43, Claim 2, second occurrence, delete "copper (I)" and insert -- copper(I) --.

Column 197, Line 44, Claim 2, first occurrence, delete "copper (I)" and insert -- copper(I) --.

Column 197, Line 44, Claim 2, second occurrence, delete "copper (I)" and insert -- copper(I) --.

Column 197, Line 45, Claim 2, first occurrence, delete "copper (I)" and insert -- copper(I) --.

Column 197, Line 45, Claim 2, second occurrence, delete "copper (I)" and insert -- copper(I) --.

Column 197, Lines 46-47, Claim 2, delete "tetrakis (acetonitrile) copper (I)" and insert -- tetrakis(acetonitrile)copper(I) --.

Column 197, Line 47, Claim 2, delete "copper (I)" and insert -- copper(I) --.

Column 197, Line 48, Claim 2, delete "copper (I)" and insert -- copper(I) --.

Column 197, Line 53, Claim 2, delete "(2-aminoethyl) ethane" and insert -- (2-aminoethyl)ethane --.

Column 198, Line 2, Claim 3, delete "copper (I)" and insert -- copper(I) --.

Signed and Sealed this
Fourteenth Day of October, 2025

John A. Squires
*Director of the United States Patent and Trademark Office*

CERTIFICATE OF CORRECTION (continued)
U.S. Pat. No. 12,365,666 B2

Column 198, Line 44, Claim 6, delete "monoperoxypthalate;" and insert -- monoperoxyphthalate; --.

Column 202, Line 18, Claim 8, delete "(3f) contacting Compound 2F with Compound 2G:" and insert the same on Column 202, Line 19, as a new subpoint.

Column 203, Line 42, Claim 13, delete "1,8-diazabicyclo [5.4.0] undec-" and insert -- 1,8-diazabicyclo[5.4.0]undec- --.

Column 203, Line 43, Claim 13, delete "1,4-diazabicyclo [2.2.2] octane," and insert -- 1,4-diazabicyclo[2.2.2]octane, --.

Column 204, Lines 3-4, Claim 15, delete "trimethylsilanoate;" and insert -- trimethylsilanolate; --.

Column 205, Line 13, Claim 18, delete "copper (I)" and insert -- copper(I) --.

Column 205, Lines 13-14, Claim 18, delete "copper (I)" and insert -- copper(I) --.

Column 205, Line 14, Claim 18, first occurrence, delete "copper (I)" and insert -- copper(I) --.

Column 205, Line 14, Claim 18, second occurrence, delete "copper (I)" and insert -- copper(I) --.

Column 205, Line 15, Claim 18, first occurrence, delete "copper (I)" and insert -- copper(I) --.

Column 205, Line 15, Claim 18, second occurrence, delete "copper (I)" and insert -- copper(I) --.

Column 205, Line 16, Claim 18, first occurrence, delete "copper (I)" and insert -- copper(I) --.

Column 205, Line 16, Claim 18, second occurrence, delete "copper (I)" and insert -- copper(I) --.

Column 205, Lines 17-18, Claim 18, delete "tetrakis (acetonitrile) copper (I)" and insert -- tetrakis(acetonitrile)copper(I) --.

Column 205, Line 18, Claim 18, delete "copper (I)" and insert -- copper(I) --.

Column 205, Line 19, Claim 18, delete "copper (I)" and insert -- copper(I) --.

Column 205, Line 24, Claim 18, delete "(2-aminoethyl) ethane" and insert -- (2-aminoethyl)ethane --.

Column 206, Line 24, Claim 20, delete "monoperoxypthalate;" and insert -- monoperoxyphthalate; --.